(12) United States Patent
Fishman

(10) Patent No.: US 7,681,572 B2
(45) Date of Patent: Mar. 23, 2010

(54) METHOD AND DEVICES FOR ADMINISTRATION OF THERAPEUTIC GASES

(75) Inventor: Royce S. Fishman, Hernando, FL (US)

(73) Assignee: AGA AB (SE)

( * ) Notice: Subject to any disclaimer, the term of this patent is extended or adjusted under 35 U.S.C. 154(b) by 1463 days.

(21) Appl. No.: 10/632,158

(22) Filed: Jul. 31, 2003

(65) Prior Publication Data

US 2004/0129270 A1 Jul. 8, 2004

Related U.S. Application Data

(60) Provisional application No. 60/404,830, filed on Aug. 20, 2002.

(51) Int. Cl.
*A61M 15/00* (2006.01)
*A61M 16/10* (2006.01)
*A61M 11/00* (2006.01)

(52) U.S. Cl. .................. 128/203.12; 128/200.14; 128/200.23

(58) Field of Classification Search ............ 128/205.21, 128/205.22, 204.18, 204.21, 203.21, 203.24, 128/200.14–200.23, 203.12–204.14; 222/145.1, 222/145.3, 145.5
See application file for complete search history.

(56) References Cited

U.S. PATENT DOCUMENTS

| | | | |
|---|---|---|---|
| 87,319 A | 3/1869 | Barker | |
| 2,185,067 A | 12/1939 | Sholes | |
| 2,388,533 A | 11/1945 | Edmondson | |
| 2,574,028 A * | 11/1951 | Fields et al. | 222/5 |
| 2,651,303 A * | 9/1953 | Johnson et al. | 128/205.21 |
| 2,944,547 A * | 7/1960 | Ziherl et al. | 128/203.21 |
| 3,192,106 A | 6/1965 | Bracken et al. | |
| 3,747,600 A | 7/1973 | Andersson | |
| 3,776,227 A | 12/1973 | Pitesky et al. | |
| 3,876,773 A | 4/1975 | Bracken | |
| 4,062,356 A * | 12/1977 | Merrifield | 128/205.22 |

(Continued)

FOREIGN PATENT DOCUMENTS

EP 1 110 547 A2 6/2001

(Continued)

OTHER PUBLICATIONS

Ammer, R, Eckhard Alt, Ayers G, Schmitt C, Pasquantonio J, Schmidt M, Putter K, Schomig A., "Pain Threshold for Low Energy Intracardiac Cardioversion of Atrial Fibrillation with Low and No Sedation," PACE 1996: 19[Pt II]: 230-236.

(Continued)

*Primary Examiner*—Patricia M Bianco
*Assistant Examiner*—Keri J Nicholson
(74) *Attorney, Agent, or Firm*—Lerner, David, Littenberg, Krumholz & Mentlik, LLP

(57) ABSTRACT

Methods for administering medical gases include providing the medical gas in compressed gas cartridges containing an amount of the medical gas preferably corresponding substantially to a unit dose of the medical gas and providing a patient with access to the medical gas from the gas cartridge upon need therefor. Apparatus for administering medical gases also includes a housing, a cassette associated with the housing containing at least one compressed gas cartridge preferably containing at least an amount of the medical gas substantially as required for a single dose and a patient supply interface to provide the medical gas to the patient.

30 Claims, 48 Drawing Sheets

U.S. PATENT DOCUMENTS

| | | | |
|---|---|---|---|
| 4,360,026 A | | 11/1982 | Venin et al. |
| 4,648,393 A | | 3/1987 | Landis et al. |
| 4,722,333 A | * | 2/1988 | Bartos .................. 128/202.27 |
| 4,771,771 A | * | 9/1988 | Walther ................. 128/201.25 |
| 5,099,834 A | | 3/1992 | Fishman |
| 5,228,434 A | | 7/1993 | Fishman |
| 5,485,827 A | | 1/1996 | Zapol et al. |
| 5,488,946 A | | 2/1996 | Calhoun et al. |
| 5,520,166 A | * | 5/1996 | Ritson et al. ........... 128/200.14 |
| 5,524,613 A | | 6/1996 | Haber et al. |
| 5,690,968 A | | 11/1997 | Ross et al. |
| 5,783,199 A | | 7/1998 | Ross et al. |
| 5,792,187 A | | 8/1998 | Adams |
| 5,846,556 A | | 12/1998 | Brooks |
| 6,016,801 A | | 1/2000 | Philips |
| 6,021,777 A | | 2/2000 | Post et al. |
| 6,125,844 A | | 10/2000 | Samiotes |
| 6,164,276 A | | 12/2000 | Bathe et al. |
| 6,168,801 B1 | | 1/2001 | Heil, Jr. et al. |
| 6,274,633 B1 | | 8/2001 | Franks et al. |
| 6,286,505 B1 | | 9/2001 | Psaros |
| 6,347,627 B1 | | 2/2002 | Frankie et al. |
| 6,484,644 B2 | | 11/2002 | Forbes et al. |
| 6,612,306 B1 | | 9/2003 | Mault |
| 6,728,574 B2 | | 4/2004 | Ujhelyi |
| 6,745,764 B2 | | 6/2004 | Hickle |
| 6,807,965 B1 | | 10/2004 | Hickle |
| 2002/0017296 A1 | | 2/2002 | Hickle |
| 2003/0078632 A1 | | 4/2003 | Ujhelyi et al. |

FOREIGN PATENT DOCUMENTS

| | | |
|---|---|---|
| WO | WO-95/18644 | 7/1995 |
| WO | WO-98/25665 | 6/1998 |
| WO | WO-00/53192 A1 | 9/2000 |
| WO | WO-01/03645 A2 | 1/2001 |
| WO | WO-01/36018 A2 | 5/2001 |
| WO | WO-01/49349 | 7/2001 |

OTHER PUBLICATIONS

Bowler SD, Green A, Mitchell CA, "Butekyo Breathing Techniques in Asthma: A Blinded Randomized Controlled Trial," MJA 1998; 169: 575-578.

Ayers GM, "New Concepts in Atrial Fibrillation," Jour of Interventional Cardiac Electrophysiology, 2000; 4: 155-161.

Browne-Heitschmidt MG, Cassidy JB, "Heliox: A New Treatment for Life Threatening Asthma," Pediatric Nursing, Sep.-Oct. 1977, 479-482.

Castera L, Negre I, Samii K, Buffet C, "Patient Administered Nitrous Oxide/Oxygen Inhalation Provides Effective Sedation and Analgesia for Percutaneous Liver Biopsy. A Randomized Placebo Controlled Trial," Am J Gastroenterol, May 2001, 96(5): 1553-1557.

Daynes G, Gillman MA, "Psychotropic Analgesic Nitrous Oxide Prevents Craving after Withdrawal for Alcohol, Cannabis and Tobacco," Intern Jour Neuroscience, 1994; vol. 76, 13-16.

Dexter SL, "Rebreathing Aborts Migraine Attacks," Br Med J (Clin Res Ed) (Jan. 30, 1982) 284(6312):312.

Freinberg WM, Blackshear JL, Laupacis A, Kronmal A, Hart RG, "Prevalence, Age Distribution and Gender of Patients with Atrial Fibrillation. Analysis and Implications," Arch Intern Med, Mar. 13, 1995; 155: 469-473.

Gall O, Annequin D, Benoit G, Van Glabeke E, Vrancea F, Murat I, "Adverse Events of Premixed Nitrous Oxide and Oxygen for Procedural Sedation in Children," The Lancet, vol. 358, Nov. 2001, 1514-1515.

Hart RG, Halperin JL, "Atrial Fibrillation and Stroke Concepts and Controversies," Stroke, 2000; 32: 803-808.

Haven, JH et al., Abstract/Presentation at 2001 Annual Scientific Assembly of the American Academy of Family Physicians.

Hirskyj L, "Use of Entonox in a General Hospital," Nursing Times, Oct. 1971, 1321-1323.

Hollman G, Shen G, Zeng L, Yngsdal-Krenz R, Perloff W, Zimmerman J, Straus R, "Helium-Oxygen Improves Clinical Asthma Scores in Children with Acute Bronchiolitis," Crit Care Med (Oct. 26, 1998(10): 1731-6.

Hornbein TF, Eger EI 2nd, Winter PM, Smith G, Wetstone D, Smith KH, "The Minimum Alveolar Concentration of Nitrous Oxide in Man," Anesth Analg Jul. 1982 61(7): 553-556.

Jung J, Heisel A, Fries R, Kollner V, "Tolerability of Internal Low Energy Shock Strengths Currently Needed for Endocardial Atrial Cardioversion," Am Jour Cardiol vol. 80, Dec. 1997: 1489-1490 ALH1.016.

Jung W, Wolpert C, Esmailzadeh B, Spehl S, Herwig S, Schumacer B, Lewalter T, Omran H, Kirchoff PG, Luderitz B, "Specific Consideratonons with the Automatic Implantable Atrial Defibrillator," J Cardiovasc Electrophysiol, vol. 9, pp. S193-S201, Aug. 1998 Supplement ALH 1.008.

Jung W, Wolpert C, Esmailzadeh B, Spehl S, Herwig S, Schmacher B, Lewalter T, Omran H, Schmipf R, Vahlhaus C, Welz A, Luderitz B., "Clinical Experience with Implantable Atrial and Combined Atrioventricular Defibrillators," Jour of Intervent Cardiac Electrophysiology, 2000: 4: 185-195.

Kass JE, Castriotta RJ, "Heliox Therapy in Acute Severe Asthma," Chest (Mar. 1995) 107(3):757-60.

Kass, JE, Terregiono CA, "The Effect of Heliox in Acute Severe Asthma: A Randomized Controlled Trial," Chest (Aug. 1999) 116(2): 296-300.

Keating HJ, Kundrat M, "Patient Controlled Analgesia with Nitrous Oxide in Cancer Pain," J of Pain and Symptom Management, vol. 11, No. 2, Feb. 1996, 126-30.

Lake FR, McCall MG, Cullen KJ, Rosman DL, de Klerk NH, "Atrial Fibrillation and Mortality in an Elderly Population," Aust NZ J Med, 1989: 19: 231-326.

Li H, Easley A, Barrington W, Windle J., "Evaluation and Management of Atrial Fibrillation in the Emergency Department Management of Cardiac Arrhythmias," Emergency Medical Clinics of NA, May 1998, vol. 16, No. 2, 389-403.

Lichtigfeld FJ, Gillman MA, "Psychotropic Analgesic Nitrous Oxide and Neurotransmitter Mechanisms Involved in the Alcohol Withdrawal State," Intern Jour Neuroscience, 1994, vol. 76, 17-33.

Martin JP, Sexton BF, Saunders BP, Atkin WS, "Inhaled Patient Administered Nitrous Oxide/Oxygen Mixture Does Not Impair Driving Ability when Used as Analgesia during Sceeening Flexible Sigmoidoscopy," Gastrointest Endosc 2001, 51, 701-703.

Murgatroyd F-D, Leenhardt A, "Non-Pharmacological Treatments for Atrial Fibrillation, A Clinical Perspective on the Status Quo," Archives des Maldies du Coeur et des Vaisseaux, 2000; 93: 7-16.

Pradalier A, Baron JF, Dry J, Launary JM, "Trial Treatment of Migraine Attack by Rebreathing of Expired Air" (Letter), Presse Med (Sep. 15, 1984) 13(31):1901.

Sundin RH, Adriani J, Alam S, Butler J, Hatrel P, Hyde P. Mangum F, Nicoletti J, Wallace J, "Anxiolytic Effects of Low Dosage Nitrous Oxide-Oxygen Mixtures Administered Continuously in Apprehensive Subjects," South Med J (Dec. 1981) 74(12): 1489-92.

Thal ER, Montgomery SJ, Atkins JM, Roberts BG, "Self Administered Analgesia with Nitrous Oxide. Adjunctive Aid for Emergency Medical Care Systems," JAMA, Nov. 1979, 242(22), 2418-2419.

Timmermans C, Rodriguez LM, Ayers GM, Lamber H, Smeets JLRM, Vlaeyen JWS, Albert A, Wellens HJJ, "Effect of Butorphanol Tartrate on Shock-Related Discomfort During Internal Atrial Defibrillation," Circulation 1999; 99:1837-1842.

Tomassoni G, Newby KH, Kearney MM, Brandon MJ, Barold H, Natale A, "Testing Different Biphasic Waveforms and Capacitances: Effect on Atrial Defibrillation Threshold and Pain Perception," Jour Amer Coll Cardiol 1996: 28: 695-699.

Tunstall ME. "Obstetric Analgesia," The Lancet, Oct. 1961, 964.

Van den Elshout FJ, van Herwaarden CL, Folgering HT, "Effects of Hypercapnia and Hypocapnia on Respiratory Resistance in Normal and Asthmatic Subjects," Thorax, Jan. 1991; 46(1): 28-32.

Wolf PA, Abbott RD, Kennel WB, "Atrial Fibrillation as an Independent Risk Factor for Stroke: The Framingham Study," Stroke, 1991:22; 15:1368-132.

Wolf PA, Mitchell JB, Baker CS, Kennel WB, D'Agostino RB, "Impact of Atrial Fibrillation on Mortality, Stroke and Medical Costs," Arch Intern Med, vol. 158, Feb. 1998; 229-234.

* cited by examiner

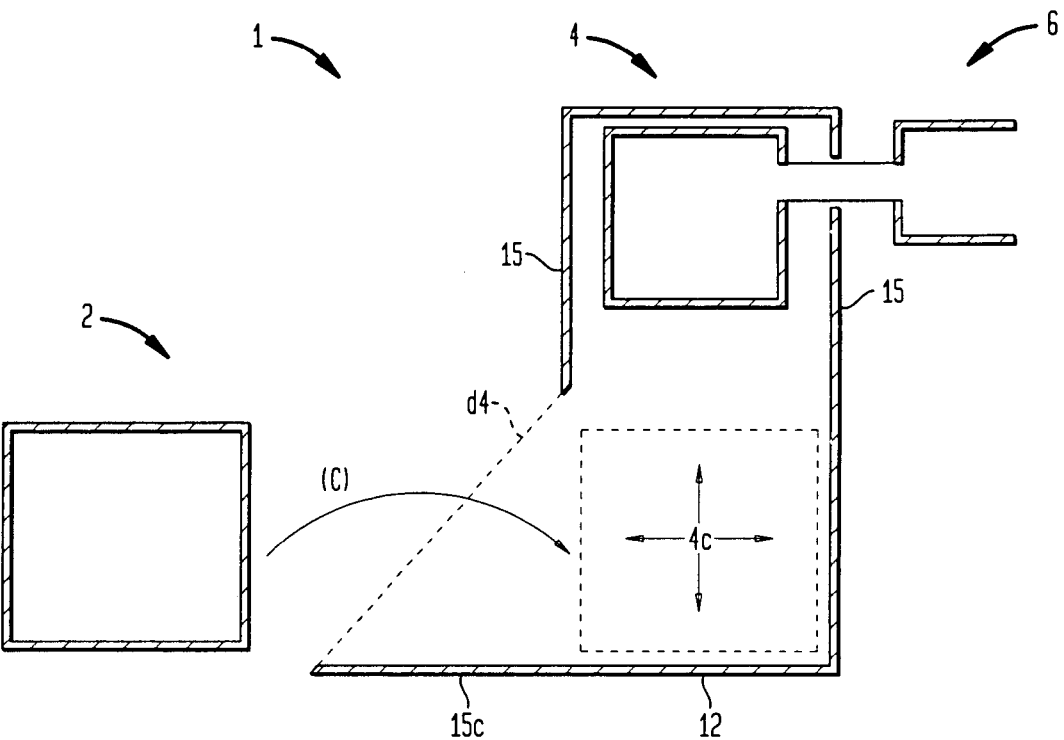
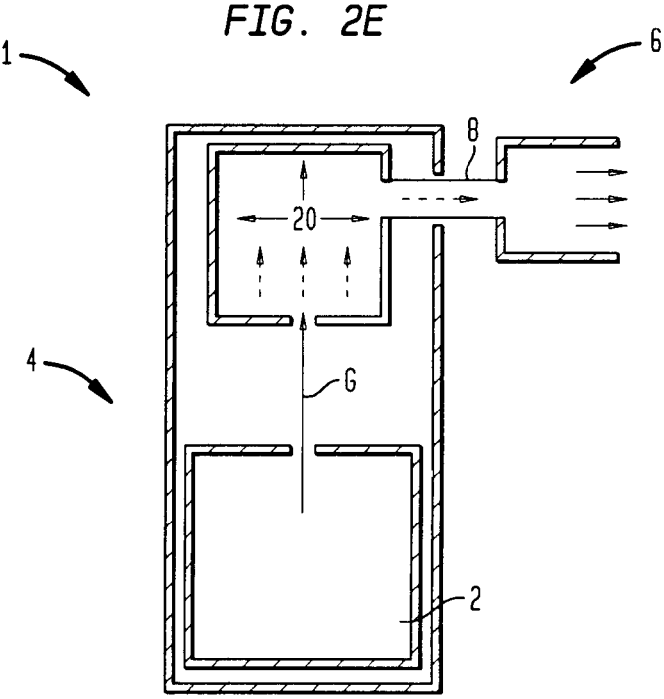

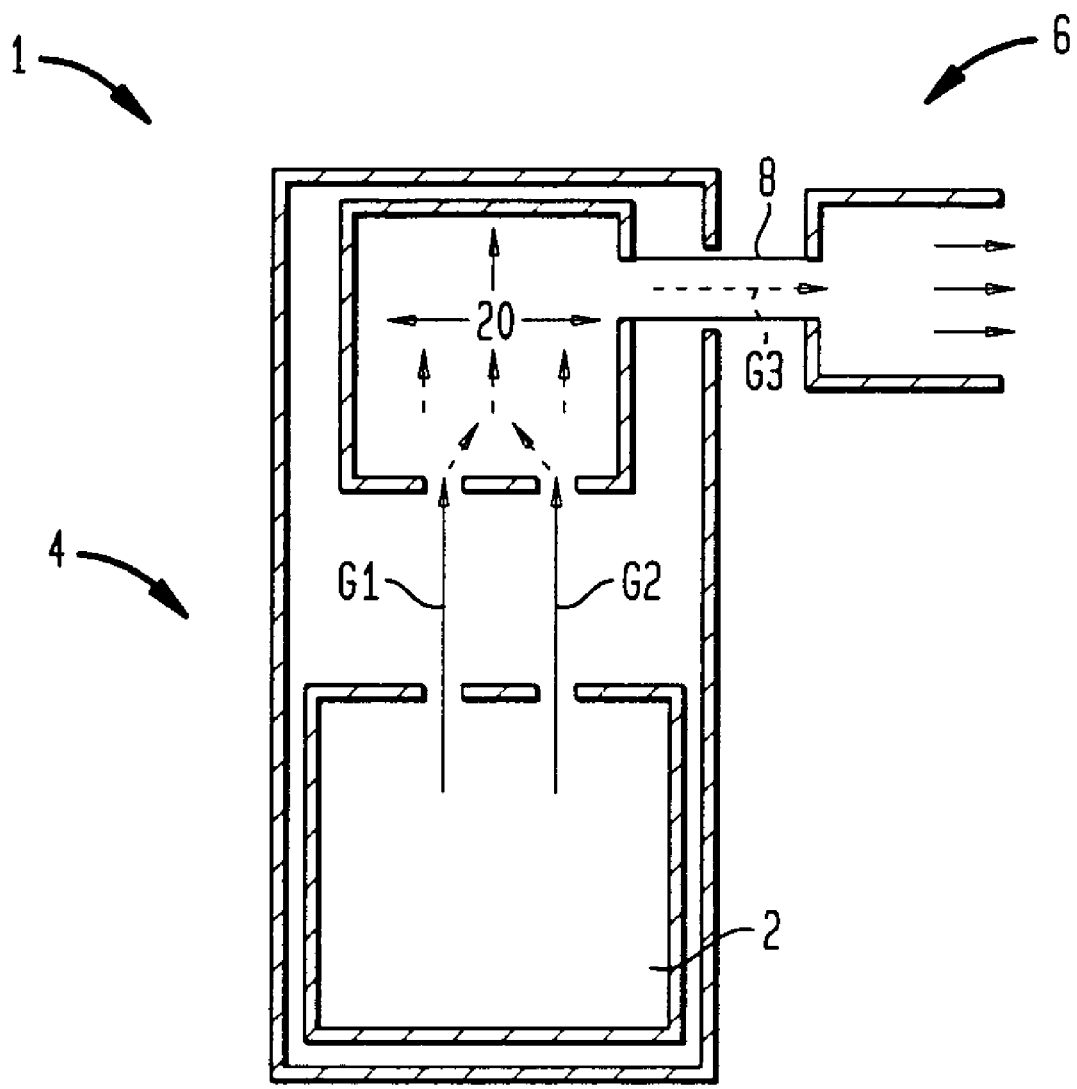

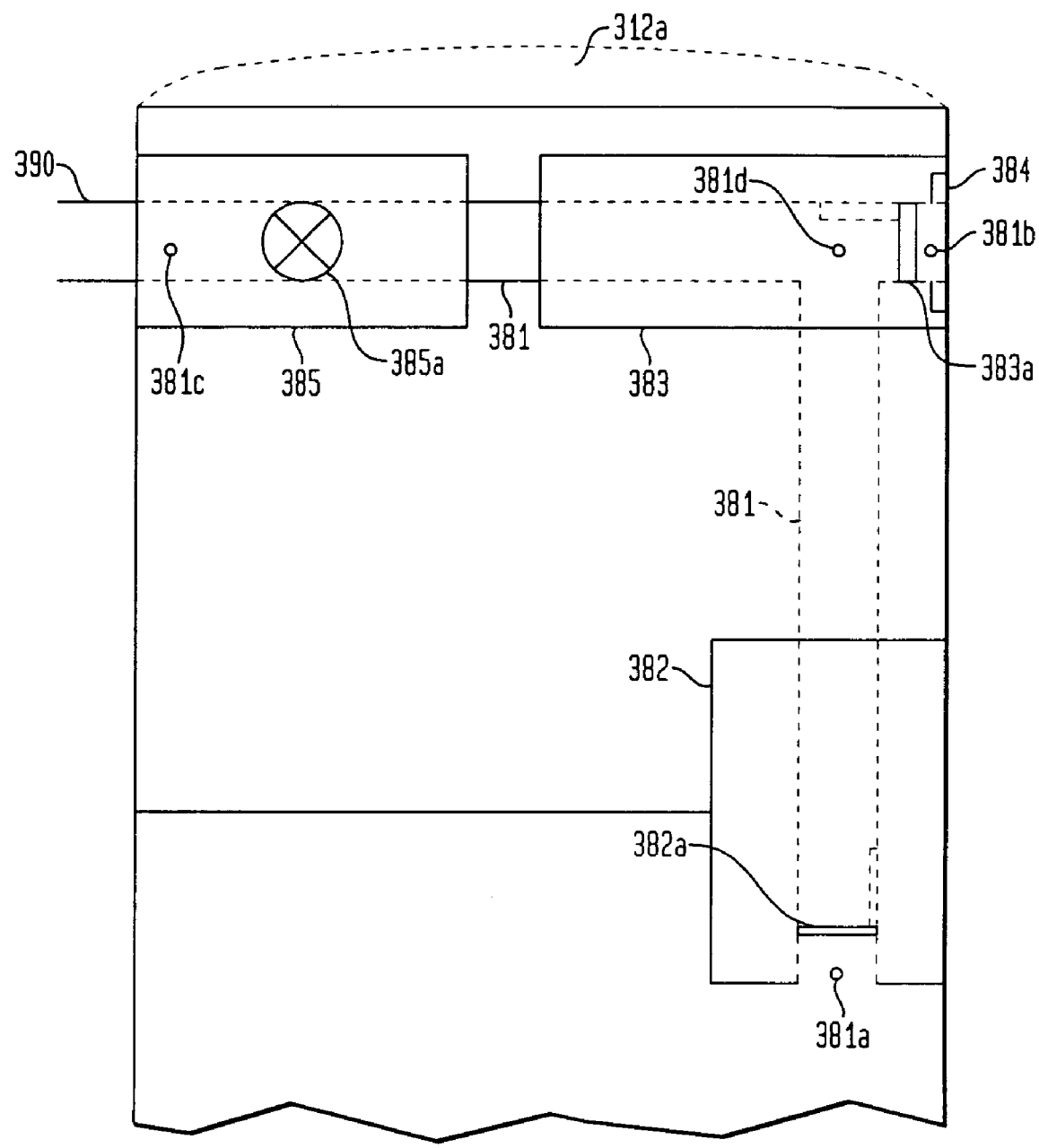

METHOD AND DEVICES FOR ADMINISTRATION OF THERAPEUTIC GASES

CROSS REFERENCE TO RELATED APPLICATIONS

The present application claims the benefit of a filing date of U.S. Provisional Application No. 60/404,830, filed on Aug. 20, 2002, the disclosure of which is incorporated herein by reference in its entirety.

BACKGROUND OF THE INVENTION

Historically, most medical gases which are considered to be pharmaceuticals by the Food and Drug Administration (FDA) whether they are USP grade or NF grade or have undergone a New Drug Approval (NDA) are supplied in the form of compressed gas cylinders, generally containing large gas volumes and for return and refilling by distributors and the like. These large cylinders create significant problems in terms of their handling and use, as well as their shipment which is generally as hazardous materials.

One exception to this is oxygen gas. Oxygen has had a long history of use by outpatients and home care patients in the form of small as well as large compressed gas cylinders. In addition, heliox, a mixture generally of 40% to 80% helium in oxygen has also sometimes been made available to home care patients.

Other gases which have been used to some extent for medical purposes such as $N_2O$ are rarely used on a home care basis and particularly are not permitted for self administration because of the dangers involved and the inability to control their use. Once again, as a general matter, with the use of medical gases including $N_2O$ in oxygen or air and other such gases, even when provided in connection with dental procedures, or during ambulance transport and the like, the gas is generally applied by professionals or in the presence of a professional on a relatively long-term basis ranging from 15 minutes to several hours. There are, in fact, other reasons why large compressed gas cylinders themselves have not been used on an outpatient basis, including the ease of access to the contents of such cylinders with standard valves, for recreational abuse in the case of certain medical gases such as $N_2O$, risk of overdosing, and other safety reasons such as enhanced flammability for certain gases and the like. In addition, these systems require the use of separate gas pressure regulators and/or blenders in order to assist in the application of these gases, and none of these known systems is present for the administration of therapeutic gases for short periods of time for specific medical purposes, and particularly not in an outpatient or home environment for self application.

Certain medical gases with therapeutic effects, such as nitrous oxide and xenon, are subject to potential recreational misuse and abuse. Cylinders of nitrous oxide and/or xenon containing large volumes of the gas and easy access to the cylinder contents by the use of traditional valves may be attractive to such non-prescribed use, or outright theft from a non-medical location, such as a patient's home, and is a major reason, in addition to concerns about overdosing, that such gases are limited to use at medical sites where security and medical supervision exists. Compressed gas cartridges containing these two gases, because of their size and the fact that they utilize a standardized, easily accessed surface for puncture and release of their contents, may be particular targets for recreational use. This is a key reason why medical gases, and in particular those with the potential for recreational abuse such as $N_2O$ or Xe, have never been approved for packaging and marketing in compressed gas cartridges. Therefore, it is highly desirable to have a sealed unit dose package and a means of delivery as described below that is strongly tamper, abuse and misuse resistant, incorporates multiple levels of safety or fail safe mechanisms, and which includes the ability to comply with new FDA regulations concerning unit dose pharmaceutical traceability as FDA considers medical gases to be regulated as pharmaceuticals.

U.S. Pat. No. 6,016,801 discloses a device for the delivery of nitrous oxide as an alternative to smoking, and to serve as a stress-reducing, recreational and nonaddictive smoking substitute. The delivery system in U.S. Pat. No. 6,016,801 mixes the nitrous oxide with ambient air from outside the device. The device includes a nitrous oxide container which includes a refilling port, and there is no discussion in this patent of the nature or duration of administration thereof. Furthermore, the device described in this patent also does not address issues of safety and control regarding the potential for misuse or recreational abuse of $N_2O$ that would be required for approval by a regulatory body such as the FDA, and therefore is not applicable to practical medical use.

U.S. Pat. No. 6,125,844 discloses a hand-held delivery system which delivers oxygen or oxygen along with a medication, so that the oxygen can act as a propellant and as a therapeutic agent in its own right. The device used in U.S. Pat. No. 6,125,844 includes a pressurized gas supply 12 in which the single gas canister can be replaced, and is said to include the possibility of other gases listed therein.

International Application No. WO 01/36018 discloses a device for the co-application of drugs, such as in a powdered form, along with short bursts of a vapor or gas, primarily $CO_2$. This device is not used for the normal respiration of a pure gas or gas mixture, but is intended to utilize a small $CO_2$ canister to entrain the drug for application to the patient's nose, mouth, eye, etc. This device is not intended for the normal respiration of a medical gas for any significant time period, and cannot accommodate a gas mixture for such purposes. A similar device is shown in International Application No. WO 01/03645 for bathing the mucous membranes of the body with a gas such as $CO_2$. In addition, U.S. Pat. No. 6,484,664 discloses a holder for a device for consumable products, such as a $CO_2$ cartridge, which includes a mechanism whereby the amount of remaining product in the dispenser can be determined based on the center of mass of the device.

Additional commercial systems for the supply of various gases and gas mixtures are also available. The NITRONOX unit from Matrx Medical, using pressure reducing regulators and a blending system combines $N_2O$ and $O_2$ from separate compressed gas cylinders into a fixed mixture of 50% $N_2O$ and 50% $O_2$ which is delivered to the patient using a demand valve and face mask. More than about a 30-minute supply of nitrous oxide is mixed with the oxygen, but this allegedly "portable" system has a weight of over 12 pounds, requires an external and separate $O_2$ source, which may be a compressed gas cylinder whose weight is not included in the above 12 pounds, or a wall outlet $O_2$ source, and also requires supervision by medical personnel trained in its use when it is self administered by a patient using the demand valve and face mask due to the medical management required in order to operate the NITRONOX blending device itself. Additional systems include the MEDIMIX unit of AGA Linde Health Care which includes a single premixed cylinder with 50 mole percent nitrous oxide and 50 more percent oxygen with a regulator, tubing, a demand valve and a face mask, and other elements, as well as the ENTONOX unit from BOC, Inc., which again requires medical personnel for use and has a weight and a size making it impossible to be carried and used with a single hand in a portable manner, and is therefore not usable for self-administration by an outpatient at home, work or other locations.

Other gases have also been utilized for patient treatment and in similar types of systems. U.S. Pat. No. 5,228,434, for example, discloses a system for the application of xenon in admixture with oxygen and helium as an anesthetic gas for administration during relatively long periods of time, such as that involved in surgical procedures.

U.S. Pat. No. 5,846,556 describes inhalant compositions for relaxation or the reduction of stress therewith. The preferred composition disclosed in this patent includes nitrogen and oxygen, and can include additional inert gases such as helium and xenon. In a preferred embodiment of this invention, the gas comprises nitrogen, oxygen, neon, argon, carbon dioxide and nitrous oxide. The patentee discloses that the inhalant can be packaged, for example, in a pressurized tank or in small pressurized containers for portable personal use. It is also stated that the product can be used for from one to 10 minutes twice per day. A number of the specific gases collectively provided in the preferred embodiment on a quantified basis provided no added medical and/or other benefit within the collective mixture.

U.S. Pat. No. 5,690,968 discloses an analgesic anesthetic composition, preferably including equal volumes of nitrous oxide and oxygen. The background of this patent discusses a prior system sold under the trademark ENTONOX which includes a demand valve by which the gas can be self-administered by a patient. The invention disclosed in this patent includes an additional ether-based anesthetic which is said to be disposable in a single container above its pseudo-critical temperature at a pressure of 2,000 psi, forming a homogeneous analgesic anesthetic composition. Use of such a product by an outpatient, or supervised by a medical person, is highly unlikely due to safety and other regulatory issues generated by the inclusion of the ether-based anesthetic in the mixture. Furthermore, in locations of treatment where medical persons are present such as hospitals, clinics and emergency medical services ambulances, the likely cost of producing and obtaining regulatory approval of such a product would require product pricing which renders alternatives that provide medical benefit of relatively equal treatment value to be far more attractive in an era of cost consciousness.

U.S. Pat. No. 2,185,067 discloses apparatus for self-administration of nitrous oxide/oxygen mixtures for analgesic purposes. This patent discloses use of this apparatus for short-term procedures. The device includes a pair of gas cylinders with pressure reducing and mixing equipment therefor.

U.S. Pat. No. 3,747,600 discloses an anesthetic apparatus for supplying oxygen/nitrous oxide gas mixtures that is primarily intended for attachment to the wall of a room in which administration is to take place, and the sources of $N_2O$ and $O_2$ include both wall outlets, and large cylinders. The device includes a homogeneous block of metal which is said to produce a very compact, light-weight version of the anesthetic apparatus, for example, one which is 5×5×15 cm, not including the reservoir bag and lever tube, and which can be attached to a wall or stand.

U.S. Pat. No. 5,485,827 discloses the administration of nitric oxide for the treatment of asthma and the like in which the gas is administered for at least three minutes, and preferably at least six minutes. This patent discloses an inhalation device as shown in FIGS. 17 and 18 in which vessel 12 includes a pressurized gas with at least 1 ppm nitric oxide dissolved in a liquefied propellant or compressed inert gas with a rebreathing chamber 22, and the total weight of the device is said to be less than 200 grams so that it is readily portable.

U.S. Pat. No. 6,164,276 discloses apparatus for delivering precise volumes of a therapeutic gas; namely, nitric oxide. The device in this patent uses a sensing device for detecting the start of a patient's spontaneous breathing for purposes of gas control regulation.

U.S. Pat. No. 5,488,946 discloses an emergency breathing supply apparatus which includes two high pressure air cartridges supplying air through demand regulators. The device is specifically for emergency purposes, so as to supply from six to eight minutes of breathable air from these cartridges.

U.S. Pat. No. 6,021,777 discloses a portable anesthesia machine which includes apparatus for delivering a mixture of oxygen and nitrous oxide combined with any known industry standard liquid anesthesia agents. This machine is said to be insensitive to the physical attitude of the machine, and is said to be transportable.

U.S. Pat. No. 6,286,505 discloses a portable anesthetic machine that utilizes liquid anesthetic and is used with an emergency kit which is said to be usable in rapid treatment of or surgery on acutely injured patients.

U.S. Pat. No. 4,648,393 discloses a breath-activated inhaler in which a pin releases a metered dose of medication for direct inhalation by the patient.

One particular area of particular application for therapeutic gases on a portable, handheld self-administration basis is in connection with atrial fibrillation implantable cardioverter defibrillators or AF-ICDs, or multi-function implants which include AF-ICD capability, which have been implanted in patients who then return to their normal lives and on an outpatient basis detect atrial fibrillation, notify the patient, and allow self-activation of a shock on a timer to effect atrial defibrillation. In connection with this procedure, there is a significant need for a co-therapy so that outpatients can reduce pain, anxiety and phobia related to self-administration of a shock of this type. It is also necessary to apply the co-therapy quickly, for it to provide a rapid onset of analgesic, anxiolytic and anterograde amnesic effects which begin prior to, last during and immediately after the atrial defibrillating shock, rapidly dissipate after use so that the patient returns to normal sensorium and can quickly resume daily routine activities supporting a quality of life, and to be safe and easy to use in this manner.

Therapeutic gases and gas mixtures are known in the art. Examples include oxygen, nitrous oxide, xenon, helium, carbon dioxide, and mixtures thereof.

SUMMARY OF THE INVENTION

In accordance with the present invention, these and other objects have now been realized by the discovery of a method of easing a patient's pain and anxiety from atrial defibrillation comprising causing the patient to inhale an effective amount of a medical gas and activating an atrial defibrillation device while the patient is under the influence of the medical gas, whereby the inhalation of the medical gas produces in the patient at least one effect such as analgesia, analgesia, anxiolysis, and anterograde amnesia immediately prior to, during and immediately after the delivery of an atrial defibrillating shock by an atrial defibrillation device.

In accordance with an embodiment of the method of the present invention, the method includes easing a patient's pain and anxiety from ventricular defibrillation comprising the automatic activation of a ventricular internal cardioverter defibrillator or VF-ICD or a multi-functional implant including VF-ICD capability, or the application of a ventricular defibrillating shock using an automatic external defibrillator or AED, and the patient subsequently inhaling an effective amount of a medical gas after the shock from the VF-ICD or AED when conscious, whereby the inhalation of the medical gas produces in the patient at least one effect such as analgesia, anxiolysis, and anterograde amnesia.

In accordance with another embodiment of the method of the present invention, the method provides a medical gas to a patient in need thereof comprising providing the medical gas in a plurality of compressed gas cartridges containing an amount of the medical gas substantially corresponding to a unit dose of the medical gas for the patient, and providing the patient with means for accessing the medical gas from the plurality of compressed gas cartridges upon that need.

In accordance with another embodiment of the method of the present invention, the method comprises providing a medical gas to a patient in need thereof comprising providing the medical gas from a compressed gas cartridge, releasing the pressurized medical gas into a pressure reducing regulator and then several chambers, and transferring the medical gas at the reduced pressure to the patient by means of a demand valve which may be of several different constructs upon that need.

In accordance with another embodiment of the method of the present invention, the method includes providing a medical gas to a patient in need thereof comprising selecting a predetermined medical gas required by the patient, providing the predetermined medical gas in at least one compressed gas cartridge and providing the patient with a means for accessing the medical gas from at least one compressed gas cartridge only if at least one compressed gas cartridge includes the predetermined medical gas.

In accordance with one embodiment of the method of the present invention, the medical gas comprises a gas such as $N_2O/O_2/He$, $N_2O/O_2$, $N_2O/O_2/N_2$, $Xe/O_2$, $Xe/O_2/N_2$ or $Xe/O_2/He$. In accordance with one embodiment, the medical gas is administered within a period of less than about 4 minutes prior to activating of the atrial defibrillation device, and more preferably within a period of less than about 2 to 3 minutes prior to such activation.

In accordance with one embodiment of the method of the present invention, the medical gas is administered within a period of about 4 minutes subsequent to the activating of the ventricular defibrillation device, and preferably within a period of about 2 to 3 minutes subsequent to such activation.

In accordance with one embodiment of the method of the present invention, the medical gas is pressurized to a pressure of up to about 2,000 psig, and preferably up to about 3,000 psig.

In accordance with another embodiment of the method of the present invention, the medical gas comprises a plurality of medical gases, and the method includes mixing the plurality of medical gases within a chamber.

In accordance with another embodiment of the method of the present invention, the method includes analyzing the medical gas at the reduced pressure and transferring the medical gas at the reduced pressure for delivery to the patient only if the analysis of the medical gas meets the predetermined therapeutic medical gas criteria. Preferably, the method includes supplying ambient air to the patient instead of the medical gas at the reduced pressure if the analysis of the medical gas does not meet the predetermined gas criteria. In one embodiment, the predetermined gas criteria comprises a predetermined oxygen content.

In accordance with one embodiment of the method of the present invention, the transfer of the medical gas comprises actuating release of the medical gas by inhalation by the patient. In a further embodiment, the actuation of the release of the medical gas comprises sensing the inhalation by the patient and releasing the medical gas when the sensor measures a predetermined inhalation pressure by the patient.

In accordance with the present invention, these and other objects have also been realized by the invention of apparatus for the administration of a medical gas to a patient comprising a housing, a cassette associated with the housing containing a compressed gas cartridge containing at least an amount of the medical gas substantially as required for a single dose for the patient where the cassette incorporates features that render it tamper, misuse and abuse resistant and trackable/traceable, and patient supply means for providing the medical gas to the patient.

In accordance with one embodiment of the apparatus of the present invention, the apparatus for administration of a medical gas to a patient comprises a portable housing, a plurality of compressed gas cartridges associated with the portable housing containing a predetermined amount of the medical gas sufficient for normal respiration by the patient, and patient supply means for providing the predetermined amount of the medical gas to the patient.

In accordance with another embodiment of the apparatus of the present invention, the apparatus for administration of a medical gas to a patient comprises a housing, a compressed gas cartridge disposed within the housing and containing a predetermined amount of the medical gas sufficient for normal respiration of the patient, and patient supply means for providing the medical gas to the patient, the housing including an upper portion and a lower portion connectable with the upper portion in a configuration in which the housing is closed, the compressed gas cartridge having a size and configuration whereby the housing may be closed with the compressed gas cartridge disposed within a cassette within the housing and the compressed gas cartridge can supply the medical gas to the patient from the housing only when the housing is closed.

In accordance with another embodiment of the apparatus of the present invention, the apparatus for administration of a medical gas to a patient comprises a sealable housing, a sealed cassette that is misuse, tamper and abuse resistant and trackable/traceable including a compressed gas cartridge which is fully mountable within the housing when the housing is sealed, a compressed gas cartridge containing a predetermined amount of the medical gas, patient supply means for providing the medical gas to the patient, and gas delivery means for sealably delivering the medical gas from the compressed gas cartridge to the patient only when the housing is sealed.

In accordance with another embodiment of the apparatus of the present invention, the apparatus for administration of a medical gas to a patient comprises a housing, a removable compressed gas cartridge in a sealed, misuse, tamper and abuse resistant and trackable/traceable cassette within the housing containing a predetermined amount of the medical gas, patient supply means for providing a predetermined amount of the medical gas to the patient, connection means for connecting the compressed gas cartridge with the patient supply means when the compressed gas cartridge is disposed within the housing for supplying the predetermined amount of the medical gas to the patient supply means, a pressure sensor for sensing the pressure of the medical gas released from the compressed gas cartridge, and control means for preventing delivery of the medical gas to the patient supply means based on a pressure sensed by the pressure sensor.

In accordance with another embodiment of the apparatus of the present invention, the apparatus for administration of a medical gas to a patient comprises a housing, a removable compressed gas cartridge within the housing containing a predetermined amount of a medical gas, and a patient interface for providing the predetermined amount of the medical gas to the patient, the apparatus having an overall weight of less than about 48 ounces, and most preferably less than about 24 ounces.

In accordance with another embodiment of the apparatus of the present invention, the apparatus for administration of a medical gas to a patient comprises a housing, a removable cassette removably mounted within the housing, a removable cassette including at least one compressed gas cartridge containing a predetermined amount of a medical gas, patient supply means for supplying the predetermined amount of the medical gas to the patient, mounting means for mounting the removable cassette within the housing, the mounting means comprising first acceptance means and the removable cassette including second acceptance means whereby the mounting means will only accept the removable cassette having second acceptance means which are compatible with the first acceptance means.

In accordance with another embodiment of the apparatus of the present invention, the apparatus for administration of a medical gas to a patient comprises a housing including an upper portion and a lower portion, a removable cassette holding at least one compressed gas cartridge within the housing, the at least one compressed gas cartridge including a predetermined amount of the medical gas, patient supply means for providing the predetermined amount of the medical gas to the patient, connection means for sealingly connecting the upper portion of the housing to the lower portion of the housing with the cassette within the housing, the connecting means including first upper connecting means disposed at the lower end of the upper portion of the housing, second upper connecting means disposed above the first upper connecting means on the upper portion of the housing, first lower connecting means disposed at the upper end of the lower portion of the housing, second lower connecting means disposed below the first lower connecting means on the lower portion of the housing, the first upper connecting means adapted to cooperatively engage the second lower connecting means to provide an intermediate closed configuration for the housing, and second upper connecting means connected to cooperatively engage the first lower connecting means to provide a sealed configuration for the housing, the distance between the first and second upper connecting means and the first and second lower connecting means being adapted so that the first upper connecting means engages the second lower connecting means before the second upper connecting means engages the first lower connecting means.

In accordance with another embodiment of the apparatus of the present invention, the apparatus for administration of a medical gas to a patient comprises a housing, a removable cassette within the housing, the removable cassette including a plurality of compressed gas cartridges, each of the plurality of compressed gas cartridges including a predetermined amount of a portion of a medical gas, patient supply means for providing the medical gas to the patient, the housing including an upper portion and a lower portion connectable to the upper portion in a configuration in which the housing is closed, the removable cassette being mounted in the lower portion of the housing, and a plurality of gas connection members corresponding to the plurality of compressed gas cartridges and mounted in the upper portion of the housing whereby when the upper portion of the housing is connected to the lower portion of the housing the plurality of gas connection members connect the upper portion of the housing with the corresponding plurality of compressed gas cartridges.

In accordance with another embodiment of the apparatus of the present invention, the apparatus for administration of a medical gas to a patient comprises a housing, a cassette mountable within the housing, the cassette including at least one compressed gas cartridge containing a predetermined amount of the medical gas, patient supply means for supplying the predetermined amount of the medical gas to the patient, and gas delivery means for delivering the medical gas from the cassette to the patient supply means.

In accordance with another embodiment of the apparatus of the present invention, the apparatus for administration of a medical gas to a patient comprises a housing, a compressed gas cartridge mountable within the housing containing a predetermined amount of the medical gas, and gas delivery means for delivering the medical gas from the compressed gas cartridge to the patient, the gas delivery means including a gas sensor for sensing a predetermined property of the medical gas, a blender chamber for receiving the medical gas from the compressed gas cartridge, a first valve for controlling the flow of the medical gas from the blender chamber to the patient and a second valve for controlling the flow of air into the housing for delivery to the patient, whereby the sensed value of the predetermined property of the medical gas controls the first and second valves for delivering either the medical gas or the air to the patient.

In accordance with another embodiment of the apparatus of the present invention, the apparatus for administration of a predetermined amount of a medical gas to a patient comprises a housing, at least one compressed gas cartridge mountable within the housing containing the medical gas, gas collection means for collecting the predetermined amount of the medical gas at a location separate from the at least one compressed gas cartridge, and gas delivery means for delivering the predetermined amount of the medical gas to the patient from the separate location.

In accordance with one embodiment of the apparatus of the present invention, the patient supply means comprises a patient interface.

In accordance with another embodiment of the apparatus of the present invention, the cassette is removably disposed within the housing.

In accordance with another embodiment of the apparatus of the present invention, the apparatus comprises a portable hand-held device.

In accordance with one embodiment of the apparatus of the present invention, the housing includes access means for providing access to the housing whereby the cassette may be inserted into or removed from the housing. Preferably, the access means comprises an upper portion of the housing and a lower portion of the housing separable from the upper portion of the housing and attachable thereto. In another embodiment, the access means comprises an openable and closable access member in the housing, and most preferably comprises a bottom portion of the housing.

In accordance with another embodiment of the apparatus of the present invention, the apparatus includes connecting means for connecting the upper portion of the housing to the lower portion of the housing. In a preferred embodiment, the connecting means comprises interconnecting threads on the upper and lower portions of the housing. Preferably, the apparatus includes a plurality of the compressed gas cartridges containing an amount of a plurality of the medical gases substantially as required for a single dose of the plurality of the medical gases, and a cassette mountable within the housing, the plurality of compressed gas cartridges being mounted on the cassette.

In accordance with a preferred embodiment of the apparatus of the present invention, the housing includes mounting means for mounting the cassette within the housing, the mounting means comprising first acceptance means and the cassette including second acceptance means, whereby the mounting means will only accept the cassette having predetermined second acceptance means which are compatible with the first acceptance means. In a preferred embodiment, the first acceptance means comprises first key means including either a male member or a female member, and the second acceptance means comprises second key means comprising the other of the male or female member. Preferably, the first key means comprises a plurality of first key means and the second key means comprises a corresponding plurality of second key means.

In accordance with another embodiment of the apparatus of the present invention, the compressed gas cartridge includes a cartridge body, a cartridge neck portion, and a puncturable sealing member closing the cartridge portion for sealing the medical gas within the cartridge, and the apparatus further includes cartridge opening means for releasing the medical gas from the compressed gas cartridge, the cartridge opening means comprising a puncturing member movable between a first position in which the puncturing member is displaced from the sealing member and a second position in which the puncturing member has punctured the sealing member. In a preferred embodiment, the apparatus includes puncturing member mounting means for mounting the puncturing member with respect to the compressed gas cartridge.

In accordance with one embodiment of the apparatus of the present invention, the apparatus includes gas delivery means in the upper portion of the housing for delivering the medical gas to the patient supply means. Preferably, the upper portion of the housing further includes gas control means for controlling the delivery of the medical gas to the patient supply means. In another embodiment, the gas delivery means includes a blender chamber for receiving the medical gas from the compressed gas cartridge at a predetermined pressure and flow rate. Preferably, the gas control means comprises a gas control sensor for sensing the content of the medical gas, and valve means for terminating the supply of the medical gas based on the sensed content of the medical gas. In a preferred embodiment, the apparatus includes room air breathing means, whereby upon terminating of the supply of the medical gas the room air breaching means supplies room air for breathing by the patient.

In accordance with another embodiment of the apparatus of the present invention, the apparatus includes gas control means comprising a gas control sensor for sensing the pressure of the medical gas entering the blender chamber, and valve means for terminating the supply of the medical gas based on the sensed pressure of the medical gas. Preferably, the apparatus includes room air breathing means, whereby upon terminating of the supply of the medical gas the room air breathing means supplies room air for breathing by the patient.

In accordance with another embodiment of the apparatus of the present invention, the gas control means comprises a second gas control means for sensing the pressure of the medical gas leaving the blender chamber, and the valve means terminates the supply of the medical gas based on the sensed pressure of either the gas control means or the second gas control sensor. Preferably, the gas control means comprises an air inlet port for permitting air into the housing for delivery to the patient supply means and an intake air valve for controlling he entry of the air when the valve means terminates the supply of the medical gas.

In accordance with one embodiment of the apparatus of the present invention, the housing includes an upper portion and a lower portion, and the apparatus includes connecting means for connecting the upper portion of the housing to the lower portion of the housing to thereby seal the housing. In a preferred embodiment, the connecting means comprises first thread means at the lower end of the upper portion of the housing and corresponding second thread means at the upper end of the lower portion of the housing. Preferably, the apparatus includes a sealing surface for providing a gas-tight seal against the upper end of the compressed gas cartridge, puncturing means for puncturing the sealing surface and releasing the medical gas from the compressed gas cartridge, and a slidable plug mounting the puncturing means for moving the puncturing means between a first position displaced from the seating surface and a second position for puncturing the sealing surface. In a preferred embodiment, the upper portion of the housing includes gas input means for accepting the medical gas from the compressed gas cartridge and plug means mounted at the lower end of the upper portion of the housing whereby when the housing is sealed the plug means contacts the slidable plug thereby moving the puncturing means into the second position. Preferably, the upper portion of the housing includes gas delivery means for delivering the medical gas to the patient supply means. In a preferred embodiment, the upper portion of the housing further includes gas control means for controlling the delivery of the medical gas to the patient supply means. Preferably, the gas delivery means includes a blender chamber for receiving the medical gas from the compressed gas cartridge at a predetermined pressure and flow rate.

In accordance with another embodiment of the apparatus of the present invention, the mounting means for a cassette comprises a rotating disk member including the first acceptance means, and a spindle rotatably mounting the disk member within the housing. Preferably, the mounting means includes a base mounted within the housing, the spindle being rotatably mounted along the base. In a preferred embodiment, the disk member is removably mounted on the base, whereby the disk member can be removed from the housing and replaced by a different disk member having a different first acceptance means. Preferably, the cassette includes first indicia and the disk member includes corresponding second indicia for matching the cassette with the disk member. In a preferred embodiment, the first and second indicia comprise coded colors. In another embodiment, the first and second indicia comprises numbers and/or letters.

In one preferred aspect, the present invention provides methods of using therapeutic gases and gas mixtures. In another preferred aspect, the present invention provides a system(s) and devices for administration of therapeutic gases and gas mixtures. In another preferred aspect, the present invention provides certain components of such system. In yet another preferred aspect, the present invention provides various methods related to the system(s) and devices for administration of therapeutic gases and gas mixtures.

The invention will be described in reference to the attached drawings, the short description of which follows:

BRIEF DESCRIPTION OF THE DRAWINGS

FIG. 2D a side, elevational, partially schematic diagram of the embodiment of a therapeutic gas administration system shown in FIG. 2A;

FIG. 2E is a side, elevational, partially schematic diagram showing operation of the therapeutic gas administration system shown in FIG. 2A;

FIG. 2F is a side, elevational, partially schematic diagram showing operation of the therapeutic gas administration system shown in FIG. 2A;

FIG. 8E is a side, elevational, schematic view of one embodiment of a gas output/control system in the upper housing of the present invention;

FIG. 10A is a top, elevational, schematic view of a lower housing with an inserted cassette in accordance with one embodiment of the present invention;

FIG. 10B is a top, elevational, schematic view of the superimposed upper housing and lower housing with the inserted cassette as shown in FIG. 10A;

FIG. 10C is a front, elevational, cross-sectional partially schematic view of the upper portion of a cassette inserted into the lower housing as shown in FIG. 10B, showing one of the sliding cannula/needle assemblies aligned with one of the gas input port assemblies of the upper housing thereof;

FIG. 10D is a front, elevational, cross-sectional, partially schematic view of one of the gas cartridges punctured by a needlepoint of the cannula/needle assembly in operation of the therapeutic gas delivery system shown in FIG. 10C;

FIG. 11A is a front, elevational, cross-sectional, schematic view of operation of one embodiment of the gas input system of the upper housing of the present invention;

FIG. 11B is a side, elevational, cross-sectional, schematic view of one variant of operation of the gas output/control system of the upper housing of the present invention;

FIG. 11C is a side, elevational, cross-sectional, schematic view of operation of the gas output/control system shown in FIG. 11*b;*

DETAILED DESCRIPTION

Figure 1:
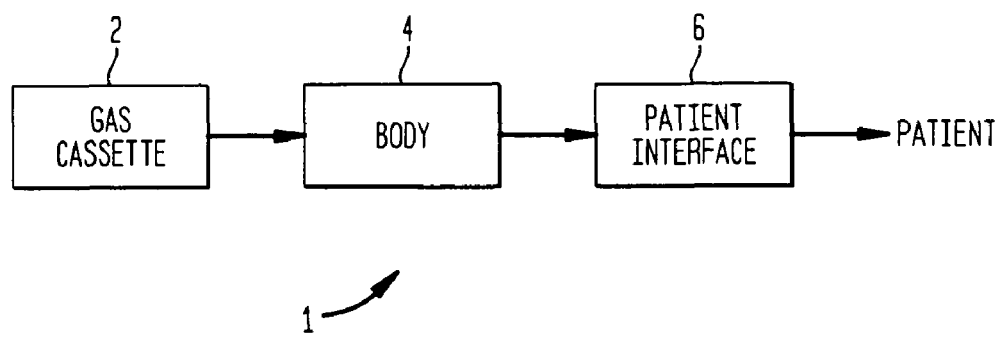
FIG. 1 is a functional block diagram of a therapeutic gas administration system in accordance with one of the preferred aspects of the invention.

For the purposes of the present invention, some of the terms used herein are defined as follows.

Cardiac arrhythmia is an irregularity of the cardiac rhythm. The term "cardiac arrhythmia" refers to several conditions, examples of which include ventricular tachycardia, ventricular fibrillation and atrial fibrillation.

Atrial fibrillation is defined as known in the medical science. Usually, the term "atrial fibrillation" is used to refer to atrial arrhythmia characterized by rapid randomized contractions of the atrial myocardium.

"Cardiac rhythm management devices" are devices that correct medically unacceptable cardiac arrhythmia through application of electrical energy, such as electrical shock. For example, the cardiac rhythm management devices may be used to correct medically unacceptable atrial or ventricular fibrillation by inducing defibrillation through delivery of the electrical shock to the heart. The cardiac rhythm management devices include implantable cardiac rhythm management devices and external cardiac rhythm management devices.

An "implantable cardiac rhythm management device" is an example of a medical device implanted into a patient's body to treat cardiac arrhythmia. The use of implantable medical devices to treat cardiac arrhythmia is described, for example, in U.S. Pat. Nos. 6,091,989 and 6,298,269, both of which are incorporated herein by reference thereto in their entirety. The implantable cardiac rhythm management device may be intended for permanent or temporary implantation. An "Atrial Fibrillation Implantable Cardioverter Defibrillator (AF-ICD)" and a "Ventricular Fibrillation Implantable Cardioverter Defibrillator (VF-ICD)" are examples of implantable cardiac rhythm management devices intended for permanent implantation.

An AF-ICD is implanted to treat atrial fibrillation by delivering electrical shock to the heart (an AF-ICD shock). An AF-ICD may allow a patient to self-initiate the AF-ICD shock. An AF-ICD may be a dedicated implant, or the AF-ICD function may also be incorporated into a device with other capabilities, including other ventricular and/or atrial pacing and defibrillation functions. AF-ICDs are described, for example, in U.S. Pat. Nos. 6,405,084, 6,067,471, 5,893,881, 5,853,426, and 5,813,999, all of which are incorporated herein by reference thereto in their entirety.

A VF-ICD is implanted to treat ventricular fibrillation. A VF-ICD shock is the electrical shock delivered by the VF-ICD. A VF-ICD may be a dedicated implant, or the AF-ICD function may be incorporated into a device with other capabilities, including other ventricular and/or atrial pacing and defibrillation functions. VF-ICDs are described, for example, in U.S. Pat. Nos. 6,377,851, 6,067,471, and 5,954,753, all of which are incorporated herein by reference thereto in their entirety.

Temporary catheters with electrodes and other types of removable implantable leads are implantable cardiac management devices that are implanted on a temporary basis. Examples of such devices, used to deliver a shock to address atrial fibrillation, are described, for example, in U.S. Pat. Nos. 5,849,033 and 5,653,734, both of which are incorporated herein by reference thereto in their entirety.

"External cardiac rhythm management devices" are medical devices used to correct medically unacceptable cardiac arrhythmia without being implanted into a patient's body. Automatic External Defibrillator (AED) is example of an external cardiac rhythm management device. AEDs are described, for example, in U.S. Pat. Nos. 6,427,083, 6,134,479 and 5,897,576, each of which is incorporated herein by reference thereto in their entirety.

An "analgesic" is an agent used to effect analgesia, which is the relief or reduction of pain without loss of consciousness. "Analgesia" is different from anesthesia, which involves causing a loss of consciousness in a patient.

Anxiety is a non-specific feeling of apprehension, worry, uneasiness or dread. "Anxiolysis" is the relief or reduction of anxiety. An anxiolytic agent is an agent that relieves or reduces anxiety. Anxiety may result in a patient treated by application of electrical energy from a cardiac rhythm management device. Cardiac shock anxiety is the anxiety associated with the shock from the cardiac rhythm management device. An example of the cardiac shock anxiety is AF-ICD anxiety, which is detailed in the medical literature, and which is associated with the AF-ICD shock in patients having an implanted AF-ICD. The AF-ICD anxiety may be observed before initiation of AF-ICD treatment in patients who previously experienced AF-ICD shock, and can be a primary reason why they do not use their AF-ICD, visit their physicians clinic to have their shock administered under intravenous sedation, or request it be removed and another potential therapy be pursued. Another example of the cardiac shock anxiety is a VF-ICD anxiety, which is detailed in the medical literature, which is associated with anticipation of the VF-ICD shock and its after effects in patients having an implanted VF-ICD, where said shock occurs automatically and without warning on a random and as-needed basis.

"Amnesia" is partial or total loss of memory. An amnesic agent is an agent that causes partial or total lost of memory. AF-ICD amnesia is an anterograde amnesia related to the period of time prior to and during administration of a shock from an AF-ICD. The term AF-ICD amnesia shall be used mostly in reference to partial loss of memory of prior AF-ICD treatment(s) in patients who experienced the prior AF-ICD shock. The AF-ICD amnesia may be especially beneficial if present at the time of initiation of new AF-ICD shock.

"Phobia" is a persistent and irrational fear of an object, activity, situation or other phenomena. AF-ICD phobia is the phobia regarding administration of AF-ICD shock. AF-ICD phobia may lead a patient having an implanted AF-ICD to avoid self-administration of the AF-ICD shock.

"Air" is a mixture of nitrogen ($N_2$) and oxygen ($O_2$) that contains minimum oxygen concentration level required by regulatory bodies to sustain life. The required oxygen concentration in the Air ranges from 19.5% to 23%. Typically, the Air is artificially produced by mechanical mixing of constituent gases, or prepared by compression of atmospheric air.

An inpatient setting ("I") is a setting at a medical facility where a patient undergoes diagnostic, therapeutic and/or other medical procedures that include at least one overnight stay. A non-limiting example of the inpatient setting is a hospital where patients occupy sleeping accommodation in the normal course of hospital's operations. Other non-limiting examples of inpatient settings include a nursing home or other institution to which patients are formally admitted for a minimum of one night. In the inpatient setting, medical treatment may occur at a patient's bed, in a surgical suite, a recovery room, a procedure room, an intensive care unit or a hospital emergency room after admission. In addition to regular hospital procedures, a wide range of short duration procedures may be conducted in the inpatient setting, including but not limited to taking of blood samples, injections, removal of bandages or dressings, arterial or venous catheterization, urinary catheterization, dermal or subcutaneous biopsy punches, insertion of aspiration needles and drainage tubes, application, removal of casts, and short term patient movement that involves pain, for example, transfer of a patient between a bed and a stretcher. A patient under care at the inpatient setting may be referred to as an in-patient.

Walk-in outpatient setting ("WIO") is a setting that includes a medical facility providing diagnostic, therapeutic and/or other medical procedures, including regular or specialty care services, to patients arriving and leaving on the same day without an overnight stay. The procedures provided in the walk-in outpatient setting typically take from minutes to several hours. The medical facility may be a clinic that is independent from a hospital, or is part of a hospital complex. Non-limiting examples of the walk-in outpatient settings include an HMO clinic, an urgent care clinic, a specialty outpatient clinic, and physician's offices. An emergency room of a hospital may be considered a walk-in outpatient setting for patients returning home after treatment and not admitted to the hospital. A patient under care at the walk-in outpatient setting may be referred to as a walk-in outpatient.

Homecare outpatient ("HC-O") setting is a setting in which a patient is treated outside a medical facility and without observation or supervision of a medical professional. Non-limiting examples of the homecare outpatient setting are patients' homes, (the HC in HC-O), a work place, a hotel, an athletic training facility, arena or playing field, and other similar locations (the O in HC-O). A patient in the homecare outpatient setting may be referred to as a homecare outpatient.

Emergency Medical Service ("EMS") setting is a setting where an individual requires emergency care as a result of a crime, fire, automobile accident, workplace accident or at-home accident, the care being delivered on the scene of the incident or accident and/or during transport to a medical facility. In the EMS setting, the care is typically provided by ambulance paramedics, fire department personnel or police department personnel. An individual in the EMS setting may be referred to as an EMS patient.

A mode of administration of a therapy or a medical procedure refers to the degree of supervision over the patient in the course of the therapy or the medical procedure. If the patient administers the therapy or the medical procedure without presence and/or direct observation of a physician or allied health professional (e.g., a nurse, physician's assistant, paramedic or technologist, etc.), the therapy or the medical procedure is administered in a self-administration mode ("S").

If the patient administers the therapy or the medical procedure under direct observation of a physician, allied health professional, police or fire emergency personnel, the therapy or the medical procedure is administered in a self-administration observed mode ("SAO").

Gases, such as nitrous oxide ($N_2O$), xenon (Xe), helium (He), carbon dioxide ($CO_2$), carbon monoxide (CO), sulfur hexafluoride ($SF_6$), neon (Ne), Air, and oxygen ($O_2$), have applications in various therapies. Mixtures of gases may also be used for therapeutic purposes. Examples of therapeutic gas mixtures include $N_2O/O_2$ mixture, $N_2O/O_2/N_2$ mixture, $N_2O/O_2/He$ mixture, $Xe/O_2$ mixture, $Xe/O_2/N_2$ mixture, $Xe/O_2/He$ mixture, $He/O_2$ mixture, $CO_2/O_2$ mixture, $CO_2/O_2/N_2$ mixture, $CO_2/O_2/He$ mixture, $CO/O_2$ mixture, $CO/O_2/N_2$ mixture, and $CO/O_2/He$ mixture.

In the therapeutic gas mixtures, different component gases may have different functions. For example, a component of a gas mixture may function as an active ingredient gas, a gas having a secondary physiological function and/or a diluent gas. Some component gases may function both as secondary function gases and as diluent gases.

One or more gases in the gas mixture may act as an active ingredient(s) to produce the intended primary effect of the therapy. For example, when the $N_2O/O_2$ mixture is used for anesthesia or analgesia depending on the concentration of $N_2O$ employed, nitrous oxide is the active ingredient that provides the desired effect.

Some therapeutic gases may be administered in pure form. For example, pure oxygen may be used as the active ingredient for certain indications. Other gases are diluted for administration. For example, administration of pure (100 mole percent) nitrous oxide is dangerous and can cause asphyxiation. Instead, nitrous oxide is usually diluted and administered as a gas mixture. Diluent gases reduce the concentration of the active ingredient gases in the therapeutic gas mixture. For, example, nitrous oxide is most often diluted with oxygen because oxygen is required to sustain life.

The gases having secondary functions do not produce the primary effect of the therapy, but their presence in the gas mixture does have physiological effect(s) on a patient, which may be related or unrelated to the primary effect of the therapy. For example, in the nitrous oxide/oxygen mixture, oxygen acts as a life support component in addition to serving as a diluent gas for nitrous oxide. The presence of oxygen in nitrous oxide/oxygen mixture allows a patient to breath the mixture without exposure to the outside air. Another example of a gas mixture component having secondary function is the inclusion of helium in mixtures with active ingredient gases (e.g., $N_2O$, $O_2$, $CO_2$ or CO). The secondary function of helium is believed to be improvement of the distribution of the active ingredient gas in the lungs.

Some components of gas mixtures have no substantial physiological effects. These components function purely as diluent gases to reduce the concentration of other gaseous components of the gas mixture. For example, nitrogen or another suitable physiologically inert gas may be mixed with nitrous oxide and oxygen. The resulting $N_2O/O_2/N_2$ ternary mixture may be used for certain indications instead of the binary nitrous oxide/oxygen mixture. The inclusion of nitrogen may be used to avoid administration of excessive oxygen concentrations, especially for situations when use of high oxygen concentrations is medically undesirable. For example, for certain indications, 65% $N_2O$/35% $O_2$ mixture may be replaced with 65% $N_2O$/21% $O_2$/9% $N_2$ mixture that has reduced oxygen concentration without substantial changes in the intended primary effect.

The therapeutic gas mixtures and/or gas components of such mixtures may also serve as a pre-, peri-, and/or post-therapy with respect to co-administration with another drug- or device-based therapy. A non-limiting example of pre-therapy is the use of the Heliox (He/$O_2$ mixture) immediately before administration of inhaled albuterol or corticosteroid in asthma patients. Heliox incorporating 80 mole percent of He is believed to facilitate deeper penetration of albuterol and drugs in micro particle powder form into the bronchi, in addition to helping to ameliorate an asthma attack directly, due to the physical properties of He which include facilitation of laminar flow deep into and throughout the bronchi.

In one of its preferred aspects, the present invention provides a method of easing administration of shock from a cardiac rhythm management device by administering an analgesic gas or gas mixture to a patient subjected to the shock. The administration of the analgesic gas or gas mixture may be carried out in conjunction with the administration of shock from an implantable cardiac rhythm management device (such as AF-ICD, VF-ICD or temporary catheter), or an external cardiac rhythm management device, such as an external ventricular defibrillator (e.g., AED) or an external atrial defibrillator. The timing of the gas administration depends on the nature of the cardiac rhythm management device and/or the underlying medical condition, as well as other factors. For example, for use in conjunction with the atrial defibrillating shock, the analgesic gas or gas mixture is preferably administered immediately prior to and up to the moment of the shock; whereas for ventricular defibrillating shock, the analgesic gas or gas mixture is preferably administered immediately after the shock.

The easing of administration of the shock from a cardiac rhythm management device results from the effects of the analgesic gas or gas mixture on the patient. Preferably, such effects include relief of pain (analgesia) and reduction of cardiac shock anxiety (anxiolysis), decrease of the phobia associated with the shock, and the presence of cardiac shock amnesia. The administration of the analgesic gas or gas mixture relieves the pain the patient experiences from the shock. The pain relief results directly from the analgesic character of the therapeutic gas or gas mixture. The administration of analgesic gas or gas mixture also reduces the feeling of unease and apprehension felt by the patient because of the shock.

The analgesic gas or gas mixture may be administered in the S, SAO, or NS modes, depending on the type of the cardiac rhythm management device and the setting. In most circumstances, the S mode of administration is preferred. Various devices for therapeutic gas administration may be used with the method of this aspect of the invention, including devices known to those of skill in the art. Examples of such devices are disclosed in U.S. Pat. Nos. 5,839,434, 5,732,694, 5,558,083 and 2,185,067, all of which are incorporated herein by reference thereto in their entirety. The preferred devices are portable and suitable for outpatient use, such as the devices described hereinbelow.

The analgesic gas or gas mixture may be administered in the HCO, WIO, I, or EMS settings, depending on the type of the cardiac rhythm management device and other factors. In most circumstances, the HCO setting is preferred.

In one preferred embodiment, the patient is placed in possession of a portable gas delivery device and a supply of analgesic gas in a suitable form. The more preferred example of such device is described hereinbelow. The use of such device in possession of a patient provides numerous advantages, some of which are described hereinbelow. For example, the device provides the patient, medical personnel or EMS personnel with ready availability of analgesia and/or anxiolysis in the immediate proximity to the patient.

Preferably, the analgesic gas or gas mixture is administered to a patient having an implanted cardiac rhythm management device.

In a preferred embodiment, the implantable cardiac rhythm management device is an AF-ICD, and the method includes easing the administration of an AF-ICD shock by administering analgesic gas or gas mixture to the patient having the implanted AF-ICD. The easing of administration of the AF-ICD shock results from the effects of administration of the analgesic gas or gas mixture on the patient immediately prior to and as of the moment of the shock. Preferably, such effects include relief of pain (analgesia), reduction of AF-ICD anxiety (anxiolysis), decrease of the AF-ICD phobia, and the presence of AF-ICD amnesia. The administration of analgesic gas or gas mixture relieves the pain the patient experiences at the time of the AF-ICD shock and immediately thereafter. The pain relief results directly from the analgesic character of the therapeutic gas or gas mixture.

The administration of an analgesic gas or gas mixture also reduces the feeling of unease and apprehension felt by the patient before AF-ICD shock is administered (AF-ICD anxiety). The AF-ICD anxiety is likely to be present if the patient had experienced pain associated with the administration of the AF-ICD shock in the past. The prior instances of pain may help produce the feeling of apprehension regarding the AF-ICD shock administration. The AF-ICD anxiety may be especially strong before another AF-ICD shock is about to be administered. Relief of the AF-ICD anxiety provided by the administration of the analgesic gas before the AF-ICD shock is initiated facilitates the administration of the shock. When the patient self-administers the AF-ICD shock, for example, in an outpatient setting, the relief of the AF-ICD anxiety makes it more likely than the patient would in fact initiate the shock.

Preferably, the administration of the analgesic gas or gas mixture also produces AF-ICD amnesia so that the period of time associated with the AF-ICD shock becomes subject to reduced recall by the patient. The amnesic function of the analgesic gas administration is especially important when the patient may be reluctant to self-initiate the AF-ICD. The reduced recall of the prior instances of pain and anxiety associated with the AF-ICD shock facilitates self-initiation of AF-ICD shocks in the future.

Preferably, the analgesic gas or gas mixture is administered immediately prior to and up to the moment of self-administration of the AF-ICD shock. More preferably, the analgesic gas or gas mixture is self-administered pursuant to the self-administration of the AF-ICD shock. However, self-administration of the analgesic gas or gas mixture in conjunction with physician-administered AF-ICD shock is also contemplated. A nurse or other medical professional may also administer the AF-ICD shock instead of the patient.

In a preferred embodiment, a patient having implanted AF-ICD administers the analgesic gas to him- or herself, and after a pre-determined period of time self-initiates his/her implanted AF-ICD. Preferably, the gas administration continues up to the moment of the AF-ICD shock. Preferably, the effect of the analgesic gas administration extends through the time of the AF-ICD shock. Preferably, at the time of the AF-ICD shock, the gas administration has produced sufficient levels of analgesia, anxiolysis, and AF-ICD amnesia in the patient. Preferably, the levels of analgesia, anxiolysis and AF-ICD amnesia are sufficient if they allow routine self-administration of the AF-ICD shock.

The length of the pre-determined period of time between the beginning of gas administration and the AF-ICD shock depends on many factors. Thus, the length of the pre-determined time period may depend on the nature and dose of the analgesic gas, among other factors. For example, administration of a 65% $N_2O$/35% $O_2$ mixture is likely to produce higher levels of analgesia than a 35% $N_2O$/65% $O_2$ mixture, when the analgesic effect is measured at the same time point after the beginning of gas administration. The dose is determined by the concentration of the active ingredient gas and the duration of gas administration.

The pre-determined time period may also vary from patient to patient, depending on factors such as age, weight and pain tolerance. Each patient is likely to respond differently to AF-ICD shock and/or experience different levels of the AF-ICD anxiety and phobia concerning future shocks. A physician may select the length of the pre-determined time period in practice sessions with a specific patient. The physician may also select the analgesic gas and the dose.

In a preferred embodiment, the length of the pre-determined time period before the AF-ICD shock is 6 minutes or less, more preferably, 4 minutes or less, yet more preferably, 2-3 minutes. In a more preferred non-limiting example, for a nitrous oxide/oxygen mixture in which the concentration of nitrous oxide varies from 55% to 70%, the maximum desirable effect of gas administration is achieved in 2 to 3 minutes after the beginning of gas administration.

Various devices for therapeutic gas administration in conjunction with the AF-ICD shock may be used, including devices known to those of skill in the art. Examples of such devices are disclosed in U.S. Pat. Nos. 5,839,434, 5,732,694, 5,558,083 and 2,185,067, which were previously incorporated herein by reference thereto. The preferred devices are portable and suitable for outpatient use, such as the devices described hereinbelow, which is especially suitable for self-administration.

It is believed that self-administration of both the analgesic gas and the AF-ICD promotes the patient's freedom of movement, for example, by allowing the patient to carry out the AF-ICD shock in an outpatient setting. The reduction in AF-ICD anxiety and other effects of analgesic gas administration decreases the patient's need for medical assistance. A patient having an implanted AF-ICD may also self-administer the analgesic gas or gas mixture while visiting a physician's office or a clinic. In addition, if a patient is unable to self-administer the analgesic gas and/or the AF-ICD shock or travel to a physician's office or a clinic, the patient may call EMS for help. The patient's possession of the analgesic gas and gas delivery device, and the consequent immediate availability of the analgesia and anxiolysis may help the EMS personnel in treating the patient. The settings suitable for administration of the analgesic gas or gas mixture are described in Table 1 below.

Therapeutic gases that produce analgesic effect in patients may be used with the methods of the invention, including analgesic gases known in the art. The preferred gases suitable for easing the administration of the AF-ICD shock are $N_2O$/$O_2$ mixture, $N_2O$/$O_2$/$N_2$ mixture, $N_2O$/$O_2$/He mixture, Xe/$O_2$ mixture, Xe/$O_2$/$N_2$ mixture, and Xe/$O_2$/He mixture.

The preferred active ingredient gas for relieving pain and anxiety associated with the AF-ICD shock is nitrous oxide ($N_2O$). Nitrous oxide is a well-known anesthetic gas, is readily available and less expensive than other suitable active ingredient gases. Nitrous oxide is usually administered in a mixture with other gases. For example, the use of nitrous oxide-containing gas mixtures for anesthesia is described in U.S. Pat. Nos. 3,876,773 and 3,192,106, both of which are incorporated herein by reference thereto in their entirety.

The preferred analgesic gas mixture for relief of pain associated with the AF-ICD and the AF-ICD anxiety is the nitrous oxide/oxygen mixture ($N_2O/O_2$) Preferably, the concentration of $N_2O$ in the mixture varies from 35% to 70%, expressed in mole percent of the component with respect to molar content of the mixture, with the balance being substantially oxygen. The content of more preferred nitrous oxide/oxygen mixtures vary from approximately 55% $N_2O$/45% $O_2$ to approximately 65% $N_2O$/35% $O_2$.

Preferably, the $N_2O/O_2$ mixture is administered 4 minutes or less before the administration of the AF-ICD shock. More preferably, the $N_2O/O_2$ mixture is administered 2.5 to 3.5 minutes prior to the administration of the AF-ICD shock. It was found that 2.5 to 3.5 minutes after the beginning of gas administration, the levels of analgesia and anxiolysis were sufficient to ease patients' self-administration of AF-ICD shock. The short period of administration reduces the likelihood of hypoxia, which was reported to occur in some instances for substantially greater periods of $N_2O/O_2$ administration.

It was found that nausea and vomiting, which sometimes had been observed in administration of the $N_2O$-containing gas mixtures, were unlikely to occur when the total duration of administration is less than about 6 minutes and especially when it is 4 minutes or less. For such duration of administration, the patients are likely to suffer little or no nausea, and vomiting was not observed. After the short-term $N_2O/O_2$ administration, patients rapidly return to normal sensory perception levels and are able to resume normal daily routines. For example, within approximately 30 minutes after gas administration, it is believed that a patient may safely drive a car or perform other tasks that demand attention. The accelerated return to normal sensory perception levels is believed to be associated with rapid elimination of $N_2O$ from the body and short duration of gas administration. For example, the current standard of care for patients seeking administration of an AF-ICD shock by a physician in the WIO setting involves sedation with a drug such as propofol, midazolam or a benzodiazapene, which are injected intravenously, or in the case of a benzodiazapene may be administered intramuscularly or orally, in which case the onset of desired effects is greatly extended. These intravenously injected drugs have short onset but relatively long offset times. As a result, the WIO patients typically remain at the site of shock administration for 3 hours after the AF-ICD shock to recover a normal sensory perception, and during this time, based on guidelines issued by the Joint Commission on Accreditation of Healthcare Organizations (JCAHO), as well as guidelines issued by professional medical organizations and societies, they must be monitored by a medical professional throughout this period, which is a major cost factor and impacts the patient's quality of life. Patients receiving such sedation must have someone drive them to the WIO setting and then drive them home, which also impacts patient quality of life and generates a burden on persons other than the patients. The use of a portable gas administration device providing an $N_2O/O_2$ mixture may in most situations permit the patient to drive to the physician's office without help and to drive back home 30 minutes after the procedure is completed, rendering the entire procedure and experience equivalent to an office visit of one hour or less.

The short duration of administration and nonsequential dosing of large numbers of patients in particular for the applications envisioned, such as those performed by but not limited to a cardiologist or electro-physiologist, is also believed to result in a small volume of exhaled nitrous oxide and its rapid dilution in the circulating room air so that scavenging and removal of the exhaled $N_2O$ is not required. However, a scavenging or decomposition system for nitrous oxide may be used if necessary to meet environmental regulations. Subject to the room air circulation and the permissible limits of $N_2O$ concentration, a simple system should be sufficient due to the low volume of $N_2O$.

In accordance with the preferred embodiment of this aspect of the invention, a patient having AF-ICD is provided with a device suitable for self-administration of a nitrous oxide/oxygen mixture in an outpatient setting, e.g., at the patient's home, while traveling, and the like. When there is a need for the AF-ICD shock, the patient first uses the device to self-administer the nitrous oxide/oxygen mixture. The inhalation of the mixture is believed to relax the patient and to reduce AF-ICD anxiety, decreasing the patient's psychological discomfort associated with self-initiation of the shock. The patient initiates the AF-ICD shock, preferably less than 4 minutes, more preferably 2 to 3 minutes, after the beginning of the $N_2O/O_2$ administration. Preferably, the effect of the gas administration fully manifests itself at the time of the AF-ICD shock. The analgesic effect of the gas administration reduces the level of pain from the AF-ICD shock. Preferably, the gas administration ends as of the AF-ICD shock. After the gas administration has ended and post-AF-ICD shock, the beneficial analgesic and anxiolytic effects of the $N_2O/O_2$ administration gradually decrease over several minutes as the $N_2O$ leaves the patients body by exhalation.

Another suitable $N_2O$-containing gas mixture is $N_2O/O_2$/He. Preferably, the concentration of $N_2O$ in the mixture varies from 35% to 70%, and the concentration of helium varies from 9% to 44%, both expressed in mole percent of the component with respect to molar content of the mixture, with the balance being oxygen. The concentration of oxygen is usually approximately 21 molar %.

Another suitable $N_2O$-containing gas mixture is $N_2O/O_2$/$N_2$. Preferably, the concentration of $N_2O$ in the mixture varies from 35% to 70%, and the concentration of nitrogen varies from 9% to 44%, both expressed in mole percent of the component with respect to molar content of the mixture, with the balance being oxygen.

Xenon is a known therapeutic gas. Thus, the use of xenon in treating neurointoxications is disclosed in International Application WO 00/53192, the disclosure of which is incorporated herein by reference thereto in its entirety. U.S. Pat. No. 5,228,434 discloses the use of xenon mixtures for anesthesia. Xenon at low concentrations may be used instead of nitrous oxide as the active ingredient gas for relief of pain and anxiety associated with AF-ICD shock. Xenon has the benefit of being a bio-chemically inert gas, making it especially suitable for pediatric patients and pregnant women. In addition, xenon is cardiotonic and thus beneficial for older patients. The drawbacks of xenon include higher cost and the consequent need for breathing circuits and recovery mechanisms in devices for administering xenon and its mixtures.

Xenon is a heavy gas and can be difficult to breathe even at low concentrations. It is therefore desirably administered in mixtures with oxygen and helium. Preferably, the mixture has sufficient xenon content to produce the desired analgesia, anxiolysis and partial amnesia.

One of the suitable xenon-containing mixtures is $Xe/O_2$ mixture. The preferred concentration of xenon in the $Xe/O_2$ mixture varies from 26% to 50%, expressed in mole percent of xenon with respect to the total molar content of the mixture, with the balance being substantially oxygen. The more preferred composition of the $Xe/O_2$ mixture is 33% $Xe$/67% $O_2$.

Another suitable xenon-containing mixture is the $Xe/O_2$/$N_2$ mixture. The preferred concentration of xenon in the mixture varies from 26% to 50%, the concentration of nitrogen varying from 29% to 53%, both expressed in mole percent of the component with respect to the total molar content of the mixture, with the balance being substantially oxygen. The concentration of oxygen is usually approximately 21 molar %. The content of a more preferred mixture is approximately 33% Xe/21% $O_2$/46% $N_2$. The use of 26% or higher concentrations, and in particular 33% of Xe for diagnostic purposes in the measurement of cerebral blood flow with a CT scanner is well known to one versed in the medical imaging art. The body of work in this area has shown that apnea may result if 33% to 40% Xenon is inhaled for periods exceeding 2.5 to 3 minutes. Therefore, the use of such gas mixtures for purposes of self-administered analgesia especially by outpatients in the HC-0 setting is preferably maintained below 2.5 to 3 minutes.

Nitrogen in the Xe/$O_2$/$N_2$ mixture may be substituted with helium. The suitable composition of the Xe/$O_2$/He mixture is the same as for the Xe/$O_2$/$N_2$ mixture. The Xe/$O_2$/He mixtures are disclosed in U.S. Pat. No. 5,228,434 ("the '343 patent") pertaining to their use in anesthesia. The disclosure of the '434 patent that is related to the composition(s) of the Xe/$O_2$/He mixtures is incorporated herein by reference thereto. The addition of helium to the mixture facilitates breathing the xenon-containing mixture, with helium acting as a carrier gas to improve xenon distribution in the breathing system. The disclosure of the '434 patent that is related to the use and function of helium in the Xe/$O_2$/He mixtures is also incorporated herein by reference thereto.

Table 1 summarizes various methods of use of the present invention for a number of indications:

TABLE 1

| Indication | Gas Mixture | Content of Mixture | Timing of Gas Administration (when used with AF ICD shock) | Duration of Gas Administration | Effect | Setting[1] | Mode of Gas Administration[2] |
|---|---|---|---|---|---|---|---|
| A. General. | $N_2O$/$O_2$ | Preferably, $N_2O$ from 35% to 70%, with the balance of $O_2$; more preferably, 65% $N_2O$/35% $O_2$. | Preferably, 4 minutes or less prior to the AF ICD shock; more preferably, from 2 to 3 minutes prior to the AF ICD shock. | Preferably, 4 minutes or less. | Analgesia, anxiolysis, and anterograde amnesia. | Preferably, HC-O, WIO, EMS or I. | Preferably, S or SAO. |
| A. | $N_2O$/$O_2$/$N_2$ | Preferably, $N_2O$ from 35% to 70%, He from 9% to 44%, with the balance of $O_2$; more preferably, 65% $N_2O$/21% $O_2$/14% $N_2$ or 55% $N_2O$/30% $O_2$/15% He. | Preferably, 4 minutes or less prior to the AF ICD shock; more preferably, from 2 to 3 minutes prior to the AF ICD shock. | Preferably, 4 minutes or less. | Analgesia, anxiolysis, and anterograde amnesia, where, for example, 21% $O_2$ balance is provided due to specific or class of patient-related concerns about a higher concentration of $O_2$ being provided. | Preferably, HC-O, WIO, EMS or I. | Preferably, S or SAO. |
| A. | $N_2O$/$O_2$/He | Preferably, $N_2O$ from 35% to 70%, He from 9% to 44%, with the balance of $O_2$; more preferably, 65% $N_2O$/21% $O_2$/14% He or 55% $N_2O$/30% $O_2$/15% He. | Preferably, 4 minutes or less prior to the AF ICD shock; more preferably, from 2 to 3 minutes prior to the AF ICD. shock. | Preferably, 4 minutes or less; more preferably from 2 to 3 minutes. | Analgesia, anxiolysis, and anterograde amnesia, with He serving to reduce the work of breathing and increase the efficient distribution of $N_2O$ in the lungs. | Preferably, HC-O, WIO, EMS or I. | Preferably, S or SAO. |
| A. | Xe/$O_2$ | Preferably, Xe from 26% to 50%, with the balance of $O_2$. More preferably, 33% Xe/67% $O_2$. | Preferably, 4 minutes or less prior to the AF ICD shock; more preferably, from 2 to 3 minutes prior to the AF ICD shock. | Preferably, 4 minutes or less; more preferably from 2 to 3 minutes. | Analgesia, anxiolysis, and anterograde amnesia. | Preferably, HC-O, WIO, VO, EMS or I. | Preferably, S or SAO. |
| A. | Xe/$O_2$/$N_2$ | Preferably, Xe from 26% to 50%, $N_2$ from 29% to 53%, with the balance of $O_2$; more preferably, 33% Xe/21% $O_2$/46% $N_2$ or 40% Xe/30% $O_2$/30% $N_2$. | Preferably, 4 minutes or less prior to the AF ICD shock; more preferably, from 2 to 3 minutes prior to the AF ICD shock. | Preferably, 4 minutes or less; more preferably from 2 to 3 minutes. | Analgesia, anxiolysis, and anterograde amnesia, where, for example, 21% $O_2$ balance $N_2$ is provided due to specific or class of | Preferably, HC-O, WIO, VO EMS or I. | Preferably, S or SAO. |

TABLE 1-continued

| | | | | | | | |
|---|---|---|---|---|---|---|---|
| A. | Xe/O₂/He | Preferably, Xe from 26% to 50%, N₂ from 29% to 53%, with the balance of O₂; more preferably, 33% Xe/21% O₂/46% N₂ or 40% Xe/30% O₂/30% N₂. | Preferably, 4 minutes or less prior to the AF ICD shock; more preferably, from 2 to 3 minutes prior to the AF ICD shock. | Preferably, 4 minutes or less; more preferably from 2 to 3 minutes. | patient-related concerns about a higher concentration of O₂ being provided. Analgesia, anxiolysis, and anterograde amnesia, with He service to reduce the work of breathing Xe which is a relatively heavy dense gas and increase the efficient distribution of Xe in the lungs. | Preferably, HC-O, WIO, EMS or I. | Preferably, S or SAO. |
| B. Reduce adverse physical and psychological effect of self-administered defibrillating shock on patients with AF ICD. | N₂O₂ | Preferably, N₂O from 35% to 70%, with the balance of O₂; more preferably, 65% N₂O/35% O₂. | Preferably, 4 minutes or less prior to the AF ICD shock; more preferably, from 2 to 3 minutes prior to the AF ICD shock. | Preferably, 4 minutes or less; more preferably, from 2 to 3 minutes. | Analgesia, anxiolysis, and anterograde amnesia. | Preferably, HC-O, WIO or EMS; more preferably, HC-O. | Preferably, S or SAO. |
| B. | N₂O/O₂/N₂ | Preferably, N₂O from 35% to 70%, N₂ from 9% to 44%, with the balance of O₂; more preferably, 65% N₂O/21% O₂/14% N₂ or 55% N₂O/30% O₂/15% N₂. | Preferably, 4 minutes or less prior to the AF ICD shock; more preferably, from 2 to 3 minutes prior to the AF ICD shock. | Preferably, 4 minutes or less; more preferably, from 2 to 3 minutes. | Analgesia, anxiolysis, and anterograde amnesia, where, for example, 21% O₂ balance N₂ is provided due to specific or class of patient-related concerns about a higher concentration of O₂ being provided. | Preferably, HC-O, WIO or EMS; more preferably, HC-O. | Preferably, S or SAO. |
| B. | N₂O/O₂/He | Preferably, N₂O from 35% to 70%, He from 9% to 44%, with the balance of O₂; more preferably, 65% N₂O/21% O₂/14% He or 55% N₂O/30% O₂/15% He. | Preferably, 4 minutes or less prior to the AF ICD shock; more preferably, from 2 to 3 minutes prior to the AF ICD shock. | Preferably, 4 minutes or less; more preferably, from 2.5 to 3.5 minutes. | Analgesia, anxiolysis, and anterograde amnesia with He serving to reduce the work of breathing and increase the efficient distribution of N₂O in the lungs. | Preferably, HC-O, WIO or EMS; more preferably, HC-O. | Preferably, S or SAO. |
| B. | Xe/O₂ | Preferably, Xe from 26% to 50%, with the balance of O₂. More preferably, 33% Xe/67% O₂. | Preferably, 4 minutes or less prior to the AF ICD shock; more preferably, from 2 to 3 minutes prior to the AF ICD shock. | Preferably, 4 minutes or less; more preferably, from 2 to 3 minutes. | Analgesia, anxiolysis, and anterograde amnesia. | Preferably, HC-O, WIO or EMS; more preferably, HC-O. | Preferably, S or SAO. |
| B. | Xe/O₂/N₂ | Preferably, Xe from 26% to 50%, N₂ from 29% to 53%, with the balance of O₂; more preferably, 33% Xe/21% O₂/46% N₂ or 40% Xe/30% O₂/30% N₂. | Preferably, 4 minutes or less prior to the AF ICD shock; more preferably, from 2 to 3 minutes prior to the AF ICD shock. | Preferably, 4 minutes or less; more preferably, from 2 to 3 minutes. | Analgesia, anxiolysis, and anterograde amnesia, where, for example, 21% O₂ balance N₂ is provided due to specific or class of patient-related concerns about a higher | Preferably, HC-O, WIO or EMS; more preferably, HC-O. | Preferably, S or SAO. |

TABLE 1-continued

| | | | | | | | |
|---|---|---|---|---|---|---|---|
| B. | Xe/O$_2$/He | Preferably, Xe from 26% to 50%, N$_2$ from 29% to 53%, with the balance of O$_2$; more preferably, 33% Xe/21% O$_2$/46% N$_2$ or 40% Xe/30% O$_2$/30% N$_2$. | Preferably, 4 minutes or less prior to the AF ICD shock; more preferably, from 2 to 3 minutes prior to the AF ICD shock. | Preferably, 4 minutes or less; more preferably, from 2 to 3 minutes. | concentration of O$_2$ being provided. Analgesia, anxiolysis, and anterograde amnesia, with He serving to reduce the work of breathing Xe which is a relatively heavy dense gas and increase the efficient distribution of Xe in the lungs. | Preferably, HC-O, WIO or EMS; more preferably, HC-O. | Preferably, S or SAO. |
| C. Reduce adverse physical and psychological effect of defibrillating shock on patients with AF ICD when shock is not self administered. | N$_2$O/O$_2$ | Preferably, N$_2$O from 35% to 70%, with the balance of O$_2$; more preferably, 65% N$_2$O/35% O$_2$. | Preferably, 4 minutes or less prior to the AF ICD shock; more preferably, from 2 to 3 minutes prior to the AF ICD shock. | Preferably, 4 minutes or less; more preferably, from 2 to 3 minutes. | Analgesia, Anxiolysis, and anterograde amnesia. | Preferably, I, WIO or EMS. | Preferably, SAO. |
| C. | N$_2$O/O$_2$/N$_2$ | Preferably, N$_2$O from 35% to 70%, N$_2$ from 9% to 44%, with the balance of O$_2$; more preferably, 65% N$_2$O/21% O$_2$/14% N$_2$ or 55% N$_2$O/30% O$_2$/15% N$_2$. | Preferably, 4 minutes or less prior to the AF ICD shock; more preferably, from 2 to 3 minutes prior to the AF ICD shock. | Preferably, 4 minutes or less; more preferably, from 2 to 3 minutes. | Analgesia, anxiolysis and anterograde amnesia, where, for example, 21% O$_2$ balance N$_2$ is provided due to specific or class of patient related concerns about a higher concentration of O$_2$ being provided. | Preferably, I, WIO or EMS. | Preferably, SAO. |
| C. | N$_2$O/O$_2$/He | Preferably, N$_2$O from 35% to 70%, He from 9% to 44%, with the balance of O$_2$; more preferably, 65% N$_2$O/21% O$_2$/14% He or 55% N$_2$O/30% O$_2$/15% He. | Preferably, 4 minutes or less prior to the AF ICD shock; more preferably, from 2 to 3 minutes prior to the AF ICD shock. | Preferably, 4 minutes or less; more preferably, from 2 to 3 minutes. | Analgesia, anxiolysis, and anterograde amnesia, with He serving to reduce the work of breathing and increase the efficient distribution of N$_2$O in the lungs. | Preferably, I, WIO or EMS. | Preferably, SAO. |
| C. | Xe/O$_2$ | Preferably, Xe from 26% to 50%, with the balance of O$_2$; more preferably, 33% Xe/67% O$_2$. | Preferably, 4 minutes or less prior to the AF ICD shock; more preferably, from 2 to 3 minutes prior to the AF ICD shock. | Preferably, 4 minutes or less; more preferably, from 2 to 3 minutes. | Analgesia, anxiolysis, and anterograde amnesia. | Preferably, I, WIO or EMS. | Preferably, SAO. |
| C. | Xe/O$_2$/N$_2$ | Preferably, Xe from 26% to 50%, N$_2$ from 29% to 53%, with the balance of O$_2$; more preferably, 33% Xe/21% O$_2$/46% N$_2$ or 40% Xe/30% O$_2$/30% N$_2$ | Preferably, 4 minutes or less prior to the AF ICD shock; more preferably, from 2 to 3 minutes prior to the AF ICD shock. | Preferably, 4 minutes or less; more preferably, from 2 to 3 minutes. | Analgesia, anxiolysis, and anterograde amnesia, where, for example, 21% O$_2$ balance N$_2$ is provided due to specific or class of patient-related concerns about a higher concentration of O$_2$ being provided. | Preferably, I, WIO or EMS. | Preferably, SAO. |

TABLE 1-continued

| | Gas Mixture | Content of Mixture | Timing of Gas Administration | Duration of Gas Administration | Effect | Setting | Mode of Gas Administration |
|---|---|---|---|---|---|---|---|
| C. | Xe/O$_2$/He | Preferably, Xe from 26% to 50%, He from 29% to 53%, with the balance of O$_2$; more preferably, 33% Xe/21% O$_2$/46% H3 or 40% He/30% O$_2$/30% He. | Preferably, 4 minutes or less prior to the AF ICD shock; more preferably, from 2 to 3 minutes prior to the AF ICD shock. | Preferably, 4 minutes or less; more preferably, from 2 to 3 minutes. | Analgesia, anxiolysis, and anterograde amnesia, with He serving to reduce the work of breathing Xe which is relatively heavy dense gas and increase the efficient distribution of Xe in the lungs. | Preferably, I, WIO or EMS. | Preferably, SAO. |

| Indication | Gas Mixture | Content of Mixture | Timing of Gas Administration | Duration of Gas Administration | Effect | Setting | Mode of Gas Administration |
|---|---|---|---|---|---|---|---|
| D. Ease administration of atrial defibrillating shock in patients having a temporary catheter-based electrode following cardiac or thoracic surgery. | N$_2$O/O$_2$ | Preferably, N$_2$O from 35% to 70%, with the balance of O$_2$; more preferably, 65% N$_2$O/35% O$_2$. | Preferably, 4 minutes or less prior to shock; more preferably, 2.5 to 3.5 minutes prior to shock. | Preferably, 4 minutes or less; more preferably, from 2 to 3 minutes. | Analgesia, Anxiolysis, and anterograde amnesia. | Preferably, I and WIO. | Preferably, SAO. |
| D. | N$_2$O/O$_2$/N$_2$ | Preferably, N$_2$O from 35% to 70%, N$_2$ from 9% to 44%, with the balance of O$_2$; more preferably, 65% N$_2$O/21% O$_2$/14% N$_2$ or 55% N$_2$O/30% O$_2$/15% N$_2$. | Preferably, 4 minutes or less prior to shock; more preferably, from 2 to 3 minutes prior to shock. | Preferably, 4 minutes or less; more preferably, from 2 to 3 minutes. | Analgesia, anxiolysis and anterograde amnesia, where, for example, 21% O$_2$ balance N$_2$ is provided due to specific or class of patient related concerns about a higher concentration of O$_2$ being provided. | Preferably, I and WIO | Preferably, SAO. |
| D. | N$_2$O/O$_2$/He | Preferably, N$_2$O from 35% to 70%, He from 9% to 44%, with the balance of O$_2$; more preferably, 65% N$_2$O/14% He or 55% N$_2$O/30% O$_2$/15% He. | Preferably, 4 minutes or less prior to shock; more preferably, from 2 to 3 minutes prior to shock. | Preferably, 4 minutes or less; more preferably, from 2 to 3 minutes. | Analgesia, anxiolysis, and anterograde amnesia, with He serving to reduce the work of breathing and increase the efficient distribution of N$_2$O in the lungs. | Preferably, I and WIO | Preferably, SAO. |
| D. | Xe/O$_2$ | Preferably, Xe from 26% to 50%, with the balance of O$_2$; more preferably, 33% Xe/67% O$_2$. | Preferably, 4 minutes or less prior to the AF ICD shock; more preferably, from 2 to 3 minutes prior to shock. | Preferably, 4 minutes or less; more preferably, from 2 to 3 minutes. | Analgesia, anxiolysis, and anterograde amnesia. | Preferably, I and WIO | Preferably, SAO. |
| D. | Xe/O$_2$/N$_2$ | Preferably, Xe from 26% to 50%, N$_2$ from 29% to 53%, with the balance of O$_2$; more preferably, 33% Xe/21% O$_2$/46% N$_2$ or 40% Xe/30% O$_2$/30% N$_2$ | Preferably, 4 minutes or less prior to shock; more preferably, from 2 to 3 minutes prior to shock. | Preferably, 4 minutes or less; more preferably, from 2 to 3 minutes. | Analgesia, anxiolysis, and anterograde amnesia, where, for example, 21% O$_2$ balance N$_2$ is provided due to specific or class of patient-related | Preferably, I and WIO | Preferably, SAO. |

TABLE 1-continued

| | | | | | | | |
|---|---|---|---|---|---|---|---|
| D. | Xe/O$_2$/He | Preferably, Xe from 26% to 50%, He from 29% to 53%, with the balance of O$_2$; more preferably, 33% Xe/21% O$_2$/46% He or 40% He/30% O$_2$/30% He. | Preferably, 4 minutes or less prior to shock; more preferably, from 2 to 3 minutes prior to shock. | Preferably, 4 minutes or less; more preferably, from 2 to 3 minutes. | concerns about a higher concentration of O$_2$ being provided. Analgesia, anxiolysis, and anterograde amnesia, with He serving to reduce the work of breathing Xe which is relatively heavy dense gas and increase the efficient distribution of Xe in the lungs. | Preferably, I and WIO | Preferably, SAO NS. |
| E. Ease of administration of atrial defibrillating shock in patients undergoing transvenous internal cardioversion administered by a physician during cardiac catheterization. | N$_2$O/O$_2$ | Preferably, N$_2$O from 35% to 70%, with the balance of O$_2$; more preferably, 65% N$_2$O/35% O$_2$. | Preferably, 4 minutes or less prior to shock; more preferably, 2.5 to 3.5 minutes prior to shock. | Preferably, 4 minutes or less; more preferably, from 2 to 3 minutes. | Analgesia, anxiolysis, and anterograde amnesia. | Preferably, I and WIO. | Preferably, SAO. |
| E. | N$_2$O/O$_2$/N$_2$ | Preferably, N$_2$O from 35% to 70%, N$_2$ from 9% to 44%, with the balance of O$_2$; more preferably, 65% N$_2$O/21% O$_2$/14% N$_2$ or 55% N$_2$O/30% O$_2$/15N$_2$. | Preferably, 4 minutes or less prior to shock; more preferably, from 2 to 3 minutes prior to shock. | Preferably, 4 minutes or less; more preferably, from 2 to 3 minutes. | Analgesia, anxiolysis and anterograde amnesia, where, for example, 21% O$_2$ balance N$_2$ is provided due to specific or class of patient related concerns about a higher concentration of O$_2$ being provided. | Preferably, I and WIO. | Preferably, SAO. |
| E. | N$_2$O/O$_2$/He | Preferably, N$_2$O from 35% to 70%, He from 9% to 44%, with the balance of O$_2$; more preferably, 65% N$_2$O/14% He or 55% N$_2$O/30% O$_2$/15% He. | Preferably, 4 minutes or less prior to shock; more preferably, from 2 to 3 minutes prior to shock. | Preferably, 4 minutes or less; more preferably, from 2 to 3 minutes. | Analgesia, anxiolysis, and anterograde amnesia, with He serving to reduce the work of breathing and increase the efficient distribution of N$_2$O in the lungs. | Preferably, I and WIO. | Preferably, SAO. |
| E. | Xe/O$_2$ | Preferably, Xe from 26% to 50%, with the balance of O$_2$; more preferably, 33% Xe/67% O$_2$. | Preferably, 4 minutes or less prior to shock; more preferably, from 2 to 3 minutes prior to shock. | Preferably, 4 minutes or less; more preferably, from 2 to 3 minutes. | Analgesia, anxiolysis, and anterograde amnesia. | Preferably, I and WIO. | Preferably, SAO. |
| E. | Xe/O$_2$/N$_2$ | Preferably, Xe from 26% to 50%, N$_2$ from 29% to 53%, with the balance of O$_2$; more preferably, 33% Xe/21% O$_2$/46% N$_2$ or 40% Xe/30% O$_2$/30% N$_2$. | Preferably, 4 minutes or less prior to shock; more preferably, from 2 to 3 minutes prior to shock. | Preferably, 4 minutes or less; more preferably, from 2 to 3 minutes. | Analgesia, anxiolysis, and anterograde amnesia, where, for example, 21% O$_2$ balance N$_2$ is provided due to specific or class of patient-related | Preferably, I and WIO. | Preferably, SAO. |

TABLE 1-continued

| | | | | | | | |
|---|---|---|---|---|---|---|---|
| E. | Xe/O$_2$/He | Preferably, Xe from 26% to 50%, He from 29% to 53%, with the balance of O$_2$; more preferably, 33% Xe/21% O$_2$/46% H3 or 40% He/30% O$_2$/30% He. | Preferably, 4 minutes or less prior to shock; more preferably, from 2 to 3 minutes prior to shock. | Preferably, 4 minutes or less; more preferably, from 2 to 3 minutes. | concerns about a higher concentration of O$_2$ being provided. Analgesia, anxiolysis, and anterograde amnesia, with He serving to reduce the work of breathing Xe which is relatively heavy dense gas and increase the efficient distribution of Xe in the lungs. | Preferably, I and WIO. | Preferably, SAO. |
| F. Ease pain and anxiety during the period immediately leading up to, during and immediately following a discreet peak period of pain generated by a variety of relatively short-term procedures and reduce recall of pain and anxiety during those periods.[3] | N$_2$O/O$_2$ | Preferably, N$_2$O from 35% to 70%, with the balance of O$_2$; more preferably, 65% N$_2$O/35% O$_2$. | Preferably, 4 minutes or less prior to peak period of pain; more preferably, from 2 to 3 minutes prior to peak period of pain. | Preferably, 4 minutes or less; more preferably, from 2 to 3 minutes. | Analgesia, Anxiolysis, and anterograde amnesia. | Preferably, I, EMS and WIO. | Preferably, SAO. |
| F. | N$_2$O/O$_2$/N$_2$ | Preferably, N$_2$O from 35% to 70%, N$_2$ from 9% to 44%, with the balance of O$_2$; more preferably, 65% N$_2$O/21% O$_2$/14% N$_2$ or 55% N$_2$O/30% O$_2$/15 N$_2$. | Preferably, 4 minutes or less prior to peak period of pain; more preferably, from 2 to 3 minutes prior to peak period of pain. | Preferably, 4 minutes or less; more preferably, from 2 to 3 minutes. | Analgesia, anxiolysis and anterograde amnesia, where, for example, 21% O$_2$ balance N$_2$ is provided due to specific or class of patient related concerns about a higher concentration of O$_2$ being provided. | Preferably, I, EMS and WIO. | Preferably, SAO. |
| F. | N$_2$O/O$_2$/He | Preferably, N$_2$O from 35% to 70%, He from 9% to 44%, with the balance of O$_2$; more preferably, 65% N$_2$O/14% He or 55% N$_2$O/30% O$_2$/15% He. | Preferably, 4 minutes or less prior to peak period of pain; more preferably, from 2 to 3 minutes prior to peak period of pain. | Preferably, 4 minutes or less; more preferably, from 2 to 3 minutes. | Analgesia, anxiolysis, and anterograde amnesia, with He serving to reduce the work of breathing and increase the efficient distribution of N$_2$O in the lungs. | Preferably, I, EMS and WIO. | Preferably, SAO. |
| F. | Xe/O$_2$ | Preferably, Xe from 26% to 50%, with the balance of O$_2$; more preferably, 33% Xe/67% O$_2$. | Preferably, 4 minutes or less prior to peak period of pain; more preferably, from 2 to 3 minutes prior to peak period of pain. | Preferably, 4 minutes or less; more preferably, from 2 to 3 minutes. | Analgesia, anxiolysis, and anterograde amnesia. | Preferably, I, EMS and WIO. | Preferably, SAO. |
| F. | Xe/O$_2$/N$_2$ | Preferably, Xe from 26% to 50%, N$_2$ from 29% to 53%, with | Preferably, 4 minutes or less prior to peak | Preferably, 4 minutes or less; more preferably, | Analgesia, anxiolysis, and anterograde | Preferably, I, EMS and WIO. | Preferably, SAO. |

TABLE 1-continued

| | | | | | | | |
|---|---|---|---|---|---|---|---|
| | | the balance of $O_2$; more preferably, 33% Xe/21% $O_2$/46% $N_2$ or 40% Xe/30% $O_2$/30% $N_2$. | period of pain; more preferably, from 2 to 3 minutes prior to peak period of pain. | from 2 to 3 minutes. | amnesia, where, for example, 21% $O_2$ balance $N_2$ is provided due to specific or class of patient-related concerns about a higher concentration of $O_2$ being provided. | | |
| F. | Xe/$O_2$/He | Preferably, Xe from 26% to 50%, He from 29% to 53%, with the balance of oxygen; more preferably, 33% Xe/21% $O_2$/46% He or 40% Xe/30% $O_2$/30% He. | Preferably, 4 minutes or less prior to peak period of pain; more preferably, from 2 to 3 minutes prior to peak period of pain. | Preferably, 4 minutes or less; more preferably, from 2 to 3 minutes. | Analgesia, anxiolysis, and anterograde amnesia, with He serving to reduce the work of breathing Xe which is relatively heavy dense gas and increase the efficient distribution of Xe in the lungs. | Preferably, I, EMS and WIO. | Preferably, SAO. |
| G. Ease pain and anxiety during initial treatment on the scene by emergency medical services, fire and police first aid responders and during ambulance transport, of accident, crime, fire and sports injury victims, and provide reduced recall of the pain and anxiety during the episode of first aid and transport. | $N_2O$/$O_2$ | Preferably, $N_2O$ from 35% to 70%, with the balance of $O_2$; more preferably, 65% $N_2O$/35% $O_2$. | Preferably, 4 minutes or less prior and/or during peak period(s) of pain; more preferably, from 2 to 3 minutes prior to and/or during peak period(s) of pain. | Preferably, 4 minutes or less; more preferably, from 2 to 3 minutes. | Analgesia, Anxiolysis, and anterograde amnesia. | Preferably, EMS. | Preferably, SAO. |
| G. | $N_2O$/$O_2$/$N_2$ | Preferably, $N_2O$ from 35% to 70%, $N_2$ from 9% to 44%, with the balance of $O_2$; more preferably, 65% $N_2O$/21% $O_2$/14% $N_2$ or 55% $N_2O$/30% $O_2$/15% $N_2$. | Preferably, 4 minutes or less prior and/or during peak period(s) of pain; more preferably, from 2 to 3 minutes prior to and/or during peak period(s) of pain. | Preferably, 4 minutes or less; more preferably, from 2 to 3 minutes. | Analgesia, anxiolysis and anterograde amnesia, where, for example, 21% $O_2$ balance $N_2$ is provided due to specific or class of patient related concerns about a higher concentration of $O_2$ being provided. | Preferably, EMS. | Preferably, SAO. |
| G. | $N_2O$/$O_2$/He | Preferably, $N_2O$ from 35% to 70%, He from 9% to 44%, with the balance of $O_2$; more preferably, 65% $N_2O$/14% He or 55% $N_2O$/30% $O_2$/15% He. | Preferably, 4 minutes or less prior and/or during peak period(s) of pain; more preferably, from 2 to 3 minutes prior to and/or during peak period(s) of pain. | Preferably, 4 minutes or less; more preferably from 2 to 3 minutes. | Analgesia, anxiolysis, and anterograde amnesia, with He serving to reduce the work of breathing and increase the efficient distribution of $N_2O$ in the lungs. | Preferably, EMS. | Preferably, SAO. |

TABLE 1-continued

| | | | | | | | |
|---|---|---|---|---|---|---|---|
| G. | Xe/O$_2$ | Preferably, Xe from 26% to 50%, with the balance of O$_2$; more preferably, 33% Xe/67% O$_2$. | Preferably, 4 minutes or less prior to and/or during peak period(s) of pain; more preferably, from 2 to 3 minutes prior to and/or during peak period(s) of pain. | Preferably, 4 minutes or less; more preferably from 2 to 3 minutes. | Analgesia, anxiolysis, and anterograde amnesia. | Preferably, EMS. | Preferably, SAO. |
| G. | Xe/O$_2$/N$_2$ | Preferably, Xe from 26% to 50%, N$_2$ from 29% to 53%, with the balance of O$_2$; more preferably, 33% Xe/21% O$_2$/46% N$_2$ or 40% Xe/30% O$_2$/30% N$_2$. | Preferably, 4 minutes or less prior to and/or during peak period(s) of pain; more preferably, from 2 to 3 minutes prior to and/or during peak period(s) of pain. | Preferably, 4 minutes or less; more preferably from 2 to 3 minutes. | Analgesia, anxiolysis, and anterograde amnesia, where, for example, 21% O$_2$ balance N$_2$ is provided due to specific or class of patient-related concerns about a higher conrentration of O$_2$ being provided. | Preferably, EMS. | Preferably, SAO. |
| G. | Xe/O$_2$/He | Preferably, Xe from 26% to 50%, N$_2$ from 29% to 53%, with the balance of O$_2$; more preferably, 33% Xe/21% O$_2$/46% N$_2$ or 40% Xe/30% O$_2$/30% N$_2$. | Preferably, 4 minutes or less prior to and/or during peak period(s) of pain; more preferably, from 2 to 3 minutes prior to and/or during peak period(s) of pain. | Preferably, 4 minutes or less; more preferably from 2 to 3 minutes. | Analgesia, anxiolysis, and anterograde amnesia, with He serving to reduce the work of breathing Xe which is relatively heavy dense gas and increase the efficient distribution of Xe in the lungs. | Preferably, EMS. | Preferably SAO. |
| H. Discomfort from radiotherapy and chemotherapy. | N$_2$O/O$_2$ | Preferably, N$_2$O from 35% to 70%, with the balance of O$_2$; more preferably, 65% N$_2$O/35% O$_2$. | Preferably, 4 minutes or less prior and/or during peak period(s) of discomfort; more preferably, from 2 to 3 minutes prior to and/or during peak period(s) of discomfort. | Preferably, 4 minutes or less; more preferably, 2 to 3 minutes. | Analgesia, Anxiolysis, and anterograde amnesia. | Preferably, WIO, HC-O and I | Preferably S or SAO. |
| H. | N$_2$O/O$_2$/N$_2$ | Preferably, N$_2$O from 35% to 70%, N$_2$ from 9% to 44%, with the balance of O$_2$; more preferably, 65% N$_2$O/21% O$_2$/14% N$_2$ or 55% N$_2$O/30% O$_2$/15% N$_2$. | Preferably, 4 minutes or less prior and/or during peak period(s) of discomfort; more preferably, from 2 to 3 minutes prior to and/or during peak period(s) of discomfort. | Preferably, 4 minutes or less; most preferably, 2 to 3 minutes. | Analgesia, anxiolysis and anterograde amnesia, where, for example, 21% O$_2$ balance N$_2$ is provided due to specific or class of patient related concerns about a higher concentration of O$_2$ being provided. | Preferably, WIO, HC-O and I. | Preferably S or SAO. |
| H. | N$_2$O/O$_2$/He | Preferably, N$_2$O from 35% to 70%, He from 9% to 44%, with the balance of O$_2$; more preferably, 65% N$_2$O/14% He or 55% | Preferably, 4 minutes or less prior and/or during peak period(s) of discomfort; more | Preferably, 4 minutes or less; most preferably, 2 to 3 minutes. | Analgesia, anxiolysis, and anterograde amnesia, with He serving to reduce the work of breathing | Preferably, WIO and I. | Preferably S or SAO. |

TABLE 1-continued

| | | N₂O/30% O₂/15% He. | preferably, from 2 to 3 minutes prior to and/or during peak period(s) of discomfort. | | and increase the efficient distribution of N₂O in the lungs. | | |
|---|---|---|---|---|---|---|---|
| I. Ease withdrawal from tobacco or alcohol addiction. | N₂O/O₂ | Preferably, N₂O from 35% to 70%, with the balance of O₂; more preferably, 65% N₂O/35% O₂. | Preferably, 4 minutes or less prior and/or during peak period(s) of craving for tobacco or alcohol; more preferably, 2 to 3 minutes prior to and/or during peak period(s) of craving for tobacco or alcohol. | Preferably, 4 minutes or less; most preferably, 2 to 3 minutes. | To provide a reduction in craving for tobacco or alcohol in part due to release of serotonin caused by N₂O. | Preferably, HC-O and WIO. | Preferably S or SAO. |
| I. | N₂O/O₂/N₂ | Preferably, N₂O from 35% to 70%, N₂ from 9% to 44%, with the balance of O₂; more preferably, 65% N₂O/21% O₂/14% N₂ or 55% N₂O/30% O₂/15% N₂. | Preferably, 4 minutes or less prior and/or during peak period(s) of craving for tobacco or alcohol; more preferably, 2 to 3 minutes prior to and/or during peak period(s) of craving for tobacco or alcohol. | Preferably, 4 minutes or less; most preferably, 2 to 3 minutes. | To provide a reduction of craving for tobacco or alcohol in part due to release of serotonin caused by N2O, where, for example, 21% O₂ balance N₂ is provided due to specific or class of patient related concerns about a higher concentration of O₂ being provided. | Preferably, HC-O and WIO. | Preferably S or SAO. |
| I. | N₂O/O₂/He | Preferably, N₂O from 35% to 70%, He from 9% to 44%, with the balance of O₂; more preferably, 65% N₂O/14% He or 55% N₂O/30% O₂/15% He. | Preferably, 4 minutes or less prior and/or during peak period(s) of craving for tobacco or alcohol; more preferably, 2 to 3 minutes prior to and/or during peak period(s) of craving for tobacco or alcohol. | Preferably, 4 minutes or less; most preferably, 2 to 3 minutes. | To provide a reduction in craving for tobacco or alcohol in part due to release of serotonin caused by N2O, with He serving to reduce the work of breathing and increase the efficient distribution of N₂O in the lungs. | Preferably, HC-O and WIO. | Preferably S or SAO. |
| J. Temporarily ameliorate asthma attacks prior to or after use of corticosteroids or other asthma specific pharmaceuticals, or as an aid if asthma specific pharmaceuticals are not immediately available; temporarily ameliorate other | He/O₂ | Preferably, He from 40% to 80%, with the balance O₂; more preferably, He from 60% to 80%, and even more preferably 80%, with the balance O₂. | Preferably, 4 minutes or less prior to or after use of asthma specific pharmaceuticals to facilitate distribution of asthma medication in the lungs, or as an aid if asthma medications are not immediately available to facilitate | Preferably, 4 minutes or less; most preferably, 2-3 minutes. | Facilitate breathing by reducing the work of breathing thereby helping to reduce the "panic" factor and increasing the distribution of O₂ in the lings via the carrier gas properties of He resulting in a greater amount of O₂ | Preferably, WIO, HC-O, I and EMS. | Preferably S or SAO. |

TABLE 1-continued

| | | | | | | | |
|---|---|---|---|---|---|---|---|
| COPD such as emphysema. | | | easier breathing and greater oxygen distribution in the lungs from the air being breathed; or more preferably, from 2-3 minutes prior to or after use of asthma specific pharmaceuticals to facilitate distribution of asthma medication in the lungs, or as an aid if asthma medications are not immediately available to facilitate easier breathing and greater oxygen distribution in the lungs from the air being breathed. | | entering the bloodstream. | | |
| K. Ameliorate and/or stop hyperventilation and certain types and phases of migraine. | $CO_2/O_2$ | Preferably, $CO_2$ from 5% to 30%, with the balance $O_2$; more preferably, $CO_2$ from 10% to 30%, with the balance $O_2$. | Preferably, 20 seconds to 4 minutes, but no more than 4 minutes if 5-10% $CO_2$ mixture is used, until hyperventilation episode and anxiety are reduced or eliminated, or migraine pain is resolved, and preferably just several breaths, until hyperventilation episode and anxiety are reduced or eliminated or migraine pain is resolved if above 10% $CO_2$, and in particular 20-30% $CO_2$ are utilized due to the associated physiological risks of breathing the latter high $CO_2$ concentrations. | Preferably, 20 seconds to 4 minutes if 5-10% $CO_2$ mixture is used; and preferably, just several breaths if above 10% $CO_2$ and in particular 20% to 30% $CO_2$. | As an aid in restoring a normal breathing pattern and to reduce anxiety during hyperventilation and reduce the time and severity of certain types and phases of migraine. | Preferably, WIO, HC-O, I and EMS. | Preferably S or SAO. |
| K. | $CO_2/O_2/N_2$ | Preferably, $CO_2$ from 5% to 30%, $N_2$ from 49% to 74%, with the balance $O_2$; more preferably, 10% $CO_2$/21% $O_2$/69% $N_2$ or 5% $CO_2$/21% $O_2$/ 74% $N_2$ or 30% $CO_2$/ 21% $O_2$/49% $N_2$. | Preferably, 20 seconds to 4 minutes, but no more than 4 minutes if 5-10% $CO_2$ mixture is used, until hyperventilation episode | Preferably, 20 seconds to 4 minutes if 5-10% $CO_2$ mixture is used; and preferably, just several breaths if above 10% $CO_2$ and in particular | As an aid in restoring a normal breathing pattern and to reduce anxiety during hyperventilation and reduce the time and | Preferably, WIO, HC-O, I and EMS. | Preferably S or SAO. |

TABLE 1-continued

| | | | | | | | |
|---|---|---|---|---|---|---|---|
| | | | and anxiety are reduced or eliminated, or migraine pain is resolved, and preferably just several breaths, until hyperventilation episode and anxiety are reduced or eliminated or migraine pain is resolved if above 10% $CO_2$, and in particular 20-30% $CO_2$ are utilized due to the associated physiological risks of breathing the latter high $CO_2$ concentrations. | 20% to 30% $CO_2$. | severity of certain types and phases of migraine, where, for example, 21% $O_2$ balance $N_2$ is provided due to specific or class of patient-related concerns about a higher concentration of $O_2$ being provided. | | |
| K. | $CO_2/O_2/He$ | Preferably, $CO_2$ from 5% to 30%, He from 49% to 74%, with balance $O_2$; more preferably, 10% $CO_2$/21% $O_2$/69% He or 5% $CO_2$/21% $O_2$/ 74% He or 30% $CO_2$/ 21% $O_2$/49% He. | Preferably, 20 seconds to 4 minutes, but no more than 4 minutes if 5-10% $CO_2$ mixture is used, until hyperventilation episode and anxiety are reduced or eliminated, or migraine pain is resolved, and preferably just several breaths, until hyperventilation episode and anxiety are reduced or eliminated or migraine pain is resolved if above 10% $CO_2$, and in particular 20-30% $CO_2$ are utilized due to the associated physiological risks of breathing the latter high $CO_2$ concentrations. | Preferably, 20 seconds to 4 minutes if 5-10% $CO_2$ mixture is used; and preferably, just several breaths if above 10% $CO_2$ and in particular 20% to 30% $CO_2$. | As an aid in restoring a normal breathing pattern and to reduce anxiety during hyperventilation and reduce the time and severity of certain types and phases of migraine, with He serving to reduce the work of breathing and increase the efficient distribution of $CO_2$ in the lungs. | Preferably, WIO, HC-O, I and EMS. | Preferably S or SOA. |
| L. Ameliorate existing cluster headache and stop the onset of cluster headache. | $O_2$ | 100% $O_2$. | Preferably, 6 minutes or less as of the onset of a cluster headache until the pain is reduced or totally eliminated. | Preferably, 6 minutes as needed until pain is reduced or ended. | In place of or in addition to other pharmaceutical medication prescribed for administration on acute basis to stop onset of a cluster headache or to ameliorate an existing cluster headache. | WIO, HC-O, I and EMS | Preferably S or SAO. |

TABLE 1-continued

| | | | | | | | |
|---|---|---|---|---|---|---|---|
| L. | He/O$_2$ | Preferably, He from 20% to 50% with the balance O$_2$; more preferably, 40% He/60% O$_2$ or 20% He/80% O$_2$ or 50% He/50% O$_2$. | Preferably, 6 minutes or less as of the onset of a cluster headache until the pain is reduced or totally eliminated. | Preferably, 6 minutes as needed until pain is reduced or ended. | In place of or in addition to other pharmaceutical medication prescribed for administration on acute basis to stop onset of or existing cluster headache, where the He acts as a carrier gas improving the efficiency of distribution of O$_2$ within the lungs facilitating more efficient delivery of O$_2$ to the bloodstream. | Preferably, WIO, HC-O, I and EMS. | Preferably S or SAO. |
| M. For other human therapeutic purposes. | CO/O$_2$ | Preferably, from 1 to 5000 ppm of CO in O$_2$. | Subject of clinical trials. | Subject of clinical trials. | Subject of clinical trials. | Preferably, WIO, HC-O, I and EMS. | Preferably S or SAO. |
| M. | CO/O$_2$/He | Preferably, from 1 to 5000 ppm of CO in 21% O$_2$, with the balance He. | Subject of clinical trials. | Subject of clinical trials. | Where, or example, 21% O$_2$ balance He is provided due to specific or class of patient-related concerns about a higher concentration of O$_2$ being provided and where He can help to reduce the work of breathing and increase the efficient distribution of CO in the lungs. | Preferably, WIO, HC-O, I and EMS. | Preferably S or SAO. |
| M. | CO/O$_2$/N$_2$ | Preferably, from 1 to 5000 ppm of CO in 21% O$_2$ with the balance N$_2$. | Subject of clinical trials. | Subject of clinical trials. | Where, for example, 20% O$_2$ balance N$_2$ is provided due to specific or class of patient-related concerns about a higher concentration of O$_2$ being provided. | Preferably, WIO, HC-O, I and EMS. | Preferably S or SAO. |

[1]WIO denotes Walk-In Outpatient setting; HC-O denotes homecare outpatient setting; EMS denotes Emergency Medical Services setting; I denotes inpatient setting; VO denotes Visiting Outpatient setting.
[2]S denotes self-administration, with no real time observation by a medical professional; SAO denotes self-administration, with real time observation by a medical professional; NS denotes not self-administered.
[3]Non-limiting examples of such procedures include venapuncture, intravenous or urinary catheter insertion, setting of a minor fracture or dislocation, application or removal of plaster casts, suturing, removal of bandages or dressings, insertion of aspiration needles, removal of warts and other topical skin growths, dermal biopsy punches, subcutaneous needle biopsies and fertility procedures. In particular, this use may be especially applicable for pediatric outpatients who are of an age capable of self administration just prior to and concomitant with procedures such as venipucture, suturing and bandage or dressing removal.

In another embodiment of the method of the preferred aspect of the present invention, the implanted cardiac rhythm management device is a VF-ICD. The method includes relief of pain and anxiety associated with the administration of a VF-ICD shock by administering analgesic gas or gas mixture to the patient having the implanted VF-ICD.

The VF-ICD shock is automatic. The after-effects of the VF-ICD shock are both physical and psychological. A patient having implanted VF-ICD experiences a constant sense of anxiety about the next shock, in part because the patients never know when the VF-ICD shock will occur. In contrast to the administration of analgesic gases in conjunction with the AF-ICD shock, in which a certain degree of control exists regarding the choice of the time of gas administration, the immediate and automatic nature of the VF-ICD shock will not allow gas administration before the VF-ICD shock. The typical status of patients during an episode of VF may also be incompatible with the pre-shock gas administration as VF can cause loss of consciousness if not immediately corrected. Therefore, the administration of the analgesic gas or gas mixture preferably begins immediately after the VF-ICD shock, rapidly providing analgesia and anxiolysis within a few minutes thereafter. Preferably, a patient having an implanted VF-ICD self-administers the analgesic gas or gas mixture with a portable gas administration device to relieve pain and anxiety the patient experiences after the VF-ICD shock. Portability of the gas administration device, its ease of use, and multiple levels of fail-safe use mechanisms provide the patient with relief from pain and VF-ICD anxiety coupled with the ability to self-administer the relief without observation, in real time, by a medical professional. Preferably, in addition to relief of pain and reduction of VF-ICD anxiety, the effects of gas administration also include decrease of the VF-ICD shock-related phobia and the presence of anterograde amnesia. The analgesic gases described in reference to the method of easing the AF-ICD shock may also be used in this embodiment.

In another embodiment of the present invention, the implanted cardiac rhythm management device is a temporary catheter or other type of easily removable implantable lead (s), such as, for example, the devices shown in U.S. Pat. Nos. 5,849,033 and 5,653,734, both of which were previously incorporated herein by reference thereto. A significant percentage of patients who undergo cardiac or thoracic surgery are prone to atrial fibrillation for several days following the surgery. These post surgery patients often not only have multiple and often serious medical conditions, but are also being treated with multiple drugs. The current standard of care for such patients is sedation by drugs, such as propofol, midazolam and benziodiazapenes, which are injected intravenously. The temporary catheters or other types of implantable lead(s) are especially useful to deliver atrial defibrillation in such post-surgery period. In this embodiment, the method of the invention includes relief of pain and anxiety associated with the administration of atrial defibrillation shock via the temporary catheter by administering analgesic gas or gas mixture. The preferred analgesic gas for use in this embodiment of the present invention is a nitrous oxide-containing gas mixture because of its lack of interaction with other drugs, lack of allergenicity, and the rapid return of the patients to normal sensory perception and a "zero" base regarding the rapid elimination of nitrous oxide and its effects. The administration of nitrous oxide results in analgesia and anxiolysis. Preferably, the analgesic gas or gas mixture is self-administered by a patient in the presence of a physician prior to the physician or other medical professional administering the atrial defibrillating shock via the temporary catheter. Preferably, the analgesic gas or gas mixture is administered with a portable gas administration device. Among the benefits is the portability of the device within the hospital, resulting in easy storage and easy access to device. It is also preferred to use gas administration devices that utilize unit dose cassettes, described in detail below. Due to their trackability, the unit dose cassettes may be assigned specifically to the patients record for purposes of medical record keeping and tracking the cost of care, thereby facilitating compliance with recent FDA regulations concerning bar coding and desired traceability of pharmaceuticals in unit dose form, and helping the healthcare institution to better assess both the cost of patient care and the outcomes/benefits ratio. The analgesic gases described in reference to the method of easing the AF-ICD shock may also be used in this embodiment.

The method of a preferred embodiment of the present invention may also be used in conjunction with the shock from external cardiac management devices. In one embodiment, the cardiac rhythm management device is an Automated External Defibrillator (AED). AEDs are typically used by first responders such as police officers, fire fighters, and emergency medical technicians to resuscitate victims of sudden cardiac arrest. AEDs are often being carried in emergency vehicles such as police cars, paramedic vehicles, and fire trucks. AEDs are also being widely deployed in areas where large numbers of people gather, such as at sports stadiums and the like.

In this embodiment, the method involves easing the administration of the shock from the AED by administering an analgesic gas or gas mixture to a patient with oxygen as part of the process of preparing the patient for or after they have undergone the Automated External (Ventricular) Defibrillation. The analgesic gases described in reference to the method of easing the AF-ICD shock may also be used in this embodiment. In addition to providing analgesia and anxiolysis, the analgesic gas or gas mixture (e.g., 65% $N_2O$/35% $O_2$) also may provide the patient with higher than normal oxygen levels, which may also be of therapeutic benefit for such patients. The preferred gas administration devices for use in conjunction with the AED are portable gas administration devices that are easy to carry and transport, can be easily secured, are easy to use and are failsafe such as the devices utilizing unit dose cassettes described herein below. This is especially the case during transport of a patient that has undergone AED in an EMS setting to a hospital Emergency Room. The benefits of the device in such situations are the ability to deliver the analgesic and anxiolytic gas mixture combined with portability, ease of use, and the ability to control handling and tracking of the unit dose cassettes which are also misuse, tamper and abuse resistant.

In accordance with another preferred embodiment of the present invention, there is provided a system 1 for delivery of therapeutic gases and gas mixtures to patients (FIG. 1). Preferably, the system 1 is suitable for self-administration by a patient. Also, the system 1 is preferably hand-held and portable. More preferably, the system 1 is suitable for operation with one hand.

As seen in FIG. 1, the therapeutic gas administration system 1 preferably includes a source gas container 2, a body 4, and a patient interface 6.

The source gas container 2 stores therapeutic gas or gas mixture for administration with the system 1. The desired therapeutic gas or gas mixture may be stored in gaseous, gas/liquid, or liquid only form. In a preferred embodiment, the source gas container 2 stores a single dose of the therapeutic gas or gas mixture (a unit dose). Generally, the dose is determined by concentration of the therapeutic gas or gas mixture and the total duration of administration, which are required to achieve the desired therapeutic effect. Preferably, the volume of the therapeutic gas or gas mixture stored in the source gas container 2 is sufficient for a single administration commensurate with the goal of the therapy (e.g., relief of AF-ICD anxiety). The source gas containers 2 may be manufactured in such unit dose form and provided to patients, physicians, and medical facilities for administration with the body 2 of the system 1.

Preferably, the source gas containers 2 are not intended for re-use, whether by the same or different patients. Since the containers 2 contain gases in amounts substantially required for a single gas administration, at least the majority of the gas stored in the containers is spent during gas administration. It is preferred that the containers be disposed of after a single use. In a preferred embodiment, the source gas containers 2 have a disposable construction.

The size of the source gas container 2, and the concentration and pressure of the gas(es) in the container depends on the type of the gas or gas mixture and the purpose of gas administration.

In one preferred embodiment, the source gas containers 2 may be provided with gas-specific and/or dose-specific indicator(s) (e.g., marked and/or equipped with such indicator(s)), which could be functional and/or non-functional. Non-limiting examples of such indicators include bar coding, alpha-numeric coding, color indicators, gas-specific interface configurations between the body 4 and the source gas container 2, gas-specific and/or dose-specific construction of the source gas containers 2 and/or the body 4, and the like.

Upon actuation, the source gas container 2 delivers the gas or gas mixture through the body 4 and the patient interface 6 to a patient (FIG. 1). The body 4 preferably provides various user controls, as well as gas control and delivery mechanisms that allow the gases to be supplied to a patient in a desired manner. Preferably, the body 4 allows easy insertion and replacement of the source gas containers 2. Preferably, the body 4 is lightweight, portable, and hand-held. More preferably, the body 4 allows the user to operate the drug delivery system with one hand. The body 4 may be constructed from materials that include, but are not limited to, aluminum, carbon steel, stainless steel, fiberglass, ceramics, PVC, styrene or other plastics, silicone, rubber, or any combination of the above. Preferably, the materials used in the construction of body 4, as well as other components of the system 1, are compatible with Food and Drug Administration regulatory requirements and are capable of operating under the necessary gas pressures and chemical conditions.

The patient interface 6 provides the therapeutic gas or gas mixture directly to a patient, preferably in the form of a gas stream. It is also possible to deliver the gas to a patient directly from the body 4 without the patient interface 6. However, the use of the patient interface 6 is preferred because it simplifies the use of the system 1, and allows delivery of gases in a desired manner. The patient interface 6 may be integral with or separate from the body 4.

Examples of patient interface components include breath-activated demand valves, manual demand valves, and gas conservation devices. The breath-activated demand valves operate by releasing therapeutic gas or gas mixture upon inspiration by the patient, typically by generating a specified negative pressure to activate the demand valve. The use of manual demand valves typically involves activation of a lever or a button during inspiration, with the therapeutic gas or gas mixture being released while the lever or the button is depressed. A fixed reservoir may be incorporated representing an average tidal volume of 500 ml to 700 ml of the gas mixture, which is released by the demand valve and is refilled by the device between inhalations. The conservation devices deliver a pre-determined amount of the therapeutic gas or gas mixture (sometimes referred to as a bolus). For example, a conservation device may be set to release 25 ml to 200 ml of gas upon activation, vis-à-vis a normal inspired tidal volume of 500 ml to 700 ml. The bolus is delivered at an exact point in the inspiration cycle so that the gas reaches the deepest and greatest portion of the lungs and has a greater effect, with the rest of the inspired gas usually being room air.

FIGS. 2A-2F show functional block/partial structural diagrams of preferred arrangements of the major components of the system 1. The structural features of the system 1 are not intended to be limiting. As seen best in FIG. 2A, the body 4 has a top wall 11, a bottom wall 12, and side walls 15. Together, the top wall 11, the bottom wall 12, and the side walls 15 enclose an upper chamber area 4a and a lower chamber area 4b. The lower chamber area 4b includes a hollow space 4c for insertion of the source gas containers 2 (shown by dotted line d1). The upper chamber area 4a contains a gas delivery and control system 20. The upper chamber area 4a borders a gas outlet 8 in the side wall 15. The gas outlet 8 may be connected to the patient interface 6. The gas outlet 8 may be integral with the body 4 or may be a separate structural element.

It should be understood that while the above arrangement of the structural elements of the system 1 is preferred, the invention also contemplates other arrangements, including an arrangement wherein the hollow space 4c is located in the upper chamber area 4a, and the gas port 8 and the gas control and delivery system 20 are located in the lower chamber area 4b.

Figure 2A:
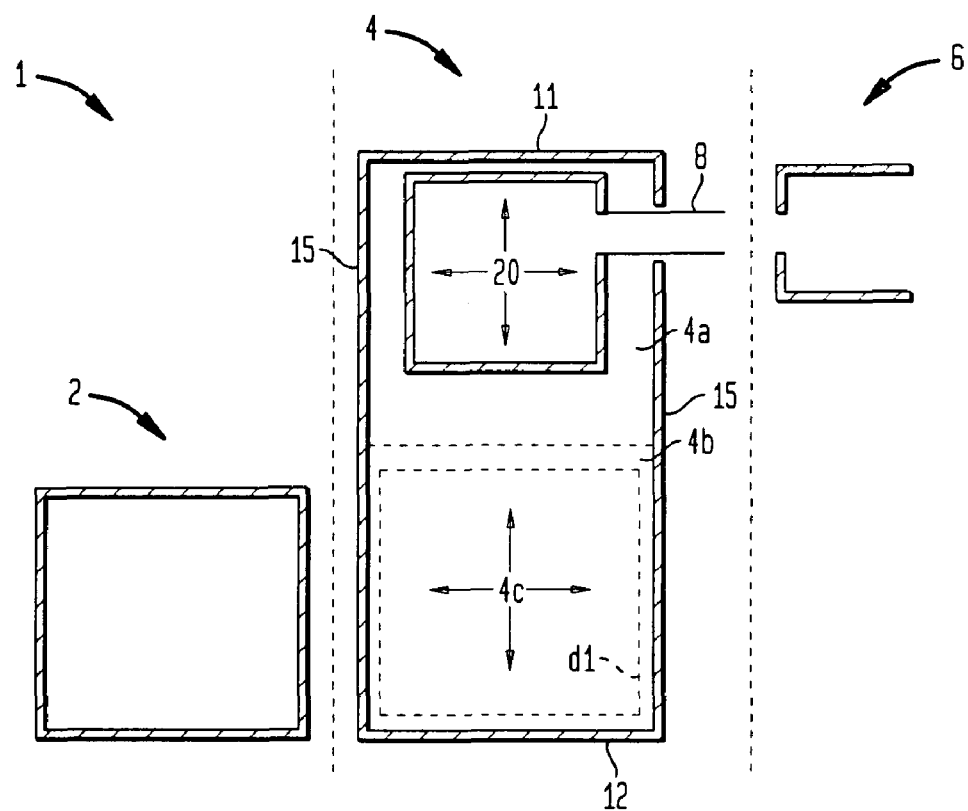
FIG. 2A is a functional block/partial structural diagram of the major components in accordance with one embodiment of the therapeutic gas administration system shown in FIG. 1.
Figure 2B:
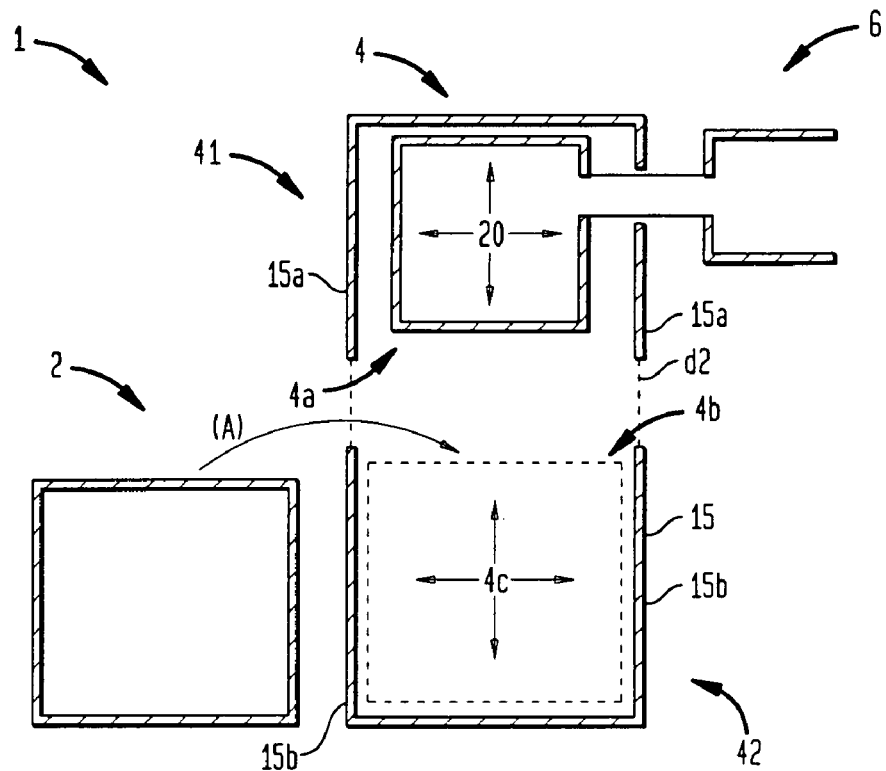
FIG. 2B is a side, elevational, partially schematic diagram of the embodiment of a therapeutic gas administration system shown in FIG. 2A.
Figure 2C:
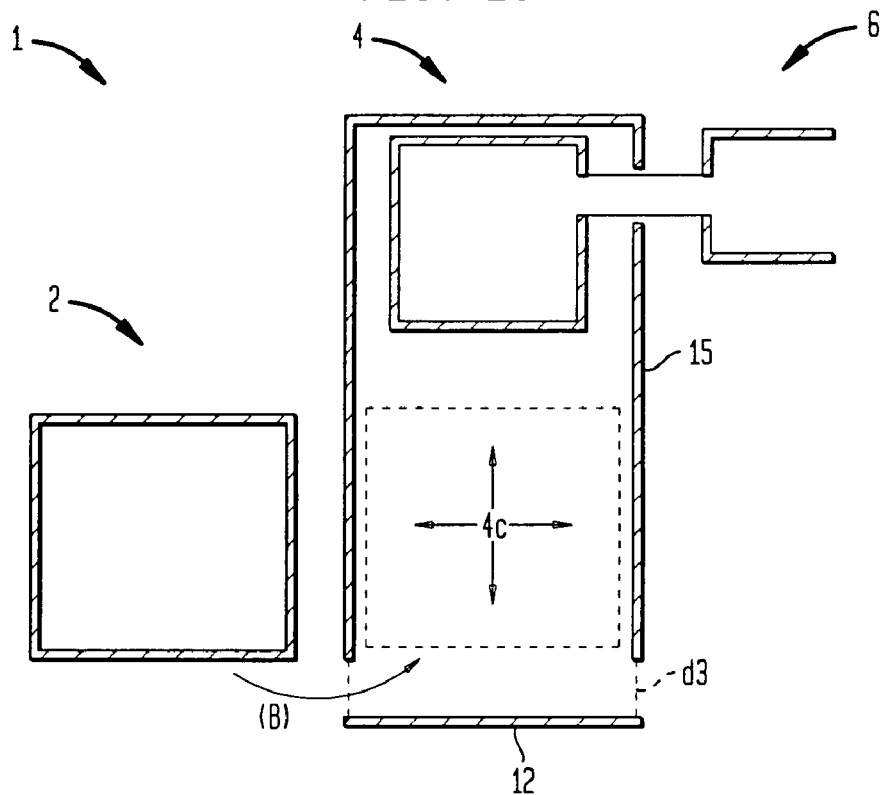
FIG. 2C is a side, elevational, partially schematic diagram of the embodiment of a therapeutic gas administration system shown in FIG. 2A.

The body 4 allows placement/insertion and removal of the source gas containers 2 from the hollow space 4c. For this purpose, one or more structural elements of the body 4 is/are releasably connected to each other and/or to the body 4. The invention contemplates releasable attachment/connection of any portion or section of the walls 15, the bottom member 12, or the top member 11 to allow insertion and replacement of the source gas container 2. FIGS. 2B-2D illustrate several of the preferred embodiments/constructions of the body 4, and the corresponding modes of inserting the source gas containers 2 (shown by arrows A, B, and C).

FIG. 2B shows one of the preferred embodiments, in which the walls 15 of the body 4 are separated into upper walls 15a and lower walls 15b, and the body 4 includes an upper portion 41 and the lower portion 42 releasably connected to each other. The methods of releasable connection may be any methods known in the art. Some of the contemplated methods will be shown in reference to more preferred embodiments.

In the embodiment shown in FIG. 2B, the upper portion 41 includes substantially the gas delivery and control system 20, and the lower portion 42 includes substantially the lower chamber area 4b and the hollow space 4c. However, the walls 15 may be separated in any location commensurate with the desired use and functioning of the system 1. Thus, in other aspects of this embodiment, the upper portion 41 may substantially contain some or most of the lower chamber area 4b and the hollow space 4c in addition to the upper chamber area 4a. Likewise, in yet other contemplated embodiments, the lower portion 42 may substantially contain some or most of the upper chamber area 4a in addition to the lower chamber area 4b and the hollow space 4c.

As shown in FIG. 2B, to load the source gas container 2, the upper portion 41 and the lower portion 42 are released from each other (shown by the dotted line d2), and the source gas container 2 is inserted into the hollow space 4c as shown by the arrow A. After the source gas container 2 is inserted, the upper portion 41 and the lower portion 42 are re-attached to each other.

FIG. 2C illustrates another embodiment of the body 4. In this embodiment, the releasably connected structural elements of the body 4 are the bottom member 12 and the walls 15 (dotted line d3). The arrow B shows the insertion of the source gas container 2.

Another embodiment is illustrated in the FIG. 2D. In this embodiment, the walls 15 include a releasable wall member 15c, which may be attached, for example, to the bottom wall 12 or the remainder of the walls 15. To insert the container, the wall member 15c is released, the source gas container 2 is inserted as shown by arrow C, and the wall member 15c is closed as shown by the dotted line d4.

Preferably, the reattachment/closure of the releasable structural element(s) of the body 4 releases the therapeutic gas or gas mixture from the source gas container 2 into the body 4. Thus, once the source gas container 2 is inserted, and the releasable structural element(s) of the body 4 is/are re-attached, the system 1 is ready for use. Preferably, a user must actuate the system 1 in some manner before the gas or gas mixture begins to flow through the patient interface 6. In one embodiment, the user may actuate the system via controls (not shown), preferably located on the body 4. In another embodiment, the user actuates the system 1 by creating negative air pressure via attempting to inhale through the patient interface 6.

Preferably, the system 1 is used for delivery of therapeutic gas mixtures. The source gas container 2 may store a pre-mixed gas mixture or separate gas components of the desired mixture for mixing in situ. Thus, the source gas container 2 may provide a single gas stream (shown as the stream G in FIG. 2E), or two or more separate gas streams (shown as the streams G1 and G2 in FIG. 2F).

After the source gas container 2 releases the gas or gas mixture, the gas stream(s) enters the gas control and delivery system 20. The gas control and delivery system 20 controls the composition of the gas, temperature, and other parameters of the gas or gas mixture, and delivers the gas or gas mixture to the gas outlet 8. The gas control and delivery system 20 may contain various sensor devices that monitor the parameters of the gas or gas mixture. If the source gas container 2 provides separate gas streams G1 and G2 (FIG. 2F), the gas control and delivery system 20 blends these gas streams and delivers a mixture stream G3 the port or outlet 8 at the desired composition, rate, temperature and the like. Through the gas outlet 8, the gas stream (e.g., the stream G3) is supplied to the patient interface 6 and subsequently to a patient.

Preferably, the patient uses the system 1 for administration of a single dose of the therapeutic gas or gas mixture provided in the source gas container 2. Once the gas or gas mixture is administered, the used source gas container 2 is removed from the body 4 and appropriately disposed. Administration of another dose of the gas requires insertion of a new gas source container 2.

The components of the system 1 and/or the system 1 as a whole may include various components, parts, and sub combinations, some of which will be discussed in reference to preferred embodiments.

The therapeutic gas administration system 1 may be used to administer various therapeutic gases and gas mixtures. Non-limiting examples of therapeutic gases include nitrous oxide ($N_2O$), xenon (Xe), helium (He), carbon dioxide ($CO_2$), carbon monoxide (CO), neon (Ne), Air, and oxygen ($O_2$). Non-limiting examples of therapeutic gas mixtures that may be used with the system 1 include $N_2O/O_2$ mixture, $N_2O/O_2/N_2$ mixture, $N_2O/O_2/He$ mixture, $Xe/O_2$ mixture, $Xe/O_2/N_2$ mixture, $Xe/O_2/He$ mixture, $He/O_2$ mixture, $CO_2/O_2$ mixture, $CO_2/O_2/N_2$ mixture, $CO_2/O_2/He$ mixture, $CO/O_2$ mixture, $CO/O_2/N_2$ mixture, and $CO/O_2/He$ mixture.

The system 1 and its various embodiments and variants may be used for administration of known therapeutic gases and gas mixtures, the use of which is commensurate with the unit dose construction of the source gas container 2. The size and construction of the source gas container 2, as well as the pressure of gas and the concentration of active ingredient gas in the container is determined by identity of the therapeutic gas or gas mixture and the goal of gas administration. Known therapeutic gases or gas mixtures may be administered in doses known in the prior or future art and for any duration known in the prior or future art and commensurate with the unit dose construction of the source gas containers 2.

The preferred gas mixture for use with the therapeutic gas administration system 1 is nitrous oxide/oxygen mixture. In a preferred example, the amount of $N_2O/O_2$ in the source gas container 2 is sufficient for about 6 minutes or less of total gas mixture administration, more preferably, up to about 4 minutes or less, yet more preferably, from about 2.5 to about 3.5 minutes of total gas mixture administration.

In accordance with another preferred aspect, the invention provides a number of uses and related methods for system 1. It should be understood that while system 1 is exemplified, these uses and methods might also be affected with other devices having a unit dose construction and/or hand-held devices that are at present not specifically disclosed herein.

Preferably, the therapeutic gas administration system 1 is intended for outpatient use at home, at work and similar settings, which lack supervision by a health professional. In the preferred embodiment, the system 1 is handheld, portable, and incorporates multiple failsafe mechanisms, simplifying the use of therapeutic gases and gas mixtures in the outpatient setting and/or unsupervised administration of therapeutic gases and mixtures. The inclusion in the system 1 of a radio frequency identification chip (RFID chip) to track its exact location provides additional levels of trackability/traceability and control over its use. Furthermore, the incorporation of optional telemetry devices whereby only the patient can activate the system 1 with a device similar to a coded telemetric automobile door lock, that is hand held, or whereby the physician can activate the system 1, or whereby the system 1 can be activated by an external second medical device, or whereby the system 1 can automatically activate an external second medical device, also enhances the suitability of system 1 for use with therapeutic gases in the unsupervised administration of therapeutic gases and mixtures by an outpatient. However, the system 1 may also be used under professional supervision and/or monitoring, for example, by patients visiting a hospital emergency room, a procedure room, a general outpatient clinic, a cardiac, fertility, cancer, mammography, dermatology, imaging or respiratory care or other specialty outpatient clinic, urgent care walk-in centers, a doctor's private office, and the like. The system 1 may also be used in an in-patient setting, where its compact size and single dose packaging facilitate easy storage, easy access and setup, tracking of use by means of and RFID chip, bar coding and bar code readers allowing tracking of physical location and assignment of a charge to the care of or the bill for a specific patient, and easy disposal of used gas sources.

The system 1 may be used for a variety of indications, disease states, and other medical situations. For example, the system 1 may be used for administration of therapeutic gases for any indication and treatment regiment/methodology known to those of skill in the art. It is especially useful when the goal of therapeutic gas administration may be achieved within the dose limits consistent with the unit dose construction of the source gas containers 2.

One of the preferred uses of the system 1 is in effecting analgesia and anxiolysis for a variety of purposes. The preferred therapeutic agents are $N_2O/O_2$ mixture, $N_2O/O_2/N_2$ mixture, $N_2O/O_2/He$ mixture, $Xe/O_2$ mixture, $Xe/O_2/N_2$ mixture, and $Xe/O_2/He$ mixture. Thus, the system 1 is especially useful in connection with the method of easing administration of shock from cardiac rhythm management devices, for example the AF-ICDs, by administering analgesic gas or gas mixture to patients having implanted AF-ICD. The method was described above and illustrated in Tables 1 and 2. The system 1 may be used with the methods illustrated in Tables 1 and 2. In the preferred portable and handheld embodiment, the therapeutic gas administration system 1 is especially suitable for self-administration of analgesic gas mixtures in homecare outpatient setting when the AF-ICD is self-initiated by the patient. Patients may use the portable embodiment of the system 1 at home, while traveling, and other HCO settings without the need for going to a hospital or clinic.

The system 1 may also be used to administer therapeutic gases or gas mixtures in conjunction with various diagnostic and/or therapeutic procedures. The non-limiting examples of suitable procedures include an insertion of a intravenous catheter prior to same day outpatient surgery or a radiological contrast procedure, outpatient same day colonoscopies, outpatient fertility clinic based procedures, setting a fracture, removing bandages from a wound, re-setting a dislocation, suturing, dermal biopsy punches, percutaneous needle biopsies, aspiration of a cyst, or, in the case of an emergency ambulance to provide analgesia and anxiolysis at the scene, during transport into the ambulance, and/or during a portion of the time the patient is actually en-route to the hospital.

The therapeutic gas administration system 1 may be especially suitable to effect analgesia or anxiolysis in patients undergoing short therapeutic or diagnostic procedures. Non-limiting examples of such procedures include insertion of urinary catheters, removal of bandages from open wounds, and post cardiac surgery prior to internal cardioversion for atrial defibrillation using a removable cardioverter defibrillator catheter, as well as to address specific diseases. In such context, the system 1 may be used with or without the presence of a medical or health professional. Non-limiting examples of possible settings include a hospital emergency room, a hospital procedure room, an outpatient clinic, a specialty outpatient clinic such as one dedicated to fertility, urgent care walk in clinic, physicians office, an emergency ambulance, and the like. For example, the use of system 1 may be especially preferred for this purpose to rapidly achieve a desired peak of pharmacological effect of $N_2O/O_2$ mixture on the patient undergoing the procedure just prior to the point in time that the maximum level of pain is expected to reduce the build-up of anxiety and the level of pain experienced. The system 1 may also be used to administer $N_2O/O_2$ mixture in an outpatient setting as a smoking cessation aid. The device 1 may also be used to administer to effect analgesia, anxiolysis and anterograde amnesia in victims of crime, accidents, and/or fire. Preferably, police and/or fire management personnel operate the system 1 in the field or provide the system 1 to the victim and closely monitor its use.

The therapeutic gas administration system 1 is believed to have several advantages. One of the advantages includes portability and low weight of the system 1. Another advantage is that the system 1 can be rapidly accessed and setup for use. Yet another advantage of the system 1 is the ease of use and gas administration, and suitability for one hand administration. Another advantage is the disposable character of the source gas containers 2. Yet another advantage is that the system 1 allows self-administration of the $N_2O/O_2$ mixture without the presence of medical or allied health professionals. Yet another advantage is that the system 1 allows the administration of therapeutic gases, including the $N_2O/O_2$ mixture, at home or in similar setting. Yet another advantage of the system 1 is that the source gas container 2 has unit dose construction and may provide a number of misuse- and abuse-related tamper-prevention features, which are especially important in the context of administration and self-administration of the $N_2O/O_2$ mixtures. Yet another advantage of the system 1 is that the unit dose construction of the source gas container 2 allows traceability and trackability of each container by a unique identifier such as but not limited to an RFID chip, bar coder or alphanumeric designation. Yet another advantage of the system 1 with respect to the administration of the $N_2O/O_2$ mixture is that the unit dose content of the source gas containers 2 when combined with a demand valve or conservation device, a patient interface, and means of administration to the patient reduces or eliminates the need for a scavenging accessory to remove exhaled $N_2O$ from the room in which the patient is located and provides for improved safety.

Figure 3:
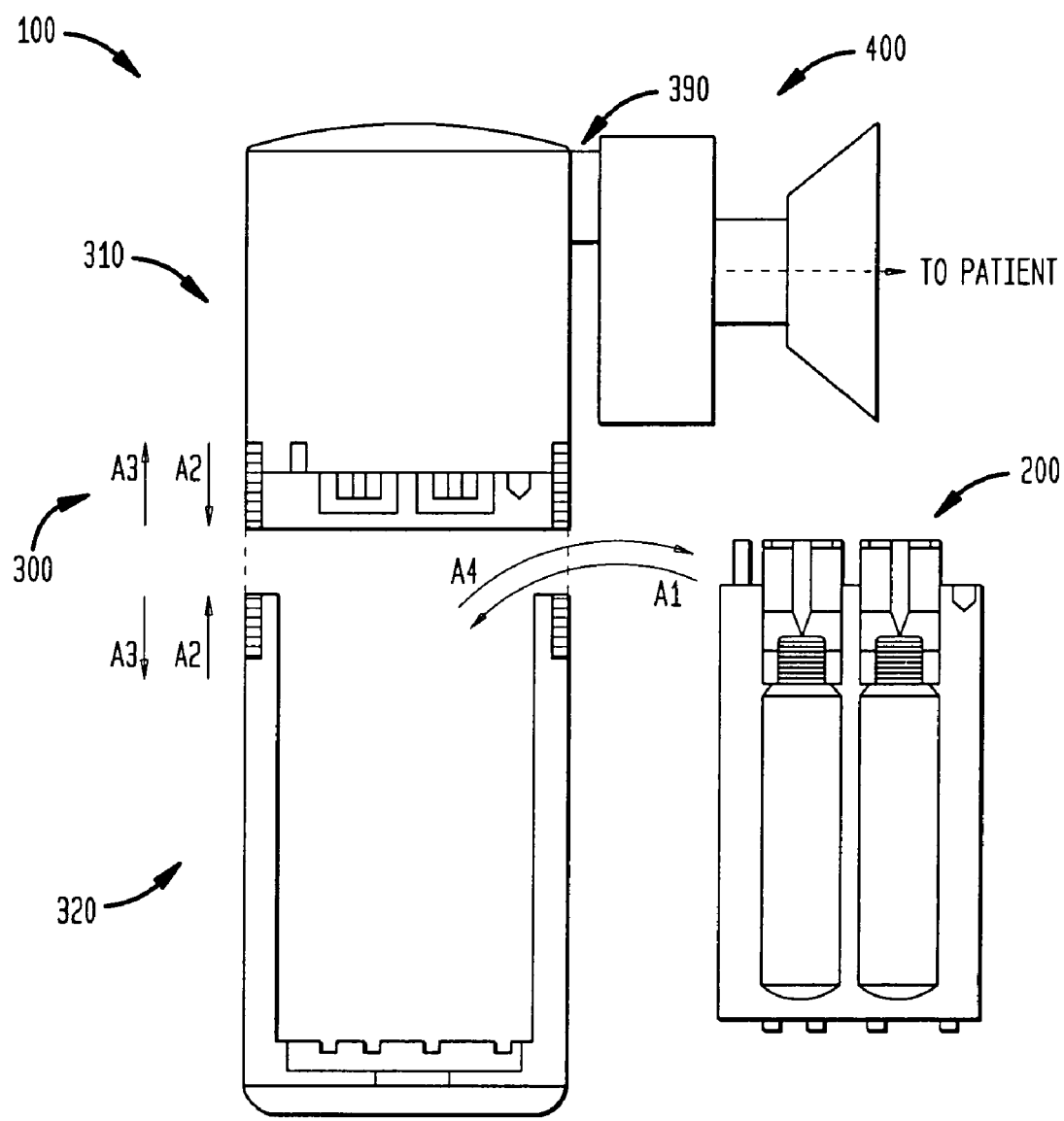
FIG. 3 is a front, elevational, cross-sectional, partially schematic view of one preferred embodiment of the therapeutic gas administration system in accordance with the present invention in a disassembled configuration.

FIG. 3 shows a portable system 100 for administration of therapeutic gases or gas mixtures in accordance with one of the preferred embodiments of the invention. With respect to the description of the system 100, the term "gas" is used to describe pure gases as well as gas mixtures. As seen from FIG. 3, the major components of the gas administration system 100 are a cassette 200, a body 300, and a patient interface assembly 400. A patient gas outlet 390 is a conduit for transferring the therapeutic gases from the body 300 to the patient interface 400. The cassette 200 is a source of therapeutic gas. The body 300 includes an upper housing 310 and a lower housing 320. In use, the cassette 200 is inserted into the lower housing 320 (arrow A1) and the housings 310 and 320 are attached to each other along the dotted lines (arrows A2). The gas administration system 100 may then be used to administer the gas from the cassette 200 to a patient. After administration of one dose of the therapeutic gas, the housings 310 and 320 are detached (arrows A3); the used cassette is removed (arrow A4) and disposed. For next gas administration, new cassette is inserted and the cycle is repeated.

Figure 4A:
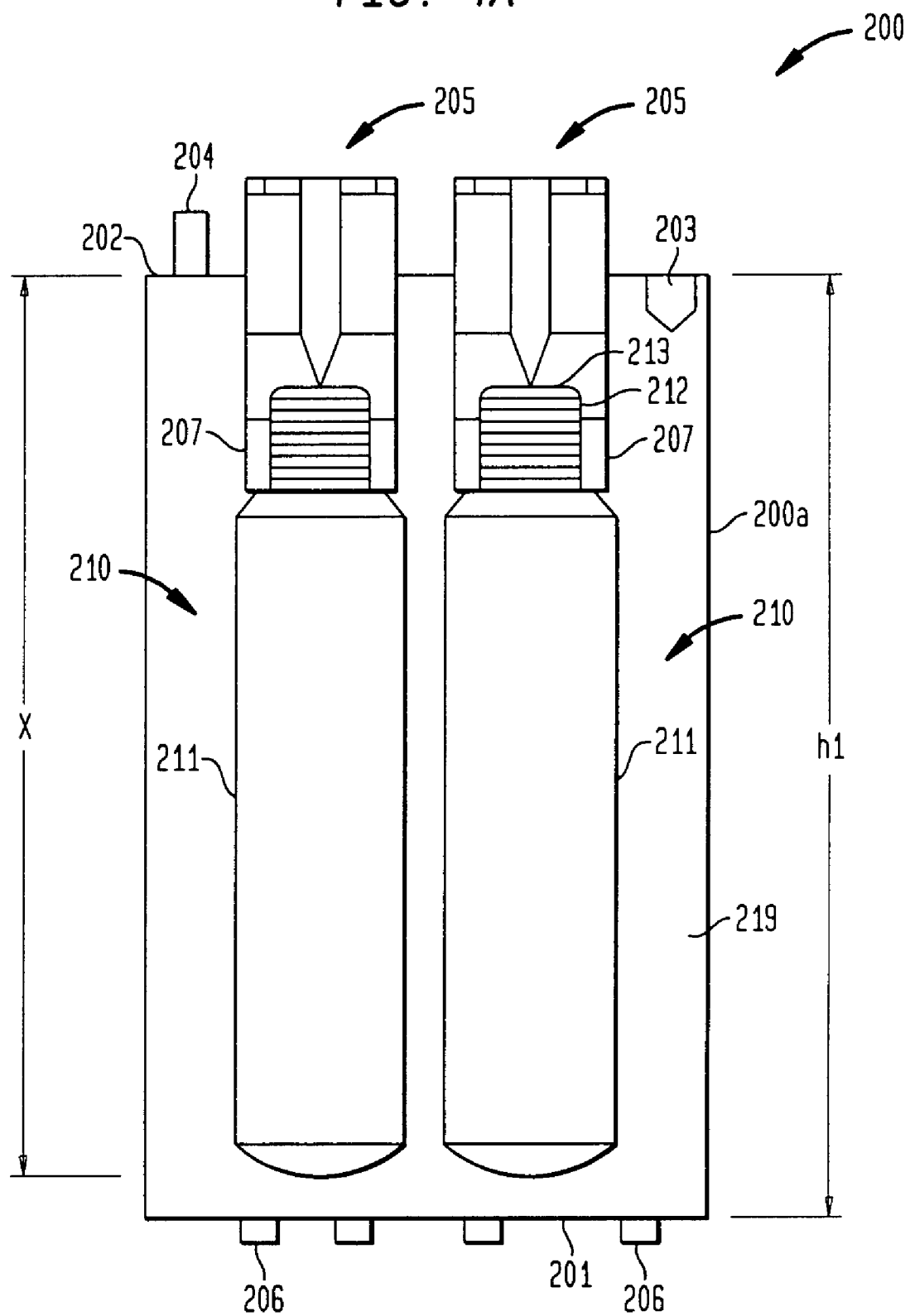
FIG. 4A is a front, elevational, partially schematic, cross-sectional view of one preferred embodiment of the unit dose cassette in accordance with another preferred aspect of the present invention that may be used with the therapeutic gas administration system shown in FIG. 3.

The cassette 200 is a unit dose, disposable source gas container for storing, transporting and dispensing therapeutic gases with the gas administration system 100 (FIGS. 4A-4F). The cassette 200 includes a cassette body 200a, two gas cartridges 210, two cannula/needle assemblies 205, and two holding members 207 (one for each cartridge 210) (FIG. 4A). It should be understood that the cassette 200 could include more than 2 gas cartridges.

Figure 4B:
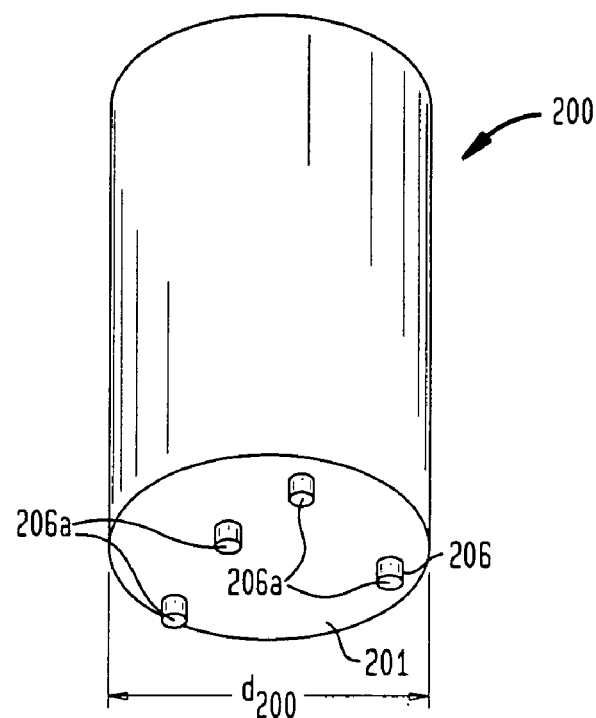
FIG. 4B is a bottom, elevational, schematic view of the cassette shown in FIG. 4A.

The cassette body 200a encloses the cartridges 210, the cannula/needle assemblies 205 and the holding members 207. In one variant, the cassette body 200a is molded together with the enclosed structural parts of the cassette 200. The molding material (e.g., plastic or composite) may form the cassette body 200a as a temper-resistant layer 219. The cassette body 200a may have various shapes, such as round, square, octagonal, and others. The round shape is preferred. The (FIG. 4B).

Figure 4C:
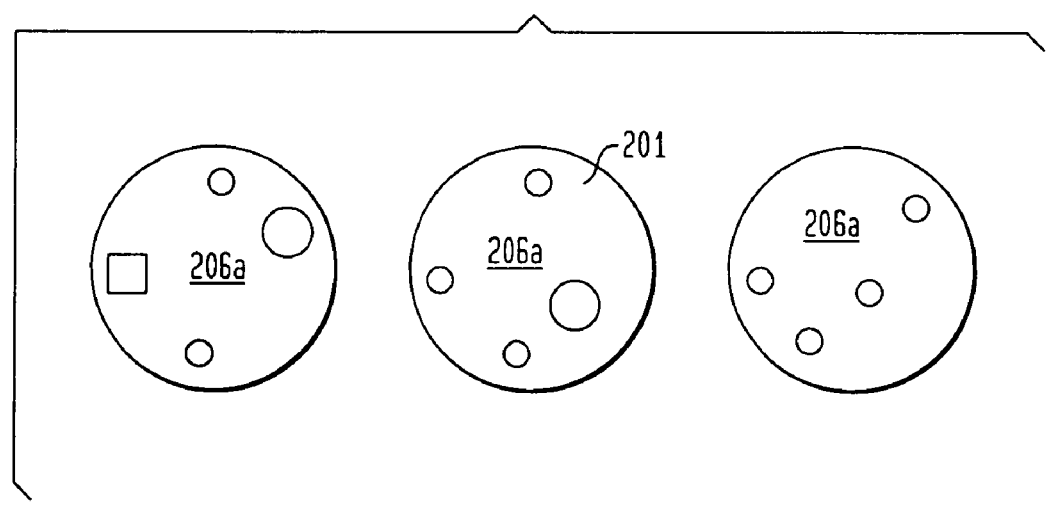
FIG. 4C is a top, elevational, schematic representation of non-limiting examples of arrays of cassette positioning keys for the cassette shown in FIG. 4A.
Figure 4D:
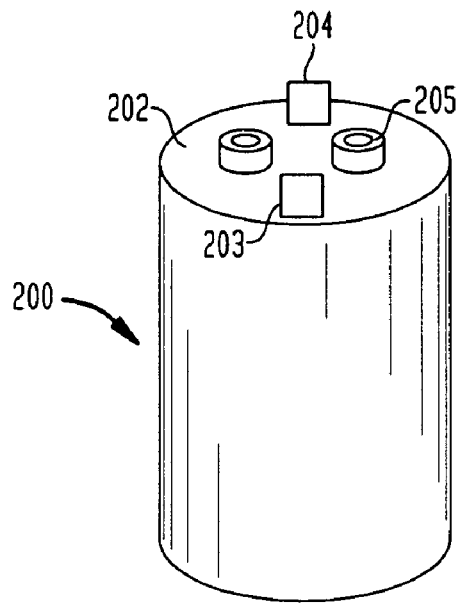
FIG. 4D is a top, perspective, partially schematic view of the cassette shown in FIG. 4A.

With reference to FIG. 4A, the cassette body 200a has a bottom surface 201 and a top surface 202. The distance between the surfaces 201 and 202 is the height h1 of the cassette 200. The bottom surface 201 of the cassette defines a circumference having a diameter $d_{200}$ (FIG. 4B). The bottom surface 201 has one or more cassette positioning keys 206 arranged in a pre-determined array 206a. Although not preferred, a single properly positioned cassette positioning key 206 may constitute an array. The cassette positioning keys 206 may be male or female, round or square, and so on. Non-limiting examples of the arrays 206a are shown in FIG. 4C. In the preferred variant, the keys 206 are male. The top surface 202 of the cassette body 200a has a female interfacing member 203 and a male interfacing member 204 (FIG. 4D). Various shapes, quantity, sizes, and arrangements of the interfacing members 203 and 204 are contemplated. Although not preferred, a single interfacing member may be substituted for the members 203 and 204. Likewise, more than two interfacing members may be present at the top surface 202. As described in greater detail below, the cassette positioning keys 206 and the interfacing members 203 and 204 take part in positioning/interfacing the cassette 200 with the body 300.

The gas cartridges 210 are pressure vessels containing therapeutic gases. Preferably, the therapeutic gases are stored in a compressed gas form at pressures of up to 2200 psig (154 bar); for certain gases and/or applications, up to about 3000 psig (207 bar). Certain gases when placed in containers of fixed dimensions under pressure exist in a liquid or combined liquid/gas phase in some ratio. Once example is $N_2O$. Because of its properties, the maximum pressure for a pressurized cartridge containing $N_2O$ is 750 psig. Of course, the larger or smaller cartridges would hold proportionately more or less compressed gas. The preferred size of the cartridges 210 and the cassette 200 depends on the goal of gas administration and the nature of the therapeutic gas. The cartridges 210 can be made from a variety of materials commensurate with the pressure requirements. The non-limiting examples of suitable materials include carbonized steel, aluminum, and composite materials, such as materials made of fiberglass, Kevlar, carbon fiber and/or epoxy and other materials, including those known to one of skill in the art.

Preferably, the cartridges 210 are embedded in the tamper-resistant layer 219 at a pre-determined depth x (FIG. 4A). Each cartridge 210 includes a cartridge body 211, a cartridge neck 212, and a sealing surface 213. The cartridge neck 212 may be threaded or smooth, long or short. The short neck saves space inside the cassette body 200a providing a wider optimization range of cassettes' width and/or length, and is therefore preferred.

The holding member 207 rigidly holds the cartridge neck 212. Preferably, the holding member 207 has a shape that matches the shape of the cartridge neck 212. The holding member 207 may be welded or otherwise permanently attached to the cartridge neck 212.

Figure 4E:
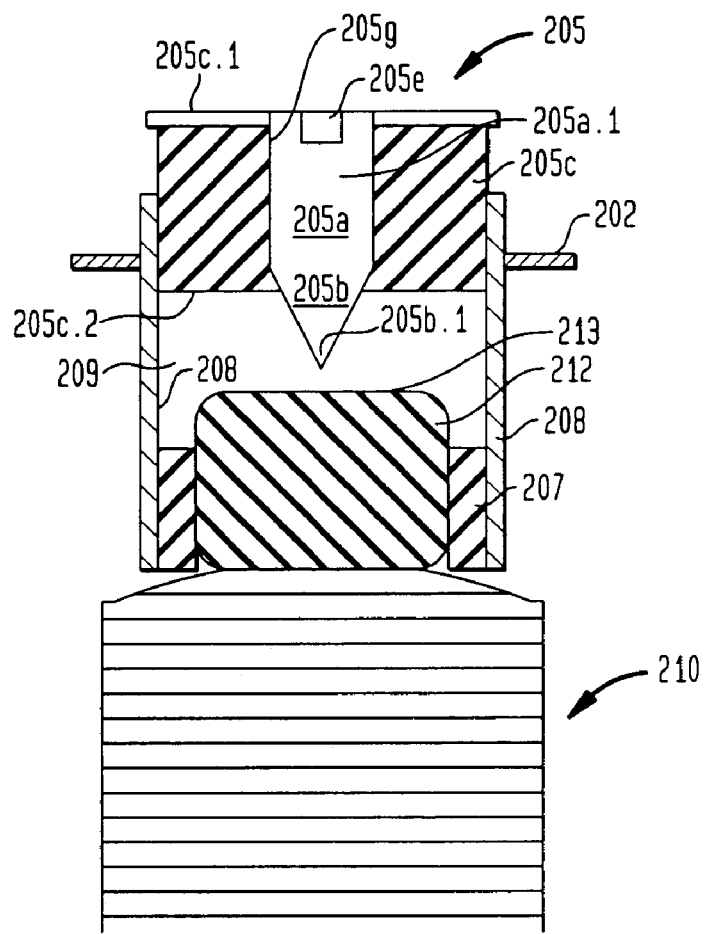
FIG. 4E is a side, elevational, partial cross-sectional view of the upper portion of the cassette shown in FIG. 4A, including one of cannula/needle assemblies and gas cartridges.

FIG. 4E shows a partial, front, cross-sectional view of an upper portion of the cassette 200, including one of the cannula/needle assemblies 205 and one of the cartridges 210. As seen from FIG. 4E, the cannula/needle assembly 205 is located opposite the sealing surface 213 of the cartridge 210. A hollow containment area 209 separates the assembly 205 and the sealing surface 213. A containment wall 208 encloses the hollow containment area 209.

The cannula/needle assemblies 205 serve to release the gases from the gas cartridges 210 for transfer to the upper housing 310. The cannula/needle assembly 205 includes a needle cannula 205a and a sliding plug 205c attached to the needle cannula 205a for movement therewith. The needle cannula 205a has a hollow needle cannula portion 205a.1, a tapered portion 205b with a needlepoint 205b.1, and a recessed coupler 205e. The needlepoint 205b.1 serves to puncture the sealing surface 213 of the gas cartridge 210. The hollow needle cannula portion 205a.1 is defined by a needle cannula wall 205g. The hollow needle cannula portion 205a.1 conveys the gas from the punctured gas cartridge 210 to the upper housing 310. The sliding plug 205c has a top surface 205c.1 and a bottom surface 205c.2. An O-ring 205f (not shown) may be placed flat on the top surface 205c.1 of the sliding plug 205c. If a force is applied to the top surface 205c.1 (shown by arrow B1), the sliding plug 205c, together with the needle cannula 205a, slides along the containment walls 208 and pushes the needlepoint 205b.1 toward the sealing surface 213 of the gas cartridge 210.

Figure 4F:
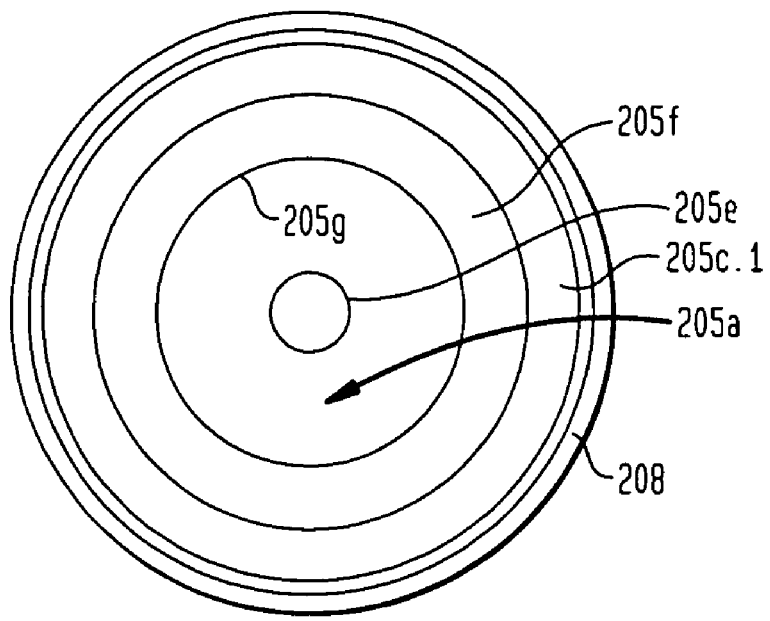
FIG. 4F is a top, elevational view of one variant of the cannula/needle assembly shown in FIG. 4E.
Figure 4G:
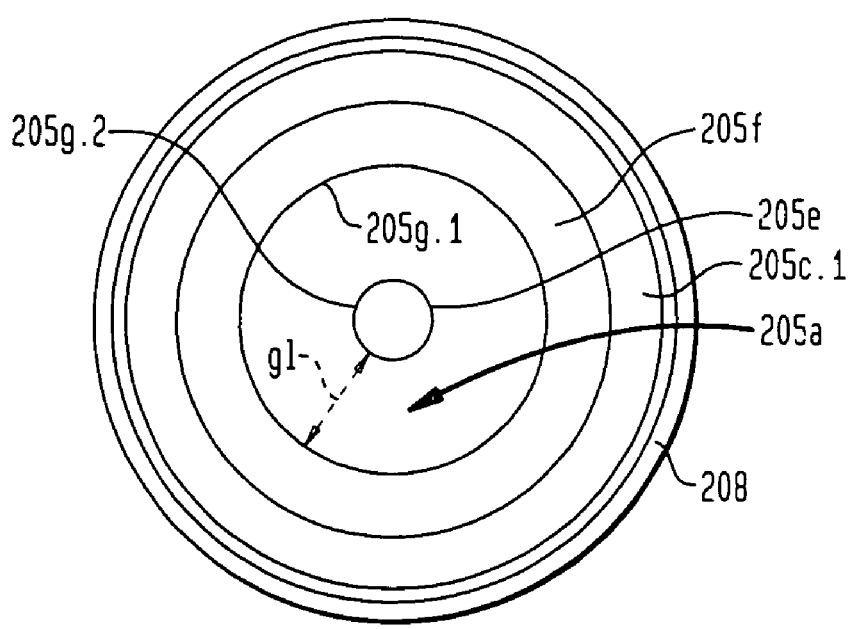
FIG. 4G is a top, elevational view of the variant of the cannula/needle assembly shown in FIG. 4E.

FIG. 4F shows a partial, top, cross-sectional view of the cannula/needle assembly 205, including the recessed cannula coupling point 205e, the containment wall 208, the top surface 205c.1 of the sliding plug 205c, and the flat O-ring 205f. The O-ring 205f may cover the entire top surface 205c.1 or a portion thereof. The needle cannula wall 205g extends vertically downward to the tapered portion 205b of the needle cannula 205a. Preferably, the needle cannula wall 205g has sufficient thickness to withstand the pressure of gas exiting the gas cartridge 210. In one of the embodiments, the needle cannula wall 205g has an external surface 205g.1 and an internal surface 205g.2, with the needle cannula wall 205g having thickness g1 (FIG. 4G).

Figure 5A:
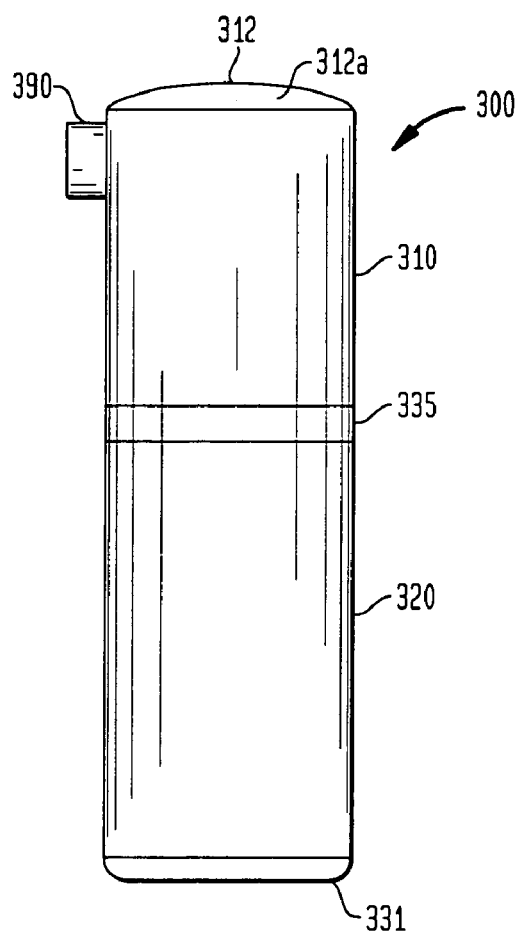
FIG. 5A is a side, elevational view of one of the embodiments of the body of the therapeutic drug delivery system in accordance with one of the preferred aspects of the present invention.
Figure 5B:
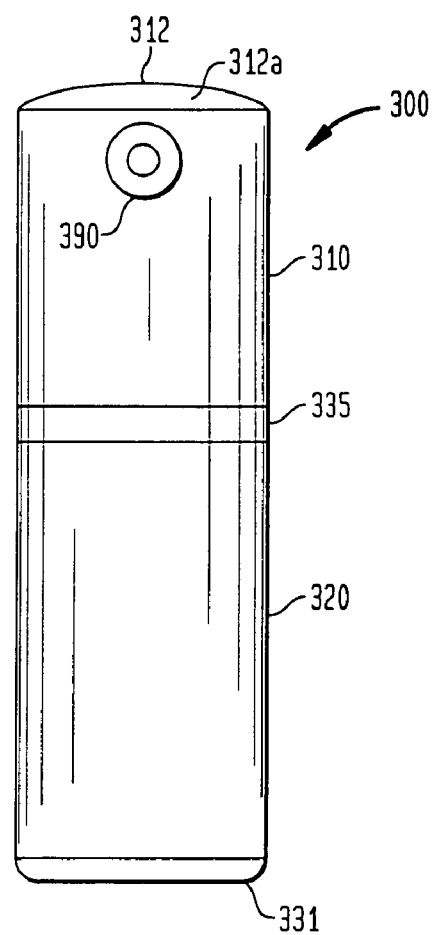
FIG. 5B is a front, elevational view of the body of the therapeutic drug delivery system shown in FIG. 5A.
Figure 5C:
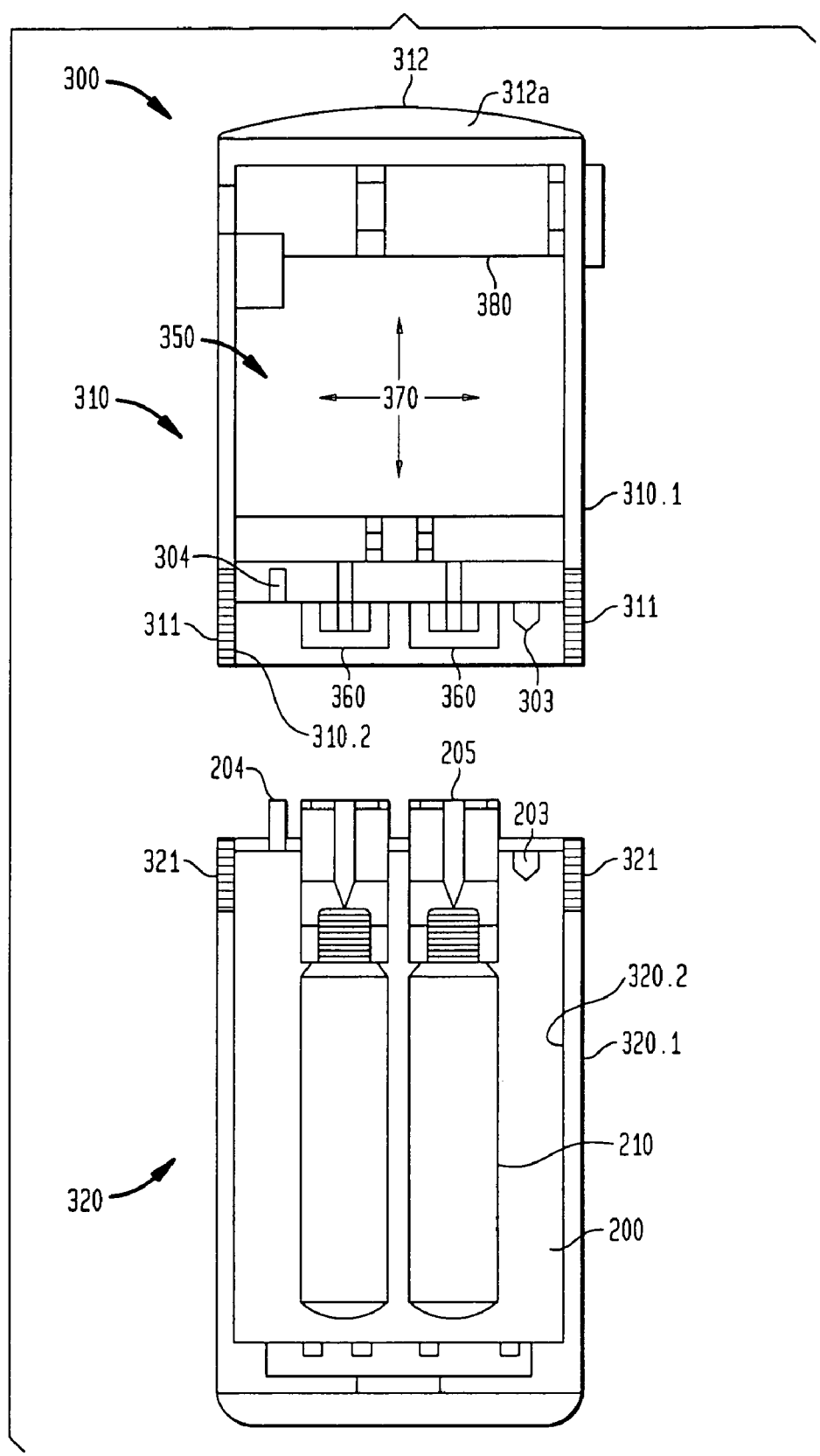
FIG. 5C is a front, elevational, cross-sectional, schematic view of a variant of the embodiment of the body shown in FIGS. 5A and 5B.

The body 300 is the principal structural component of the therapeutic gas administration system 100 (FIGS. 5A-5C). The body 300 processes the gas from the cassette 200, delivers the gas from the cassette 200 to the patient interface assembly 400, seals the gas from the outside environment and permits a user to hold and handle the system 100. The upper housing 310 and the lower housing 320 of the body 300 are releasably connected to each other. The system 100 has at least two configurations: a released configuration and a ready-to-use configuration. In the released configuration, the housings 310 and 320 are detached from each other. In the ready-to-use configuration, the housings 310 and 320 are fully re-attached with the cassette 200 inserted inside the lower housing 320.

FIGS. 5A and 5B show the body 300 in the ready-to-use configuration of the therapeutic gas administration system 100. Preferably, the body 300 has a non-skid bottom surface 331 and a gripping surface 335. The gripping surface 335 makes holding the body 300 easier and facilitates use of the gas administration system 100 with one hand. The gripping surface 335 may reside on the upper housing 310 or the lower housing 320. The body 300 has a domed top surface 312 that cover a domed area 312a. The domed shape of the top surface 312 provides additional space inside the body 300. The domed area 312a may be used, for example, to locate various electronics components. Thus, the domed area 312a may contain components of a processor/controller (not shown) that directs and controls the operation of the system 100 and functioning of its structural parts.

FIG. 5C shows a front cross-sectional view of the body 300 in the released configuration. The upper housing 310 has an external surface 310.1 and an internal surface 310.2. Likewise, the lower housing 320 has an external surface 320.1 and an internal surface 320.2. The upper housing 310 has threads 311. The lower housing 320 has threads 321. In one variant, the threads 311 are located on the external surface 310.1 of the upper housing 310 and the threads 321 are located on the internal surface 320.2 of the lower housing 320. In another variant, the threads 311 are located on the internal surface 310.2 of the upper housing 310 and the threads 321 are located on the external surface 320.2 of the lower housing 320. The threads 311 and 321 allow attachment and release of the housings 310 and 320. The attachment of the housings 310 and 320 transfers the system 100 from the released configuration to the ready-to-use configuration. Conversely, the detachment (or release) of the housings 310 and 320 transfers the gas administration system 100 to the released configuration after gas administration is concluded. The threads 311 and 321 may be simple continuous threads of any structure, including those known to those skilled in the art. In the preferred embodiment, the housings 310 and 320 are connected by a specialized threaded connection, which shall be described below. The upper housing 310 and the lower housing 320 also may be connected to each other using a variety of other methods, for example, a single direction screw, luer or otherwise threaded method, or a pin and track thread.

Figure 6A:
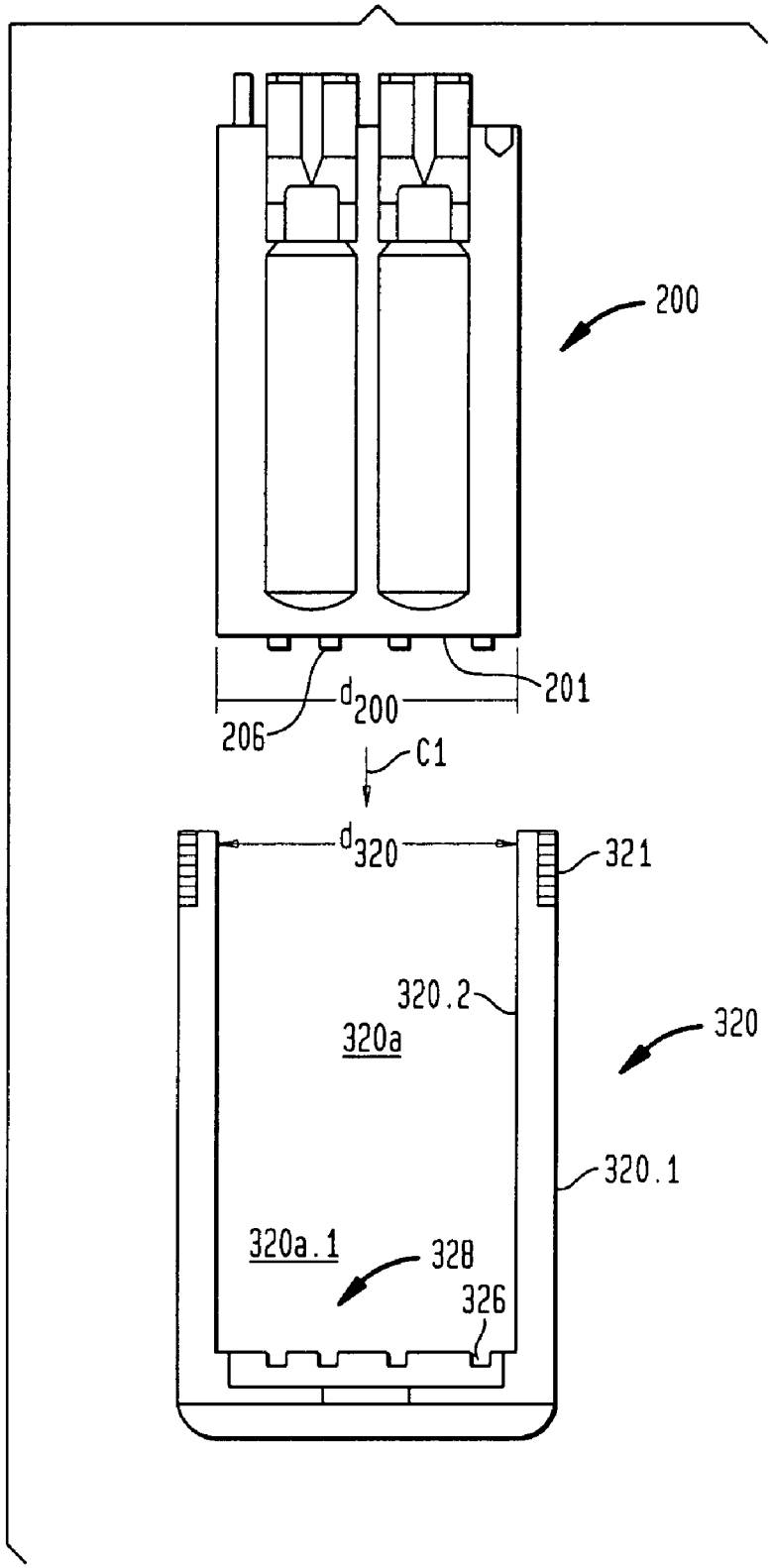
FIG. 6A is a front, elevational, cross-sectional, disassembled view of a lower housing of the body of the therapeutic drug delivery system of the present invention, and illustrates insertion of a cassette into the lower housing.
Figure 6B:
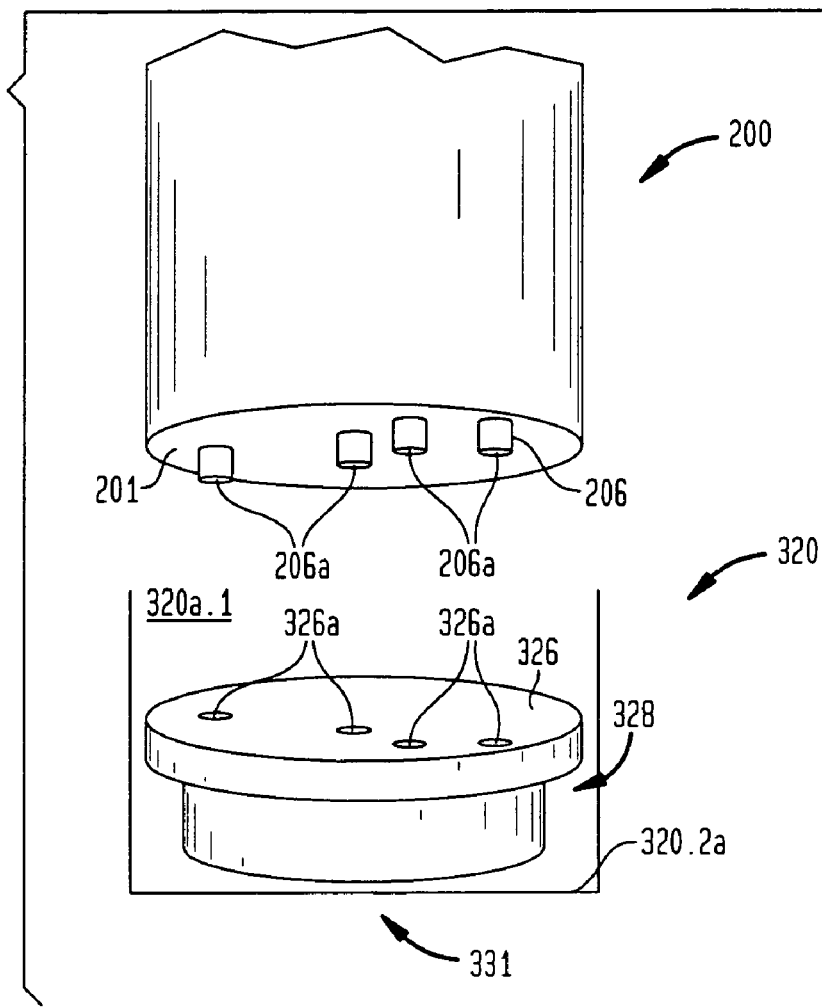
FIG. 6B is a side, perspective, partially schematic view of a preferred embodiment of the gas-specific insertion mechanism of the cassette and the body of the therapeutic drug delivery system shown in FIG. 3.

The lower housing 320 provides a hollow space 320a for the cassette 200 (FIG. 6A). The internal surface 320.2 of the lower housing 320 defines a circular opening having diameter $d_{320}$. In one variant, the diameter $d_{320}$ is smaller than the diameter $d_{200}$ defined by the bottom surface 201 of the cassette 200 to allow the insertion of the cassette (shown by arrow C1). The internal surface 320.2 surrounds the hollow space 320a and includes a horizontal bottom surface 320.2a (FIG. 6B). In reference to FIG. 6A, the hollow space 320a includes a lower portion 320a.1 containing a bearing member 328 with one or more housing positioning keys 326. The number, shapes, sizes and arrangements of the housing positioning keys 326 may vary. The keys 326 may be male or female, round or square, and so on. In the preferred variant, the keys 326 are female.

Figure 6C:
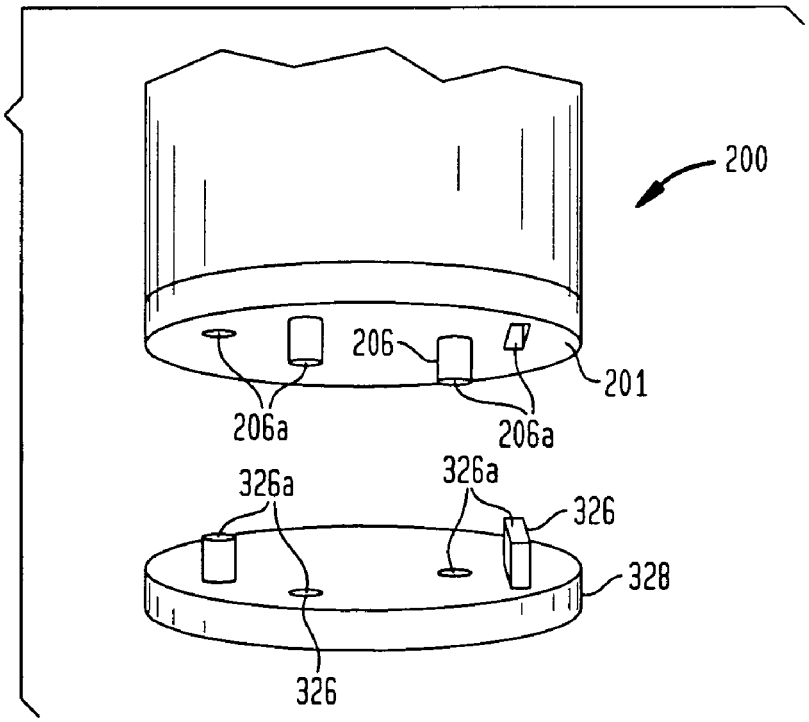
FIG. 6C is a side, perspective, partially schematic view of a preferred embodiment of the gas-specific insertion mechanism of the cassette and the body of the therapeutic drug delivery system shown in FIG. 3.
Figure 6D:
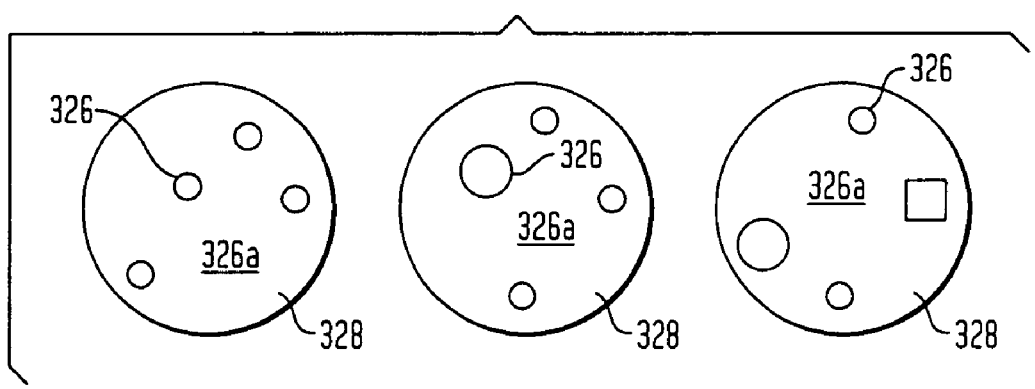
FIG. 6D is a top, elevational, schematic representation of non-limiting examples of arrays of housing positioning keys that match the arrays of cassette positioning keys shown in FIG. 4C.

The housing positioning keys 326 are arranged into a pre-determined array 326a (FIGS. 6B and 6C). In a variant, a single properly positioned housing key 326 may constitute an array. The pre-determined array 326a of the one or more housing positioning keys 326 matches the pre-determined array 206a of the one or more cassette positioning keys 206 on the bottom surface 201 of the cassette 200. Upon insertion of the cassette 200 in the lower housing 320, the arrays 206a and 326a must match to allow insertion of the cassette positioning keys 206 into the housing positioning keys 326, or visa versa. Unless the arrays 206a and 326a match, the cassette 200 cannot be fully inserted into the body 300 and the system 100 cannot be brought to a ready-to-use configuration. Preferably, the arrangement/shape of the positioning keys 206 and 326, and the corresponding arrays 206a and 326a, is unique for each therapeutic gas and/or dose. Some of the non-limiting alternatives of the arrays 326a of the housing positioning keys 326 are shown in FIG. 6D. The arrays 326a shown in FIG. 6D match the array 206a shown in FIG. 4C.

Figure 7A:
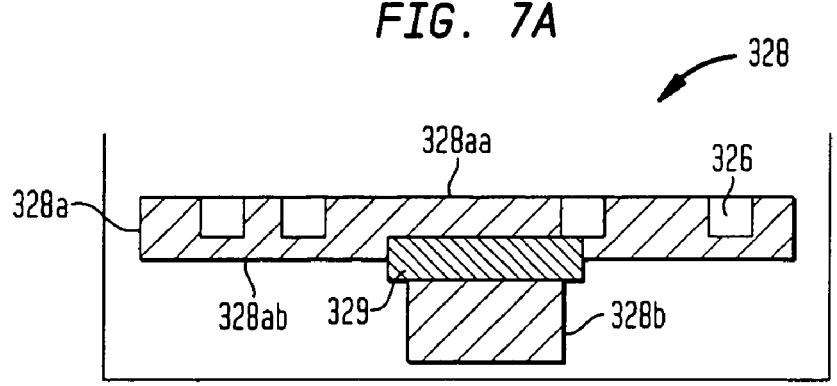
FIG. 7A is a side, elevational, partially schematic view of a rotating disk assembly bearing member for housing positioning keys used in accordance with the present invention.

In the preferred variant, the bearing member 328 has a structure shown in FIG. 7A. The bearing member 328 includes a disk 328a and a spindle 328b attached to the disk 328a for rotation therewith. The disk 328a has a top surface 328aa and a bottom surface 328ab. The spindle 328b is supporting the disk 328a. The top surface 328aa of the disk 328a has the positioning keys 326 arranged in the pre-determined array 326a.

Figure 7B:
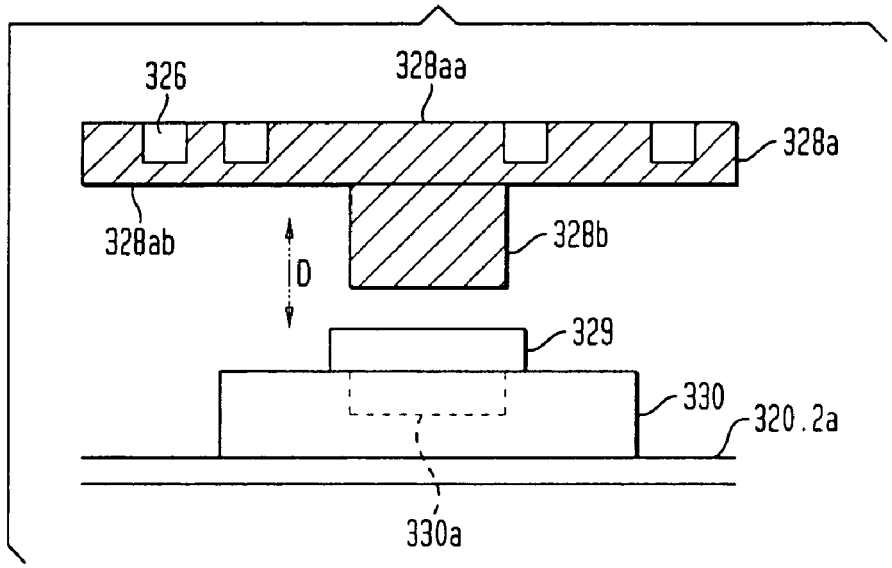
FIG. 7B is a side, elevational, partially exploded schematic view of a preferred embodiment of a rotating disk assembly bearing member for the housing positioning keys of the present invention.
Figure 7C:
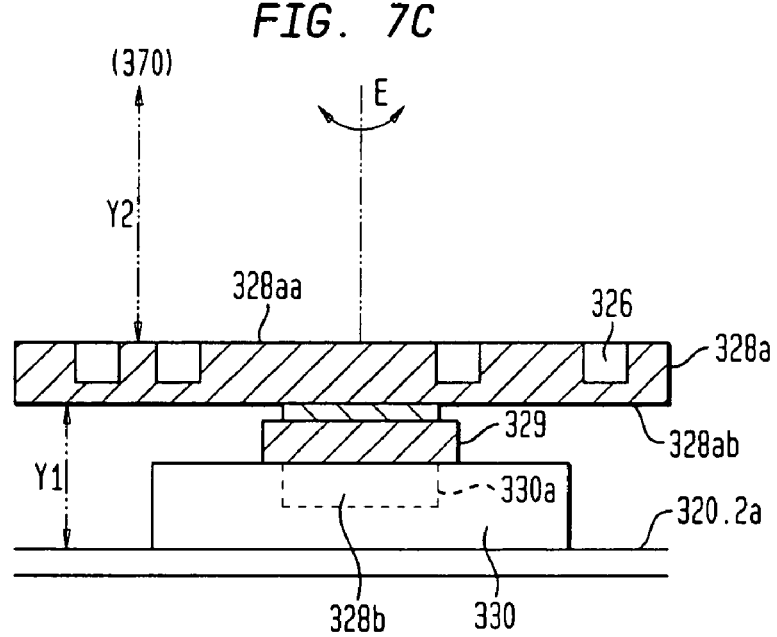
FIG. 7C is a side, elevational, partially schematic view of preferred embodiment of a rotating disk assembly bearing member for the housing positioning keys of the present invention.

The disk 328a is supported, directly or indirectly, by the horizontal bottom surface 320.2a of the lower housing 320 (FIGS. 7B-7C). The surface 320.2a supports, directly or indirectly, a washer 329 and a platform 330. Preferably, the washer 329 is a self-lubricating washer. The platform 330 has a recess 330a for the spindle 328b. The disk 328a can be inserted into/removed from the lower housing 320 by inserting/detaching the spindle 328b from the recess 330a (shown by arrow D). Thus, a given disk 328a can be removed from the platform 330 and replaced with another disc 328a having a different array 326a. When the spindle 328b is inserted into the recess 330a, the disk 328a may be freely rotated around the axis of rotation of the spindle (shown by arrow E), while the platform 330 remains stationary and coupled to the lower housing 320. The washer 329 facilitates the free rotation of the spindle 328b and the disk 328a. When the disk 328a is inserted into the recess 330a, a distance Y1 separates the bottom surface 328ab from the horizontal bottom surface 320a.2 and the distance Y2 separates the top surface 328aa from the upper housing 310.

The array 326a of the disk 328a must match the array 206a of the cassette 200 to allow proper insertion of the cassette. For each prescribed dose and/or indication, different cassettes 200 and disks 328a may have different and unique matching arrays 206a and 326a, respectively, with unique and matching number, pattern and types or shapes of the keys 206/326. Thus, only cassettes having proper gas and/or dose can be used with the body 300 equipped with a given disc 328a. Likewise, only proper disks 328a can be used with given cassettes.

Referring back to FIG. 5C, the upper housing 310 houses a gas control and delivery system 350. The upper housing 310 also has a male interfacing key 303 and a female interfacing key 304, which cooperate with the interfacing members 203 and 204, respectively, of the cassette 200.

Figure 8A:
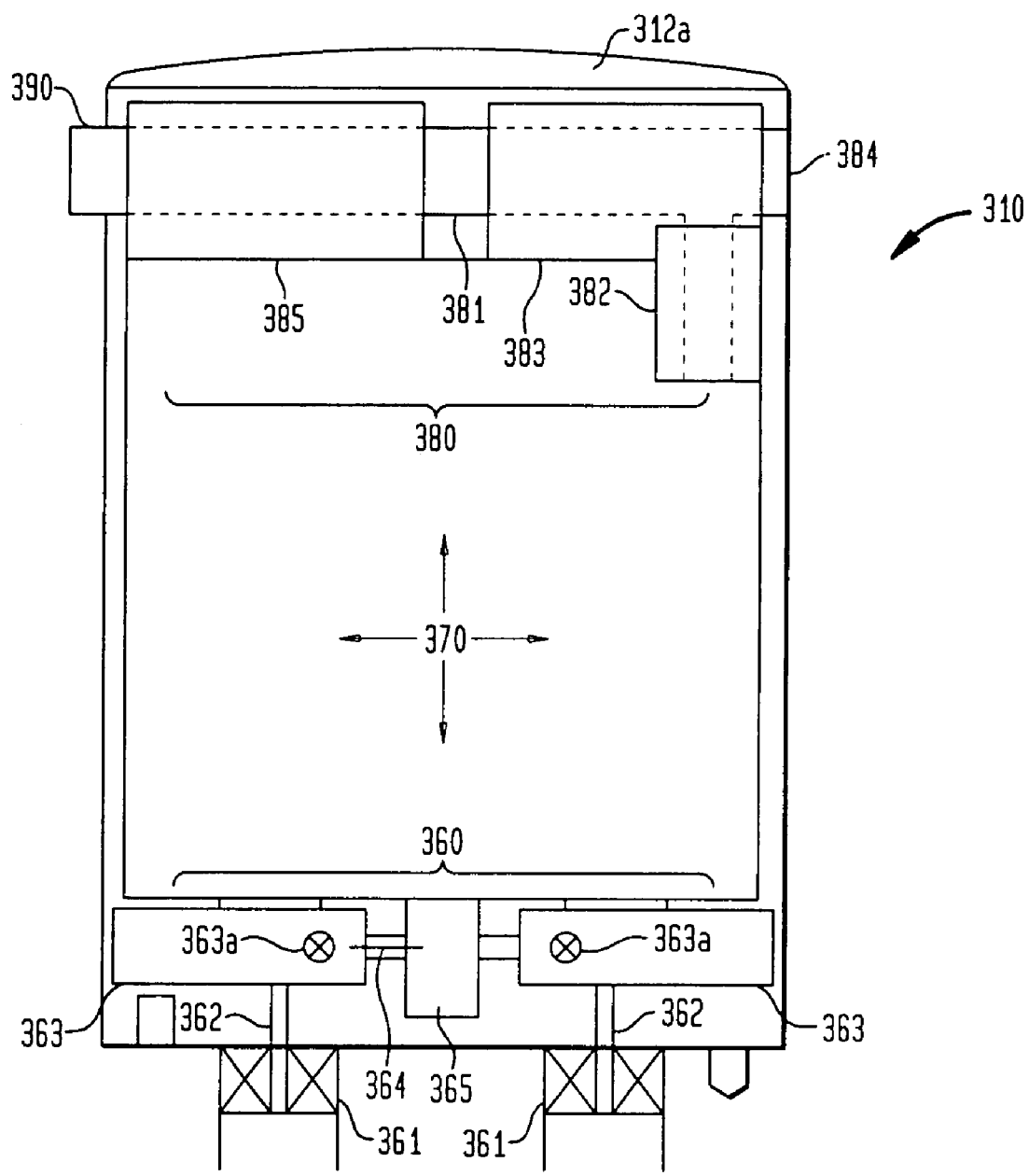
FIG. 8A is a front, elevational, schematic, cross-sectional view of a preferred embodiment of a gas delivery and control system in the upper housing of the present invention.

The gas control and delivery system 350 processes and delivers gases from the cassette 200 to the patient interface assembly 400 (FIGS. 8A-8D). FIG. 8A shows a block functional/partial structural diagram of one of the preferred embodiments of the gas control and delivery system 350 that includes a gas input system 360, a blender 370, and a gas output/control system 380.

The gas input system 360 cooperates with the needle/cannula assemblies 205 of the cassette 200 to release the gases from the cartridges 210 and to deliver them to the blender 370. The gas, input system 360 includes two gas input ports assemblies 361 (one for each cartridge 210), two input cannulas 362, two input pressure sensing blocks 363 containing pressure sensors 363a, two upper cannulas 364, and a pre-mixer 365.

Figure 8B:
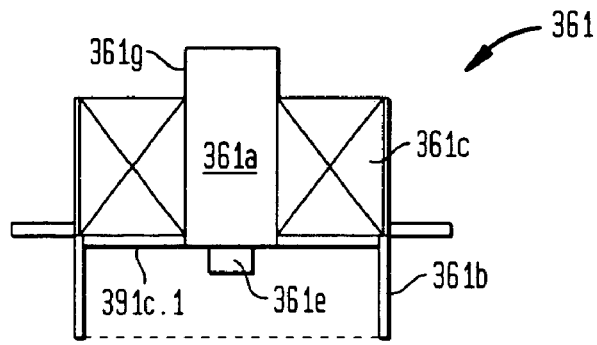
FIG. 8B is a side, elevational, partially schematic view of an input port assembly of the gas delivering control system in the upper housing in accordance with the present invention.

The gas input port assemblies 361 interface with the cannula/needle assemblies 205 of the cassette 200 in the lower housing 320. As shown in FIG. 8B, each gas input port assembly 361 includes a port cannula 361a, an outer port wall 361b, and a stationary plug 361c.

The port cannula 361a is a conduit for gases exiting from the gas cartridge 210 via the needle cannula 205a. A port cannula wall 361g defines the port cannula 361a. The port cannula 361a includes a hollow port cannula portion 361a.1 and a port coupler 361e that matches the recessed coupler 205e of the cannula/needle assembly 205 of the cassette 200.

The outer port wall 361b extends downward from and surrounds the stationary plug 361c. The stationary plug 361c has a puncturing surface 361c.1. In operation, the puncturing surface 361c.1 comes in contact with the top surface 205c.1 of the sliding plug 205c. A flat O-ring 361f (not shown) may cover the puncturing surface 361c.1. The O-ring 205f may cover all of the surface 361c.1 or a portion thereof.

Figure 8C:
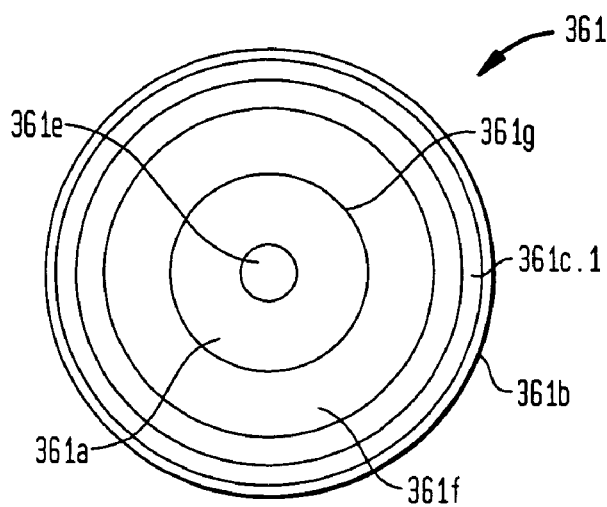
FIG. 8C is a top, elevational, perspective view of the input port assembly shown in FIG. 8B.
Figure 8D:
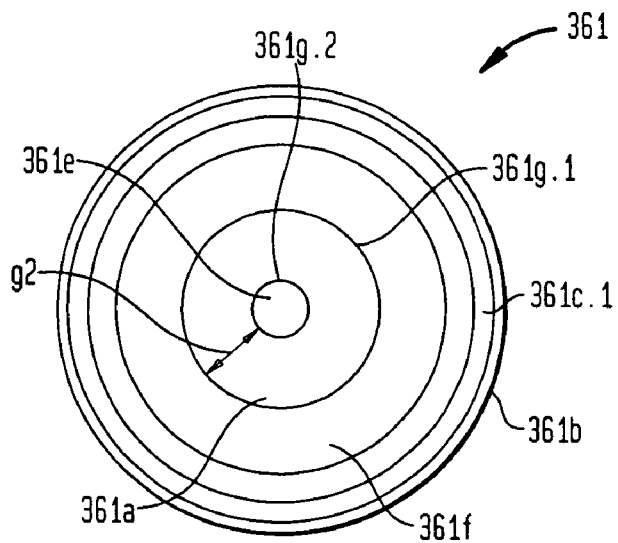
FIG. 8D is a top, elevational, perspective view of the input port assembly shown in FIG. 8B.

FIG. 8C shows the bottom view of the gas input port assembly 361, including the flat O-ring 361f, the port coupler 361e, and the port cannula wall 361g. Preferably, the thickness of the port cannula wall 361g is sufficient to withstand the pressure of gases exiting the gas cartridge 210. In one of the embodiments, the port cannula wall 361g has an external surface 361g.1 and an internal surface 361g.2, with the port cannula wall 361g having thickness g2 (FIG. 8D).

The input cannulas 362 are conduits for gases that enter the gas control and delivery system 350 from the cartridges 210. The input pressure sensors 363a of the pressure sensing block 363 measure the pressure of gases entering from the cartridges 210. The pre-mixer 365 is a small mixing chamber at the entrance point to the blender 370.

The blender 370 is an aspiration chamber of pre-determined volume. One of the functions of the blender 370 is to reduce the pressure of gases stored in the gas cartridges 210 to a level suitable for patient administration. As known to those of skill in the art, the pressure is reversibly proportional to the volume. Thus, preferably, the chamber volume of the blender 370 is substantially greater than the volume of the cartridges 210 to permit gas expansion and the consequent desired reduction in gas pressure. If the therapeutic gas administration system 100 is used for administration of a gas mixture, the blender 370 also serves to improve content uniformity of the gas mixture, especially if the cartridges 210 contain a pre-mixed gas that may develop a certain degree of content non-uniformity during storage. Finally, the blender 370 is used to mix the gases and/or to stabilize the composition of the mixture before it is provided to a patient.

The gas output/control system 380 delivers the gas from the blender 370 to the patient interface assembly 400. The system 380 also controls the quality of the gas. If the properties (e.g., content) of the gas do not fit pre-determined-parameters, the system 380 may block administration of the gas to the patient. FIG. 8E shows a block functional/partial structural diagram of one of the preferred embodiments of the system 380. As seen from FIG. 8E, the gas output/control system 380 includes a connective tubing system 381, a primary control block 382 with a primary control valve 382a, an air intake block 383 with an air intake valve 383a, an air intake port 384, and a content sensor block 385 having at least one gas content sensor 385a.

The connective tubing system 381 is a conduit for passage of gases from the blender 370 to the patient gas outlet 390. With reference to FIG. 8E, for the purposes of illustration, the connective tubing system 381 includes entrance/exit points 381a, 381b, 381c, and a switching point 381d. The entrance point 381a is located at the entrance from the blender 370 to the connective tubing system 381 and the primary control block 382. The entrance point 381b is located between the air intake valve 383a and the air intake port 384. The exit point 381c is located between the patient gas outlet 390 and the gas content sensor 385a. The switching point 381d is located between the gas content sensor 385a and the air intake valve 383a.

The primary control valve 382a controls the entry of gases from the blender 370. If the primary valve 382a is open, the gas flows from the entrance point 381a through the switching point 381d to the exit point 381c. If the primary control valve 382a is closed, the gas from the blender 370 cannot enter at the point 381a.

The air intake valve 383a controls the passage of outside air from the air intake port 384. If the valve 383a is open, the outside air may flow from the air intake port 383 through the entrance point 381b. The outside air may then be allowed to flow further through the switching point 381d to the exit point 381c and the patient outlet 390. The air intake port 384 allows outside air to reach the air intake valve 383. The air intake port 384 may remain always open.

Preferably, only one of the valves 382a and 383a is open at a time. If the primary control valve 382 is open, the air intake valve 383 is closed. If the primary control valve 382a is closed, the air intake valve 383a is open. The primary control valve 382 may be controlled by signals from the gas mixture/oxygen content sensor 385a, input pressure sensors 363a or another component(s) of the system 100. In a preferred variant, the primary control valve 382a is directed by a processor/controller (not shown) that controls the operation of the system 100.

The gas content sensor 385a analyzes the composition of the gas that flows through the connective tubing system 381 before the gas passes through the exit point 381c. In essence, the gas content measured by the sensor 385a is substantially identical to the composition of the gas to be inhaled by a patient. In the simpler variant, the sensor 385a is an oxygen sensor that measures only the oxygen content of the gas. The oxygen content may provide information sufficient to control the quality of therapeutic gas and may be important to measure from the regulatory standpoint. For example, if the gas administration system 100 is used to administer nitrous oxide/oxygen mixture, the determination of the oxygen content may provide sufficient information about the binary mixture. Also, Food and Drug Administration regulations are believed to require that the oxygen content of the $N_2O/O_2$ mixture be not lower than required to sustain life. Preferably, the oxygen content measured by the sensor 385a is substantially identical (within acceptable pre-set deviation parameters) to the oxygen content of the mixture inhaled by a patient. The gas content sensor 385a may also measure concentration of other gases (e.g., mixture components), with or without also measuring the oxygen content, or other parameters of the gas that reaches the content sensor block 385.

The patient gas outlet 390 connects the upper housing 310 to the patient interface assembly 400. The outlet 390 may be integral with the body 300 or may be a separate structural element. It should be understood that the patient gas outlet 390 might also be located partially or entirely within the body 300.

Figure 9:
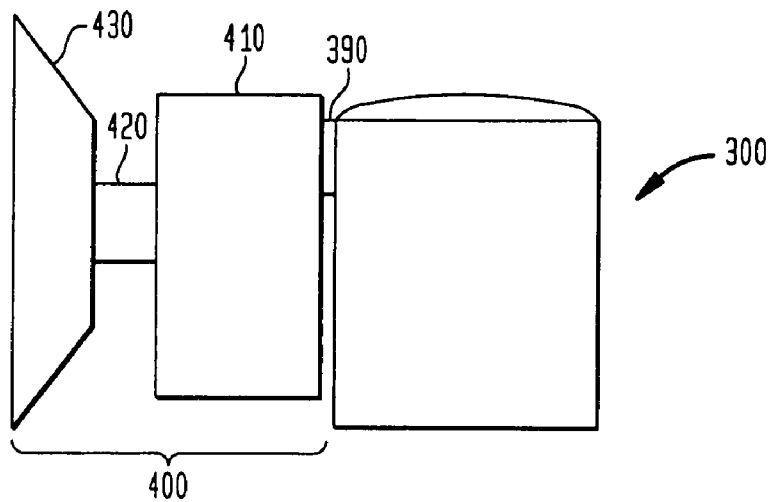
FIG. 9 is a side, elevational, schematic view of a patient interface assembly of the therapeutic gas administration system in accordance with a preferred embodiment of the present invention.

The function of the patient interface assembly 400 is to provide the gas directly to a patient. The important requirements to the patient interface assembly 400 are safety and gas conservation. The assembly 400 includes a demand valve 410, a connector 420 and a facemask 430 (FIG. 9). The demand valve 410 controls the flow of gases from the body 300 to a patient. The negative pressure generated by patient's inspiration activates the demand valve 410. The demand valve 410 may have any suitable structure, including structures known to those skilled in the art. The connector 420 may be any type of tubing or other similar conduit suitable for transmitting the therapeutic gases. The facemask 430 may be of any form and material known to those of skill in the art and would preferably be silicone so as to avoid allergic reactions from latex, and also desirably impregnated with vanilla or another pleasing scent. Preferably, the facemask 430 allows formation of a tight seal between a patient's face and the facemask 430 that facilitates creation of negative pressure upon the patient's inspiration.

The system 100 may be used for administering pre therapeutic gases or therapeutic gas mixtures. For delivery of mixtures, the gas components may be stored pre-mixed or the mixing of the gas components may occur in situ inside the system 100. If the gas components are stored pre-mixed in the cassette 200, both cartridges 210 may contain the pre-mixture. In the alternative, which is preferred, each cartridge may store different mixture component(s). For example, if the system 100 is used for administration of the nitrous oxide/oxygen mixture, one of the cartridges may store pure nitrous oxide and another pure oxygen. In another non-limiting example, if the system 100 is used for administration of $Xe/O_2/He$ mixture, one of the cartridges may store pure xenon and another helium/oxygen mixture.

When the therapeutic gas mixture is generated in situ inside the system 100, the proportions of the mixture components need to be controlled in mixing. One of the preferred methodologies for this purpose is metering of the desired molar amounts of the components into the cartridges during manufacturing of the cassettes. Since the cassettes are not re-used, complete release and mixing of the content of the cartridges provides a mixture of desired composition. As an example not intended to be self-limiting, in a cassette intended for 2.5 minutes administration of 65% $N_2O$/35% $O_2$ mixture, assuming the inhalation volume of 700 ml and an average of 15 breaths per minute (26.25 liters total gas volume including 17.06 liters of nitrous oxide and 9.19 liters of oxygen), one of the cartridges may store 18.2 liters of nitrous oxide and another 9.8 liters of oxygen. The additional gas volume provides a margin of safety.

In accordance with one variant, to operate the therapeutic gas administration 100, a patient inserts a cassette into the lower housing and attaches the housings to each other. When the housings are fully attached, the gas cartridges are punctured, and the contents are released into the body of the system 100. The patient needs to actuate the system to begin gas administration. The patient places the facemask over the mouth tightly pressing the facemask against the skin and attempts to inhale. The inhalation creates negative inspiration pressure in the demand valve, actuating the system 100 that begin to deliver therapeutic gas to the patient. In one variant, if at any time the patient is unable to continue pressing the facemask against the skin, the seal is broken at the interface of the mask and facial skin and the therapeutic gas flow stops. After the end of gas administration, the user detaches the housings, removes the spent cassette, which may then be disposed.

Now, the functioning of parts and components of the system 100 is described.

Referring back to FIG. 6A, with the gas administration system 100 being in the released configuration, the cassette 200 is inserted into the hollow space 320a of the lower housing 320. The cassette 200 is inserted with the bottom surface 201 of the cassette facing the top surface 328aa of the disk 328a. If the arrays 206a and 326a match, the cassette positioning keys 206 are inserted into the housing positioning keys 326 of the disk 328a (or visa versa).

Figure 10A:
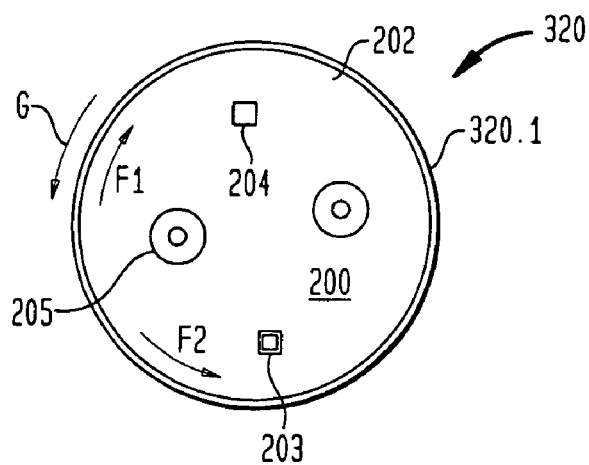
FIGS. 10A-10D and 11A-11C illustrate the functioning of the therapeutic gas administration system in accordance with another preferred aspect of the invention.

FIG. 10A shows a schematic top view of the lower housing 320 after matching/insertion of the positioning keys 206/326. The cassette 200 is inserted into the hollow space 320a. The cassette 200 is detachably coupled to and supported on the disk 328a. The inserted cassette 200 can be freely rotated inside the hollow space 320a (shown by arrows F1 and/or F2). Thus, if the lower housing 320 is rotated circularly (shown by arrow G), the position of cassette 200 may be stationary relative to the housing 320.

Figure 10B:
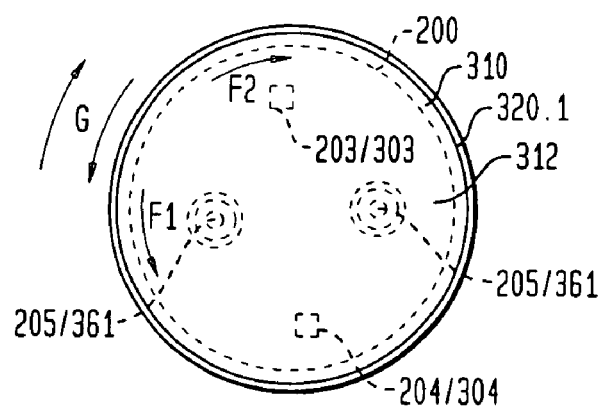

After the cassette is inserted, the upper housing 310 is placed over the lower housing 320 with the upper surface 202 of the cassette 200 facing the gas input port assemblies 361. FIG. 10B shows a schematic top view of the housings 310 and 320 with the upper housing 310 placed over the lower housing 320 with the inserted cassette. The housings 310 and 320 are rotated circularly relative to each other (arrows G) until the interfacing members 203 and 204 of the cassette 200 match the corresponding interfacing keys 303 and 304 of the upper housing 310. Upon match, the male interfacing member 204 is partially inserted into the female interfacing key 304 and the male interfacing key 303 is partially inserted into the female interfacing member 203. The housings 310 and 320 move vertically towards each other, allowing the threads 311 and 321 to establish an initial connection. Unless the arrays 206a and 326a match, the initial connection between the threads 311 and 321 cannot not be established.

Figure 10C:
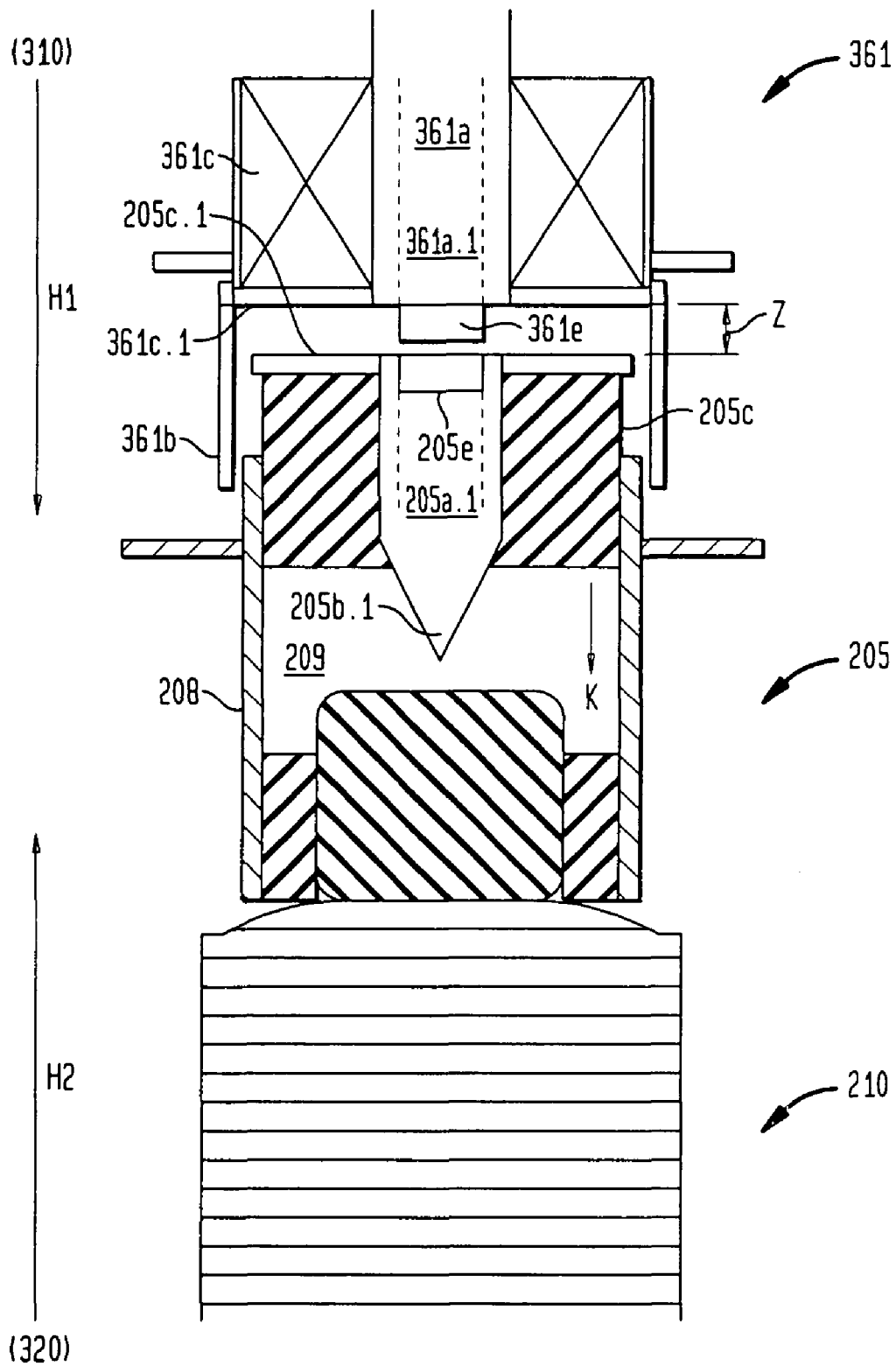

The partial insertion/connection of the interfacing members 203 and 204 with the interfacing keys 303 and 304 aligns the cannula/needle assemblies 205 of the cassette 200 with the gas input port assemblies 361 of the upper housing 310. FIG. 10C shows one of the input port assemblies 361 and cannula/needle assemblies 205 after the initial connection of the housings 310 and 320 is established. As seen from FIG. 10C, the top surface 205c.1 of the sliding plug 205c and the puncturing surface 361c.1 of the fixed plug 361c are placed opposite to each other and are separated by a distance z. The distance z is commensurate with the traveling distance of the threads 311 and 321, which in turn preferably depends on the distance required for substantially complete re-attachment of the housings 310 and 320. The distance z may be varied, for example, by varying the depth x at which the cartridges 210 are embedded, or the distances Y1 and/or Y2 that determine the depth of the disk 328a inside the hollow space 320a. The hollow needle cannula portion 205a.1 of the needle cannula 205a is aligned with the hollow port cannula portion 361a.1 of the port cannula 361a. The port coupler 361e is also aligned with the recessed coupler 205e.

The engagement of the threads 311 and 321 involves lateral, circular movement of the housings 310 and/or 320 in the opposite directions (e.g., clockwise and counterclockwise, as shown by arrows G in FIG. 10B), or one of the housings moving circularly while the other is held in place. The circular movement via the threads 311 and 312 is accompanied by vertical axial movement of the housings 310 and 320 toward each other (shown by arrows H1 and H2). The insertion/connection of the interfacing members 203/204 with the interfacing keys 303 and 304 fixes the relative position of the cassette 200 with respect to the upper housing 310. Referring back to FIG. 10B, the circular movement of the housings 310 and 320 along the threads 311 and 321 (arrows G) does not affect the relative position of the cassette and upper housing. Instead, the cassette 200 coupled to the disk 328a via the positioning keys 206/326 rotates relative to the lower housing 320 (arrows F1 and/or F2). The vertical alignment of the assemblies 205 and 361 is therefore maintained throughout the circular and vertical/axial movements of the housings 310 and/or 320.

Figure 10D:
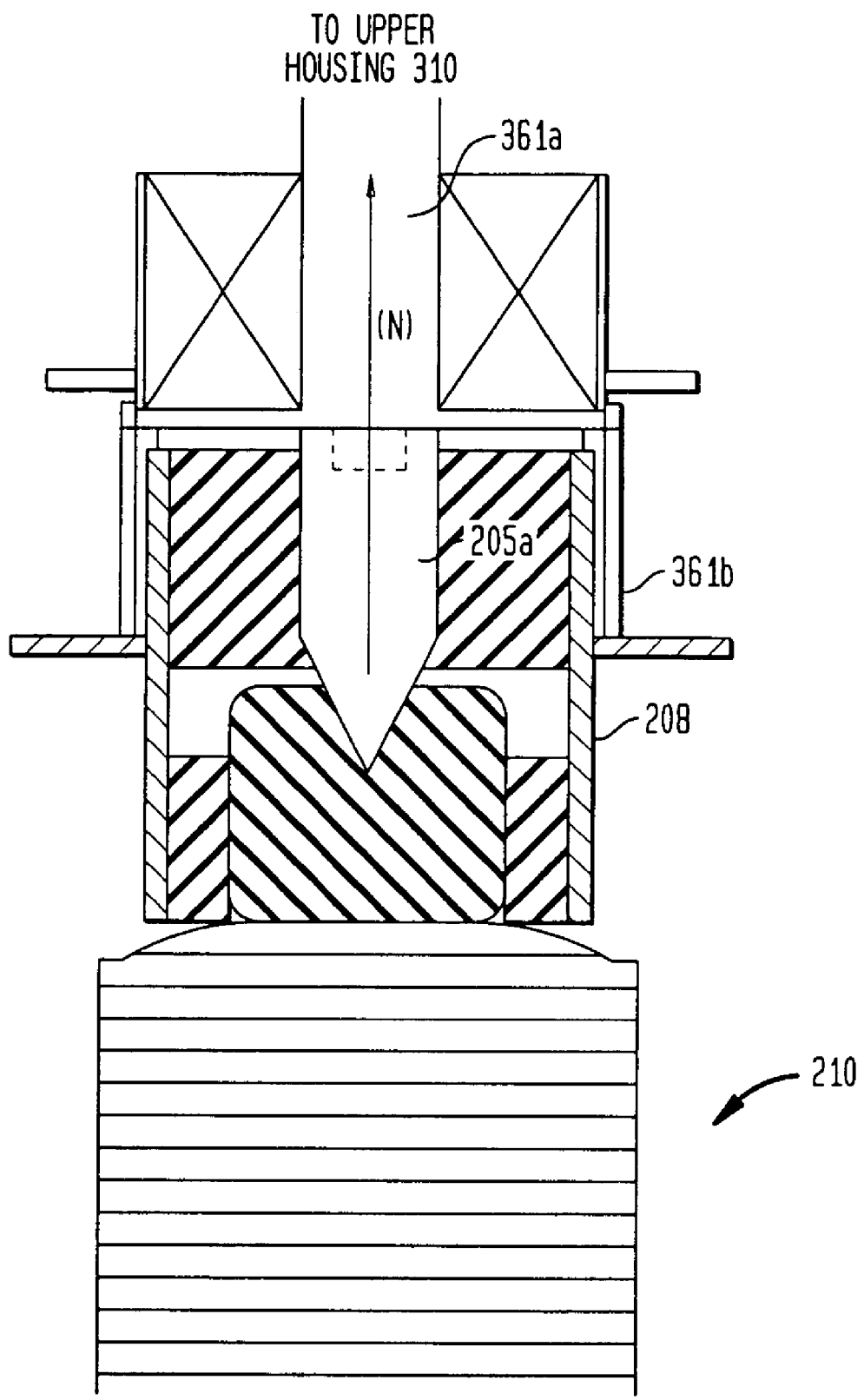

After the initial connection between the threads 311 and 321, the user continues to engage the threads 311 and 321. As a result, the housings 310 and 320 continue to move axially toward each other (arrows H1 and H2). The port coupler 361e is inserted into the recessed coupler 205e. The engagement of the couplers 205e and 361e, if necessary, corrects the alignment between the port cannula 361a and the needle cannula 205a. The puncturing surface 361c.1 of the fixed plug 361c comes in contact with the top surface 205c.1 of the sliding plug 205c, and the surfaces 205c.1 and 361c.1 exert forces on each other. The position of the puncturing surface 361c.1 is fixed. The force exerted onto the surface 205c.1 causes the sliding plug 205c, together with the needle cannula 205a, to move toward the sealing surface 213 of the cartridge 210 (shown by arrow K). The needlepoint 205b.1 comes in contact with and ruptures the sealing surface 213 of the cartridge 210 (FIG. 10D).

The gas stored in the cartridges 210 is released. The gas pressure in the cartridges 210 causes the gas to move through the needle cannula 205a and the port cannula 361a into the upper housing 310 (shown by arrow IV). The O-rings 205f and 361f (not shown) form a gas-tight seal at the interface between the surfaces 205c.1 and 361c.1 that reduces or eliminates gas leaks during the transfer of the gases from the cartridges 210 to the upper housing 310. The containment wall 208 and the port wall 361b may provide additional gas containment.

Figure 11A:
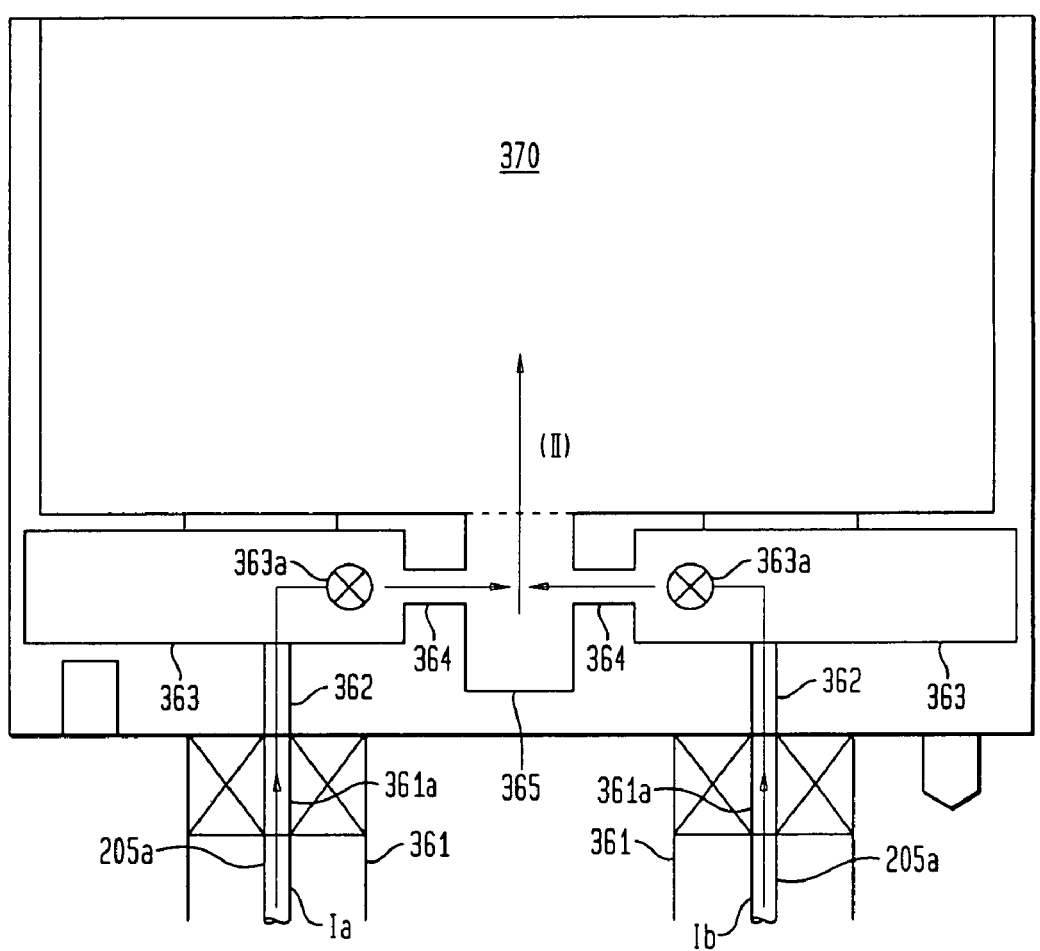

FIG. 11A illustrates the movement of gas through the gas input system 360 to the blender 370. The gas streams from the cartridges 210 move through the needle cannulas 205a and the port cannulas 361a (arrows 1a and 1b), pass through the input cannulas 362 and enter the pressure sensing blocks 363. The pressure sensors 363a measure the pressure of the incoming gas. If the pressure measured by one and/or both of the sensors 363a is lower than a pre-determined desired pressure(s) (e.g., if the pressure is insufficient to produce the intended gas mixture in the expected dose), the gas delivery and control system 350 may prevent administration of the gas to a patient. For example, the gas may be prevented from reaching the patient gas outlet 390. Thus, if the pressure is insufficient, the primary control valve 382a is closed and the air intake valve 383a is opened, providing the patient with an outside air through the air intake port 384. If the pressure measured by the pressure sensors 363a correspond with the pre-determined value(s), the gas flow through the pressure sensing blocks 363 and the upper cannulas 364 into the pre-mixer 365 and then into the blender 370 (shown by arrow II). The gas, which is stored under substantial pressure in the cartridges 210, possesses substantial kinetic energy after the cartridges are punctured. The kinetic energy of the expanding gas and the internal shape of the blending vessel help to facilitate a thorough mixing of gases in the blender 370. The release of gases from the cartridges 210 into the blender 370 brings the gas administration system 100 to the ready-to-use configuration. In this configuration, the gas output and controls system 380 and/or the demand valve 410 prevent flow of the gas from the blender 370 to the patient outlet 390 and/or from the patient outlet 390 to the facemask 430.

From the ready-to-use configuration, the system 100 is actuated to deliver the gas to the patient. The actuation begins gas administration to a patient. In the preferred variant, to actuate the gas administration system 100, the patient creates negative inspiration pressure in the demand valve 410. The demand valve 410 opens when the inspiration pressure reaches a pre-determined threshold level (in a non-limiting example, the threshold negative or crack pressure may be 0.5 to 2.5 cm $H_2O$ and the flow rate pressure may be 140 to 160 liters per minute peak inspiration for an adult and 40 liters per minute for a child. Alternatively, the demand valve measures the inspiration pressure and after the threshold pressure is reached, provide a signal to a processor/controller (not shown) that directs the demand valve to open. When the demand valve 410 is open, the gas can flow from the outlet port 390 through the demand valve 410 and the connector 420 to the facemask 430 (where the gas is inhaled by the patient).

Figure 11B:
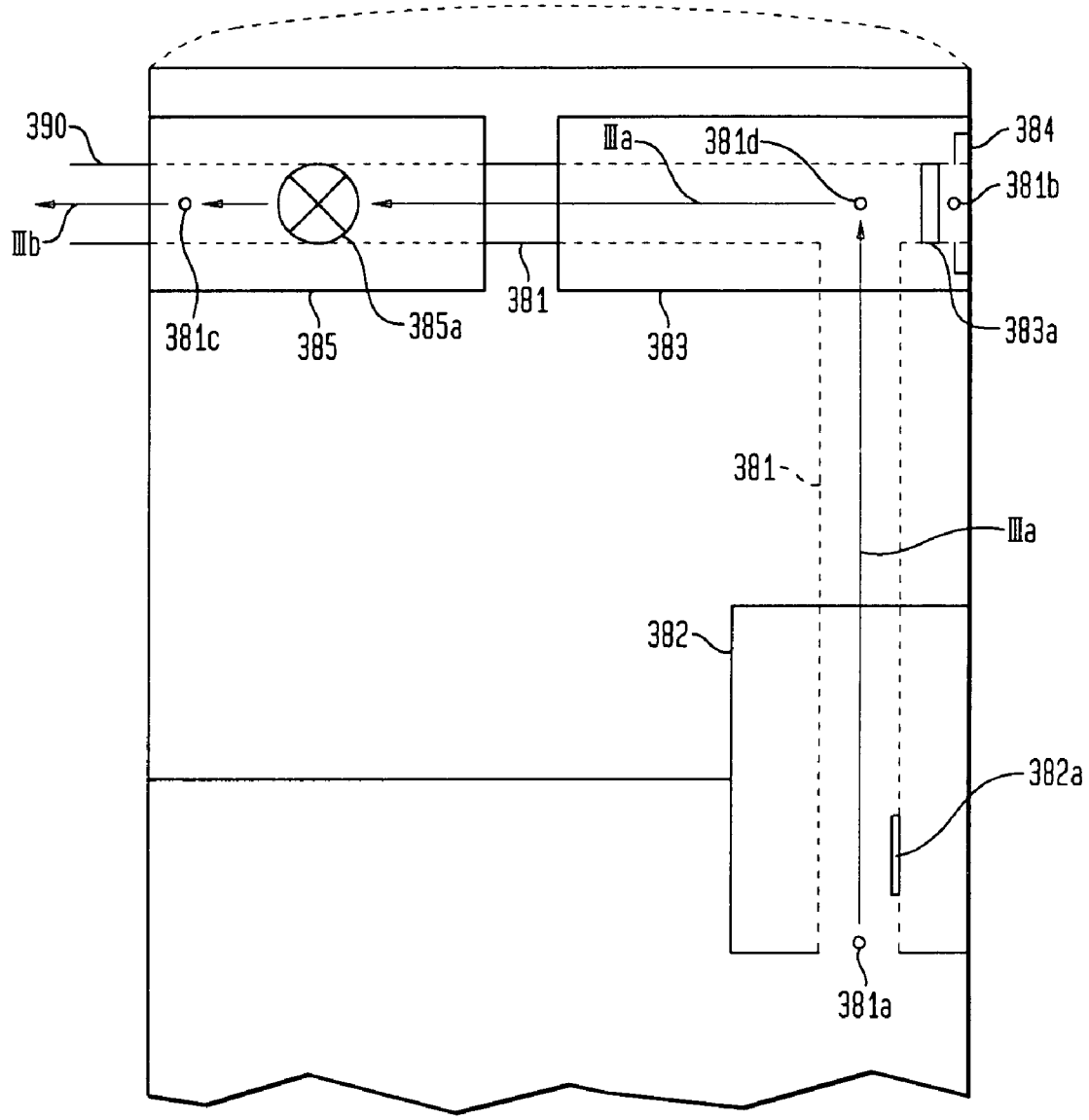
Figure 11C:
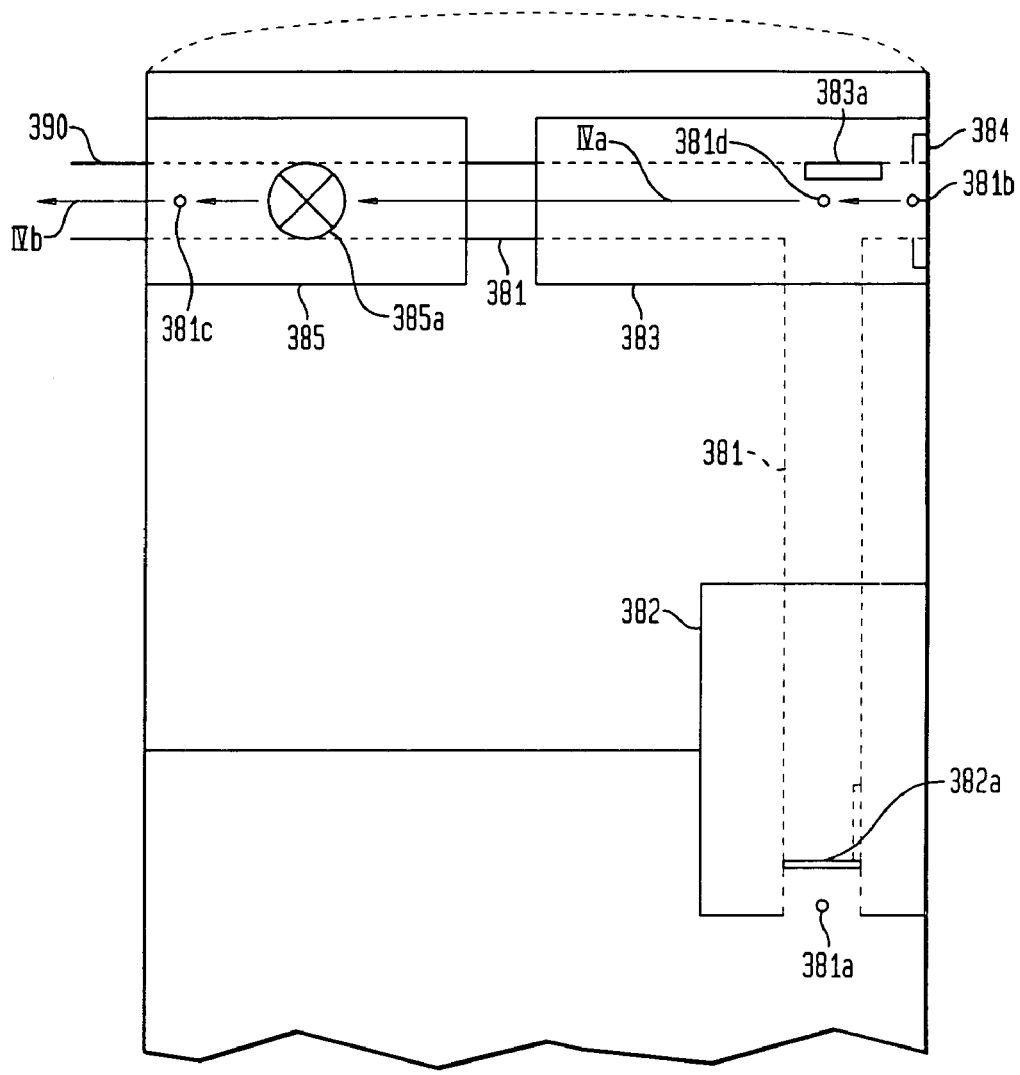

The demand valve 410 also provides a signal to the gas output/control system 380 to allow the gas flow from the blender 370 to the patient outlet 390. The actuation signal may be provided directly or through a processor/controller. FIGS. 11B and 11C illustrate one of the preferred variants of operation of the gas output/control system 380. Upon an actuation signal from the demand valve 410, the system 380 opens the primary control valve 382a and closes the air intake valve 383a. In the ready-to-use configuration of the system 100, the air intake valve 383a may have been closed before the signal from the demand valve 410. If so, the valve 383a is directed to remain closed. The gas from the blender 370 enters the connective tubing system 381 at the entrance point 381a and flows through the switching point 381d to the content sensor 385a (shown by arrow 111a). The gas content sensor 385a determines the composition of the gas (in the simpler variant, the sensor 385a measures only the oxygen content of the gas). If the composition of the gas is in line with pre-determined desired value or range of values, the primary control valve 382a remains open. The gas continues to flow from the blender 370 through the points 381a, 381d and the exit point 381c to the patient outlet 390 and further to the patient (shown by the arrow IIIb). The patient inhales the therapeutic gas.

If the composition of the gas determined by the gas content sensor 385a is not in the pre-determined range of the measured parameter(s) (e.g., if the oxygen content is below the pre-determined desired value), the primary control valve 382a is closed and the air intake valve 383a is opened (FIG. 11C). The closure of the primary control valve 382a prevents entry of therapeutic gas from the blender 370 at the entrance point 381a. The opening of the air intake valve 383a permits the outside air to flow from the air intake port 384, through the entrance point 381b and the switching point 381d to the exit point 381c (shown by arrow IVa) and further to the patient (arrow IVb). The opening of the air intake valve 383a purges the connective tubing system 381. The patient inhales the outside air rather than the therapeutic gas having undesired composition.

In other preferred aspects, the invention provides numerous additional, preferred and/or alternative features of the system 100.

The system 100 may include various electronic components. The electronic components may be included in structural parts and components of the system 100, such as the gas control and delivery system 350, the patient interface assembly 400, and others. For example, electronic components may be used in the input pressure sensing blocks 363, the gas content sensing block 385, the demand valve 410, and others. The electronic components may also direct the overall operation of the system 100. The suitable electronic components may be located in the domed area 312a and/or in other locations. Power for the electronic components of system 100 may include self-contained sources of power, as in the case of an RFID, other components which require external sources of electrical power provided by a small replaceable battery or rechargeable battery system incorporated into the device (neither of which is shown), or further yet, as in the case of the disposable unit dose cassette, a one-time use battery incorporated s part of the structure to provide the electrical energy necessary to heat the cartridge and gas-warming components.

Figure 12:
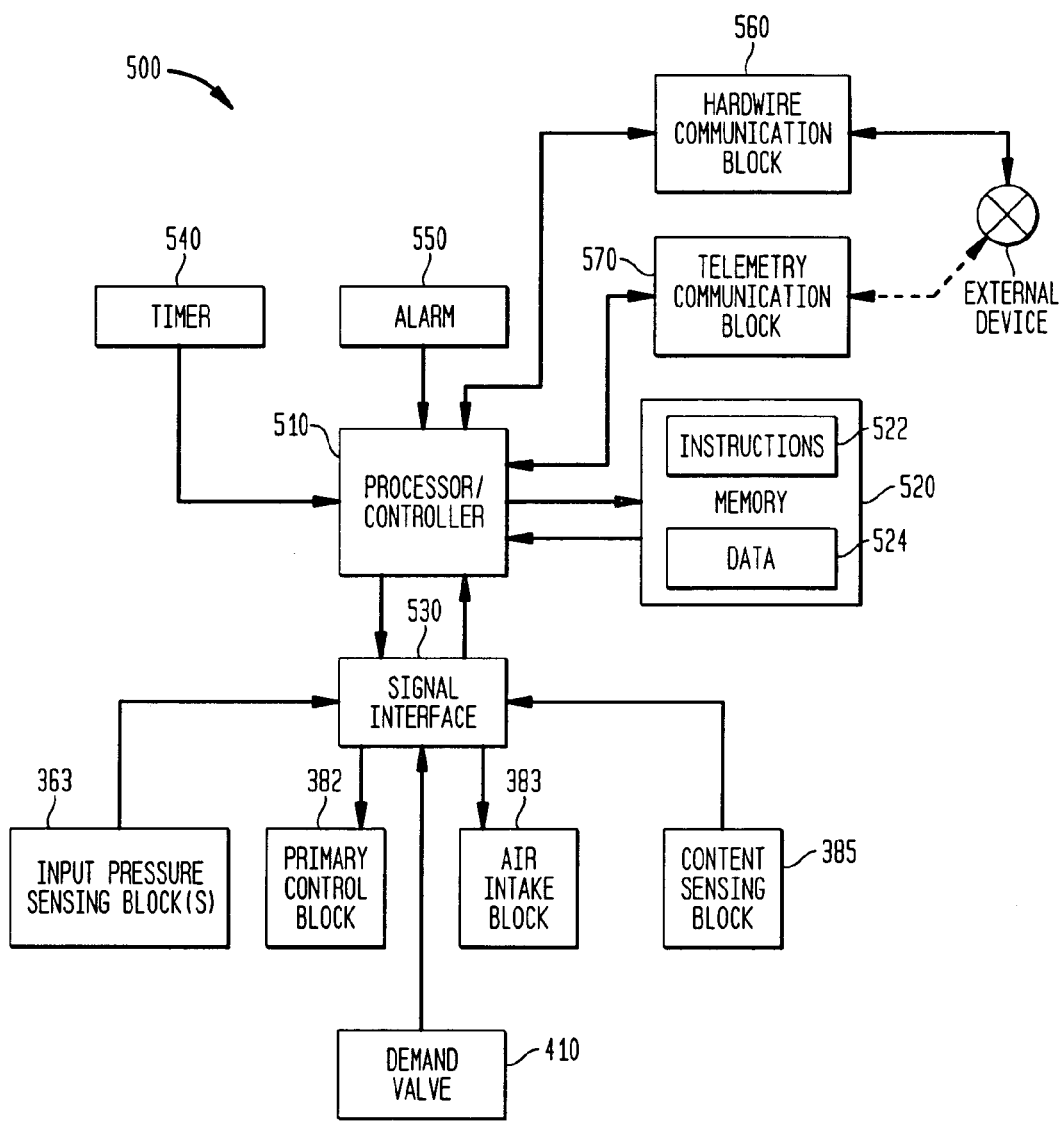
FIG. 12 is functional block diagram of an operational control system of a therapeutic gas administration system in accordance with another preferred embodiment of the present invention.

In a preferred embodiment, the gas administration system 100 includes an operational control system 500 that directs the overall operations of the system 100 and affects the operation of and the communication between its various structural blocks and components, such as valves, sensors, and the like. FIG. 12 shows a block functional diagram of one embodiments of the system 500. It should be understood that some of the functional blocks and/or system components shown in FIG. 12 may be absent and that additional functional blocks and/or system components may be present.

The operational control system 500 includes a processor/controller 510 and a memory 520. The processor/controller 510 and the memory 520 may be parts of the same structural part or may be located in different structural parts. The processor/controller 510 may be a microprocessor, a CPU of a personal computer or a PDA, and so on. Preferably, the processor/controller 510 is a microprocessor located inside the system 100. Preferably, the processor/controller 510 is located inside the domed area 312a of the body 300.

The processor/controller 510 processes data and signals received from the components and parts of the system 100. For example, the controller 510 may receive and process signals from the blocks 363 and 385, the demand valve 410, the cassette 200, and others. The processor/controller 510 also may direct functioning of components and parts of the system 100. For example, the processor/controller 510 may direct the valves 382a and 383a to open or close, control and operate components of the patient interface assembly 400 (e.g., the demand valve 410 or a conservation device), activate aural or visual alarms, operate a timer, and so on.

The memory 520 includes an instructions block 522 and a data block 524. It should be understood that the instructions block 522 and the data block 524 might be part of the same program. The program may be stored in the memory 520 as software, firmware or in any other form.

The instructions block 522 stores various instructions for operation of the therapeutic gas administration system 100. The instructions may include, for example, pre-determined modes of operation for components and parts of the system 100. The data block 524 stores data relevant to the operation of the system 100. The data stored in the data block 524 may include pre-set values, such as levels of various operational parameters, pre-determined desired values of measured gas parameters, pre-set timer data and the like; as well as data collected in the course of use of the therapeutic gas administration system 100. For example, the data block 524 may store pre-set values for pressure, oxygen content, and the like, and the information regarding the number of times the system 100 was used.

The processor/controller 510 addresses the instructions block 522 and receives instructions therefrom for processing. The processor/controller 510 also retrieves data from the data block 524 and causes the acquired/collected data to be stored in the memory 520 in accordance with instructions provided by the instructions block 522.

The processor/controller 510 may communicate with the structural parts and components of the therapeutic gas administration system 100, such as the input pressure sensing blocks 363, the primary control block 382, the air intake block 383, the gas content block 385, and the demand valve 410. The controller 510 may receive signals from the demand valve 410, the input pressure sensing blocks 363 and the gas content block 385. The processor/controller 510 may issue commands to the primary control block 382, the air intake block 383, and the demand valve 410. The blocks 363, 382, 383, 385, and the valve 410 may include mechanical components as well as structures for communicating with the processor/controller 510. The communication structures in the blocks 363, 382, 383, 385, and the valve 410 may include electrical components that provide and receive analog signals. If the blocks 363, 382, 383, 385, and the valve 410 provide and receive analog signals, the operational control system 500 may include a signal interface 530 for converting the analog signals into digital signals readable by the processor/controller 510 and for converting the digital signal from the processor/controller 510 into analog signals. The signal interface 530 may have any structure that permits communication between a processor and electromechanical components, including structures known in the art.

Instead of electrical components, the communication structures in the blocks 363, 382, 383, 385, and the valve 410 may include electronic components that provide and receive digital signals. In such case, the presence of the signal interface 530 may not be necessary.

The following non-limiting example illustrates some aspect of functioning of the therapeutic gas administration system 100 having the operational control system 500. Suppose, a patient has the system 100 equipped for administration of nitrous oxide/oxygen mixture. The memory 520 is programmed with pre-set data and instructions particular to the gas mixture, the dose, and the patient. The patient wants to administer the nitrous oxide/oxygen mixture stored in the cassette 200. The patient inserts the cassette and fully attaches the housings 310 and 320 to each other. The cartridges 210 are punctured. The pressure sensors 363*a* determine the pressure of oxygen and/or nitrous oxide released from the cartridges. The input pressure sensing blocks 363 forward the pressure measurement data to the processor/controller 510. The processor/controller 510 retrieves the pre-set values of desired pressure from the data block 524 of the memory 520. If the data from the input pressure sensing blocks 363 indicate that the pressure of the incoming gases is insufficient, the processor/controller 510 directs the primary control block 382 to close the primary control valve 382*a*. The patient is unable to actuate the system 100 and to begin gas administration. If the gas pressure is sufficient (e.g., equal to the stored pre-determined value or within the permitted range of predetermined pressure values), the processor/controller 510 directs the primary control block 382 to open the primary control valve 382*a* or to maintain the valve 382*a* open. In essence, if the input pressure is sufficient, the processor/controller 510 does not prevent opening of the primary control valve 382*a* on the basis of the input pressure data.

The system 100 is in the ready-to-use configuration. The patient attempts to inhale through the facemask 430, creating negative pressure at the demand valve 410. The demand valve 410 provides information about the inspiration pressure to the processor/controller 510, which compares the information with a pre-determined threshold value or range of values stored in the data block 524. When the pre-determined threshold inspiration pressure is reached, the processor/controller 510 signals the demand valve 410 to open. Alternatively, the demand valve 410 may have an independent electronic or mechanical mechanism for opening once the inspiration pressure reaches the threshold value. Also, once the threshold pressure reaches the threshold value, the processor/controller 510 opens the primary control valve 382*a* (depending on programming in the memory 520, the valve 382*a* may be kept open unless a command to close is received, or may remain closed unless it receives a command to open). The gas flows to the gas content block 385. The oxygen sensor 385*a* determines the oxygen concentration in the mixture that flows through the block 385 and forwards the data to the processor/controller 510. If the oxygen concentration is in the desired range, the controller 510 directs the primary control valve 382*a* to remain open (or provides no command to close). If the oxygen concentration is outside the desired range, the controller 510 closes the valve 382*a* and opens the air intake valve 383*a*.

A timer may be incorporated as one of the preferred features of the therapeutic gas administration system 100. Any suitable timer mechanism, including those known in the art, may be used. Preferably, the system 100 includes a timer based on microelectronic component(s). A battery located in the cassette 200, in the upper housing 310 or elsewhere may power the timer.

Referring to FIG. 12, in the preferred embodiment, the operational control system 500 includes a timer block 540. The timer block 540 stores pre-set instructions regarding the timing and/or duration of certain operations of the system 100 and/or associated devices or therapies. The timer 540 may be part of the instructions block 522, data block 524 or an independent component. The instructions stored in the timer block 540 may include, for example, the total duration of administration for a given gas or gas mixture, the length of a pre-set time period before the end of gas administration for activation of an alarm, the lengths of various relevant pre-set time periods after the beginning of administration when the patient is advised to take a given action, and on. For example, the timer block 540 may store data on the length of a pre-set time period after the beginning of gas administration when the patient should initiate AF-ICD, administer co-therapy, and so on. The timer block 540 may also store instruction for the type of warning or alarm to be given to the patient. Preferably, the timer block 540 is pre-set by the patient's physician or in the factory. The instructions stored in the timer block 540 may correspond to the prescribed therapeutic gas and dose. The processor 510 executes the instructions from the timer block 540. The timer block 540 may also issue a hardwire or telemetric signal to an external medical device to activate a timer or on switch for an external device delivering a secondary or co-therapy as described in further detail herein below.

The system 100 may include an alarm 550. Generally, the alarm 550 provides certain information to a patient and/or informs the patient that a certain action is required or suggested. Preferably, the alarm 550 is activated by a command from the processor/controller 510. The processor/controller 510 may activate the alarm 550 on the basis of instructions from the timer 540. The controller 510 may also activate the alarm 550 based on signals from other components of the system 100, such as the primary control block 382, the air intake block 383 and the input pressure sensing block 363.

The alarm 550 may include visual and/or aural indicators. A non-limiting example of the visual indicators is a light source (not shown) located on a frontal external surface of the body 300. The light source may display bright flashes of light immediately visible to the patient who holds the body 300. The visual and/or aural indicators of the alarm 550 may be different for different instructions provided by the timer block 540. For example, at a given time after the beginning of gas administration, the alarm 550 may give two flashes and sound twice; after a cassette is empty, the alarm 550 may give 3 flashes and one long audible signal, and so on. For example, the alarm 550 may let the patient know that it is time to cease gas administration. In another non-limiting example, the alarm 550 may inform the patient that an amount of gas remaining in the cassette is sufficient for a specific remaining inhalation time known to the patient. The information about the remaining inhalation time may be based on data from the input pressure sensing block(s) 363.

The following non-limiting example is helpful to illustrate the operation of the alarm 550. Suppose, a physician has conducted practice sessions with a patient having AF-ICD. The purpose of the sessions was to determine the optimal length for administration of nitrous oxide/oxygen mixture (e.g., 65% $N_2O$/35% $O_2$) to achieve the desired analgesia, anxiolysis and AF-ICD amnesia. The practice sessions showed that the optimal time for AF-ICD shock for the patient is 3 minutes after the beginning of gas administration. The physician may then set the timer 540 to activate the alarm 550 at 2 minutes and 40 seconds after the beginning of gas administration. As the system 100 is brought into the ready-to-use configuration, the input sensing block 363 signals to the controller 510 that the gas pressure is sufficient. The controller 510 opens the primary control valve 382a. The patient attempts to inhale, creating negative pressure at the demand valve 410. The demand valve 410 provides information about the inspiration pressure to the controller 510, which compares the information with the threshold value stored in the data block 524. When the threshold pressure is reached, the controller 510 signals the demand valve 410 to open. The time of opening of the demand valve 410 signals the time of beginning of gas administration. The controller 510 compares this time with the information stored in the timer block 540. 2 minutes and 40 seconds later, the controller 510 activates the alarm 550. The alarm 550 suggests to the patient that it is time to activate the AF-ICD timer so that the AF-ICD shock coincides with the peak effect from the nitrous oxide/oxygen mixture at 3 minutes. Similarly, the timer 540 may be utilized with other devices or co-therapies used with the system 100.

In another preferred additional feature, the system 100 may communicate with an external medical device via a wired connection or telemetry. To conduct the communication with the external device, the operational control system 500 may include a hardwire communication block 560 and/or a telemetry communication block 570 (FIG. 12). The system 100 may receive signals from an external medical device. The system 100 may also direct operation of the external medical devices. The signals are received by the hardwire communication block 560 and/or the telemetry communication block 570, and communicated to the controller 510. The hardwire communication block 560 has structural and/or data components necessary for wired interface with the external medical device, including components and structures known in the art. Likewise, the telemetry communication block 570 includes structural and/or data components necessary for wireless interface with the external medical device, including components and structures known in the art.

In one of the preferred embodiments, the therapeutic gas administration system 100 may be interfaced with an implanted AF-ICD. The system 100 can communicate with the interfaced AF-ICD through the hardwire communication block 560 and/or the telemetry communication block 570 of the operational control system 500. The interfaced AF-ICD also should have components and structures necessary for wired or wireless communication with the system 100. For the purpose of illustration, it is assumed that the interfaced AF-ICD has its own timer and is capable of detecting patient's atrial fibrillation.

The following non-limiting example illustrates one variant of the interaction between interfaced system 100 and AF-ICD. The instructions block 522 stores instructions for the controller 510 to prevent opening of the primary control valve 382a without a signal from an AF-ICD. The nature of the expected AF-ICD signal is pre-determined and stored in the data block 524. Unless the system 100 receives the pre-determined AF-ICD signal, the primary control valve remains closed and the gas administration is precluded. The system 100 is unavailable for use.

If the hardwire communication block 560 and/or the telemetry communication block 570 receives a signal from the interfaced implanted AF-ICD, the processor/controller 510 compares the signal with the pre-determined signal stored in the data block 524 to verify the authenticity of the signal. If the received signal is identical to the pre-set signal stored in the data block 524, the processor/controller 510 recognizes the received signal as authentic and directs the primary control valve 382a to open. The system 100 is released for use.

The authentication mechanism can reduce the risk of misuse or abuse of analgesic gases, such as the $N_2O/O_2$ mixture. The authentication may be premised on a model and/or a manufacturer of AF-ICDs. For example, all AF-ICDs of a given model would be recognized as authentic.

The authentication also may be based on the unique AF-ICDs of each patient. In a non-limiting example, only patient X having AF-ICD with unique identifier U34GDF3 may use body 300 with identifier 7YW345. A patient Y having AF-ICD with different identifier would not be able to use X's body 300. The mechanism of authentication may involve, for example, a specified frequency or amplitude modulation pattern, a series of separate signals broken by intervals of time, and so on.

In another non-limiting example, the interfaced system 100 and AF-ICD may cooperate to alert a patient of an atrial fibrillation incident and to encourage the patient to use the system 100. Suppose, the AF-ICD determines that the patient is in atrial fibrillation. The AF-ICD sends a pre-determined signal to the hardwire communication block 560 and/or the telemetry communication block 570. The block(s) 560 and/or 570 forward the signal from the interfaced AF-ICD to the processor 510. The signal contains information about the identity of the interfaced AF-ICD and the fact that the patient is in atrial fibrillation. The processor/controller 510 authenticates the signal with the memory 520 and recognizes that the patient is in atrial fibrillation. The processor/controller directs the primary control block 382 to open the primary valve 382a and activates the alarm 550. The alarm 550 alerts the patient. The type of the alarm indicates to the patient that the system 100 is released and ready for use and that the patient has atrial fibrillation.

In another non-limiting example, suppose a physician has determined in practice sessions with the patient that the optimal time for the AF-ICD shock is 3 minutes after the beginning of administration. In accordance with physician's directions, the patient's AF-ICD and system 100 are programmed on the basis of the information obtained in the practice sessions. The timer 540 is set to provide a pre-determined signal to the interfaced AF-ICD two minutes and 40 seconds after the beginning of gas administration. The timer of the interfaced AF-ICD is set to initiate AF-ICD shock 20 seconds after receipt of the pre-determined signal from the system 100.

The patient wants to administer nitrous oxide/oxygen mixture. The patient inserts the cassette 200 and fully attaches the housings 310 and 320 to each other. As the system 100 is brought into the ready-to-use configuration, the input pressure sensing block(s) 363 determines the pressure of the gas released from the cartridges 210 and forwards the pressure measurement to the processor/controller 510, which the pre-determined value of the desired pressure from the data block 524 of the memory 520.

If the gas pressure is sufficient (e.g., equal to the stored pre-determined value or within the permitted range of predetermined pressure values), the processor/controller 510 directs the primary control block 382 to open the primary control valve 382a or to maintain the valve 382a open. The patient attempts to inhale, creating negative pressure at the demand valve 410. The demand valve 410 provides information about the inspiration pressure to the controller 510, which compares the information with a pre-determined threshold value or range of values stored in the instructions block 522. When the desired threshold pressure is reached, the controller 510 signals the demand valve 410 to open. The time of opening of the demand valve 410 is the time when gas administration began.

The demand valve 410 forwards the opening/beginning time to the processor/controller 510. The controller 510 compares the opening/beginning time with the information stored in the timer block 540. In accordance with instructions and data stored in the memory 520, the processor controller 510 activates the hardwire communication block 560 or the telemetry communication block 570 two minutes and 40 seconds after the beginning of gas administration. The block(s) 560 and/or 570 sends a signal to the AF-ICD. The signal from the blocks 560 and/or 570 causes the patient's AF-ICD to activate the AF-ICD timer (set for 20 seconds). AF-ICD initiates the AF-ICD shock 20 seconds after receiving the predetermined signal from the system 100 without any additional actions by the patient. In effect, instead of separately actuating the system 100 and the AF-ICD, the patient self-administers the AF-ICD shock by beginning the gas administration.

If the input pressure sensor block(s) 363 signals to the controller 510 that the pressure of the incoming gas is insufficient. The controller 510 signals the primary control block 382 to close the primary control valve 382a. Depending on the programming, the controller 510 may also provide no signal to the blocks 560 and/or the block 570, or may cause the blocks 560 and/or the block 570 to signal to the AF-ICD not to administer the shock.

Suppose, for example, that the patient deviates from the instructions of a physician and continues the administration of the gas after an AF-ICD shock is administered at 3.5 minutes. Suppose also that the cassette stored gas amount sufficient for 4 minutes of gas administration. After 3 and half minutes of gas administration, the appropriately pre-set timer 540 may cause the alarm 550 to warn the patient that only 30 seconds of gas administration is remaining in the cassette.

The telemetry communication block 570 may also be used to remotely communicate with a physician, paramedics, fire or police personnel and other authorized persons. For example, a physician may monitor a patient from a remote location. Any location that does not involve a direct physical contact with a patient may be considered remote. Such remote monitoring may involve, for example, periodical downloads of data from the patient's AF-ICD and system 100, including numbers of occurrences of atrial fibrillation events, AF-ICD shock administrations and therapeutic gas administrations. The physician may use the downloaded data to evaluate the patient's use of the system 100. The downloaded data may be used for medical purposes, for example, to compile the patient's medical history for future treatment. Also, the data may be used to monitor whether the analgesic gas cassettes provided to the patient are used as intended.

The remote communication between the patient's AF-ICD and system 100 and the physician may also allow the physician to administer or affect therapy from the remote location. For example, the physician may remotely initiate the AF-ICD shock (e.g., if the patient is unable or anxious to self-administer the shock) while the patient is self-administering the analgesic gas mixture with the system 100. Also, a physician, paramedic, fire or police personnel or other authorized persons may remotely release the system 100 for use.

The cassette 200 may have various additional features, variants and alternatives. In one embodiment, both cartridges 210 may contain the same gas or gas mixture. Non-limiting examples of therapeutic gases that may be dispensed with the cartridges having the same gas include pure oxygen, helium/oxygen mixture (e.g., 80% He/20% $O_2$), nitrous oxide/oxygen mixture (e.g., 50% $N_2O$/50% $O_2$) at pressures and temperatures that assure mixture stability, and carbon dioxide/oxygen mixture (e.g., 10% $CO_2$/90% $O_2$). One of the benefits of this embodiment for certain applications is the increased maximum duration of gas administration using the unit dose cassette 200. The maximum pressure in the cartridges 210 and the dimensions of the cassette 200 control the maximal duration of administration for the unit dose cassettes. For example, if oxygen and carbon dioxide (for the 10% $CO_2$/90% $O_2$ mixture) were placed in separate cartridges, the total maximal duration of administration would be smaller due to the constrains in regards to the pressure and size of the cartridge containing the oxygen.

One of the preferred applications of the system 100 is the administration of nitrous oxide/oxygen mixture in an outpatient setting. As known to those of skill in the art, the prevention of nitrous oxide abuse is an important consideration. For this reason, the cassette 200 may have features designed to minimize the opportunity for misuse of the gases contained in the cassettes. Thus, preferably, the cartridges 210 are permanently fixed and rigidly attached to body 200a of the cassette 200, and the holding members 207 are attached to the cartridge necks 212 in a manner that makes it difficult to puncture and/or to remove the cartridges without possession of the body 300. The body 200a may be a unitary molded structure in which the cartridges 210 and the needle/cannula assemblies 205 are firmly embedded. In reference to FIG. 4A, the depth x at which the cartridges 210 are embedded is selected to make removal and puncturing of the cartridge 210 as difficult as possible. Deep embedding of the cartridges 210 minimizes opportunities for recreational abuse. Furthermore, inclusion of an RFID chip within or permanently attached to the outer body allows real time physical tracking of the location of a specific cassette. In the case of cassettes containing gases such as nitrous oxide or xenon, which may be the subject of potential theft for recreational abuse, the inclusion of an RFID chip provides an additional level of control, trackability and traceability.

In another embodiment, the cassette body 200a may include two or more sections (more preferably, two sections) permanently attached to each other. The sectional structure provides improved integral strength.

In a preferred non-limiting example, the cartridges 210 have a nominal volume of 50 ml (based on water fill volume). At the pressure of 3000 psig (207 bar), the 50 ml cartridge holds a nominal fill volume of up to 15 liters for oxygen and up to 18.57 liters for nitrous oxide. The cartridge may be smaller or larger then 50 ml dependent on application. Other suitable preferred sizes of the cartridge 210 are 25 ml, 75 ml, and 100 ml. Cartridges larger than 100 ml are also contemplated.

Yet another preferred feature(s) relates to various temperature control devices. As described, compressed gas cartridges 210 are filled with gases at high pressures. Venting of gas, which is stored in a closed vessel under high pressure, in a short period of time leads to rapid decrease in temperature. With respect to the operation of the system 100, the rapid venting of gas from the cartridges 210 may result in a rapid decrease of the temperature of walls of the gas cartridges, the cooling of the gas itself, and a rapid decrease in the temperature of materials/components of the system 100 that come in contact with the venting gases. The ultra cold gas exiting the cartridges 210 may be further cooled by the effect of high-pressure gas flowing through small orifices/passages at the exit from the cartridges 210.

Potentially, the cooling can lead to several undesirable effects. A portion of the gas may be converted to solid (e.g., crystal) or liquid form. In some cases, the ultra cold gases may form crystals and block various gas passage elements of the system 100, or may cause malfunctioning of the mechanical components (e.g., valves). Such blockage and/or malfunctioning may partially or completely prevent effective use of the system 100. It should also be kept in mind that mixtures of gases pre-mixed in a single container, for example, nitrous oxide/oxygen mixtures containing 50% or more of nitrous oxide, are unstable when compressed and exposed to temperatures of minus 5 to minus 7 degrees Centigrade. The gas cartridges may be exposed to such temperatures for a number of reasons, such as an external temperature on the metal of the cartridge transferred to the cartridge contents and/or the cooling effect on the small surface area of the cartridge metal during rapid venting of the cartridge contents through a small orifice under pressure further decreasing the temperature of the remaining contents and gas exiting from the cartridge inside the system 100. The result may be the liquefaction of the nitrous oxide that leads to sequential exit of gases from the cartridge, with the gaseous oxygen exiting the cartridge first, followed by pure nitrous oxide.

Figure 13A:
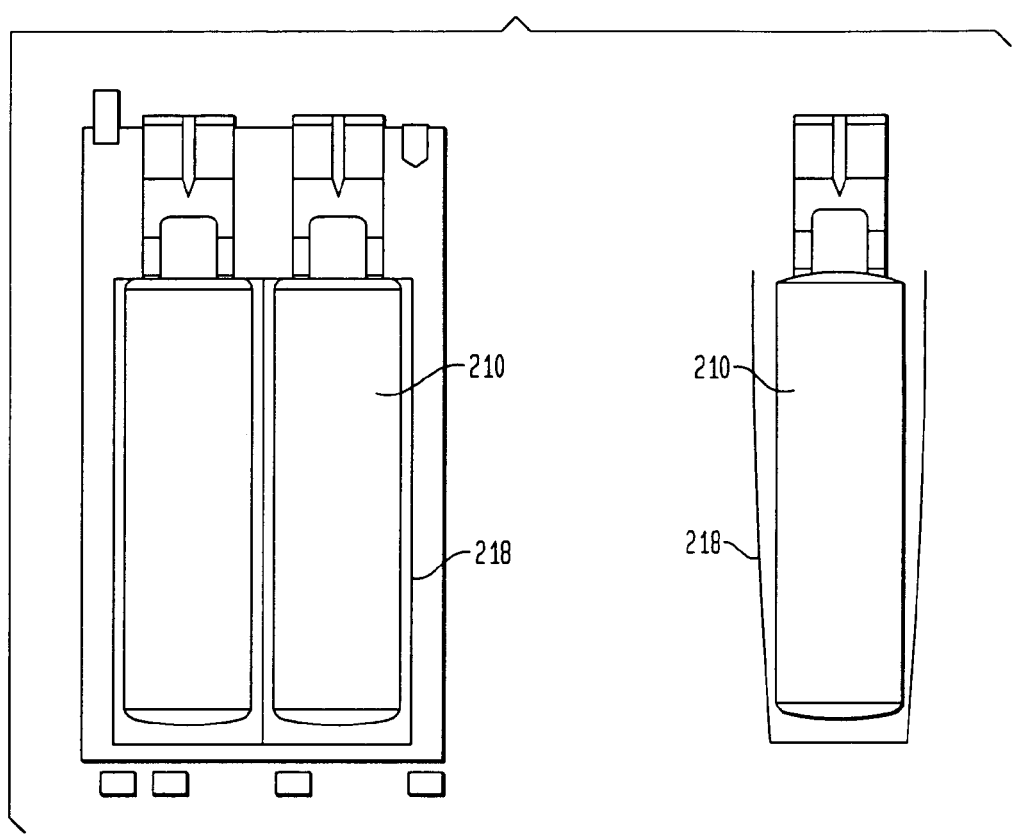
FIG. 13A is a side, elevational, partially schematic view of a cold sink component for the therapeutic gas administration system in accordance with one embodiment of the present invention.

One of the methods of dealing with the cooling is to incorporate cold sink material into the cassette 200 (FIG. 13A). A non-limiting example of suitable cold sink materials is aluminum. As shown in FIG. 13A, the cassette 200 may include a cold sink structure 218, surrounding and in close contact with the surface of the cartridges 210. For example, the cold sink structure 218 may be in a form of a layer. As the gas is vented from the cartridge, the cold sink structure 218 absorbs some of the temperature decrease, thus minimizing the cooling effect on the operation of the system 100.

Another method of counteracting the gas-induced cooling is to heat the gas and/or the components of the gas administration system 100 that come in contact with the gas. Preferably, the heat is provided by a suitable energy element incorporated into the system 100, for example, disposable or rechargeable battery. The battery may be located in the cassette 200 or the body 300.

The use of rechargeable batteries is contemplated, but is believed to be less desirable. It is not feasible to equip cassettes with rechargeable batteries since preferably the cassettes are disposed after a single use. The rechargeable battery may be located in the body 300. However, a patient may forget to recharge the battery. The disposable battery may be also located in the body 300, but is also less desirable since the patient may forget to replace the disposable battery. It is important to have the system 100 immediately available and therefore, if possible, reliance on patients' memory should be avoided.

The preferred form of energy element is a disposable battery located in the disposable cassette 200. With a new cassette for administration of each dose of therapeutic gas, the use of disposable battery in each cassette increases the likelihood that fully charged battery is available for each gas administration. This provides a measure of assurance to a patient that the system 100 will function correctly. The disposable battery in the cassette 200 may also be used to power other operations of the system 100. It should be understood that an energy element might be used with the system 100 regardless of whether or not the system 100 includes any heating structures.

A choice of structure and locations of heating structures for the therapeutic gas administration system 100 depends at least in part, on the desired timing for gas heating. The methodology and structures for heating may vary, and may include methodologies and structures known in the art. An example of a portable medical gas warming system is disclosed in U.S. Pat. No. 4,597,917, which is incorporated herein by reference in its entirety.

The gas may be heated as the system 100 is brought to a ready-to-use configuration, and/or before/when it is actuated to begin gas administration. Referring back to FIG. 8A, it is desired to stabilize the temperature of the gas before it reaches the input pressure sensing blocks 363. The pressure of gases depends on their temperature. Therefore, if the gas temperature changes after the pressure was measured, the pressure measurement may not be sufficiently reliable. In a system with a manual demand valve, the initial pressing on the demand valve lever or button by the patient would activate the flow of current from the battery to the heating elements. When the required temperature was achieved and the patient notified by the alarm, the patient would be able to press the manual demand valve lever fully to activate the flow of gas. As another alternative not meant to be self limiting, upon initial pressing of a startup button prior to actual use, power from the battery would sufficiently warm heating elements incorporated in the variant of the system 100, and a green light would flash on top of the unit to indicate it is ready for use. At that time, the patient would firmly bring together the two halves of system 100 so as to puncture the cartridges in cassette 200 releasing their gas contents.

Figure 13B:
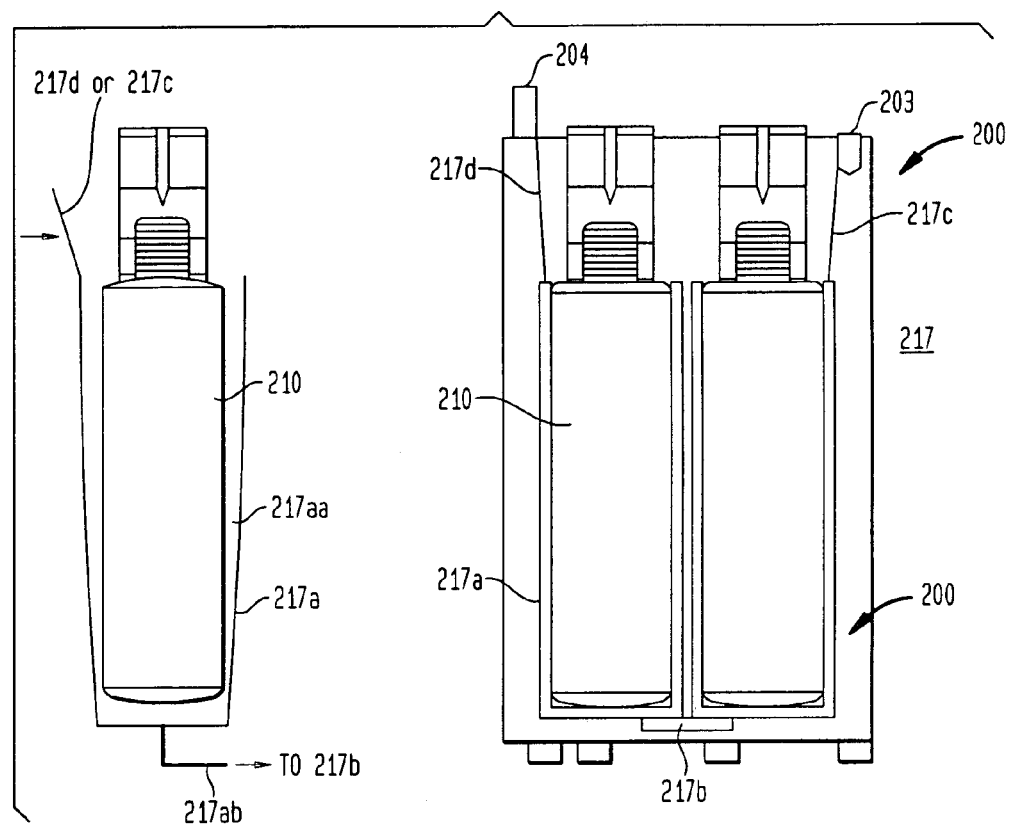
FIG. 13B is a side, elevational, partially schematic view of a heating component for the therapeutic gas administration system in accordance with another embodiment of the present invention.

One of the preferred locations for the heating the gas is the cassette 200. The cassette 200 may include a cassette heating system 217. In one preferred variant, the cassette heating system 217 includes cartridge heaters 217a, an energy element 217b, and activation connectors 217c and 217d (FIG. 13B). The cartridge heaters 217a separately heat the cartridges 210. Alternatively, the cassette heater may include a single heating element for all cartridges in the cassette. The cartridge heater 217a (one for each cartridge 210) includes a heating element 217aa and an energy connector 217ab. The heating element 217aa surrounds the cartridge 210, for example, as shown in FIG. 13B. The heating element 217aa is preferably an electrically conductive/heat-producing layer. It can be made from such materials as metal and metal-coated plastic. For example, the heating element 217aa may include heat-conducting plastic material containing metallic structural elements in the form of metal plates or metal wires set in a parallel or grid formation. The energy connector 217ab connects the heating element 217aa to the energy element 217b. The energy connector 217ab may be, for example, a metallic wire or other electrically conductive structure.

The energy element 217b serves to provide heat to the cassette 200 at a desired time. The energy element 217b has to last only for a short period of time (while the gas is released from the cartridge 210). Therefore, the energy can be rapidly drawn down and provided to the heating elements 217aa to effect rapid heating of the cartridges 210. Preferably, the energy element 217b is a disposable battery. Various shapes, makes and types of energy sources, including batteries, are contemplated. Thus, the battery may be flat, coin shaped, elongated such as standard AAA or AA batteries). The battery may be placed in various locations in the cassette 200, for example, at the bottom of the cassette and/or horizontally (as shown in FIG. 13B), or vertically and parallel to the length of the cartridges 210.

The activation connectors 217c and 217d serve to deliver a signal to the cartridge heaters 217a and the energy source 217b to begin heating. The connectors 217c and 217d may be, for example, metallic wires or other electrically conductive structures. The connector 217c is connected to the female interfacing key 203 and the connector 217d is connected to the male interfacing key 204. The keys 203 and 204 of the cassette 200, as well as the corresponding interfacing members 303 and 304 of the upper housing 310, may be coated with a suitable conducting material (e.g., a metallic coating).

Describing the operation of the cassette heating system 217, a closed circuit is created when the interfacing keys 203 and 204 contact the interfacing members 303 and 304 as the housings 310 and 320 are attached. In one variant, the establishment of the closed circuit itself activates the battery 217b that begins heating immediately after the circuit is established. In this variant, the timing of heating may be varied via a number of methods, including for example proper placement of locations of the conductive coatings on the interfacing members and keys. In another variant, the establishment of the circuit allows the controller 510 to signal the cassette heating system 217 to begin heating. The signal causes the battery 217b to provide heating energy to the cartridge heaters 217aa via the energy connectors 217ab. Preferably, the controller 510 provides the heating signal at a pre-determined time, for example, as the system 100 is brought to the ready to use configuration or as/before the system 100 is actuated.

Figure 13C:
FIG. 13C is a side, elevational, schematic view of a heating component for use in accordance with the system of the present invention.
Figure 13D:
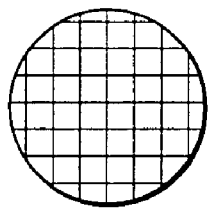
FIG. 13D is a top, elevational, perspective view of another heating component for use in accordance with the system of the present invention.
Figure 13E:
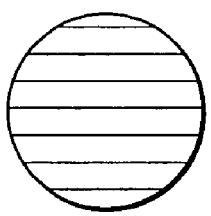
FIG. 13E is a top, elevational, perspective view of another heating components for use in connection with the system of the present invention.

Yet another method of counteracting the gas-induced cooling is the use of various heating structures for the input cannula 361a of the gas input port assembly 361 of the upper housing 310. FIGS. 13C-13E illustrate contemplated structures of heating elements for the input cannula 361a. In FIG. 13C, an electrical wire is wrapped around the cannula 361a. In FIG. 13D, a wire grid is placed inside the cannula. In FIG. 13E, a network of parallel electrical wires is placed inside the gas input cannula 361a. In the variants shown in FIGS. 13C-13E, the wires may be supplied with an electrical current upon the closing of the closed circuit and/or a signal from the processor/controller 510 as described in reference to FIG. 13B. In a preferred example, the cannula heater provides rapid warming of the gas stream, building up to a maximum heat output within 1-2 minutes. Various heating structures may be combined. For example, the use of one of the heating structures for the input cannula 361a may be combined with the cassette heating system 217 and/or a cold sink 218.

In yet another preferred specific feature, the system 100 may use cassettes containing therapeutic gas stored substantially or entirely in a liquid form. An example of a device for gasifying liquid is disclosed in U.S. Pat. No. 5,978,548, which is incorporated herein by reference. Liquefied gases may also contain some ultra cold gaseous fraction, or be initially converted into the ultra cold gas upon heating. Non-limiting examples of gases that may be stored in a liquid form include $N_2O$, $CO_2$ and $O_2$. Liquefied gases occupy substantially smaller volume than compressed gases. Therefore, the size of a cartridge or other storage container, as well as the unit dose cassette, can be smaller, which is a substantial advantage.

The liquefied/ultra cold gas should be converted to gas at a desired temperature before it can be administered to a patient. Preferably, the heating of the gas is completed prior to the pressure sensor block(s) 363 to obtain reliable pressure measurements.

Thus, the use of liquid phase storage for therapeutic gases may require incorporation of vaporizer component(s) in the system 100. The vaporizer heats the liquefied gas, converting it to a gaseous form. The vaporizer component(s) may also be used to raise the temperature of the ultra cold gas to a level suitable for the gas control and delivery system 350. The vaporizer component(s) may be powered by a disposable battery or re-chargeable battery.

Figure 13F:
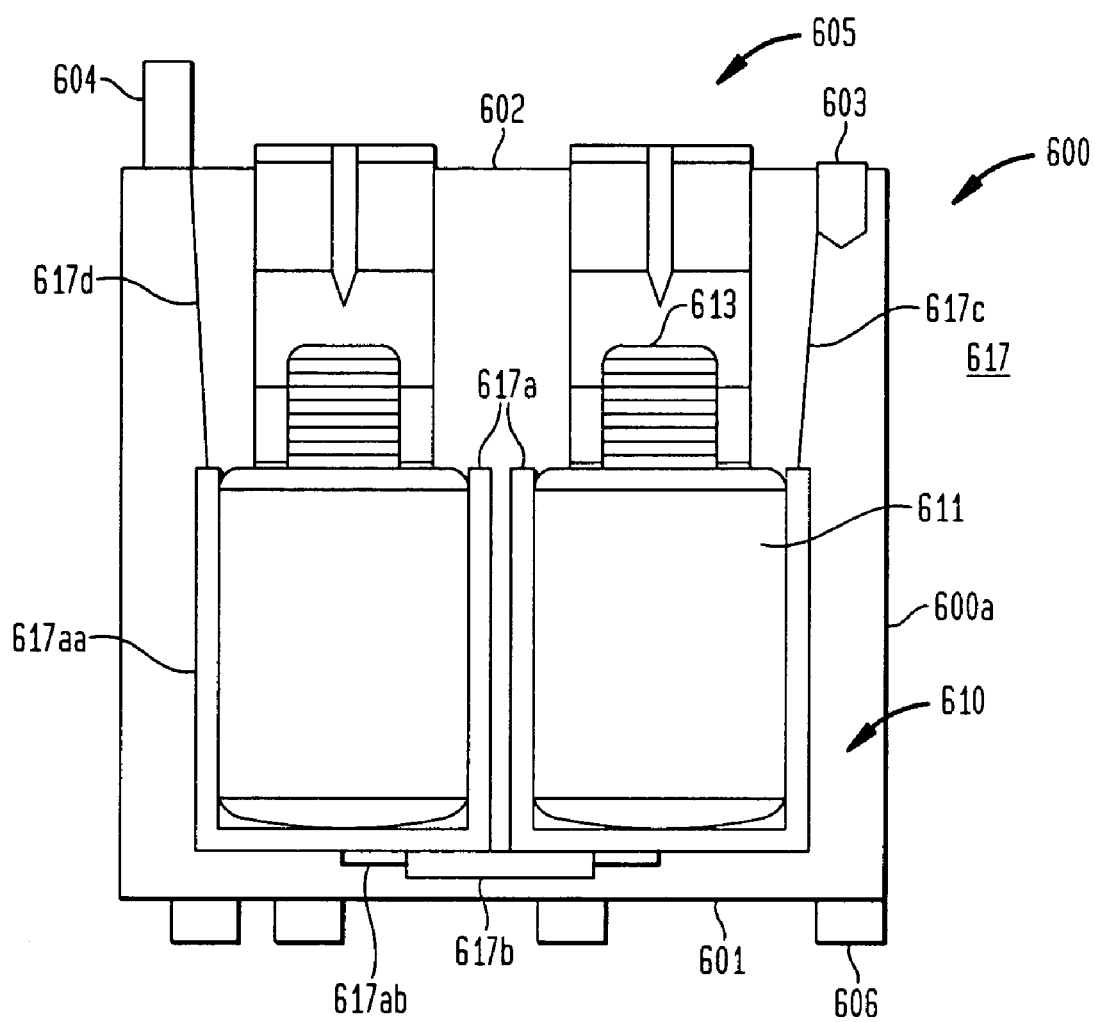
FIG. 13F is a side, elevational, partially cross-sectional, schematic view of a cassette for storing therapeutic gases in a liquid form in accordance with the present invention.
Figure 13G:
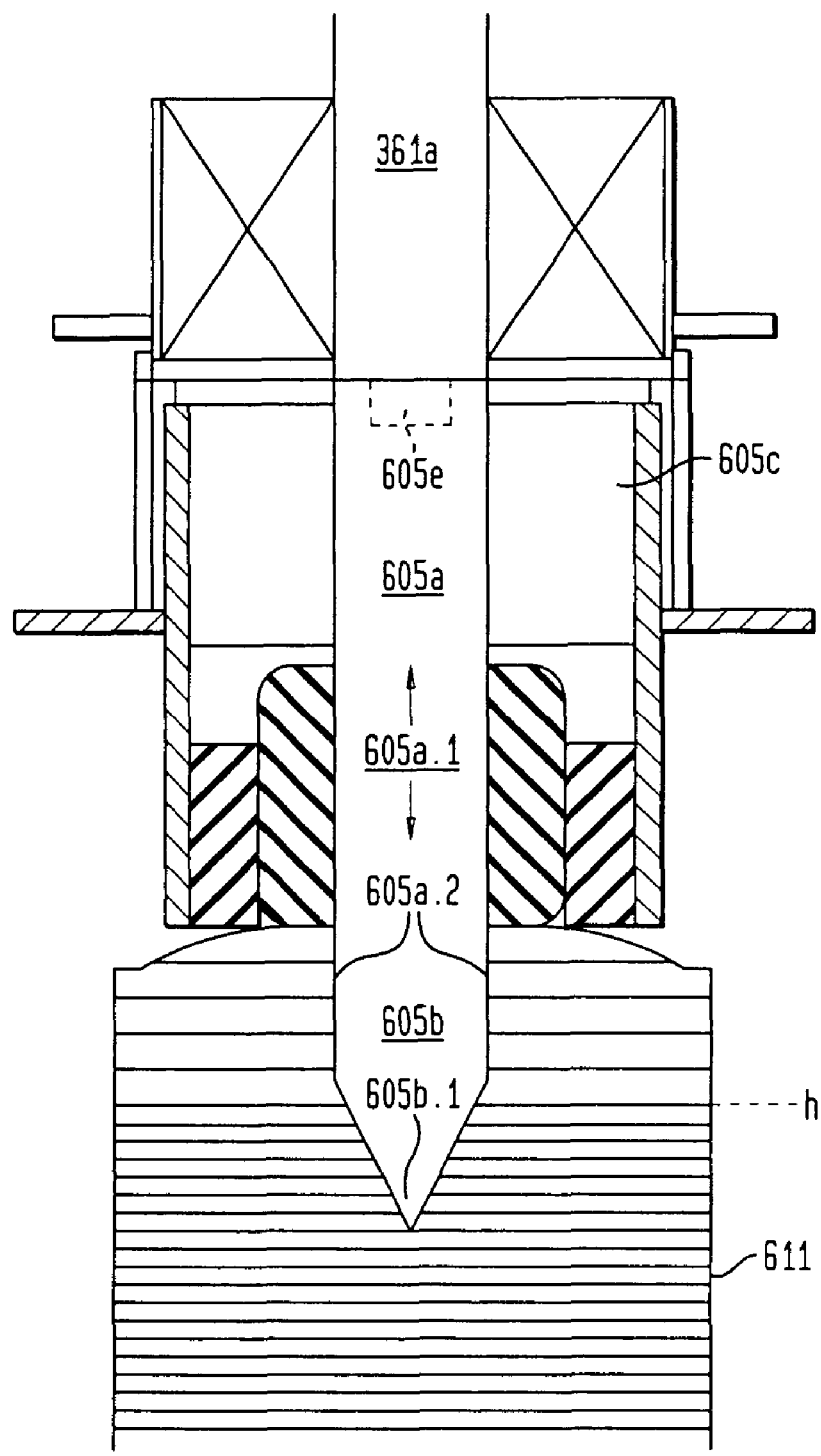
FIG. 13G is a side, elevational, partially, cross-sectional, perspective view of a cassette for use in storing therapeutic gases in a liquid form in accordance with the present invention.

The vaporizer components suitable for use in the system 100 may have various structures. For example, a cassette heater similar to one described in reference to FIGS. 13A-13B may be used to vaporize the liquefied gas. FIG. 13F shows a modified cassette 600 for storing and dispensing liquefied/ultra cold gases with the system 100 in accordance with an embodiment of the invention. FIG. 13G shows the cassette 600 after the cartridges had been punctured. Generally, the cassette 600 is similar to the cassette 200 described above. The description of components and functioning of the cassette 200 is applicable to the cassette 600 with the exception of certain structural and functional aspects, which are described briefly below.

The cassette 600 includes a cassette body 600a, two cannula/needle assemblies 605 and two cartridges 610. Similarly to the cassette 200, the cassette body 600a has a bottom surface 601 with cassette positioning keys 606 and a top surface 602 with a female interfacing member 603 and a male interfacing member 604.

The cartridges 610 contain therapeutic gases in liquefied/ultra cold gas form. Each cartridge 610 includes a cartridge body 611 and a sealing surface 613. The cartridge body 611 has walls 611a and a hollow interior 611b (FIG. 13G). The hollow interior 611a is filled with liquefied gas up to the level h, and may be divided into a liquid portion 611b.1 and a head volume 611b.2. In the sealed cartridge, the head volume 611b.2 is filled with gas.

The cannula/needle assemblies 605 are located opposite the sealing surface 613 of the cartridge 610, and include a needle cannula 605a and a sliding plug 605c attached to the needle cannula 605a for movement therewith. The needle cannula 605a has a hollow needle cannula portion 605a.1 with micro holes 605a.2, a tapered portion 605b with a needlepoint 605b.1, and a recessed coupler 605e. As shown in FIG. 13F, the relative proportions of the needle cannula 605a and the cartridge 610 of the cassette 600 are modified in comparison with the cassette 200. The hollow needle cannula portion 605a.1 of the needle cannula 605a is elongated relative to the cartridge body 611. Gases occupy substantially smaller space in liquid form, permitting the reduction in the length of the cartridge body 611 without substantial loss in molar content of the stored gas.

The cassette 600 also includes a cassette heater/vaporizer 617 having cartridge heaters 617a, a battery 617b, and activation connectors 617c and 617d (FIG. 13F). The connector 617c is connected to the female interfacing key 603 and the connector 617d is connected to the male interfacing key 604. The cartridge heaters 617a, one for each cartridge in the cassette, each include a heating element 617aa and an energy connector 617ab. The heating element 617aa surrounds the cartridge 610. The energy connector 617ab connects the heating element 617aa to the battery 617b.

The closed circuit is created when the interfacing keys 603 and 604 contact the interfacing members 603 and 604 as the housings 310 and 320 are attached. In comparison with the cassette 200, after the sealing surface 613 is punctured by the needlepoint 605b.1, the longer cannula needle 605a penetrates deeper into the cartridge 610 and increases the travel length for the exiting gases (FIG. 13G). Through the established closed circuit, the battery 617b is drawn down heating and vaporizing the liquefied/ultra cold gas in the cassette 600. The elongation of the heated hollow needle cannula portion 605a.1 results in a more efficient heating of the cartridge contents. The liquid phase is drawn upwards into the hollow needle cannula portion 605a.1 through the needlepoint 605b.1 while gases are drawn from the upper part of the cartridge 610 through the micro holes 605a.2. The vaporized gases travel upwards through the hollow needle cannula portion 605a.1 into the input cannula 361a of the gas input port assembly 361.

The gas heating components shown in FIGS. 13C-13E may also perform the functions of the vaporizer components. Also, to use the cassettes 600, the input cannula 361a may have a coiled shape to maximize the heating efficiency and expansion volume of the gas before it enters the pressure sensing block(s) 363.

The heating of the cassette 600 may be initiated when the cartridges are punctured and/or when the system 100 is actuated. The timing procedures described in reference to the FIGS. 13A-13E may be also applicable for activation of the vaporizer component(s). In one variant, the vaporizer component(s) are activated just prior to or simultaneously with actuation of the system 100 that initiates gas administration to a patient. The actuation of the system 100 and the activation of the vaporizer components may be affected together. For example, if the demand valve 410 is used to actuate the system 100, the signals providing the inspiration pressure may cause the processor/controller 510 both to begin gas administration and to activate the vaporizer component(s). For example, to activate the vaporizer components before a patient takes a first breath, the processor/controller 510 may activate the vaporizer component(s) at the inspiration pressure lower than the threshold pressure for opening the demand valve 410. Likewise, if the actuation is carried out manually, the press of the button or the pull of the lever may signal the processor/controller 510 to begin gas administration and to activate the vaporizer component(s). For separate actuation/activation, the first press of the button may activate the vaporizer component(s), while the second would begin gas administration. The actuation of the system 100 and the activation of the vaporizer components may also be affected separately. For example, a dedicated button for activating the vaporizer component(s) may be located on the body 300.

A preferred specialized connection between the housings 310 and 320 is also provided. It should be understood that the specialized connection disclosed herein may be used for any structural components of gas administration systems that have functions similar to the housings 310 and 320, for example, the function of allowing a gas administration system to provide for inserting a gas source and reattaching with the inserted gas source inside the reattached components. A non-limiting example of such structural components is shown in reference the embodiment of the body 300 shown in FIGS. 15A and 15B and described below.

In general, the connection between the housings 310 and 320 presents a number of issues. First, the movement of the housings 310 and 320 toward each other should be properly coordinated with the puncture of the cartridges 210. If the cartridges are punctured prematurely, the gas-seal integrity of the system 100 may be compromised. If the cartridges are not punctured after the housings 310 and 320 are fully re-attached, the movement of the housings is no longer available to affect the puncturing and the system 100 cannot be actuated. Further, referring back to FIGS. 10A and 10B, the vertical alignment between the gas input port assemblies 361 and the cannula/needle assemblies 205 is preferably maintained while the housings 310 and 320 move toward each other axially with the circular movement associated with the engagement of the connection mechanism (e.g., the threads). These goals may be achieved by using the continuous threaded connection already described.

However, it is also desirable to enable a patient to store the cassette 200 inside the body 300 so that the system 100 is always ready for immediate use by the patient. To begin using the system 100 from the released configuration, a patient must insert a cassette, align the interfacing members and keys, and attach the housings. These actions take time, which may be in short supply in certain medical situations, especially for patients with implanted AF-ICD. On the other hand, storing the system 100 in the ready-to-use configuration may raise other issues. In the ready-to-use configuration, the cartridges had already been punctured and the system 100 is under internal gas pressure. The storage of the body 300 under internal gas pressure may raise issues of safety, pressure integrity of the body 300, and excessive wear and tear of the components. Also, in the ready-to-use configuration, the system 100 may be actuated incidentally, which is undesirable. Therefore, while the continuous threaded connection may be adequate and desirable for many situations and/or indications, it is desired to address the above issues. It is also desirable to utilize a connection mechanism unique to the system 100 to minimize the likelihood of misuse.

Figure 14A:
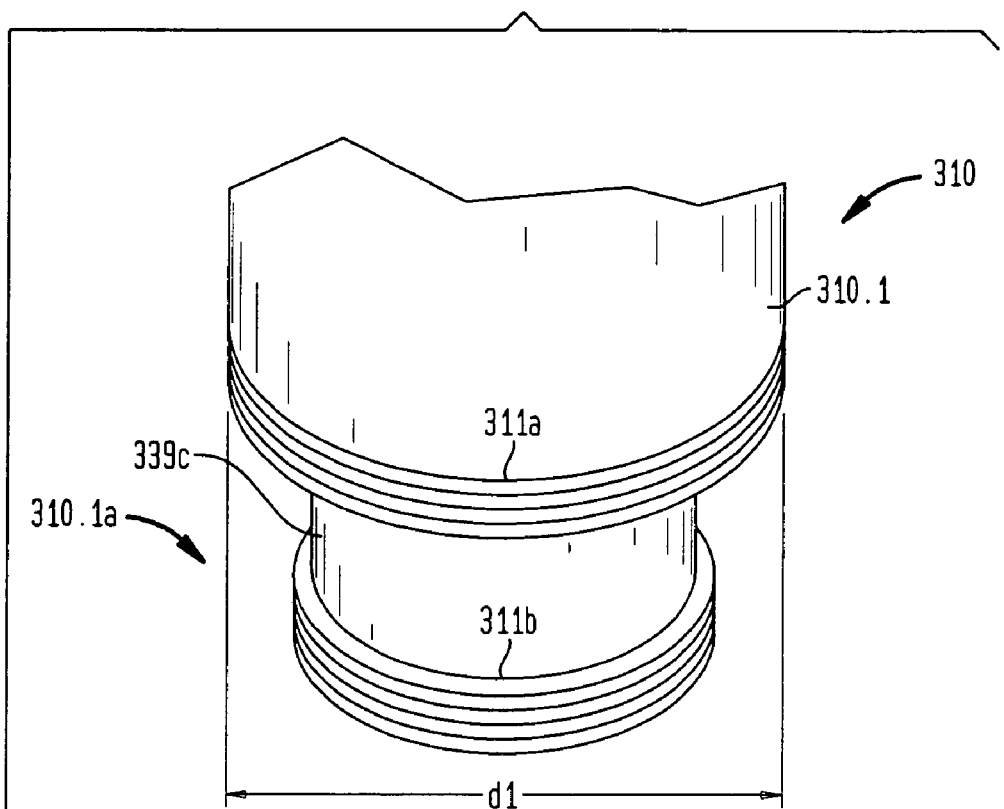
FIG. 14A is a side, perspective, schematic view of one embodiment of a specialized threaded connection between the upper housing and lower housing of the system of the present invention.
Figure 14A:
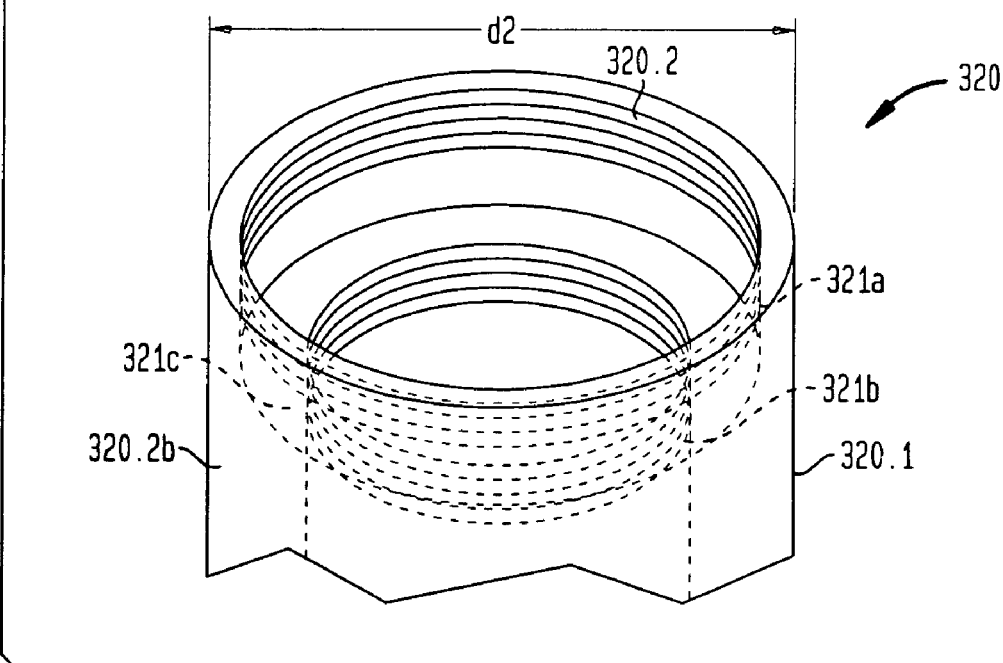

One of the preferred embodiments of the specialized threaded connection between the housings 310 and 320 is illustrated in FIG. 14A. As seen in FIG. 14A, the external surface 310.1 of the upper housing 310 defines a circumference with external diameter d1. The internal surface 320.2 of the housing 320 defines a circumferential opening with internal diameter d2. In one embodiment, the internal diameter d2 of the lower housing 320 is larger than the external diameter d1 of the upper housing 310. It should be understood that in other embodiments, the internal diameter d2 of the lower housing 320 may be smaller than the external diameter d1 of the upper housing 310.

As seen from FIG. 14A, the external surface 310.1 of the upper housing 310 has a threaded area 310.1a that includes lower threads 311a and upper threads 311b. The threads 311a and 311b are separated by a non-threaded area 311c. The internal surface 320.2 of the lower housing 320 has a threaded area 320.2a that includes upper threads 321a and lower threads 321b.

Figure 14B:
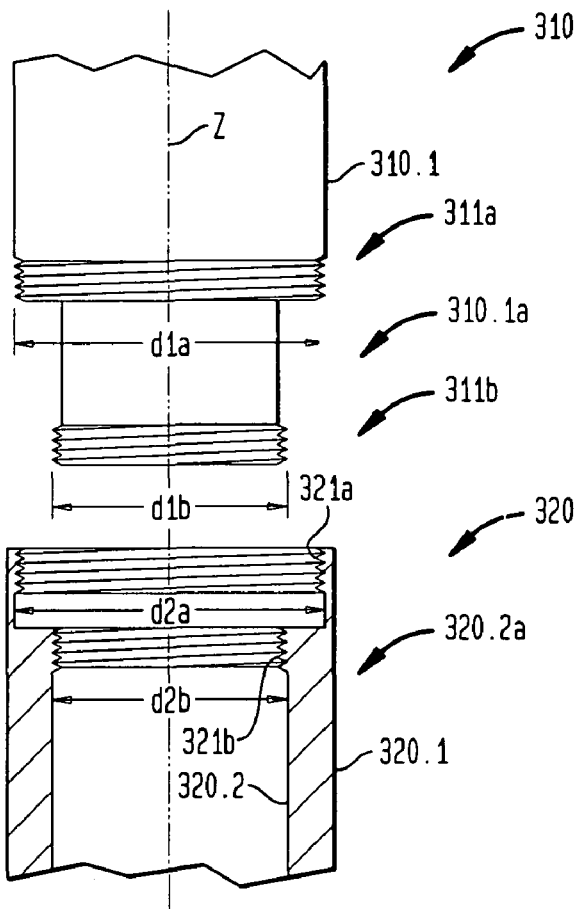
FIG. 14B is a side, elevational, cross-sectional, schematic view of an embodiment of the specialized threaded connection shown in FIG. 14A.

FIG. 14B shows a side cross-sectional view of the threaded areas 310.1a and 320.2a in one of the variants of the embodiment shown in FIG. 14A. As seen in FIG. 14B, the threads 311a have a larger diameter than the threads 311b (d1a>d1b). Likewise, the threads 321a have a larger diameter than the threads 321b (d2a>d2b). The upper threads 311a are adopted for engaging the upper threads 321a, and the lower threads 311b are adopted for engaging the lower threads 321b.

Figure 14C:
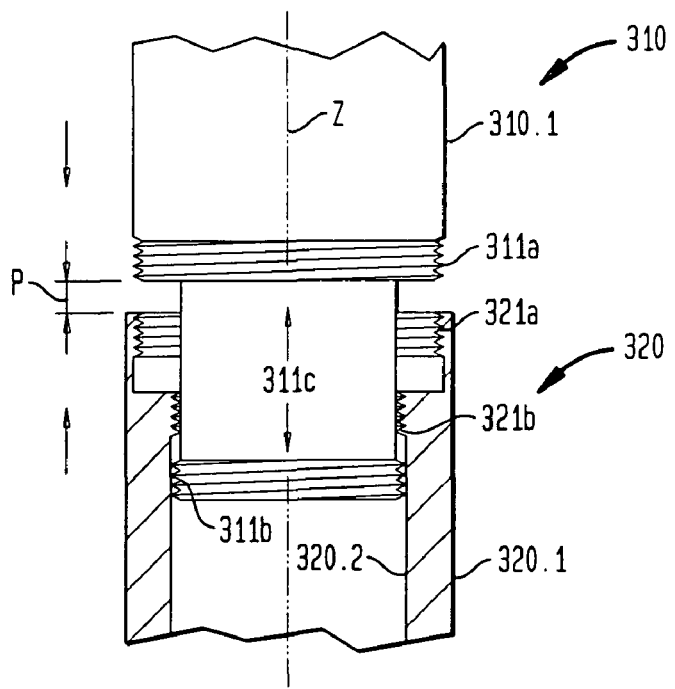
FIG. 14C is a side, elevational, cross-sectional, schematic view of the embodiment shown in FIG. 14B.

As the user begins to attach the housings 310 and 320, the external surface 310.1 of the upper housing 310 fits inside the external surface 320.2 of the lower housing 320 (d1<d2). The threaded areas 310.1a and 320.2a are moving toward each other vertically along the axis Z (FIG. 14B). The diameter d2a of the threads 321a is too large to permit interaction between the threads 311b and 321a. Therefore, the threads 311b clear the threads 321a, and than come in contact and engage the threads 321b. The user continues to attach the housings 310 and 320 until the threads 321b clear the threads 311b so that the threads 321b are above the threads 311b (FIG. 14C). In this position of the housings 310 and 320, the gas input port assemblies 361 and the cannula/needle assemblies 205 are vertically aligned, but not yet in direct contact. The threads 321a are not yet engaged to the threads 311a, being separated by a distance p. The threads 311b prevent loose detachment of the housings 310 and 320. The cartridges 210 have not yet being punctured. If desired, the system 100 may be brought back to the released configuration with the cassette 200 intact. However, the cassette 200 is inside the body 300. The system 100 is on stand-by for immediate use. For example, a patient having AF-ICD does not have to spend time to insert the cassette, align the housings, etc. Such configuration of the system 100 may be referred to as a stand-by configuration.

To bring the system 100 to the ready-to-use configuration from the stand-by configuration, the user pushes the housings 310 and 320 toward each other along the axis Z (passing the distance p). The axial movement brings the threads 321a and 311a in contact and permits their engagement. The user continues to attach the housings via the threads 311a and 321a. As the housings move toward each other via the threads 311a/321a, the gas input port assemblies 361 and the cannula/needle assemblies 205 cooperate to puncture the cartridges 210. The system 100 is in the ready-to-use configuration.

The diameters of the threads, the order of engagement, and other connection elements may be varied as would be understood by one of skill in the art. In one of the preferred embodiments, the threads may be in a form a wide channel and corresponding channel guide. Any combinations of the two threads are contemplated. The threads that are engaged are preferably the same type or threads. For example, if the upper threads 311a are right threads, the upper threads 321a are also right threads. However, the pairs of upper and the lower threads may be same or different, right threads or left threads, the upper threads may be right threads and the lower threads may be left threads and visa versa and so on. For example, in reference to the variant shown in FIG. 14B, the threads 311a and 321a may be right threads or left threads, and the threads 311b and 321b may be right threads or left threads, and so on. Preferably, the direction of the upper threads and the lower threads is different.

Also, in a different embodiment, the internal diameter of circumferential opening of the lower housing 320 may be smaller than the external diameter of the upper housing 310, with the external surface of the lower housing 320 and the internal surface of the lower housing 310 each having a set of upper and lower threads. In this embodiment, the connection mechanism is similar to the mechanism in the embodiment shown in reference to FIG. 14A.

Figure 14D:
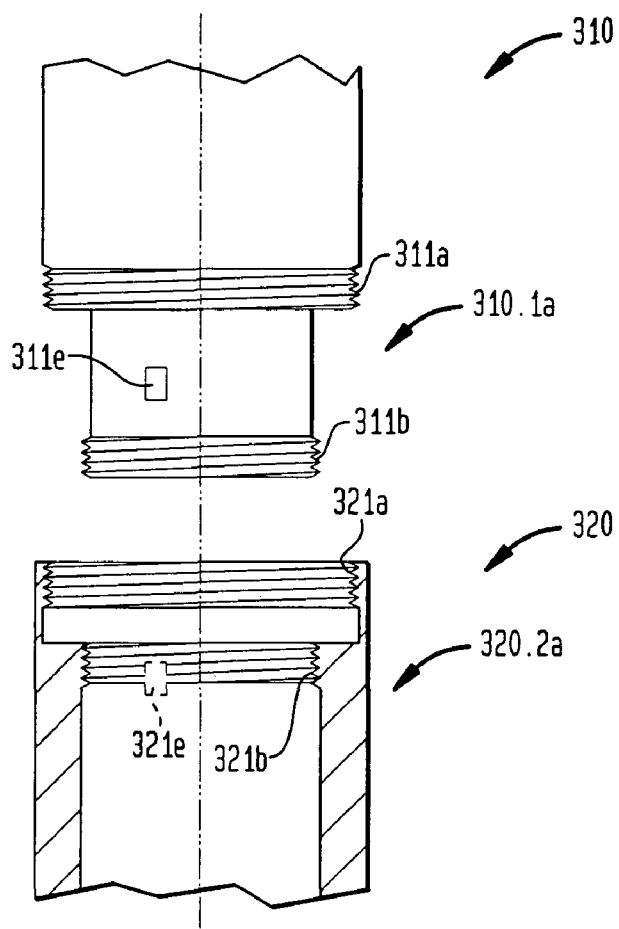
FIG. 14D is a side, elevational, cross-sectional, schematic view of another embodiment of the specialized threaded connection shown in FIG. 14A.

Referring to FIG. 14C, the relative lateral stability of the housings 310 and 320 may be improved by incorporating a directional channel or stop/slot arrangement between the upper and lower threads. FIG. 14D shows a side cross-sectional view of the threaded areas 310.1 and 320.1 in one of the preferred variants of the embodiment shown in FIG. 14A. As seen in FIG. 14D, the threaded area 310.1a includes at least one raised extension 311e located in the area 311c between the threads 311a and 311b. The extension 311e may have various shapes, such as convex, round, square and rectangular shapes. The threaded area 320.2a has a corresponding recessed slot 321e located at the threads 321b. The shape of the slot 321e matches the shape of the extension 311e. Preferably, the extension 311e and the slot 321e extend vertically along the axis Z. More preferably, the extension 311e, if inserted into the slot 321e, can be moved up and down along the slot 321e. The locations of the extension 311e and the corresponding slot 321e may be indicated on the external surfaces 310.1 and 320.1 of the housings 310 and 320.

Figure 14E:
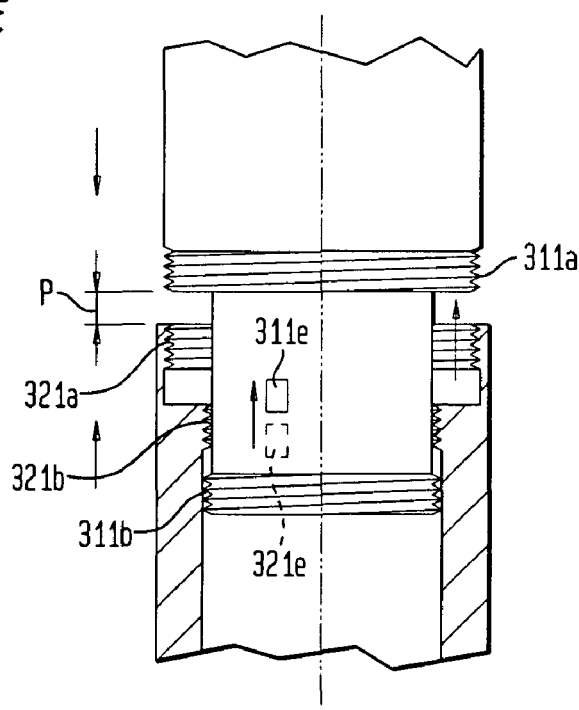
FIG. 14E is a side, elevational, cross-sectional, schematic view of the embodiment shown in FIG. 14D.

The housings 310 and 320, which have the specialized threaded connection showed in FIG. 14D, are transferred to a standby configuration in the same manner as shown in reference to FIG. 14B. The threads 311b clear the threads 321a, and then come in contact and engage the threads 321b. The threads 321b are engaged via the threads 311b until the threads 321b are above the threads 311b. FIG. 14E shows the locations of the threaded areas 310.1 and 320.1 in the standby configuration of the system 100. The threads 321a are not yet engaged to the threads 311a, being separated by the distance p. The threads 311b prevent loose detachment of the housings 310 and 320. The extension 311e and the slot 321e are aligned. The extension 311e and the slot 321e may be aligned by virtue their positions on the respective housings. In another variant, the alignment is achieved by preventing further circular movement along the threads 311b and 321b. In another variant, after the housings 310 and 320 clear the lower threads 311b and 321b, the user may manually align the extension 311e and the slot 321e on the basis of the alignment indicators on the external surfaces 310.1 and 320.1.

To transfer the system 100 to the ready-to-use configuration, the user pushes the housings 310 and 320 toward each other. The extension 311e engages the slot 321e, guiding the housings 310 and 320 toward each other in the course of the axial movement. After the extension 311e travels the distance p in the slot 321e, the threads 321a engage the threads 311a.

In the preferred variant, the upper threads 311a/321a and the lower threads 311b/321b have different thread direction. Thus, the upper threads may be right threads and the lower threads may be left threads, or visa versa.

In use, the patient inserts the cassette 200 into the lower housing, places the upper housing 310 over the lower housing 320 until the initial connection between the interfacing members/keys is achieved and the lower threads 311b are in contact with the lower threads 321b. Then, holding the upper housing still, the patient turns the lower housing 320 in a first circular direction (e.g., clockwise) until the lower threads clear each other and/or the extension 311e prevents further engagement of the lower threads. The extension 311e/slot 321e may be positioned to align at the point the lower threads are cleared. Alternatively, the arrangement of the extension 311e/slot 321e may involve the extension 311e stopping further clockwise movement of the lower housing 320. The patient pushes the housings 310 and 320 together via the extension 311e/slot 321e and the upper threads 311a and 321a come in contact. The direction of the upper threads is reversed, and the patient must now turn the housing 320 in a second circular direction (e.g., counterclockwise).

Figure 14F:
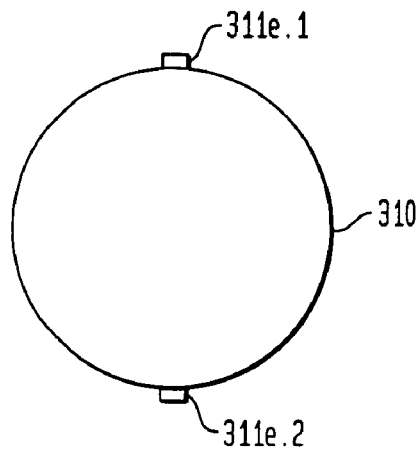
FIG. 14F is a top, elevational, schematic view of another embodiment of the specialized threaded connection used in the system of the present invention.
Figure 14G:
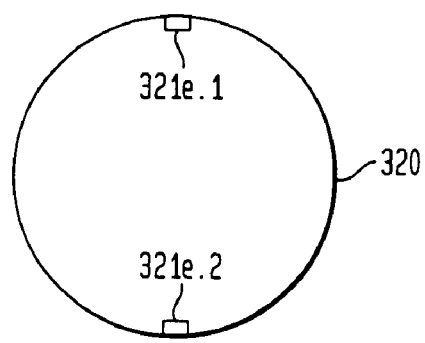
FIG. 14G is a top, elevational, schematic view of the embodiment shown in FIG. 14F.

In another embodiment, there may be two raised extensions 311e.1 and 311e.2 and two corresponding slots 321e.1 and 321e.2 (FIGS. 14F and 14G). The use of two extension/slot pairs provides additional strength to the threaded connection. The locations of the extensions, slots and threads may vary, including any variation known to those of skill in the art. For example, the upper housing 310 may have the slot(s) and the lower housing 320 may have the extension(s).

Figure 15A:
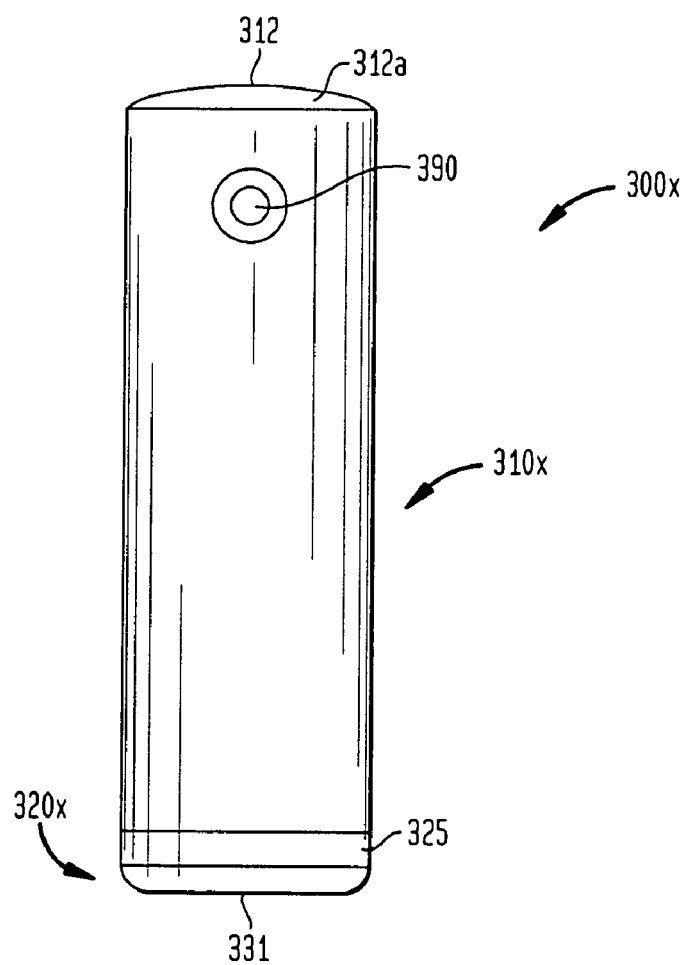
FIG. 15A is a side, elevational, schematic view of an alternative embodiment of the body of the therapeutic gas administration system in accordance with the present invention.
Figure 15B:
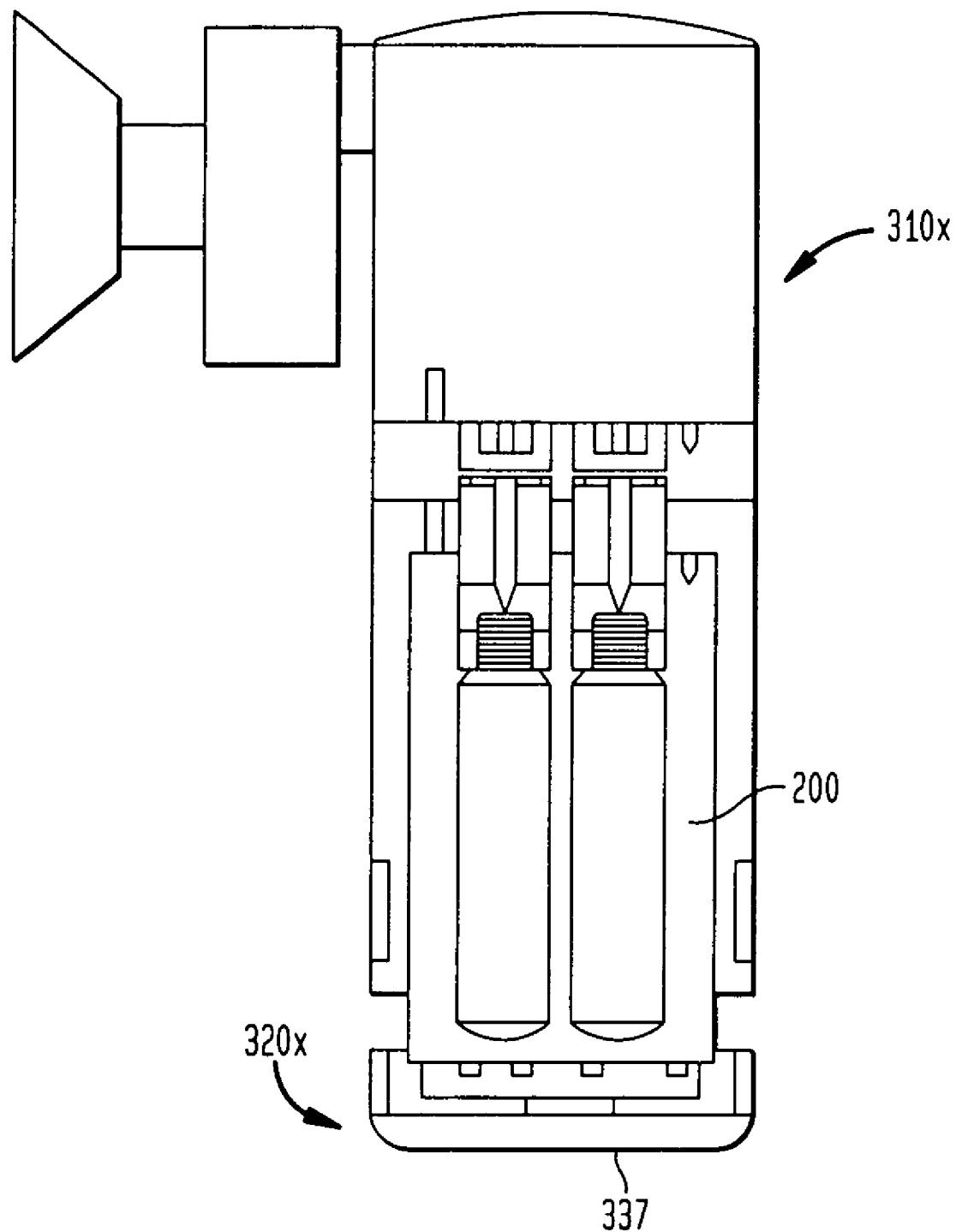
FIG. 15B is a side, elevational, partially cross-section, schematic view of the body shown in FIG. 15A.

An alternative embodiment of the body of the therapeutic gas administration system 100 is shown in FIGS. 15A and 15B. In this embodiment, the body 300x includes an upper housing 310x and a bottom cap 320x. All other features of the system 100, the cassette 200 and the cartridges 210, with the exception of the different structural division of the body 300x, have been described in reference to the system 100 and may be present with respect to this embodiment.

The gas control and delivery system 350 may include a number of preferred, additional, and/or alternative features some of which are briefly described below. The components of the system 350, such as valves and sensors, may have various structures, including those known in the art.

In reference to FIG. 11A, the gas input system 360 may include one input pressure-sensing block 363. Also, the structure of the block 363 may include elements and components known to those skilled in the art. For example, a miniature pressure sensor for a metered dose inhaler is disclosed in U.S. Pat. No. 6,138,669, which is incorporated herein by reference. Although such inhalers greatly differ from the system 100, some of the structures, components and operations of the pressure sensor may be suitable for use with the system 100 and the description of such structures, components and operations in the '669 patent are incorporated herein by reference.

In reference to FIG. 8A, if the natural pressure-driven movement of gases from the cartridges 210 into the blender 370 may be insufficient to effect good mixing. In another embodiment, the interior shape of the blender 370 may be modified to increase gas turbulence. The inclusion of appropriately placed gas baffles is one of the possible modifications. In another modification, the blender 370 may include a mixing fan. The mixing fan may be powered by a battery or may be driven by the flow of the incoming gas. Also, the structure of the blender 370, as well as the mixing structures of the system 350 as a whole, may include elements and components known to those skilled in the art. For example, various gas mixing devices and structures are disclosed in U.S. Pat. Nos. 5,887,611, 5,727,545, 4,722,333 and 5,159,924. Although such devices and structures greatly differ, some of the structures, components and operations of these devices and structures may be suitable for use with the system 100 and the description of such structures, components and operations in the '611, '545, '333, and '924 patents are incorporated herein by reference.

The gas output and control system 380 may include various structures and components, including those known to those skilled in the art. For example, U.S. Pat. No. 5,034,107 discloses a method of identifying nitrous oxide and determining its concentration. Although the devices and structures of the '107 patent greatly, some of the structures, components and operations of these devices and structures may be suitable for use with the system 100 and the description of such structures, components and operations in the '107 patent is incorporated herein by reference.

Figure 16A:
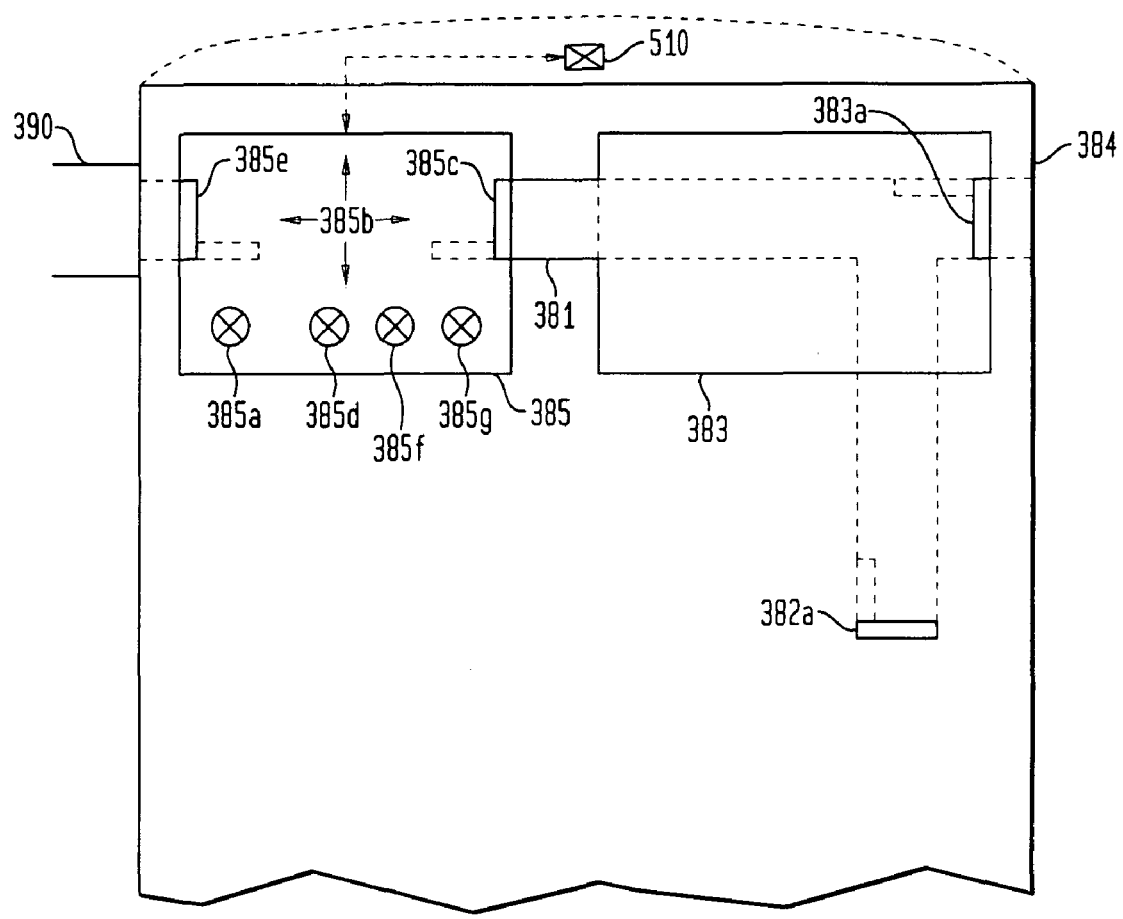
FIG. 16A is a side, elevational, cross-sectional, schematic view of one embodiment of a gas content block of the gas output/control system used in the system of the present invention.

FIG. 16A shows an embodiment of the gas content block 385. In addition to the content sensor 385a, the block 385 may include a holding chamber 385b, a holding chamber entry valve 385c, a pressure sensor 385d, a holding chamber exit valve 385e, a non-oxygen gas content sensor 385f, and a temperature sensor 385g. Each of the sensors and valves may be present or absent. The sensors may be separate devices or may be part of the same structural component. The holding chamber 385b has a pre-determined volume. It serves to accumulate the gas before it is provided to a patient. The holding chamber entry valve 385c control entry of gases from the connective tubing system 381 into the holding chamber 385b. The pressure sensor 385d measures pressure of gases in the holding chamber 385b. The holding chamber exit valve 385e controls exit of gases from the holding chamber 385b to the patient outlet 390. The non-oxygen gas content sensor 385f measures concentration of gases other than oxygen, such as $N_2O$ or $CO_2$. The temperature sensor 385g measures the temperature inside the holding chamber 385b. The sensors and valves of the gas content block 385 may contain other component, including electronic components that communicate with the processor/controller 510 in the domed area 312a.

Figure 16B:
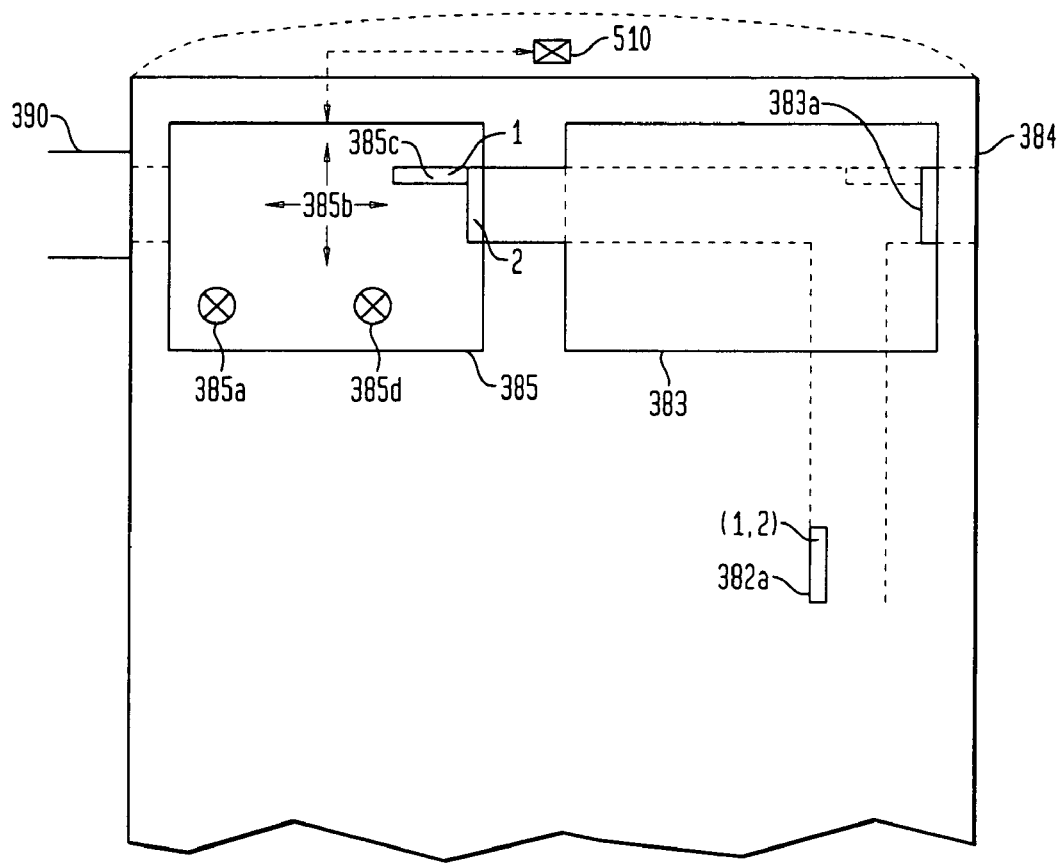
FIG. 16B is a side, elevational, cross-sectional, schematic view of operation of one embodiment of the gas content block shown in FIG. 16A.

One mode of operation of the sensing block 385 is illustrated in FIG. 16B. Upon a signal from the patient interface assembly (e.g., from the demand valve 410), the processor/controller 510 opens the primary control valve 382a and the sensor chamber entry valve 385c (position 1). The gas enters the holding chamber 385b fro the blender 370. The pressure sensor 385d measures the pressure in the holding chamber 385b. The volume of the holding chamber 385b is pre-determined, known and stored in the data block 524. The combination of known volume and pressure measured by the pressure sensor 385d provides information about the molar amount of the gas. Once the desired amount of gas is in the holding chamber 385b, the holding chamber entry valve 385c is closed (position 2). The gas accumulated in the holding chamber 385b is provided to a patient via the patient outlet 390. The timing of closing of the valve 385c may be selected to accumulate the gas in the holding chamber 385c prior to each breath by the patient.

The gas content block 385 may function as a gas conservation device. A conserving device for use with administration of oxygen is disclosed in U.S. Pat. No. 6,220,244, the disclosure of which is incorporated herein by reference in its entirety. A gas conservation device may conserve gas by providing the gas to a patient at a proper time in the inspiration cycle. The conservation device may provide a patient with a properly timed tidal volume of therapeutic gas that is smaller then the total volume of gases the patient inhales. The tidal volume of the gas is delivered as a bolus at the appropriate point in the inhalation cycle, followed by inhalation of room air. The total inhaled volume includes both the therapeutic gas and the room air.

With reference to FIG. 16A, timely opening of the valves 382a, 383a, 385c, and/or 385e may allow the use of the gas content block 385 in a conservation device mode. The room air may be provided via the air intake port 384. The operation of the gas content block 385 in the conservation device mode may be controlled by the processor/controller 510 on the basis of instructions and data stored in the memory 520. The gas content block 385 may function in a conservation device mode with or without the holding chamber exit valve 385e.

Figure 16C:
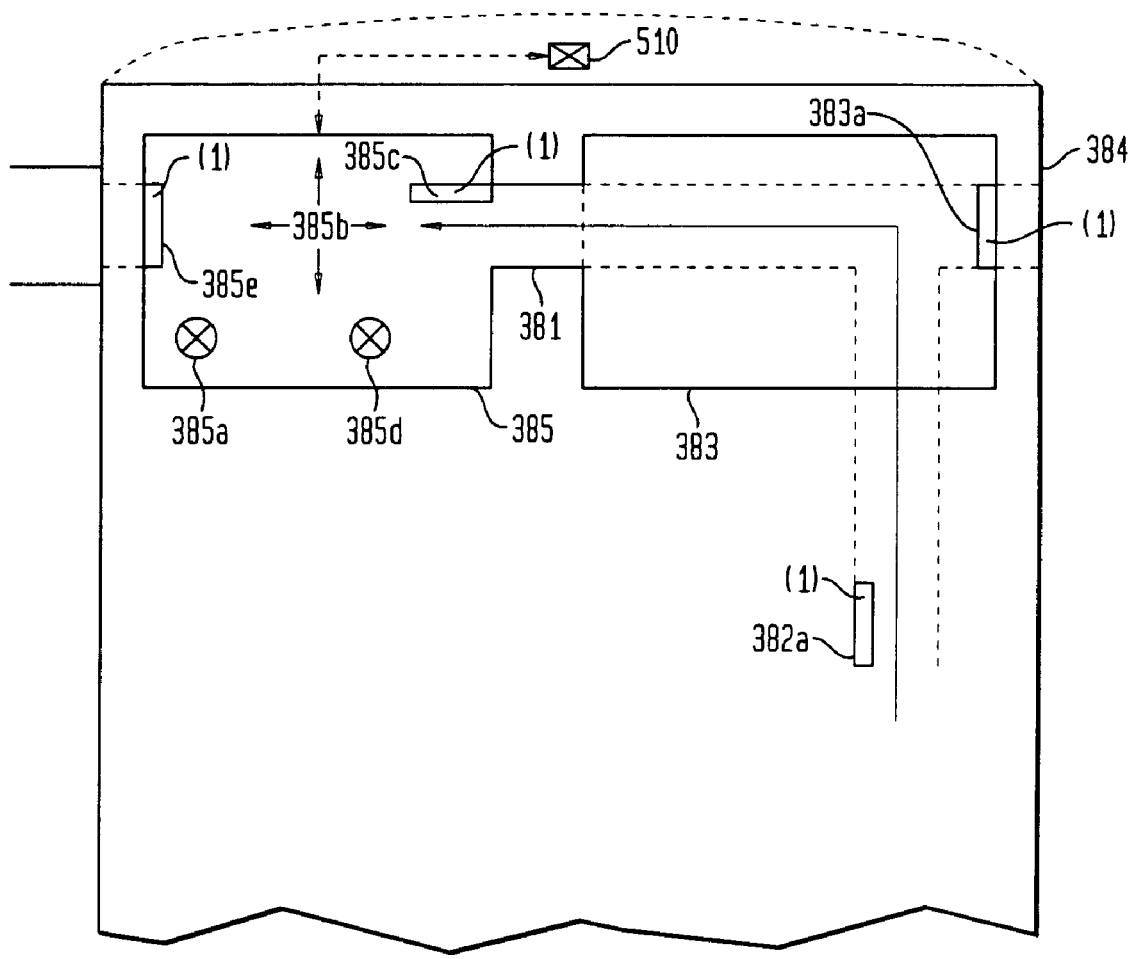
FIG. 16C is a side, elevational, cross-sectional, schematic, partially schematic diagram of one embodiment of operation of the gas content block in a conservative device mode of the system of the present invention.
Figure 16D:
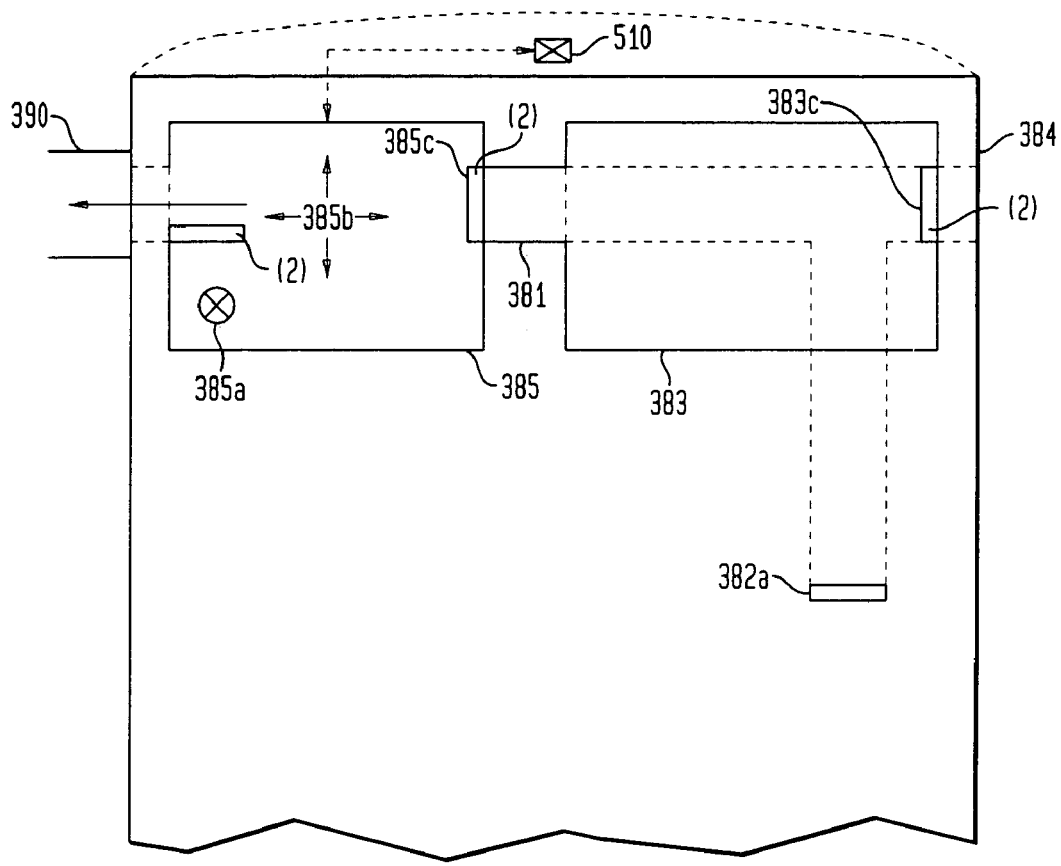
FIG. 16D is a side, elevational, cross-sectional, partially schematic view of the embodiment shown in FIG. 16C.
Figure 16E:
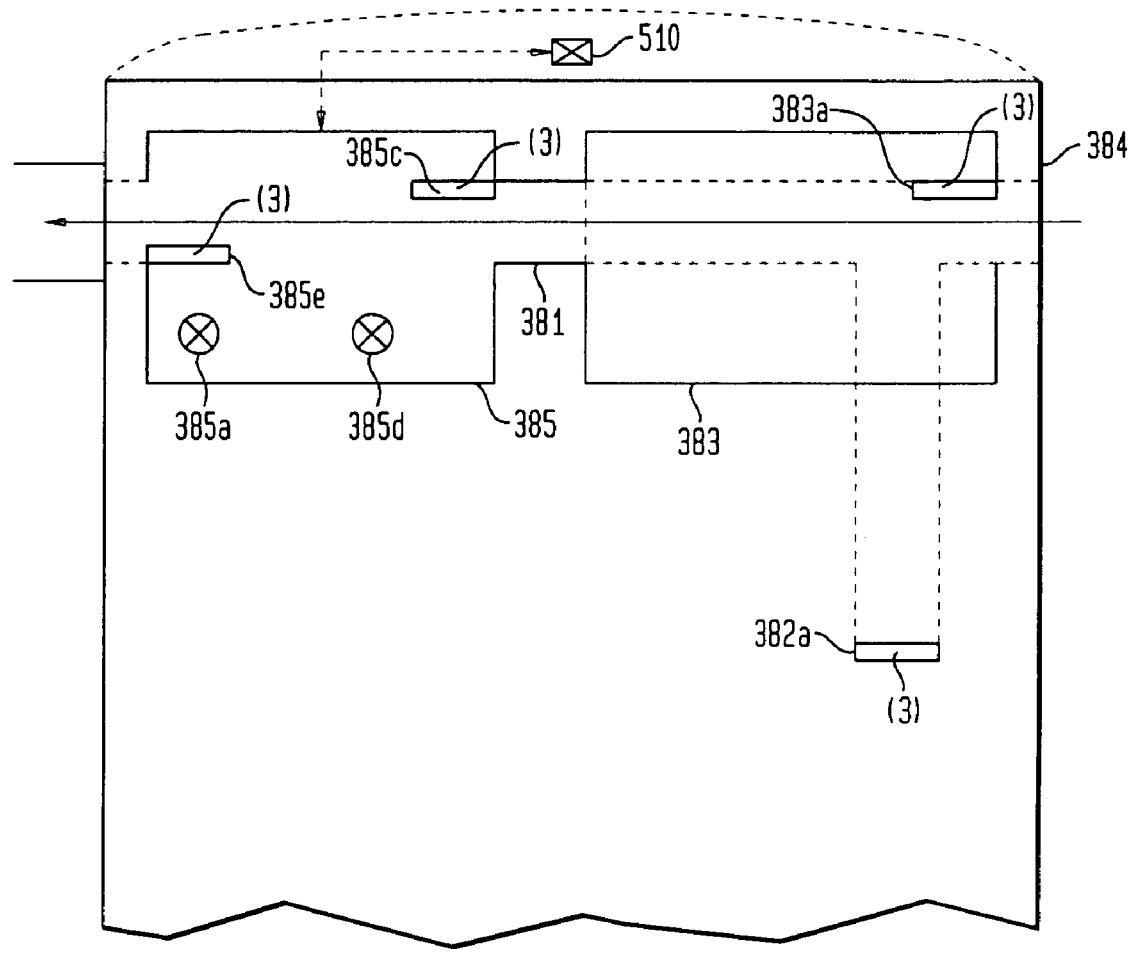
FIG. 16E is a side, elevational, cross-sectional, partially schematic diagram of the embodiment shown in FIG. 16C.

One variant of the conservation device mode operation of the block 385, which includes the valve 385e, is illustrated in FIGS. 16C-16E. As shown in FIG. 16C, in the position (1), the valves 385c and 382a are open. The gas flow from the blender 370 into the holding chamber 385c. Once the pressure in the holding chamber 385c reaches the desired value (e.g., as measured by the pressure sensor 385d), the valve 385c is closed and the valve 385e is opened (FIG. 16D, position (2)). The therapeutic gas flow from the holding chamber 385b through the patient outlet 390. The amount of gas in the holding chamber 385c is selected to provide a patient with smaller volume of gas than the total inhaled volume. The timing of the opening of the valve 385e is selected to provide the patient with therapeutic gas at the desired point in the inhalation cycle. Next, at the desired time in the inhalation cycle, the primary valve 382a is closed, and the holding chamber valve 385c and the air intake valve 383a are opened (FIG. 16E, position (3)). Air flows from the air intake port to the patient outlet valve 390. After the desired amount of air is provided, the system returns back to the position (1) (FIG. 16C).

In general, it is important to minimize the possibility that a wrong gas or gas mixture is used. It is also important to prevent misuse of the system 100, such as in using unauthorized gases or gas mixtures. For this purpose, the cassette 200 and the body 300 may have various gas-specific structural features or elements. Some of such features had been already described (e.g., the matching of arrays 206a and 326a). Other gas- and/or dose-specific features may include, for example, varying the distance Y1 from the bottom surface 328ab of the disk 328a to the horizontal bottom surface 320.2a of the lower housing and/or the distance Y2 from the top surface 328aa of the disk 328a to the gas input port assemblies 361 (FIG. 7C). Unless the height h1 of the cassette 200 (FIG. 4A) and the distances Y1 and Y2 are correct, the cassette 200 cannot be used with a given body 300. Thus, the height h1 and the distances Y1 and Y2 may be made different for different gases and doses, providing additional gas- and dose-specificity. The embedding depth X of the cartridges 210 may also be used in this manner if desired. Also, the cassettes 200 and/or the disk 328a may have different colors for different doses and/or indicated gas mixtures.

In yet another specific preferred feature, the cassette 200 may be identified with a unique identifier for each individual cassette. The unique identifier, such as a serial number or the like, may be embedded, imprinted or otherwise permanently affixed to the exterior surface of the cassette. An alternative unique identifier is an RFID chip. In addition to providing information about the gas or gas mixture and the dose contained in the identified cassette, the identifier allows tracing and/or tracking the origin, distribution route and use of the cassettes. Since each cassette represents a single dose, the unique identifiers assigned to each cassette can be used to track distribution and use of each cassette.

The following non-limiting example is useful. 12 unit dose cassettes containing 65% $N_2O$/35% $O_2$ mixture for 4 minutes of gas administration are shipped to a patient with an AF-ICD. The patient claims to have used each of the 12 cassettes in connection with AF-ICD use. The patient's physician determines, upon routinely downloading data from the patient's AF-ICD, that the patient's AF-ICD was used only 8 times. The physician may request an explanation for the discrepancy.

In another non-limiting example, a physician based in an office or a small clinic orders 32 unit dose cassettes of $N_2O$ and $O_2$ for use during dermal biopsy punches. The serial numbers of the cassettes are noted on shipping and receiving records. The use of each cassette might therefore be accounted for by keeping records of which patient each cassette was used for. In addition to the permanently affixed unique identifiers, the cassette may be labeled by tear-off label strip that covers the top surfaces of the cannula/needle assemblies. The tear-off strip may list the contents and the serial number of the cassette. The strip may be removed from the cassette and placed in a logbook by the patient or medical staff member after the cassette is used, providing an additional method of controlling the use of the cassettes. The physician may later review the log to confirm that the cassettes were used as intended.

Figure 17A:
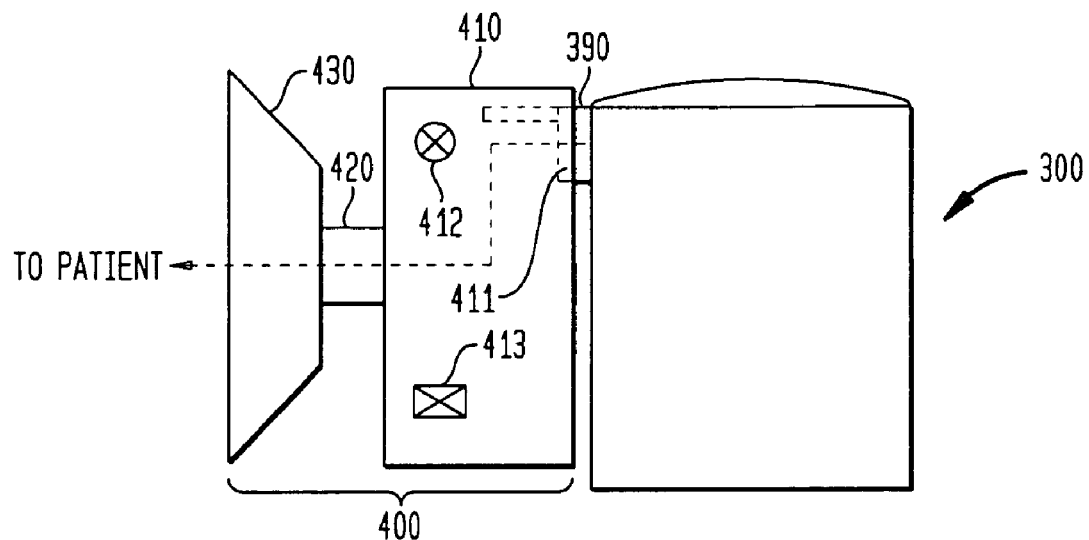
FIG. 17A is a side, elevational, schematic view of an embodiment of the patient interface of the therapeutic gas administration system of the present invention.

Various features, additions and alternatives of the patient interface assembly 400 are also provided. The assembly 400 may include any demand valve 410, including those known in the art. The demand valve 410 is a component that controls the flow of gas from the patient outlet 390 to a patient upon the action/demand by the patient. The patient can exercise control in various ways, for example, by creating negative inspiration pressure inside the demand valve 410 or by manually pressing a button or a lever. In one embodiment, the demand valve 410 may include, for example, a demand-controlled valve 411, an inspiration pressure sensor 412, and a communication block 413 (FIG. 17A). The demand-controlled valve 411 opens and closes the flow of gases from the patient outlet 390. The valve 411 may be directed by the processor/controller 510. Alternatively, the valve 411 is controlled directly by the inspiration pressure sensor 412. The inspiration pressure sensor 412 measured the inspiration pressure created by the patient at the facemask 430. The communication block 413 includes electronic components for communicating with the processor/controller 510. For example, the block 413 may inform the processor/controller 510 of the inspiration pressure measured by the sensor 412, provide the controller 510 with the time of the beginning of gas administration, and so on. Also, the communication block 413 may receive signals from the processor/controller 510. For example, the processor/controller 510 may signal to the block 413 to close the demand-controlled valve 411 regardless of the inspiration pressure. Such closing signal may be communicated, for example, if the processor/controller 510 received a signal from the input pressure sensing block(s) 363 that the pressure of incoming gas is outside the pre-determined range. The closing of the valve 411 may provide an added measure of safety.

In another variant, a patient manually activates the demand-controlled valve 411, for example, by pressing a button or pulling a lever.

Alternative embodiments of the patient interface assembly 400 are also provided (FIGS. 17B-17E). Also, the patient interface assembly 400 may include elements and components known to those skilled in the art. For example, demand-activated gas control components are disclosed in U.S. Pat. Nos. 5,839,436 and 5,692,492. Although the devices disclosed in these patents greatly differ from the system 100, some of the structures, components and operations may be suitable for use with the system 100 and the description of such structures, components and operations in the '436 patent and '492 patent are incorporated herein by reference.

Figure 17B:
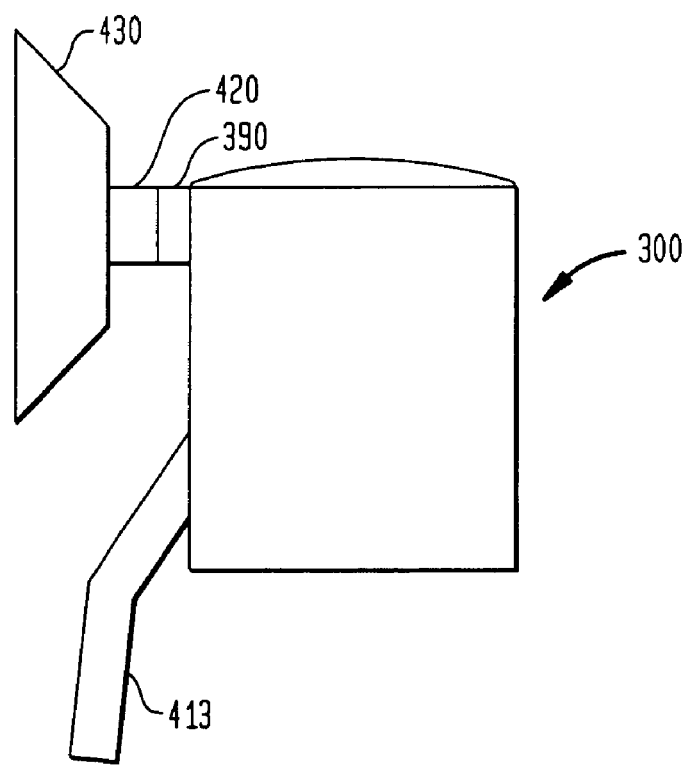
FIG. 17B is a side, elevational view of another embodiment of the patient interface of the therapeutic gas administration system of the present invention.
Figure 17C:
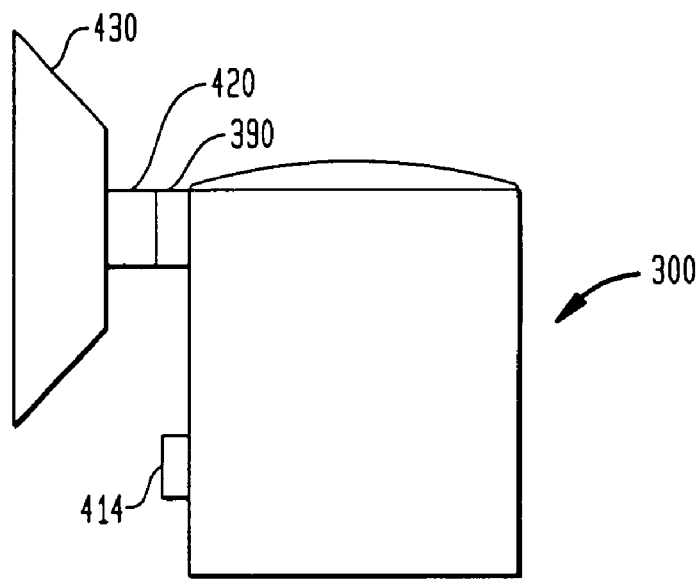
FIG. 17C is a side, elevational view of another embodiment of the patient interface of the therapeutic gas administration system of the present invention.

In the embodiment shown in FIG. 17B, the patient interface assembly 400 does not include an inspirationally activated demand valve. Instead, a lever 413 initiates the flow of therapeutic gas to a patient functioning as a manually activated demand valve. Once the lever 413 is pulled, the gas begins to flow through the connector 420 into the facemask 430. In one of the preferred variants, the flow is stopped upon an expiration of a pre-determined period of time or upon flow of a pre-determined volume of gas through the gas control and delivery system 350. A non-limiting example of such pre-determined volume is about 500 ml to 700 ml. The interruption of the flow may be effected for example by a signal from the processor/controller 510 to the primary control valve 382a. In another embodiment, shown in FIG. 17C, the lever may be replaced with a button 414.

A normal tidal volume inspired by a patient is believed to be approximately 500 ml to 700 ml. To conserve therapeutic gas, it may be desired to provide the patient with therapeutic gas that comprises only a portion of the tidal volume (e.g., 25 ml to 200 ml) at a point in the inspiration cycle when the inhaled gas reaches deeper and greater portion of the lungs so it has greater effect. The outside air is usually provided as the rest of the inspired tidal volume. The therapeutic gas portion delivered in such a manner is sometimes referred to as a bolus.

Figure 17D:
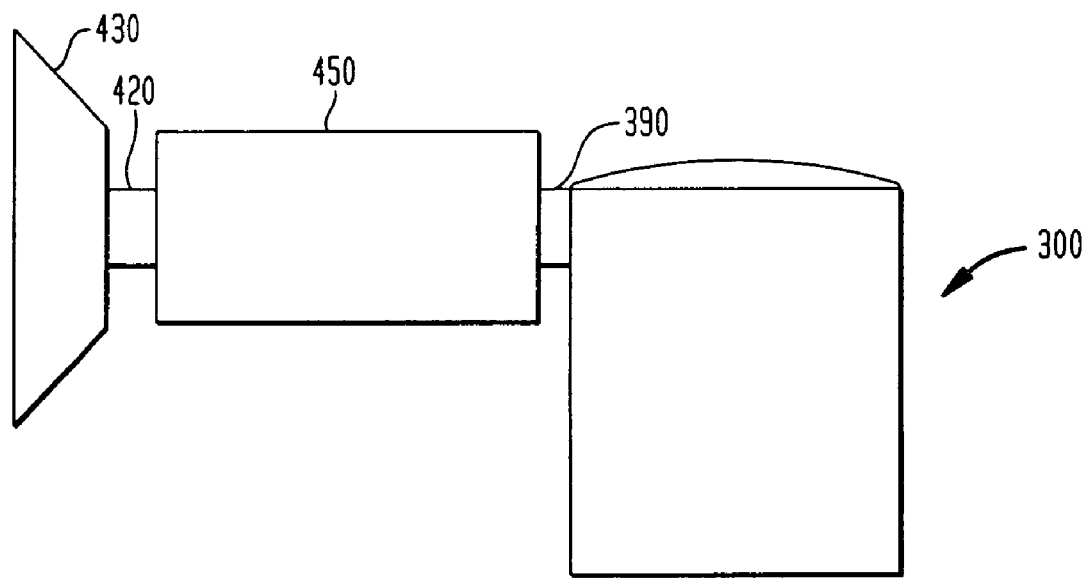
FIG. 17D is a side, elevational view of another embodiment of the patient interface of the therapeutic gas administration system of the present invention.

In general, the demand valve 410 and the gas conservation device may be completely outside the body 300, partially inside/outside the body 300, or completely internal. An example of internal gas conservation device was described in reference to FIGS. 16C-16E. The demand valve 410 may replaced by an external gas conservation device 450 (FIG. 17D). The structure and operation of the gas conservation demand 450 may vary, including structures known to those of skill in the art. The description of the variant of the internal conservation device (FIGS. 16C-16E) provides good illustration of the suitable structure and operation of the device 450.

Figure 17E:
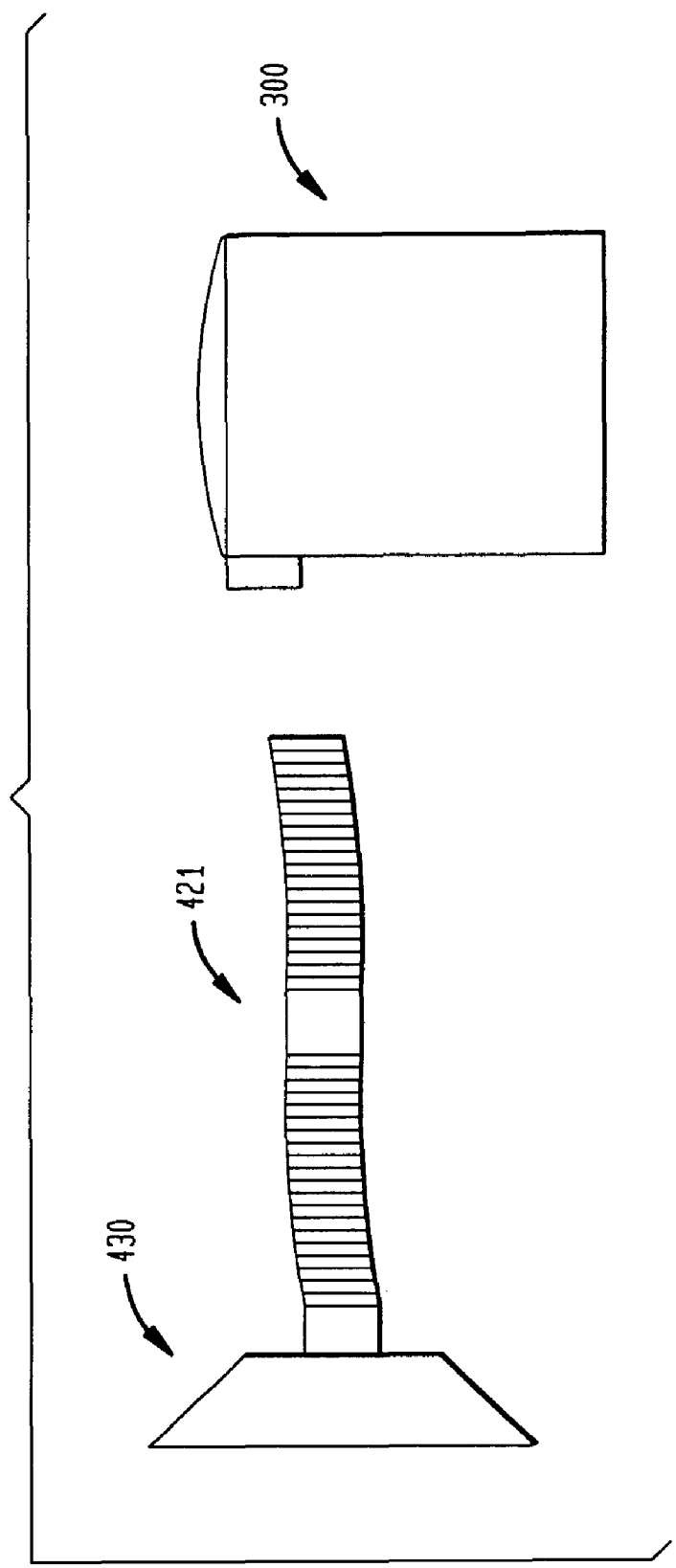
FIG. 17E is a side, elevational exploded view of another embodiment of the patient interface of the therapeutic gas administration system of the present invention.

An alternative embodiment of the connector 420 is also provided (FIG. 17E). In this embodiment, the connector 420 is a flexible tube 421, preferably having sufficient length to allow a patient to use the system 100 with the body 300 being in the patient's lap or side, while the facemask is pressed against the patient's face.

The facemask 430 may be replaced with a mouthpiece. A nose clip can be used with the mouthpiece to prevent the intake of air through the nose that would dilute the gas inhaled through the mouthpiece. A nose mask may also replace the facemask 430. While using the nose mask, the patient is expected to keep the mouth closed in order to prevent the dilution of gas inhaled through the nose mask. It should be noted that use of facemask is preferred for gas mixtures that produce some relaxation/loss of control in a patient (e.g., $N_2O$- or Xe-containing mixtures). The relaxation and the attendant loss of control may result in dilution of intended inhaled gas by outside air if mouthpiece or nose mask is used.

Xenon is a rare and expensive noble gas. Xenon is produced from air via an air liquefaction process. Xenon is present in the atmosphere at concentrations of less than 1 part per million, and therefore should be conserved as much as possible. Therefore, when using a therapeutic gas mixture containing xenon, it is desirable to recover all that is used, such as the Xe-containing exhaled gas mixture (that may also contain oxygen, carbon dioxide, methane, water vapors, and other constituents). The exhaled xenon-contain ng gas mixture may be processed to extract xenon, which may then be reused after sterilization for the manufacture of a medical gas product for patient use. Xenon recycling may reduce the overall cost of xenon therapy and conserve a rare gas.

Figure 18:
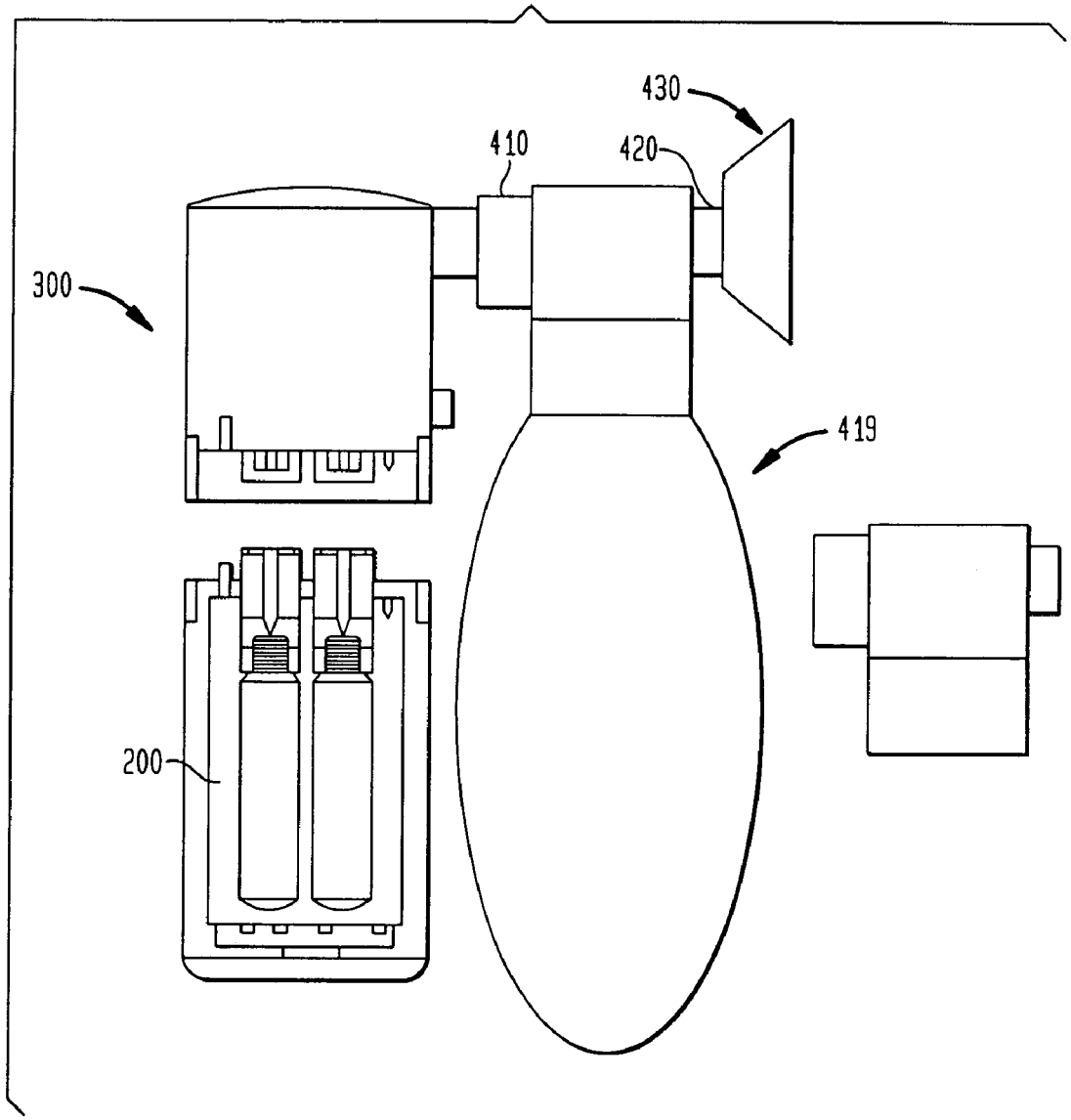
FIG. 18 is a side, elevational view of another embodiment of the therapeutic gas administration system of the present invention suitable for administration of gas mixtures containing xenon.

In another preferred embodiment, in relation to the administration of xenon-containing gases or mixtures, the invention provides a modification of the patient interface 400 designed to conserve xenon and to reduce the cost per dose related to xenon. In this embodiment, the patient interface assembly 400 may include a disposable, hollow re-breathing container 419 having a highly compressible empty balloon 419a (not shown) within the container 419 (FIG. 18). The re-breathing container 419 is attached to the demand valve 410. The balloon 419a can be made of Mylar or other similar material.

In operation, the cassette 200 containing for example $Xe/O_2$ mixture is inserted into the body 300 and system 100 is used in the usual manner. The cassette may contain separate cartridges of 100% xenon and 100% oxygen or two cartridges each containing the xenon/oxygen mixture. The contents of the cassette 200 are blended in the blender 370, flow through the demand valve 410, and are vented into the re-breathing balloon 419a. The mixture in the re-breathing balloon 419a thus contains a proper composition of the $Xe/O_2$ mixture to achieve the desired therapeutic effect. The patient breathes in and out of the breathing balloon 419a via the demand valve 410. The exhaled mixture is returned to the balloon 419a. The re-breathing balloon 419a may be returned to the vendor for reprocessing and extraction of the remaining xenon.

Preferably, the therapeutic gas administration system 100 is portable and may be used in various locations, including hotels, offices and other locations of work, gymnasiums, athletic fields, and the like. To facilitate portability and convenient use, a belt clip may be affixed to the body 300. Also, a lanyard may be connected to the body 300. The lanyard may be attached to a wrist strap (e.g., made of Velcro or similar material). The lanyard may also be connected to a patient's belt. The lanyard is useful for certain therapies that may involve involuntary muscle movement. For example, in regards to self-administration of nitrous oxide/oxygen mixture together with AF-ICD shock, a patient may experience involuntary movement during shock initiation. The involuntary movement (e.g., an outward fling of an arm) may result in loss of control and release of grip on the body 300. The lanyard is intended to prevent the body 300 from flying in the air and causing damage to the patient, other persons, physical surroundings or the system 100 itself.

Figure 19:
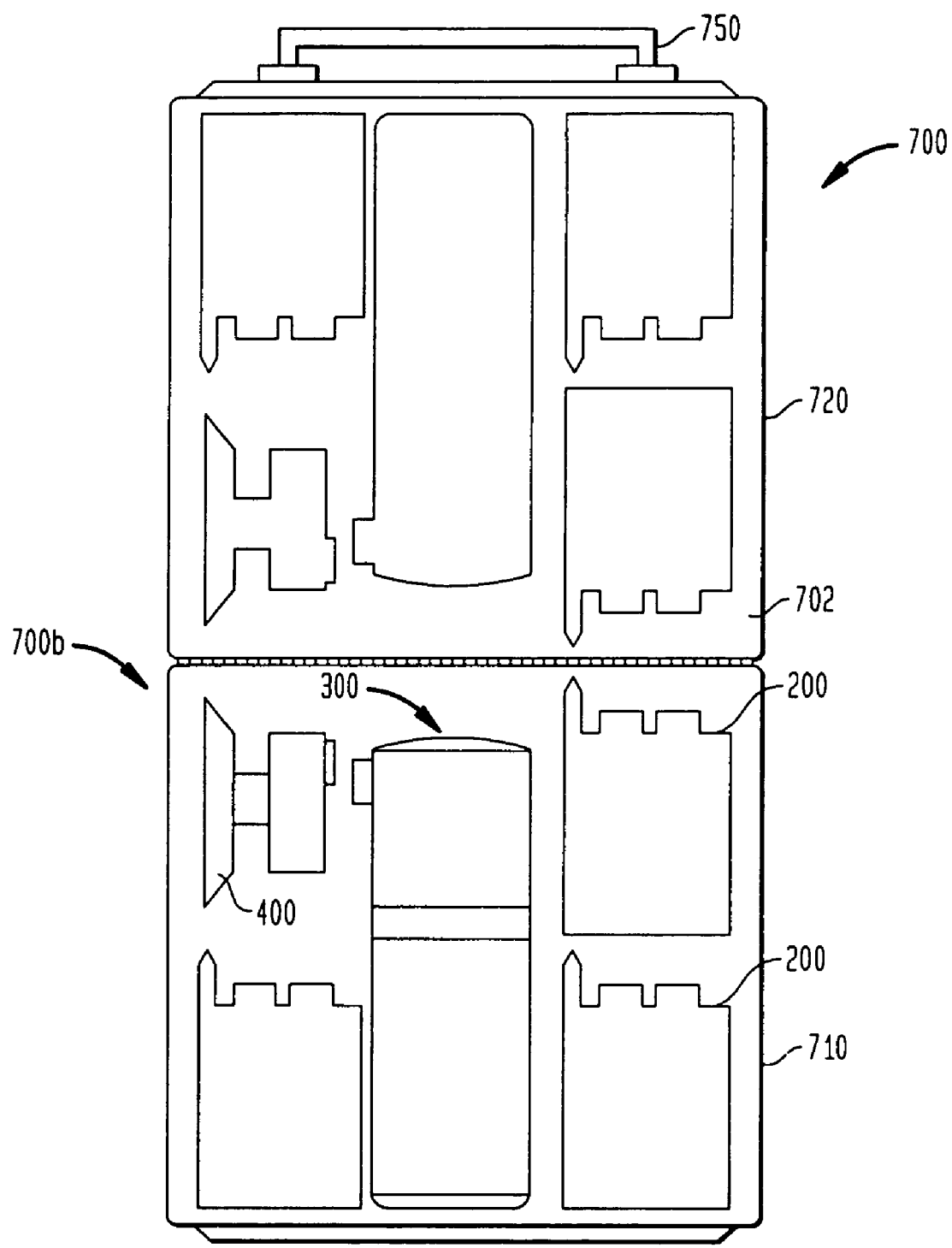
FIG. 19 is a side, elevational view of an embodiment of a hard case for carrying the therapeutic gas administration system of the present invention.

The therapeutic gas administration system 100 may be provided with a hard carrying case 700 (FIG. 19). The case 700 facilitates portability and may be used to transport the system 100. As seen from FIG. 19, the carrying case 700 includes a bottom portion 710 and a top portion 720. The case is opened and closed by attaching and releasing the portions 710 and 720. In FIG. 19, the case 700 is shown opened.

The case 700 includes an external covering 700a (not shown) and an internal area 700b. The external covering 700a may be made of a plastic (e.g., PVC, PET or styrene), metal (e.g., aluminum), or a combination of plastic and metal. The covering 700a additionally may be coated with a soft, impact-resistant and skid-resistant substance, for example, incorporating silicone. The internal area 700b is the space for placing the components of the system 100. The internal area 700b preferably contains a foam layer 702. The foam layer 702 protects the components of the system 100 and is shaped to firmly hold them inside the case 700. The internal area 700b may be used to place several cassettes 200, the body 300 and the components of the patient interface assembly 400. The carrying case 700 also may include a handle 750 that is hinged and folds flat against the external covering 700a of the carrying case 700.

Figure 20A:
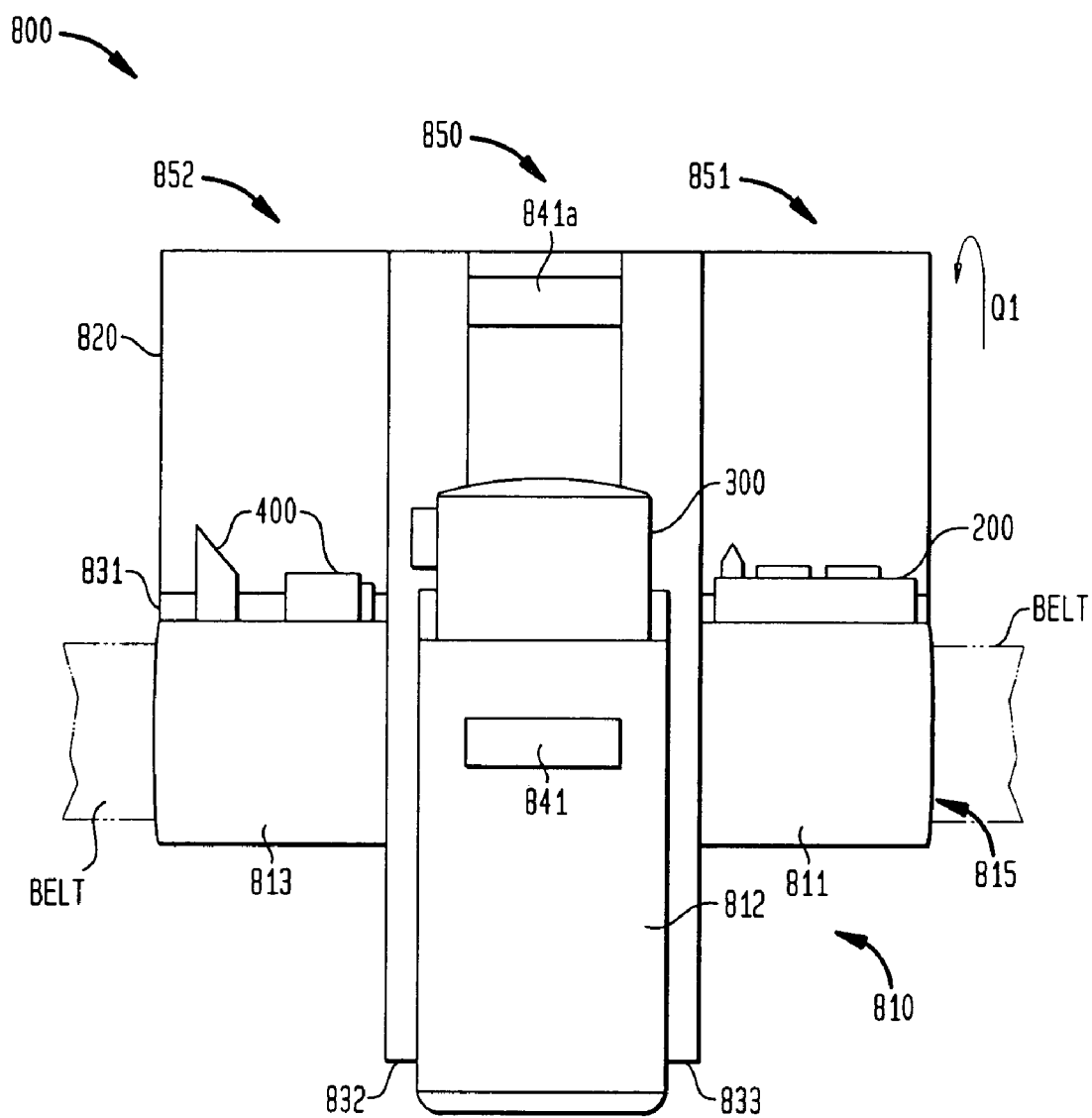
FIG. 20A is a front, elevational view of one embodiment of a soft case for carrying the therapeutic gas administration system of the present invention.
Figure 20B:
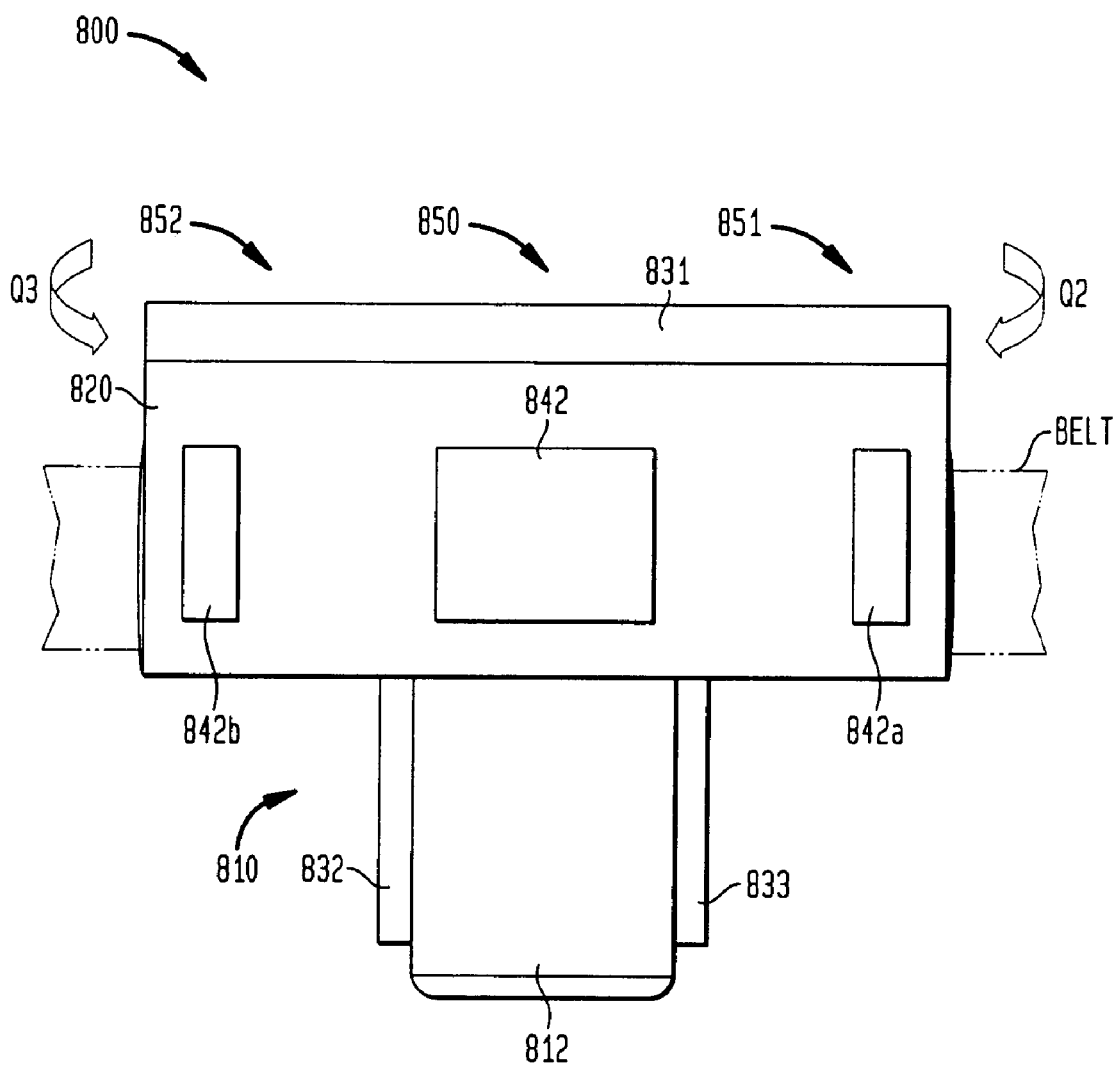
FIG. 20B is a front, elevational view of another embodiment of a soft case for carrying the therapeutic gas administration system of the present invention.
Figure 20C:
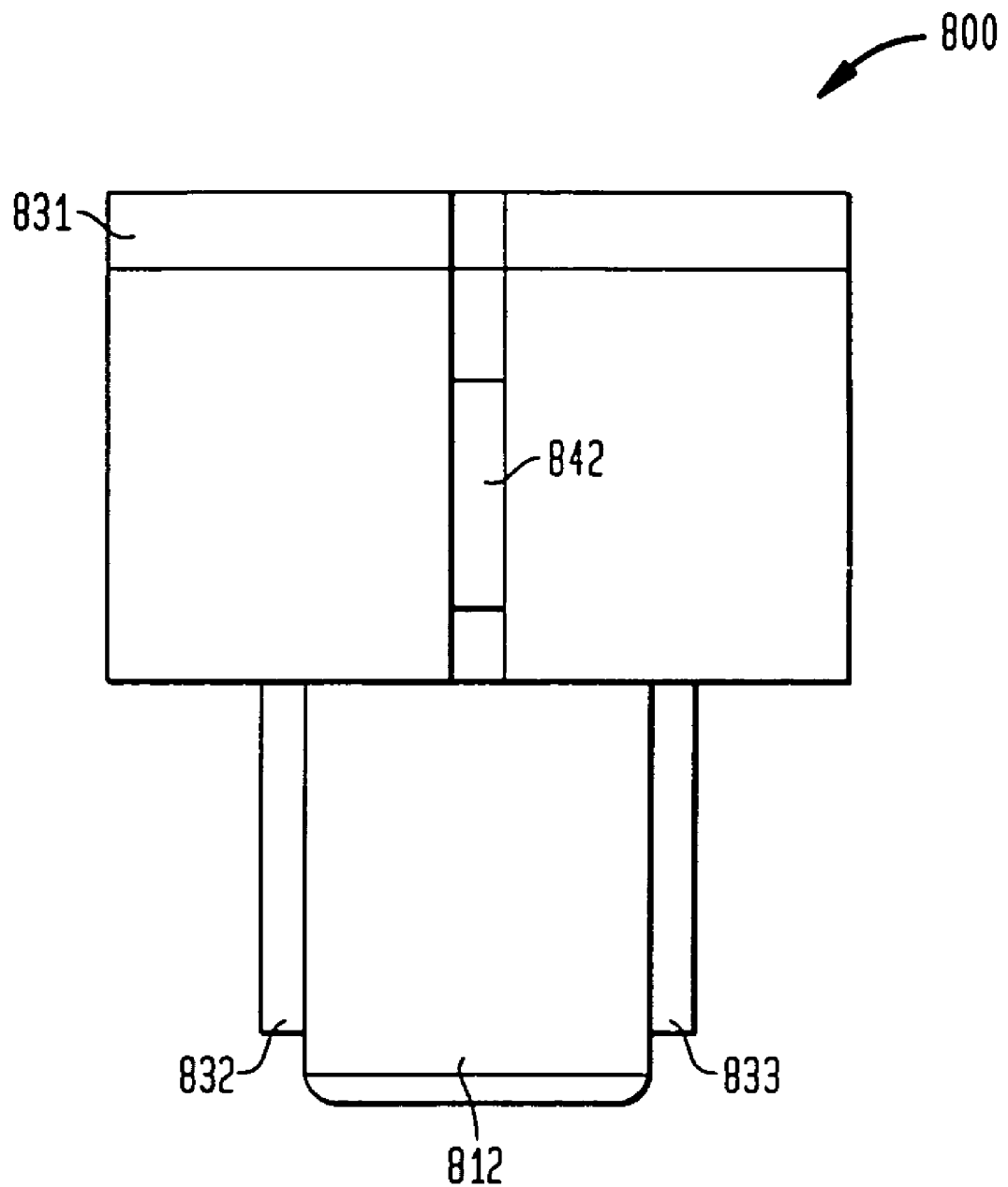
FIG. 20C is a front, elevational view of another embodiment of a soft case for carrying the therapeutic gas administration system of the present invention.

In another variant, a soft carrying case 800 may be provided with the therapeutic gas administration system 100 (FIGS. 20A-20C). The case 800 can be made from soft, durable material that allows folding the case (e.g., nylon or like material). The case 800 includes a pocket portion 810 and a top closure flap 820. The pocket portion 810 has an attachment member 841 and the top closure flap 820 has matching attachment member 841a. The members 841 and 841a may be any typical attachment structures, such as buttons/buttonhole, snap attachment, etc. Preferably, the members 841 and 841a are Velcro strips. An elasticized strip 831 divides the portion 810 and the flap 820. The strip 831 allows folding of the case 800 as shown by arrow Q1. The strip 831 may be made from a suitable elastic material.

The pocket portion 810 has a cassette pocket 811, a body pocket 812, and a patient interface pocket 813 for placing the cassette 200, the body 300 and the components of the patient interface assembly, respectively. The pocket portion 810 may also include a belt opening 815 located transversally to the direction of the pockets. The belt may be threaded through the opening 815, thus attaching the case 800 to a person wearing the belt. Alternatively, the case 800 may be clipped to a belt.

Elasticized strips 832 and 833 divide the case 800 into a central portion 850 and peripheral portions 851 and 852. The central portion includes the body pocket 812, the portion 851 includes the cassette pocket 811, and the portion 852 includes the patient interface pocket 813. The elasticized strips 832 and 833 divide the portions 852/850 and 850/851, respectively. The strips 832 and 833 allow folding of the case 800 in vertical direction. In reference to FIG. 20B, the central portion 850 has an attachment member 842, and the peripheral portions 851 and 852 have attachment members 842a and 842b, respectively. Preferably, the attachment members 842, 842a, and 842b are Velcro strips.

FIG. 20A shows the case 800 in a completely unfolded configuration. The top closure flap 820 can be folded along the elasticized strip 831 (shown by arrow Q1). After folding the attachment member 841a contacts the attachment member 841, holding the folded closure flap 820 in place. FIG. 20B shows the case 800 after it is folded along the portion 831. In the configuration shown in FIG. 20B, the case 800 may wore by threading a belt through the belt opening 815. For storage, the case 800 may then be further folded along the elasticized strip 832 and 833 (shown by arrows Q2 and Q3), with the attachment members 842a and 842b coming in contact with the attachment member 842 to hold the peripheral portions 852 and 853 attached to the central portion 851. FIG. 20C shows the completely folded case 800.

The inventions described herein are further illustrated below in the following non-limiting examples.

EXAMPLE 1

Administration of Nitrous Oxide/Oxygen Mixture to Healthy Volunteers

Initially, pilot studies were conducted on 5 healthy volunteers having medical experience of dealing with patients with AF-ICDs. The volunteers of different ages and weights were selected. The volunteers had experience with $N_2O$ ranging from none to some and from long ago to recent. The volunteers were witnessed and interviewed about their experience. They were asked to visualize their worse historical pain. The volunteers were also asked to provide an input from their patients on how an AF-ICD shock feels, including information about the anxiety generated by memory of the prior shocks before the next shock is initiated.

The volunteers, while being videotaped, were then asked to breathe 65% $N_2O$/35% $O_2$ mixture (expressed in molar percents) for 4 minutes while periodically pressing an activator button to simulate pressing of the shock timer button on an AF-ICD, and to determine the ability to press the timer button while under the effect of gas administration. In one case, the gas administration was extended to 5.5 minutes for the purpose of collection of additional data. The nitrous oxide/oxygen mixture was administered using a prior art $N_2O/O_2$ device using an inspiration-activated demand valve. The prior art device was a typical gas mixing system with an external oxygen source. The purpose of the experiment was to evaluate the volunteers' responsiveness to commands and the ability to self-activate an AF-ICD shock timer. In all cases, the volunteers reported that 2-3 minutes of inhalation were, in their view, sufficient in terms of reduction of anxiety and to allow the volunteers' patients to self-initiate an AF-ICD shock. According to the interviews with the volunteers, the observed anxiolysis was at a level that would be needed for their patients prior the self-initiation of the AF-ICD shock. Within minutes following the end of the nitrous oxide/oxygen administration, all volunteers returned to normal sensory perception levels and their normal work routine. Also within minutes, no residual effects from the administration of nitrous oxide/oxygen mixture were reported.

EXAMPLE 2

Administration of Nitrous Oxide/Oxygen Mixture to Actual Patient Volunteers Having an Implanted AF-ICD Eleven patients having an existing implanted AF-ICD for atrial fibrillation participated in a study that included self-administration of nitrous oxide/oxygen mixture prior to administration of an AF-ICD shock. The patients were asked to breathe 65% $N_2O$/35% $O_2$ mixture for 4 minutes. The nitrous oxide/oxygen mixture was self-administered using the prior art $N_2O/o_2$ mixing system described in Example 1 using an inspiration-activated demand valve under observation. The patients were asked to periodically press an activator button, which was not connected to the AF-ICD, to evaluate their responsiveness to commands and ability to self-initiate an AF-ICD shock timer during the short period of nitrous oxide/oxygen administration. When a patient indicated that he/she was ready to actually self-activate the AF-ICD timer to administer a shock and pressed a button to simulate the self-activation, a physician actually initiated the shock instead of the patient to facilitate gathering of additional behavioral and clinical data during the study.

Physiological data were recorded electro-mechanically and observational data was recorded manually, and the instructions to the patient, therapy session itself and the questioning of the patient after the therapy session were videotaped. All data were collected pre-, peri- and immediately post-study. Additional information generated by the study was based on interviews of the patients by medical staff pre and post study. From baseline starting levels just prior to the study, 65% $N_2O$/35% $O_2$ inhaled by the patients immediately prior to and up to the moment of shock reduced pre-shock anxiety by 48%, shock related intensity by 45%, pain by 60%, and discomfort by 78%, and there were no adverse events. All patients returned to normal sensory perception within 5 minutes after the nitrous oxide/oxygen administration ended. The study showed that a short-term administration of 65% $N_2O$/35% $O_2$ mixture was effective, safe and allowed a rapid return to normal sensory perception and activity. Of note was the fact that the spouses of these patients, who are routine observers of the patients attitudes before, during, and after self-administration of an AF-ICD shock, stated that they observed a marked difference in the attitudes and feelings of the patients after the AF-ICD shock was administered in conjunction with administration of nitrous oxide/oxygen in comparison with usual circumstances. The patients were also asked to complete questionnaires over a period extending to 24 hours post-study. The evaluation of the questionnaires showed reduced memory of pain and anxiety, providing evidence of anterograde amnesia.

EXAMPLE 3

Prescription of System 100 and Cassette 200 for Patients Having Implanted AF-ICD A physician wishes to prescribe the 65% $N_2O$/35% $O_2$ mixture to patient X who has an implanted AF-ICD. The prescribing physician is cardiologist K. The prescription is intended for self-administration of the nitrous oxide/oxygen mixture to relieve the pain and anxiety associated with self-initiation of the patient X's AF-ICD in outpatient setting. In practice sessions with the patient X, the cardiologist K had determined that approximately 4 minutes of gas administration are sufficient to produce the desired analgesia and anxiolysis for the patient X.

The patient X first obtains the body 300 (as well as the patient interface assembly 400). The electrophysiologist or cardiologist K may directly provide the patient X with the body 300 and the assembly 400. Alternatively, a pharmacist or a manufacturer provides the body 300 to the patient X on the basis of the prescription from the electrophysiologist or cardiologist K. The body 300 is suitable only for administration of nitrous oxide/oxygen mixture in the prescribed dose. The body 300 provided to the patient X is equipped with the freely turning disk 328a having the array 326a that corresponds to the prescribed dose of nitrous oxide/oxygen mixture. The disk 328a has orange color that indicates that the array 326a would match cassettes containing also corresponds to the color of the cassettes containing the prescribed nitrous oxide/oxygen dose (65% $N_2O$/35% $O_2$ mixture with maximum administration time of 4 minutes).

K writes a prescription for the cassettes to be provided to X. The prescription indicates the type of the prescribed gas mixture ($N_2O/O_2$), the dose (65% $N_2O$/35% $O_2$; 4 minutes of maximum administration), and the quantity. The cassettes have orange color, matching the color of the disk 328a of the body 300 provided to X. K uses X's history of atrial fibrillation to select the quantity of the cassettes to be provided to X. K determines how many times X will likely need to administer the AF-ICD shock over a 3 months period based on X's frequency of prior atrial fibrillation incidents. X submits the prescription to a local or mail order pharmacy. Alternatively, K may forward the prescription directly to the manufacturer or distributor of the cassettes. If X submitted the prescription the mail order pharmacy, the prescribed quantity of cassettes is shipped by regular U.S. mail to X's home, place of work, or other location indicated by X. The cassettes are provided in individual packaging or in cartons containing from 2 to 48 cassettes.

EXAMPLE 4

Prescription of System 100 and Cassette 200 for Patients Having a Temporarily Implanted Catheter with Electrodes Capable of Providing Atrial Defibrillation A large percentage of patients undergoing cardiac surgery such as coronary artery bypass grafts and valve replacements, or other thoracic surgery, experience atrial fibrillation for several days or weeks after surgery. A new method to address this is the placement of a temporary catheter with electrodes that provides the same benefit as an AF-ICD in terms of low energy internal cardioversion vs. high-energy external cardioversion. In the hospital, AF cardioversion shocks using the temporary implanted catheter electrodes would be activated by a physician, but the patient would be able to self administer a mixture of nitrous oxide/oxygen using system 100 in the presence of the physician prior to being shocked.

EXAMPLE 5

Advantage of Analgesic Gas Administration over Intravenous Drugs used in the Prior Art The male patient X with an AF-ICD does not feel capable of activating a shock for whatever reason. The patient X drives to see a physician. In an examination room, the patient X self-administers nitrous oxide/oxygen using the system 100, while the physician or a properly trained nurse activates the shock timer on the patient's AF-ICD. The patient X is able to drive home after 30 minutes by which time the patient has returned to fully normal sensory perception including additional time that provided a margin of safety. In contrast, if the patient X would have been given propofol or midazolam, the patient X would have had to stay at the physician's office for 3 hours after the AF-ICD shock and would have needed someone else to both drive him to the physician's office and back home.

The patient that has undergone cardiac artery bypass graft also known as CABG surgery generally is suffering from multiple clinical conditions and is on multiple medications. It is therefore highly desirable to use an analgesic and anxiolytic drug that has rapid onset and rapid offset, does not interact with other therapeutic drugs, and is non-allergenic, when providing an atrial defibrillation shock using a temporary catheter with electrodes implanted during surgery. It is also desirable to have an administration system such as the system 100 that is easily stored, securely stored, easily used, easily held by the patient, contains multiple safeguards and which incorporates unit doses which can be tracked and assigned to the specific patients chart and cost account.

EXAMPLE 6

Combination of Nitrous Oxide/Oxygen and Propofol

A patient X comes to a hospital and requires external atrial cardioversion. In contrast to the internal atrial cardioversion, the administration of nitrous oxide/oxygen mixture by itself is insufficient to provide sufficient pain relief because of the higher voltage required for external atrial cardioversion. A combination of nitrous oxide/oxygen and propofol is provided to the patient X. Propofol is provided in lower-than-usual dose (e.g., lower amount and/or strength). The patient X returns to normal sensory perception faster than if a usual dose of propofol were administered.

EXAMPLE 7

Combination of Nitrous Oxide/Oxygen and Midazolam

A patient. X comes to a hospital and requires external atrial cardioversion. In contrast to the internal atrial cardioversion, the administration of nitrous oxide/oxygen mixture by itself is insufficient to provide sufficient pain relief because of the higher voltage required for external atrial cardioversion. A combination of nitrous oxide/oxygen and midazolam is provided to the patient X. Midazolam is provided in lower-thanusual dose (e.g., lower amount and/or strength). The patient X returns to normal sensory perception faster than if a usual dose of midazolam were administered.

EXAMPLE 8

Matching of Cassette/Freely Rotating Disk

Suppose, a physician prescribes helium/oxygen mixture to a patient (80% He/20% $O_2$ for a maximum gas administration of A minutes). The physician or a pharmacy provides the patient with the system 100, including the body 300 and the disk 328*a*. Before the system 100 is provided to the patient, the physician or the pharmacy installs the disc 328*a* having the array 326*a* unique to the prescribed gas mixture (He/$O_2$) and the dose (80% He/20% $O_2$ for a maximum gas administration of A minutes). The patient can use the system 100 only with the cassettes containing the prescribed gas at the prescribed dose. For example, if the patient obtains a cassette containing nitrous oxide/oxygen mixture (e.g., 65% $N_2O$/ 35% $O_2$ for a maximum administration period of 4 minutes), such unauthorized cassette cannot be used with the system possessed by the patient. Likewise, if an unauthorized person possesses nitrous oxide/oxygen cassettes, such cassette can be used only with the body 300 authorized for nitrous oxide/oxygen use. If the prescribed therapeutic gas and/or the dose the indicated prescription changes, the disk 328*a* is replaced with a disk having the corresponding array 326*a*. The gas- and/or dose-specific matching of the arrays 206*a* and 326*a* minimizes the possibility that a patient may select a wrong cassette and thus use the wrong gas or gas mixture, and reduces the risk of unauthorized use.

EXAMPLE 9

An FDA Submission Quality Phase I, Double Blind, Randomized, Placebo Controlled, 4-Way Crossover Study to Investigate the CNS Pharmacodynamics of $N_2O/O_2$ Mixtures Administered for Short Periods of Time to Healthy Volunteers The study was conducted in 2002 on 16 normal volunteers to evaluate the pharmacodynamic effects of 3 different concentrations of nitrous oxide mixed with oxygen when administered for 4 minutes, as compared to placebo. These mixtures fall within the range described within this application. The subjects underwent a physical examination, vital sign measurement, blood chemistry, urinalysis and a host of additional screening and baseline evaluations. Objective and subjective measures of sedation and levels of consciousness were employed. During administration of the nitrous oxide in oxygen mixtures and placebo, an EEG was recorded, cognitive tests were performed, Bond and Lader questionnaires completed and saccadic eye movements measured. The study clearly showed that with the concentrations of $N_2O$ used which are described in this application, the end tidal $N_2O$ and therefore desired effect reached a peak equilibrium within a 4 minute period regardless of concentration, with higher concentrations reaching a peak level and therefore providing a desired effect at the earliest time periods. The maximum change in peak saccadic velocity was similar to that induced by a sedative dose of 10 mg of benzodiazipene, with the advantage being that the effects of Nitrous Oxide have a far more rapid offset post administration and desired effect that is measured in minutes, versus the hours required to fully offset the effect of benzodiazapenes. This makes Nitrous Oxide a more ideal agent for use in outpatient procedures, as the patients can leave earlier and in fact drive home by themselves. In addition, memory of events during nitrous oxide in oxygen administration for such short periods was shown to decline post administration. To the best of our knowledge, no such evaluation concerning the short term administration and beneficial effects of a nitrous oxide in oxygen mixture have been previously conducted on a formal Phase I basis or published. The ability of nitrous oxide in oxygen mixtures as described herein to provide a level of desirable pain reduction and anxiety relief in the case of cardiac rhythm shock based therapies, as well as other short time frame diagnostic and therapeutic procedures involving anxiety with a peak point of pain, is further supported by this study, as is the decline in memory of events occurring during such an event.

Unless stated to the contrary, any use of the words such as "including," "containing," "comprising," "having" and the like, means "including without limitation" and shall not be construed to limit any general statement that it follows to the specific or similar items or matters immediately following it. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. Apparatus for the administration of a medical gas to a patient comprising a housing, a compressed gas cartridge disposed within said housing and containing a predetermined amount of said medical gas sufficient for normal respiration by said patient, patient supply means for providing said medical gas to said patient, and a cassette, said compressed gas cartridge being mounted on said cassette, said housing including an upper portion and a lower portion connectable with said upper portion in a configuration in which said housing comprises a completely enclosed configuration, and mounting means for mounting said cassette within said housing, said mounting means comprising first acceptance means associated with said housing and said cassette including second acceptance means, whereby said mounting means will only accept said cassette within said second acceptance means which are compatible with said first acceptance means, and said upper and lower portions of said housing are only connectable with each other in said completely enclosed configuration and said upper and lower portions of said housing cannot be connected to each other so as to form said completely enclosed configuration if said second acceptance means is not compatible with said first acceptance means, said compressed gas cartridge having a size and configuration whereby when said housing is in said completely enclosed configuration said compressed gas cartridge is contained entirely within said housing and said compressed gas cartridge can supply said medical gas to said patient from said housing only when said housing is in said completely enclosed configuration.

2. The apparatus of claim 1 wherein said first acceptance means comprises first key means including at least one member selected from the group consisting of a male member and a female member and said second acceptance means comprises second key means including a member selected from the group consisting of the other of said male member and said female member.

3. The apparatus of claim 2 wherein said first key means comprises a plurality of said first key means and said second means comprises a corresponding plurality of said second key means.

4. The apparatus of claim 1 wherein said cassette includes a plurality of said compressed gas cartridges containing a corresponding plurality of medical gases substantially as required for a single dose of said plurality of medical gases.

5. The apparatus of claim 4 wherein said first acceptance means comprises first key means including at least one member selected from the group consisting of a male member and a female member and said second acceptance means comprises- second key means including at least one member selected from the group consisting of the other of said male member and said female member.

6. The apparatus of claim 5 wherein said first key means comprises a plurality of said first key means and said second key means comprises a corresponding plurality of said second key means.

7. The apparatus of claim 1 including gas delivery means in said upper portion of said housing for delivering said medical gas to said patient supply means.

8. The apparatus of claim 7 wherein said upper portion of said housing further includes gas control means for controlling said delivery of said medical gas to said patient supply means.

9. The apparatus of claim 8 wherein said gas control means comprises a gas control sensor for sensing the content of said medical gas, and valve means for terminating said supply of said medical gas based on said sensed content of said medical gas.

10. The apparatus of claim 9 including room air breathing means, whereby upon said terminating of said supply of said medical gas said room air breathing means supplies room air for breathing by said patient.

11. The apparatus of claim 7 wherein said gas delivery means includes a blender chamber for receiving said medical, gas from said compressed gas cartridge at a predetermined pressure and flow rate.

12. The apparatus of claim 11 including gas control means for controlling said delivery of said medical gas to said patient supply means.

13. The apparatus of claim 12 wherein said gas control means comprises a gas control sensor for sensing the pressure of said medical gas entering said blender chamber, and valve means for terminating said supply of said medical gas based on said sensed pressure of said medical gas.

14. The apparatus of claim 13 including room air breathing means, whereby upon said terminating of said supply of said medical gas said room air breathing means supplies room air for breathing by said patient.

15. The apparatus of claim 13 wherein said gas control means comprises a second gas control means for sensing the pressure of said medical gas leaving said blender chamber, and wherein said valve means terminates said supply of said medical gas based on said sensed pressure of either said gas control means or said second gas control means.

16. The apparatus of claim 15 wherein said gas control means comprises an air inlet port for permitting air to enter said housing for delivery to said patient supply means and an air intake valve for controlling said entry of said air when said valve means terminates said supply of said medical gas.

17. Apparatus for the administration of a medical gas to a patient comprising a housing, a compressed gas cartridge disposed within said housing and containing a predetermined amount of said medical gas sufficient for normal respiration by said patient, patient supply means for providing said medical gas to said patient, said housing including an upper portion and a lower portion connectable with said upper portion in a configuration in which said housing comprises a completely enclosed configuration , and gas delivery means in said upper portion of said housing for delivering said medical gas to said patient supply means, said compressed gas cartridge having a size and configuration whereby when said housing is in said completely enclosed configuration said compressed gas cartridge is contained entirely within said housing and is not accessible from the outside of said housing and said compressed gas cartridge can supply said medical gas to said patient from said housing only when said housing is in said completely enclosed configuration.

18. The apparatus of claim 17 wherein said upper portion of said housing further includes gas control means for controlling said delivery of said medical gas to said patient supply means.

19. The apparatus of claim 18 wherein said gas control means comprises a gas control sensor for sensing the content of said medical gas, and valve means for terminating said supply of said medical gas based on said sensed content of said medical gas.

20. The apparatus of claim 19 including room air breathing means, whereby upon said terminating of said supply of said medical gas said room air breathing means supplies room air for breathing by said patient.

21. The apparatus of claim 17 wherein said gas delivery means includes a blender chamber for receiving said medical gas from said compressed gas cartridge at a predetermined pressure and flow rate.

22. The apparatus of claim 21 including gas control means for controlling said delivery of said medical gas to said patient supply means.

23. The apparatus of claim 22 wherein said gas control means comprises a gas control sensor for sensing the pressure of said medical gas entering said blender chamber, and valve means for terminating said supply of said medical gas based on said sensed pressure of said medical gas.

24. The apparatus of claim 23 including room air breathing means, whereby upon said terminating of said supply of said medical gas said room air breathing means supplies room air for breathing by said patient.

25. The apparatus of claim 23 wherein said gas control means comprises second gas control means for sensing the pressure of said medical gas leaving said blender chamber, and wherein said valve means terminates said supply of said medical gas based on said sensed pressure of either said gas control means or said second gas control means.

26. The apparatus of claim 25 wherein said gas control means comprises an air inlet port for permitting air to enter said housing for delivery to said patient supply means and an air intake valve for controlling said entry of said air when said valve means terminates said supply of said medical gas.

27. Apparatus for the administration of a medical gas to a patient comprising a housing, a compressed gas cartridge disposed within said housing and containing a predetermined amount of said medical gas at a predetermined pressure sufficient for normal respiration by said patient, patient supply means for providing said medical gas to said patient, gas delivery means for delivering said medical gas from said compressed gas cartridge to said patient supply means, said gas delivery means including a blender chamber for receiving said medical gas from said compressed gas cartridge and for maintaining said medical gas at a substantially reduced pressure as compared to said predetermined pressure, and a demand valve for delivering said medical gas from said blender chamber to said patient based upon the inhalation pressure created by said patient, said housing including an upper portion and a lower portion connectable with said upper portion in a configuration in which said housing comprises a completely enclosed configuration, whereby said compressed gas cartridge is fully enclosed within said housing and access to said compressed gas cartridge is prevented.

28. The apparatus of claim 27 including a cassette, said compressed gas cartridge being mounted on said cassette, said housing including mounting means for mounting said cassette within said housing, said mounting means comprising first acceptance means and said cassette including second acceptance means, whereby said mounting means will only accept said cassette having second acceptance means which are compatible with said first acceptance means, and said housing can only close if said first acceptance means and said second acceptance means are compatible with each other.

29. The apparatus of claim 28 wherein said first acceptance means comprises first key means including at least one member selected from the group consisting of a male member and a female member and said second acceptance means comprises second key means including a member selected from the group consisting of the other of said male member and said female member.

30. The apparatus of claim 29 wherein said first key means comprises a plurality of said first key means and said second means comprises a corresponding plurality of said second key means.

* * * * *